(12) United States Patent
Pincetic et al.

(10) Patent No.: US 12,258,410 B2
(45) Date of Patent: Mar. 25, 2025

(54) ANTI-SIRPα ANTIBODIES AND METHODS OF USE THEREOF

(71) Applicant: Alector LLC, South San Francisco, CA (US)

(72) Inventors: Andrew Pincetic, San Francisco, CA (US); Wei-Hsien Ho, Belmont, CA (US); Patricia Culp, Oakland, CA (US); Arnon Rosenthal, Woodside, CA (US)

(73) Assignee: Alector LLC

( * ) Notice: Subject to any disclaimer, the term of this patent is extended or adjusted under 35 U.S.C. 154(b) by 0 days.

(21) Appl. No.: 18/627,754

(22) Filed: Apr. 5, 2024

(65) Prior Publication Data

US 2024/0301071 A1 Sep. 12, 2024

Related U.S. Application Data

(62) Division of application No. 17/707,637, filed on Mar. 29, 2022, now Pat. No. 11,976,119, which is a division of application No. 16/421,692, filed on May 24, 2019, now Pat. No. 11,319,373.

(60) Provisional application No. 62/676,813, filed on May 25, 2018.

(51) Int. Cl.
| | |
|---|---|
| *C07K 16/28* | (2006.01) |
| *C07K 16/24* | (2006.01) |
| *C07K 16/40* | (2006.01) |
| *C07K 16/42* | (2006.01) |
| *C12N 15/85* | (2006.01) |

(52) U.S. Cl.
CPC ......... *C07K 16/283* (2013.01); *C07K 16/246* (2013.01); *C07K 16/2818* (2013.01); *C07K 16/2827* (2013.01); *C07K 16/40* (2013.01); *C07K 16/4283* (2013.01); *C12N 15/85* (2013.01); *C07K 2317/21* (2013.01); *C07K 2317/24* (2013.01); *C07K 2317/32* (2013.01); *C07K 2317/55* (2013.01); *C07K 2317/567* (2013.01); *C07K 2317/622* (2013.01); *C07K 2317/732* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 6,180,370 B1 * | 1/2001 | Queen ................... | A61P 19/02 |
| | | | 435/69.6 |
| 8,562,997 B2 | 10/2013 | Jaiswal et al. | |
| 9,399,682 B2 | 7/2016 | Jaiswal et al. | |
| 9,493,575 B2 | 11/2016 | Jaiswal et al. | |
| 9,605,076 B2 | 3/2017 | Jaiswal et al. | |
| 9,611,329 B2 | 4/2017 | Jaiswal et al. | |
| 9,624,305 B2 | 4/2017 | Jaiswal et al. | |
| 9,624,329 B2 | 4/2017 | Aida et al. | |
| 9,765,143 B2 | 9/2017 | Jaiswal et al. | |
| 10,081,680 B2 * | 9/2018 | Weiskopf ................ | A61P 35/00 |
| 2002/0090674 A1 | 7/2002 | Rosen et al. | |
| 2002/0114807 A1 | 8/2002 | Berg et al. | |
| 2003/0054415 A1 | 3/2003 | Buhring et al. | |
| 2016/0333093 A1 | 11/2016 | Weiskopf et al. | |
| 2017/0247464 A1 | 8/2017 | Poirier et al. | |
| 2018/0105600 A1 | 4/2018 | Pons et al. | |
| 2019/0359707 A1 | 11/2019 | Pincetic et al. | |

FOREIGN PATENT DOCUMENTS

| | | |
|---|---|---|
| CL | 2019003266 A1 | 3/2020 |
| CL | 2020002305 A1 | 2/2021 |
| CL | 2021000738 A1 | 8/2021 |
| CL | 2021001260 A1 | 12/2021 |
| CL | 2021001627 A1 | 1/2022 |
| CN | 105026426 A | 11/2015 |
| CN | 107106679 A | 8/2017 |
| EP | 2953633 B1 | 10/2017 |
| WO | 2001040307 A1 | 6/2001 |
| WO | 2002092784 A2 | 11/2002 |
| WO | 2009046541 A1 | 4/2009 |
| WO | 2009091547 A1 | 7/2009 |
| WO | 2009091601 A1 | 7/2009 |
| WO | 2009131453 A1 | 10/2009 |
| WO | 2010130053 A1 | 11/2010 |
| WO | 2013056352 A1 | 4/2013 |
| WO | 2013063076 A1 | 5/2013 |
| WO | 2014072876 A1 | 5/2014 |
| WO | 2014123580 A1 | 8/2014 |
| WO | 2014124028 A1 | 8/2014 |
| WO | 2015138600 A3 | 11/2015 |

(Continued)

OTHER PUBLICATIONS

Janeway, Charles A. "Immunobiology: The Immune System in Health and Disease." 2001 (Year: 2001).*

Kipriyanov, Sergey M., and Fabrice Le Gall. "Generation and production of engineered antibodies." Molecular biotechnology 26.1 ( 2004): 39-60.(Year: 2004).*

Adams et al., "Signal-Regulatory Protein Is Selectively Expressed by Myeloid and Neuronal Cells," J Immunol 1998; 161:1853-1859.

(Continued)

*Primary Examiner* — Michael Szperka
*Assistant Examiner* — Lia E Taylor
(74) *Attorney, Agent, or Firm* — McNeill PLLC

(57) ABSTRACT

The present disclosure is generally directed to compositions that include antibodies, e.g., monoclonal, antibodies, antibody fragments, etc., that specifically bind a SIRPA polypeptide, e.g., a mammalian SIRPA or human SIRPA, and use of such compositions in preventing, reducing risk, or treating an individual in need thereof.

76 Claims, 38 Drawing Sheets
Specification includes a Sequence Listing.

(56) References Cited

FOREIGN PATENT DOCUMENTS

| | | |
|---|---|---|
| WO | 2015177360 A1 | 11/2015 |
| WO | 2016023019 A2 | 2/2016 |
| WO | 2016063233 A1 | 4/2016 |
| WO | 2016205042 A1 | 12/2016 |
| WO | 2017068164 A1 | 4/2017 |
| WO | 2017178653 A2 | 10/2017 |
| WO | 2017180519 A1 | 10/2017 |
| WO | 2017184553 A1 | 10/2017 |
| WO | 2017197495 A1 | 11/2017 |
| WO | 2018013534 A1 | 1/2018 |
| WO | 2018026600 A1 | 2/2018 |
| WO | 2018057669 A1 | 3/2018 |
| WO | 2018107058 A1 | 6/2018 |
| WO | 2017178653 A3 | 7/2018 |
| WO | 2018190719 A2 | 10/2018 |
| WO | 2018210795 A1 | 11/2018 |
| WO | 2018210793 A3 | 12/2018 |
| WO | 2019022600 A1 | 1/2019 |
| WO | 2019023347 A1 | 1/2019 |
| WO | 2019175218 A1 | 9/2019 |
| WO | 2020068752 A1 | 4/2020 |
| WO | 2020099653 A1 | 5/2020 |
| WO | 2020127373 A1 | 6/2020 |

OTHER PUBLICATIONS

Ahmad, K., "Insulin sources and types: a review of insulin in terms of its mode on diabetes mellitus," Journal of Traditional Chinese Medicine, vol. 34, issue 2 (2014).

Alblas et al., "Signal Regulatory Protein a Ligation Induces Macrophage Nitric Oxide Production through JAK/STAT- and Phosphatidylinositol 3-Kinase/Rac1/NAPDH Oxidase/H2O2-Dependent Pathways", Molecular and Cellular Biology, vol. 25, No. 16, pp. 7181-7192, Aug. 15, 2005.

Anonymous, "MABS164 | Anti-SHPS-1 Antibody, clone P84," 4 pages (Jan. 1, 2016). Retrieved from the Internet: http://www.merckmillipore.com/NL/en/product/Anti-SHPS-1-Antibody,-clone-P84,MM N F-MABS164#anchorPackaging%20Information.

Barclay et al., "Signal regulatory protein alpha (SIRPα) / CD47 interaction and function," Curr Opin Immunol. Feb. 2009 ; 21(1): pp. 47-52.

Berglund, L., et al., "The epitope space of the human proteome," Protein Science, vol. 17, pp. 606-613 (2008).

Bio-Rad Antibodies, formerly AbD Serotec; Summary.

Bostrom et al., "Improving antibody binding affinity and specificity for therapeutic development", Methods in Molecular Biology, 2009; vol. 525, pp. 353-376.

Chao et al., "Mechanisms of targeting CD47-SIRP in hematologic malignancies," Blood, vol. 119, No. 18, pp. 4334-4336, May 3, 2012.

Chen, L., et al., "Epitope-directed antibody selection by site-specific photocrosslinking," Science Advances, vol. 6, No. 14, p. eaaz7825 (2020).

Chiavenna et al., "State of the art in anti-cancer mAbs," Journal of Biomedical Science (2017) 24:15.

Cosmetology, vol. 18, pp. 57-61 (2010).

De Vries et al., "Signal-regulatory protein alpha-CD47 interactions are required for the transmigration of monocytes across cerebral endothelium," The Journal of Immunology, vol. 168, No. 11, pp. 5832-5839 (Jun. 1, 2002).

Edwards, B., et al., "The Remarkable Flexibility of the Human Antibody Repertoire; Isolation of Over One Thousand Different Antibodies to a Single Protein, BLyS," Journal of Molecular Biology, vol. 334, pp. 103-118 (2003).

Fournier et al., "Surfactant Protein D (Sp-D) Binds to Membrane-proximal Domain (D3) of Signal Regulatory Protein (SIRPα), a SiteDistant from Binding Domain of CD47, while Also Binding to Analogous Region on Signal Regulatory Protein β ((SIRPα)", J Biol Chem, 2012, 287:19386-19398.

Gonzales, et al., "Minimizing the Immunogenicity of Antibodies for Clinical Application", Tumour Biol., Jan.-Feb. 2005, vol. 26, No. 1, pp. 31-43.

Hatherly et al., "Polymorphisms in the Human Inhibitory Signal-regulatory Protein Do Not Affect Binding to Its Ligand CD47," The Journal of Biological Chemistry, vol. 289, No. 14, pp. 10024-10028, Apr. 4, 2014.

Huang, R., et al., "Trastuzumab-cisplatin conjugates for targeted delivery of cisplatin to HER2-overexpressing cancer cells," Biomedicine & Pharmacotherapy, vol. 72, pp. 17-23 (2015).

International Search Report and Written Opinion of International Application No. PCT/US2019/0363884, dated Aug. 27, 2019 (16 pages).

International Search Report and Written Opinion of PCT/US2017/065366 dated Mar. 26, 2018, (18 pages).

Janeway, C. A., Jr., et al., "The interaction of the antibody molecule with specific antigen", Immunobiology: The Immune System in Health and Disease, 5th Edition, New York: Garland Science (2001).

Janeway, Charles A., "Immunology: The Immune System in Health and Disease," (2001).

Kipriyanov et al., "Generation and production of engineered antibodies," Molecular Biotechnology, vol. 26, No. 1, pp. 39-60 (2004).

Kunik et al., "Structural consensus among antibodies defines the antigen binding site", PLoS Comput Biol., Feb. 23, 2012, vol. 8, No. 2.

Lee et al., "Novel Structural Determinants on SIRPα that Mediate Binding to CD47," Journal of Immunology, Jan. 1, 2007, vol. 179, No. 11, pp. 7741-7750.

Liu et al., "Functional Elements on SIRPα IgV domain Mediate Cell Surface Binding to CD47," J Mol Biol. Jan. 19, 2007; 365(3): 680-693.

Liu et al., "Signal regulatory protein (SIRPα), a cellular ligand for CD47, regulates neutrophil transmigration," The American Society for Biochemistry and Molecular Biology, J Biol Chem, 2002, 277:10028-10036.

Liu, Q., et al., "Inhibition of SIRP[alpha] in dendritic cells potentiates potent antitumor immunity," Oncoimmunology, vol. 5, No. 9, p. e1183850 (2016).

Matozaki et al., "Functions and molecular mechanisms of the CD47—SIRPα signalling pathway," Trends Cell Biol, 2009, 19:72-80.

Mimoto, F., et al., "Engineered antibody Fc variant with selectively enhanced FcγRIIb binding over both FcγRIIa(R131) and FcγRIIa(H131)," Protein Eng Des Sel, vol. 26, No. 10, pp. 589-598 (2013).

Muchtar, E., et al., "Immunoglobulin Light-Chain Amyloidosis: From Basics to New Developments in Diagnosis, Prognosis and Therapy," Acta Haematol, vol. 135, No. 3, pp. 172-190 (2016).

Murata et al., "The CD47SIRPa signalling system: its physiological roles and therapeutic application," J. Biochem. 2014;155(6):335-344.

Oldenborg, "Cd47-Signal Regulatory Protein α (Sirpα) Regulates Fcy and Complement Receptor-Mediated Phagocytosis," The Journal of Experimental Medicine, vol. 193, No. 7, pp. 855-861, Apr. 2, 2001.

Padlan, E., "X-ray Crystallography of Antibodies", Advances in Protein Chemistry, vol. 49, pp. 57-134 (1996).

Pan et al., "Signal Regulatory Protein a Is Associated With Tumor-Polarized Macrophages Phenotype Switch and Plays a Pivotal Role in Tumor Progression," Hepatology, vol. 58, No. 2, pp. 680-691, 2013.

Ratnikova, et al., "CD47 receptor as a primary target for cancer therapy", Mol Biol (Mosk), 51(2), 2017, 251-261 (11pgs.).

Ring, et. al., "Anti-SIRPα antibody immunotherapy enhances neutrophil and macrophage antitumor activity", PNAS, vol. 114 (49), 2017, E10578-E10585, 8 pages.

Rissiek, B., et al., "Nanobodies as modulators of inflammation: potential applications for acute brain injury," Front Cell Neurosci, vol. 8, p. 344 (2014).

Rudikoff, S. et al: "Single amino acid substitution altering antigen-binding specificity", Proceedings of the National Academy of

(56) References Cited

OTHER PUBLICATIONS

Sciences, National Academy of Sciences, vol. 79, Mar. 1, 1982 (Mar. 1, 1982), pp. 1979-1983 (7 pgs.).

Seiffert et al., "Human Signal-Regulatory Protein Is Expressed on Normal, But Not on Subsets of Leukemic Myeloid Cells and MediatesCellular Adhesion Involving Its Counterreceptor CD47," Blood, vol. 94, No. 11, pp. 3633-3646, Dec. 1, 1999.

Seiffert et al., "Signal-regulatory protein α (SIRPα) but not SIRPβ is involved in T-Cell activation, binds to CD47 with high affinity, and is expressed on immature CD34+CD38-hematopoietic cells," Blood, vol. 97, No. 9, pp. 2741-2749, May 1, 2001.

Sharma, G., et al., "The Role of Cell-Penetrating Peptide and Transferrin on Enhanced Delivery of Drug to Brain," International Journal of Molecular Sciences, vol. 17, No. 6, p. 806 (2016).

Sim, J., et al., "Discovery of high affinity, pan-allelic, and pan-mammalian reactive antibodies against the myeloid checkpoint receptors SIRP[alpha]", mAbs, vol. 11, No. 6, pp. 1036-1052 (Jul. 1, 2019).

Van Beek et al., "Signal Regulatory Proteins in the Immune System," J Immunol 2005; 175:7781-7787.

Wark et al., "Latest technologies for the enhancement of antibody affinity", Advanced Drug Delivery Reviews, Elsevier, vol. 58, No. 5-6, Aug. 7, 2006, pp. 657-670.

Weiskopf et al., "Cancer immunotherapy targeting the CD47/SIRPα axis", Trends Cell Biol, 2009, 19:72-80.

Willingham et al., "The CD47-signal regulatory protein alpha (SIRPa) interaction is a therapeutic target for human solid tumors," PNAS, vol. 109, No. 17, pp. 6662-6667, Apr. 24, 2012.

Yanagita et al., Anti-SIRPα antibodies as a potential new tool for cancer immunotherapy, JCI Insight, vol. 2, No. 1, pp. 2379-3708, Jan. 12, 2017.

Zhao et al., "CD47-signal regulatory protein-α (SIRPα) interactions form a barrier for antibody-mediated tumor cell destruction," PNAS, vol. 108, No. 45, pp. 18342-18347, Nov. 8, 2011.

Zhao et al., "Is targeting of CD47-SIRP enough for treating hematopoietic malignancy?" Blood, vol. 119, No. 18, pp. 4333-4334, 2012.

\* cited by examiner

| | | |
|---|---|---|
| Human | 100.0% | EEELQVIQPDKSVLVAAGETATLRCTATSLIPVGPIQWFRGAGPGRELIYNQKEGHFPRV |
| Cyno | 88.6% | EEELQVIQPEKSVSVAAGDSAILNCTVSSLIPVGPIQWFRGAGPGRELIYNLKEGHFPRV |
| Marmoset | 86.0% | EEELQVVQPEKSVSVAAGETATLHCTVTSLVPVGPIQWFRGAGPGRELIYNQKEGQFPRV |
| Rabbit | 71.2% | QEKLQVTQPDRWVSVAEGEAATLRCTINTLLPVGPMKWFRGAGPDRKMIYNFKGDQDPRV |
| Dog | 71.8% | EAELQVIQPEKSVSVAAGETATLRCTLTSLIPVGKVEWFRGTGPGRELIFHFKGGHFPRV |
| | | : :***:* * * * *:.* : . .: :*** |

| | | |
|---|---|---|
| Human | 100.0% | TTVSDLTKRNNMDFSIRIGNITPADAGTYYCVKFRKGSPDDVEFKSGAGTELSVRAKPSA |
| Cyno | 88.6% | TPVSDPTKRNNMDFSIRISNITPADAGTYYCVKFRKGSPD-VELKSGAGTELSVRAKPSA |
| Marmoset | 86.0% | TAVADQTKRNNMDHSIRISNITPADAGTYYCVKFRKASPIDVELKSGPGTELSVRAKPSA |
| Rabbit | 71.2% | TNVSDTTKRNNMDFSIRIRDITPADAGTYYCVKFQKKGADDEEFKSGGGTQVSVSAKPST |
| Dog | 71.8% | TNVSDSTKRRNNTDFSIRISNITPADTGTYYCVKFQKGNPD-VELKSGPGTLVTVSAKPSP |
| | | * *: **** *. * : **::*.* :*** |

| | | |
|---|---|---|
| Human | 100.0% | PVVSGPAARATPQHTVSFTCESHGFSPRDITLKWFKNGNELSDFQTNVDPVGESVSYSIH |
| Cyno | 88.6% | PVVSGPAVRATAEHTVSFTCESHGFSPRDITLKWFKNGNELSDFQTNVDPAGKSVSYSIR |
| Marmoset | 86.0% | PVVSGPATRVTPEDTVSFTCESHGFSPRDITLKWFKNANELSALQTTVDPAGESVSYSIR- |
| Rabbit | 71.2% | PKVSGPGARSTPEQIVDFTCESHGFSPRNISLKWFKNGNELPAFQTSVYPAGESVSYNVT |
| Dog | 71.8% | PVVSGPTARATPQQTVNFTCKSHGFSPRNITLRWFKNGNELTASQTTVYPEEDNASYSIS |
| | | * **** .*:*.* ** *:*.  ..** :.: :..:*:.: |

| | | |
|---|---|---|
| Human | 100.0% | STARVVLTREDVHSQVICEVAHVTLQG-DPLRGTANLSETIRVPPTLEVTQQPVRAENQV |
| Cyno | 88.6% | STARVVLTRRDVHSQVICEVAHVTLQG-DPLRGTANLSEAIRVPPFLEVTQQSMRADNQV |
| Marmoset | 86.0% | STARVGLTRGDVRSQVICEVAHVTLQG-DPLRGTANLSEAIRVPPTLEVTHQPMRAENQV |
| Rabbit | 71.2% | STVGLASSDVHSQVICEVAHITLQGGSPLRGTANLSETIRVPPTVEVTQQPMGAGTQV |
| Dog | 71.8% | STTKLVLAPGDVRSQVICEVAHVTLQGGPPLRGTANLSETLRVPPTLEVSQHPMAGD-QV |
| | | **.:.: * : :*****:. :.::::. . :* |

| | | |
|---|---|---|
| Human | 100.0% | NVTCQVRKFYPQRLQLTWLENGNVSRTETASTVT---ENKDGTYNWMSWLLVNVSAHRDD |
| Cyno | 88.6% | NVTCQVTKFYPQRLQLTWLENGNVSRTEMASALP---ENKDGTYNWTSWLLVNVSAHRDD |
| Marmoset | 86.0% | NVTCQVKKFYPQSLQLTWLENGNVSRTETASTLI---ENKDGTYNWASWLLVNSSAHRDG |
| Rabbit | 71.2% | NVTCHVDKFYPRDMQLSWLENGNVSRTETAWTIV---ENKDGTYNRTSWLLVNSSAHRED |
| Dog | 71.8% | NVTCQVKKFYPQRLQLTWLENGNVSRTETPSVASNLLENKDGTFNWTSWLLVNSSTHRED |
| | | ** ::* : ******* :. . ****:* :****..: |

| | | |
|---|---|---|
| Human | 100.0% | VKLTCQVEHDGQPAVSKSHDLKVSAHPKEQGSNTAAENTGSNERNIY |
| Cyno | 88.6% | VKLTCQVEHDGQPAVNKSFSVKVSAHPKEQGSNTAAENTGTNERNIY |
| Marmoset | 86.0% | VVLTCQVEHDGQPAVSKSLRLEVSAHRKEQGSDTAAEKTGTNERNIY |
| Rabbit | 71.2% | VVLSCQVEHDGQPAVTRSHTLQVSAPPKEQGTDTSLDQADNWNVF-- |
| Dog | 71.8% | VVFTCQVQHDGQPAVTKNHTLVASARQKDQETLKPEDNDSRSIF-- |
| | | * :*:******.:. . .* * ::*: . : |

Fig. 1

```
Potential humanized sequence based on IGHV3-23*01 acceptor framework (AbM CDR definition)
IGHV3-23*01  EVQLLESGGGLVQPGGSLRLSCAASGFTFSSYAMSWVRQAPGKGLEWVSAISGSGGSTYYADSVKG
             RFTISRDNSKNTLYLQMNSLRAEDTAVYYCAK
Joining region  IMGT J00256|IGHJ4*01|YFDYWGQGTLVTVSS 10          20          30          40          50          60
seq                                                                              ab
AbM         b b b   p       p b b b       b b     b b i l     i ibb b
SB-3F9      EVKLVESGGGLVQPGGSLKLRLSCAAS GFTFSSYAMS WVRQTPEKRLEWVA TISDYGGSTY
                *                         *  *  *                   *
IGHV3-23*01 EVQLLESGGGLVQPGGSLRLSCAAS GFTFSSYAMS WVRQAPGKGLEWVS AISG-SGGSTY
hSB-3F9-H1  EVQLLESGGGLVQPGGSLRLSCAAS GFTFSSYAMS WVRQAPGKGLEWVS TISDYGGSTY
hSB-3F9-H2  EVQLLESGGGLVQPGGSLRLSCAAS GFTFSSYAMS WVRQAPGKGLEWVA TISDYGGSTY 70          80  abc     90          100         110  100abcd  120       110
seq                                                                                               b b b
AbM         i b b b x   b b b   b     bibibb
SB-3F9      YPDSVKGRFTISRDNAKYTILYLQMSSLRSEDTALYYCAR PPIDDYYGGFAY WGQGTLVTVSA
             p                  *    *                              *
IGHV3-23*01 YADSVKGRFTISRDNSKNTLYLQMNSLRAEDTAVYYCAK
hSB-3F9-H1  YADSVKGRFTISRDNSKNTLYLQMNSLRAEDTAVYYCAR PPIDDYYGGFAY WGQGTLVTVSS
hSB-3F9-H1  YADSVKGRFTISRDNSKNTLYLQMNSLRAEDTAVYYCAR PPIDDYYGGFAY WGQGTLVTVSS
                                                  L Fig. 2A
```

Potential humanized sequence based on IGKV3-11*01 acceptor framework (AbM CDR definition)
IGKV3-11*01 EIVLTQSPATLSLSPGERATLSCRASQSVSSYLAWYQQKPGQAPRLLIYDASNRAT
            GIPARFSGSGSGTDFTLTISSLEPEDFAVYYCQQRSNWPP
Joining region IMGT J00242|IGKJ2*01|YTFGQGTKLEIK

```
                         10             20              30             40         50          60
seq                      10             20            30abcd           40         50
AbM              b b b    p p     b b b  b    b    bi b   b    bi bi i     ii ibbi   i
SB-3F9       DIVLTQSPASLAVSLGQRATISC RASQSVS-----SYLA    WYQQKPGQAPRLLIY DASNRAT
                 *  ***  *     * *    **** *             *
3-11*01      EIVLTQSPATLSLSPGERATLSC RASQSVS-----SYLA    WYQQKPGQAPRLLIY DASNRAT
hSB-3F9-L1   EIVLTQSPATLSLSPGERATISC RASKSVSSSGYSYMH     WYQQKPGQAPRLLIY LASNLES
hSB-3F9-L2   EIVLTQSPATLSLSPGERATISC RASKSVSSSGYSYMH     WYQQKPGQAPRLLIY LASNLES
hSB-3F9-L3   EIVLTQSPATLSLSPGERATISC RASKSVSSSGYSYMH     WYQQKPGQAPRLLIY LASNLES
                                            V                   P                  #

70           80             90             100           110
                  70           80             90             100
AbM        b  b    b b b     ib b    ibi ib i   i   b b b
SB-3F9     GVPARFSGSGSGTDFTLNIHPVEEDAATYYC QHNRELPCT FGGGTKLEIK
            *
3-11*01    GIPARFSGSGSGTDFTLTISSLEPEDFAVYYC QQRSNWPP
hSB-3F9-L1 GIPARFSGSGSGTDFTLTISSLEPEDFAVYYC QHNRELPCT FGGGTKLEIK
hSB-3F9-L2 GVPARFSGSGSGTDFTLTISSVEPEDFAVYYC QHNRELPCT FGGGTKLEIK
hSB-3F9-L3 GVPARFSGSGSGTDFTLTISSVEPEDFAVYYC QHNRELPST FGGGTKLEIK
                                      A                #
```

Fig. 2B

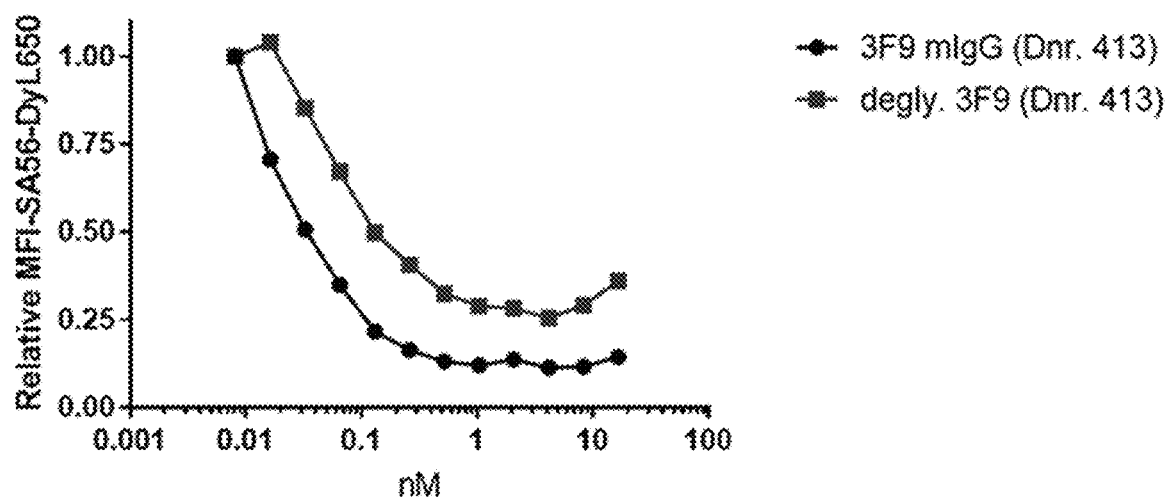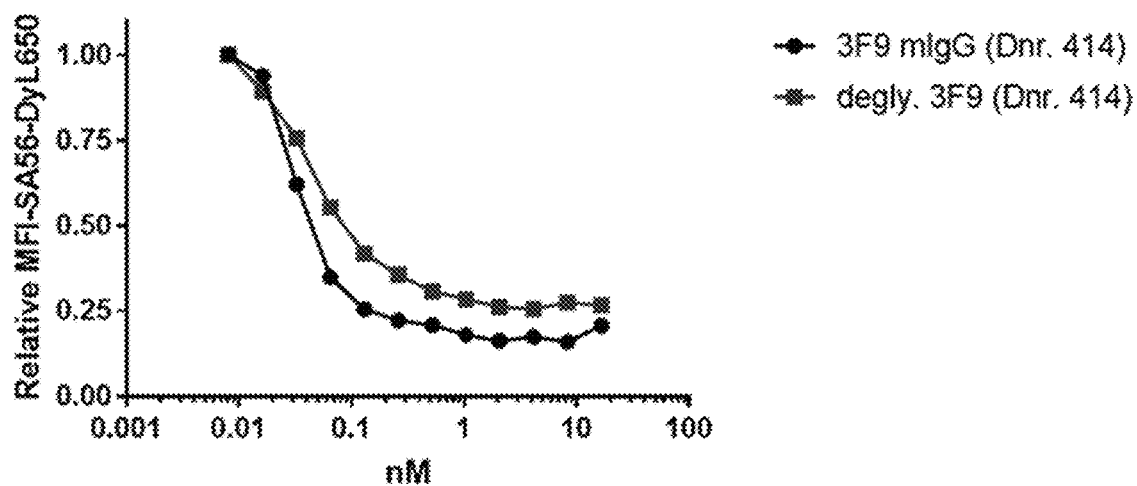
Fig. 4A

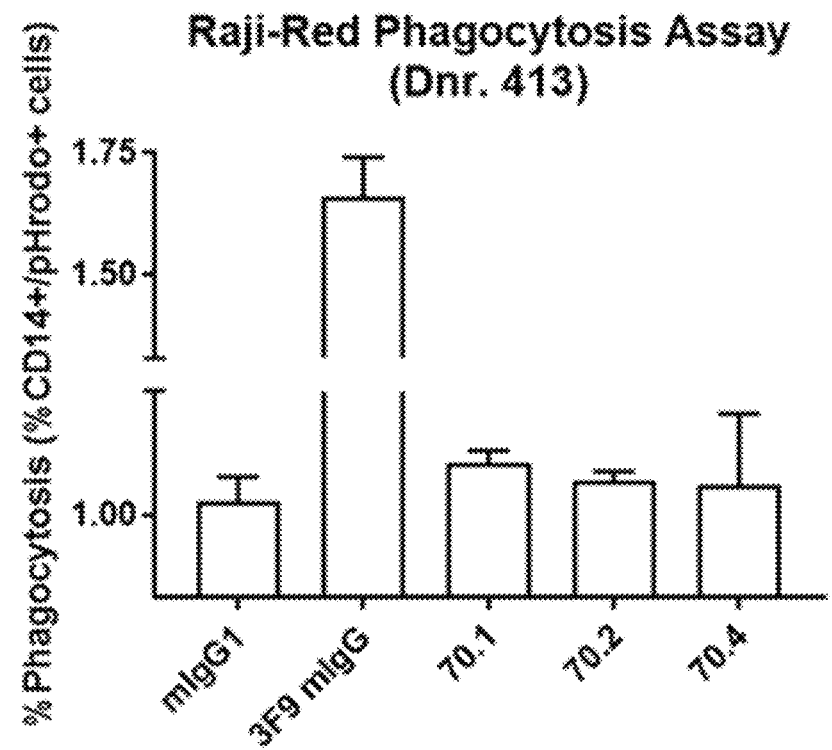
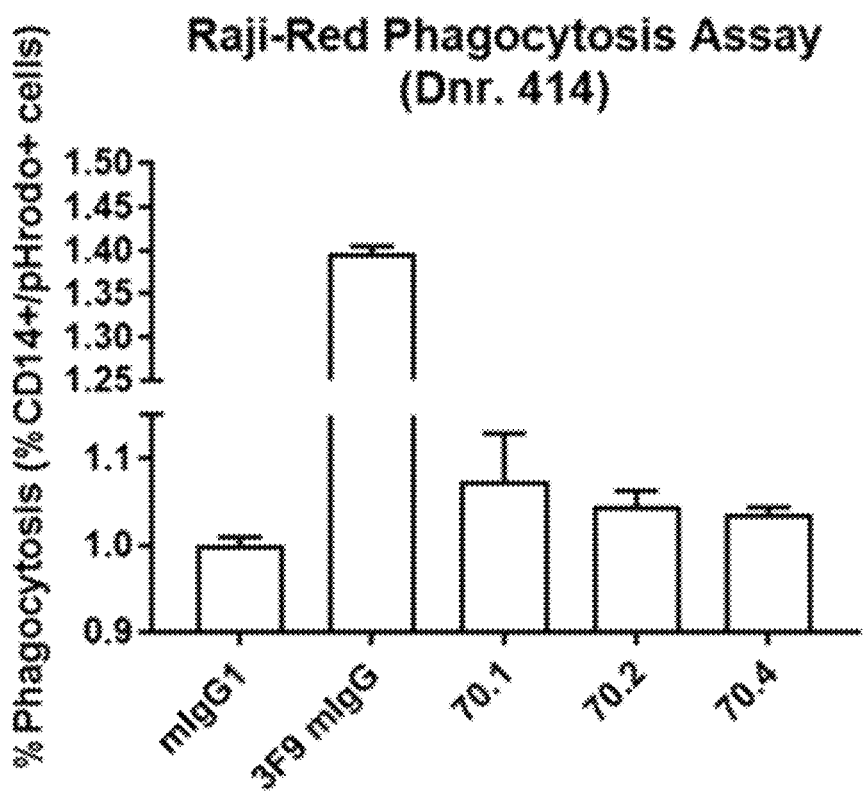
Fig. 5A

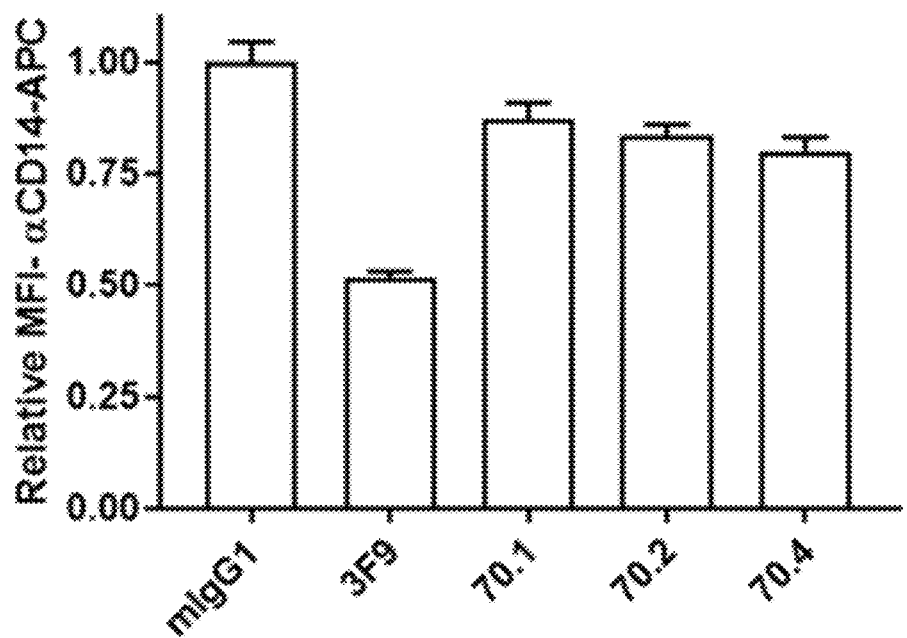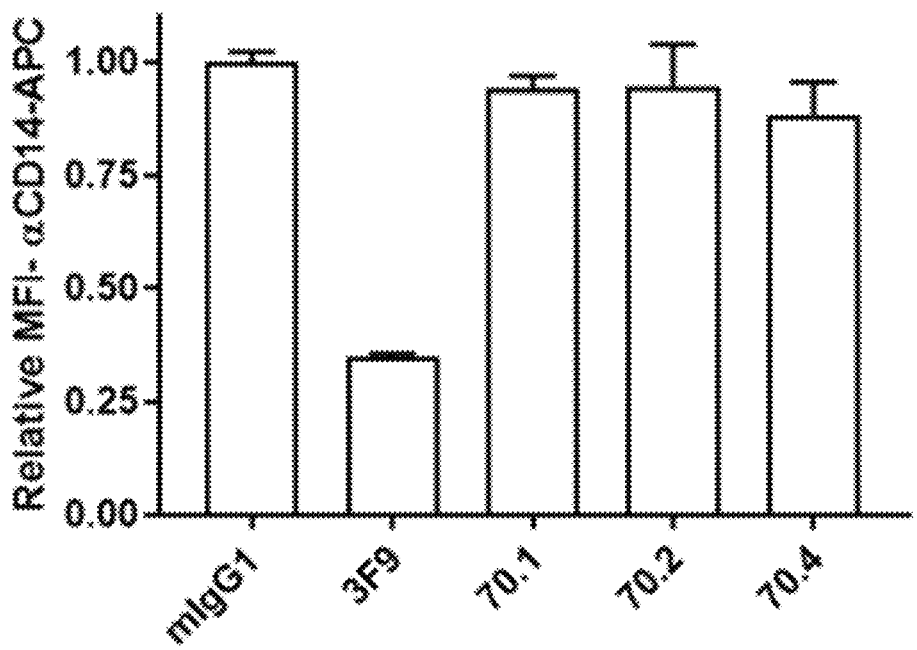
Fig. 5B

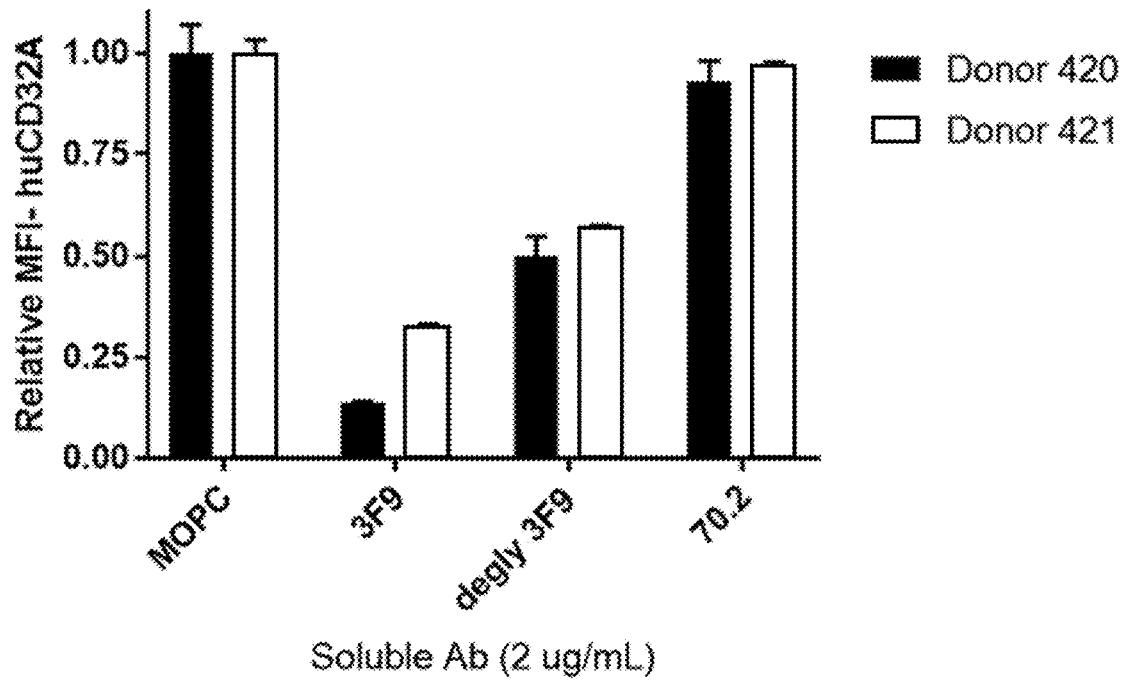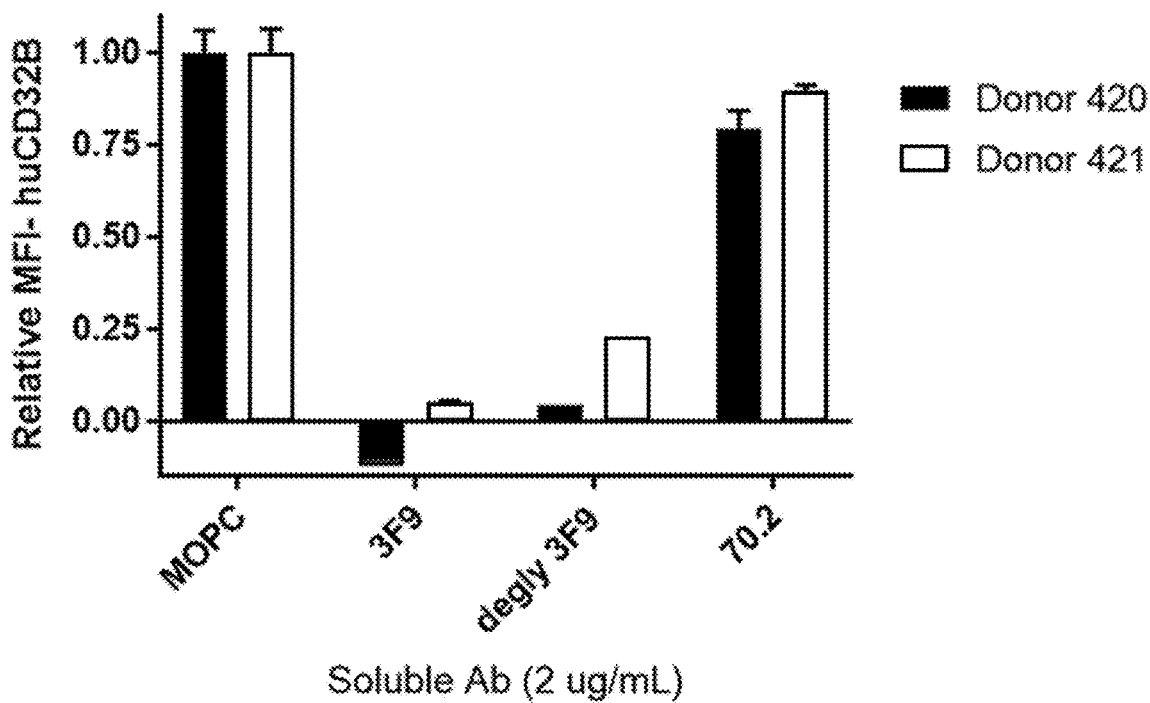
Fig. 6B

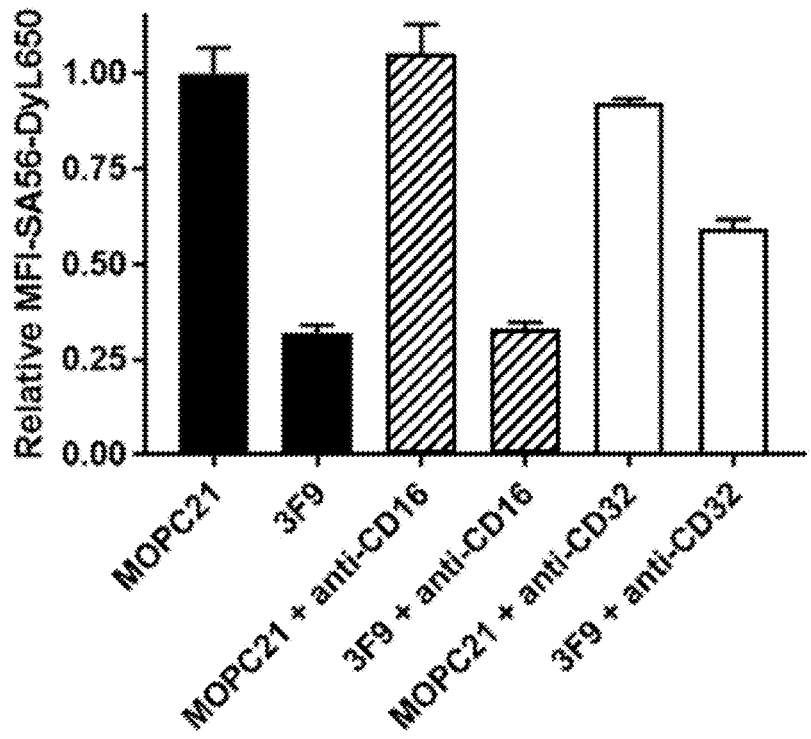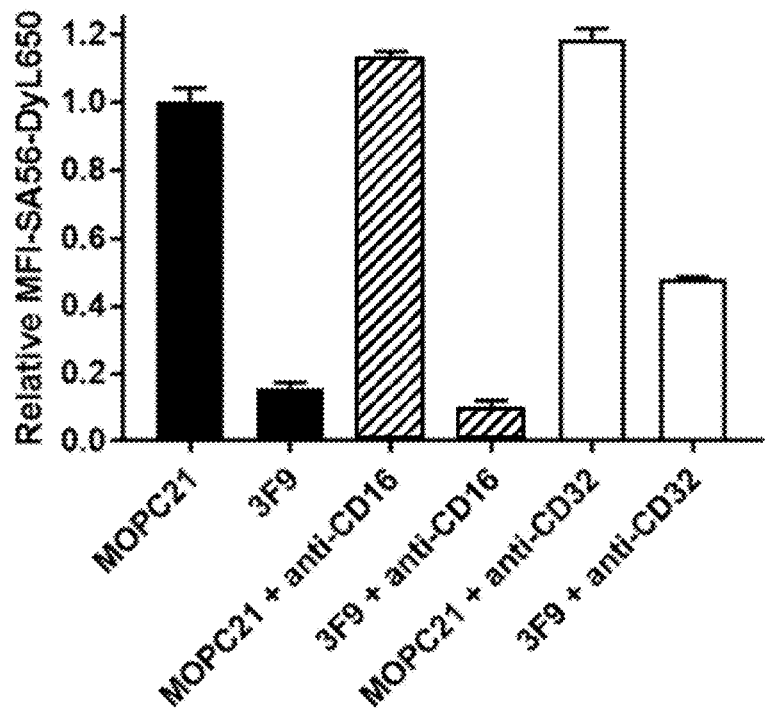
Fig. 7A

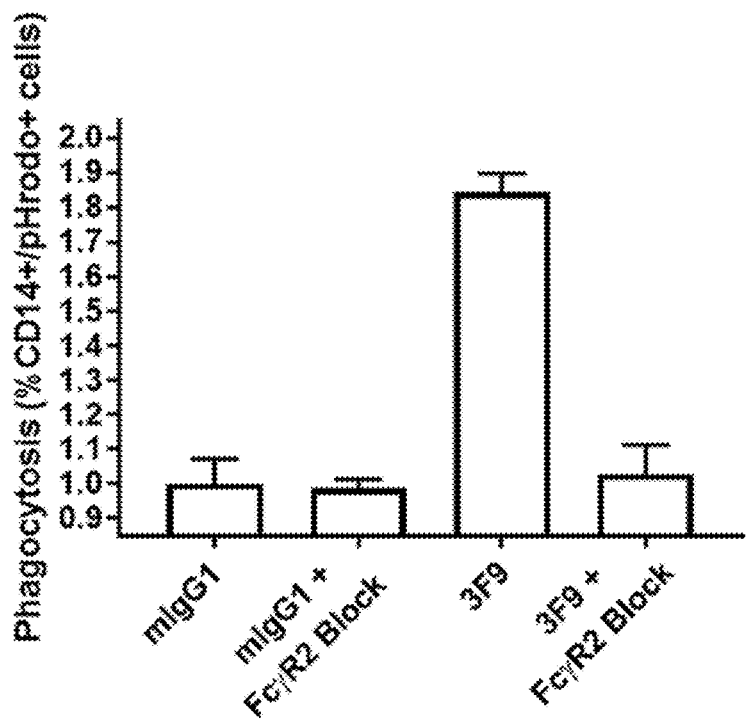
(Human Macrophage Dnr. 432)
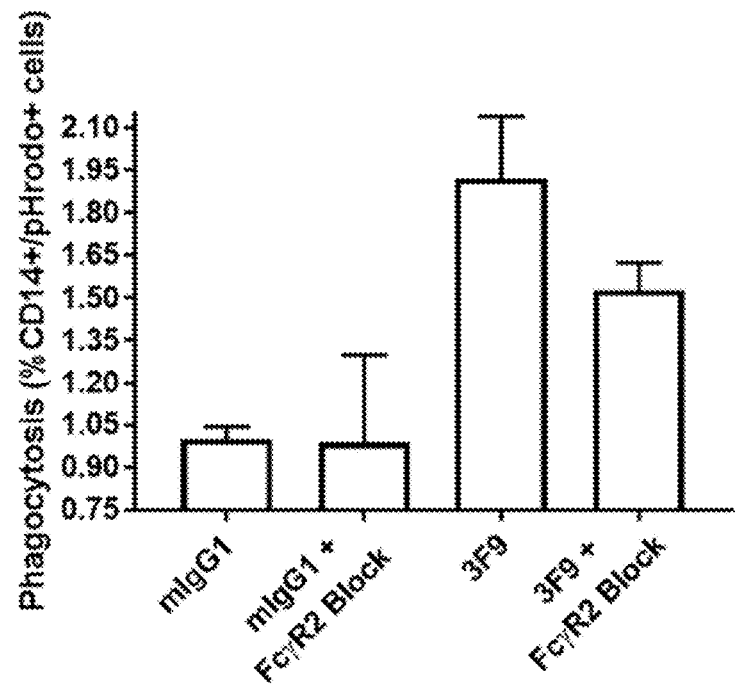
(Human Macrophage Dnr. 433)
*Fig. 7B*

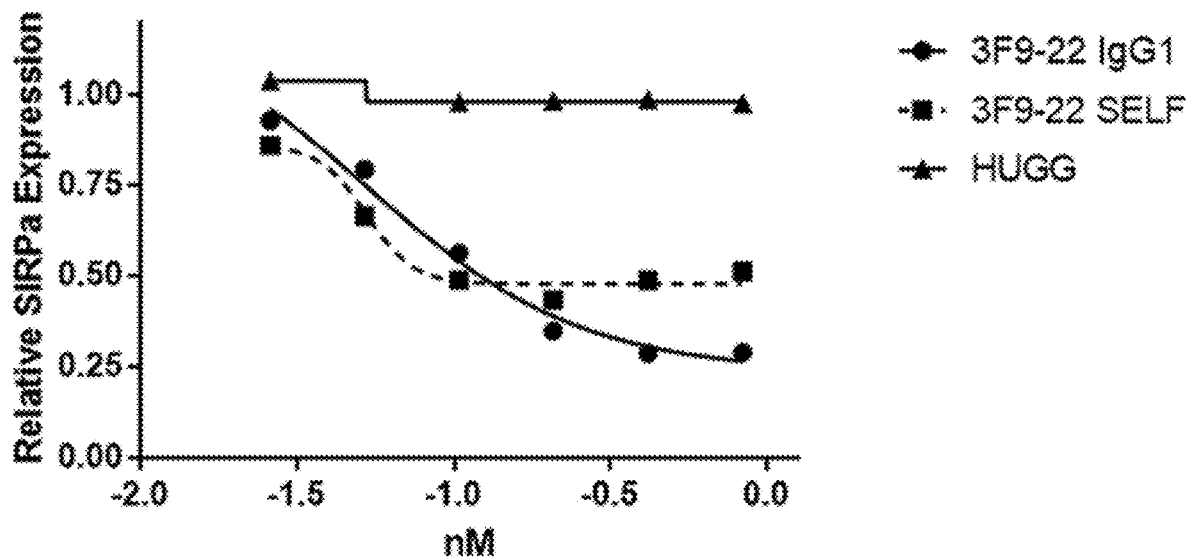
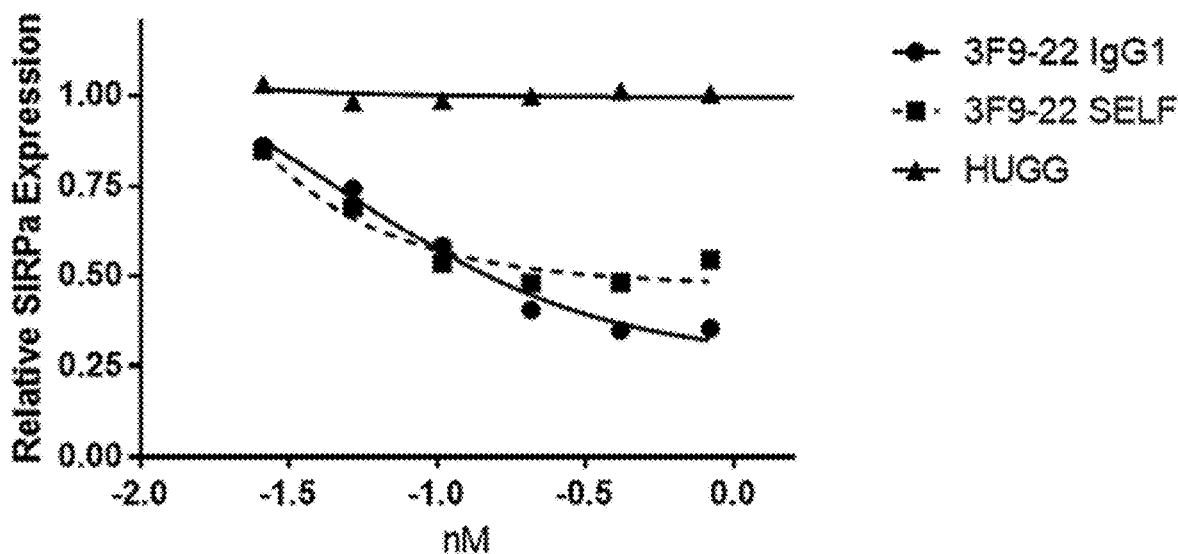
Fig. 8A

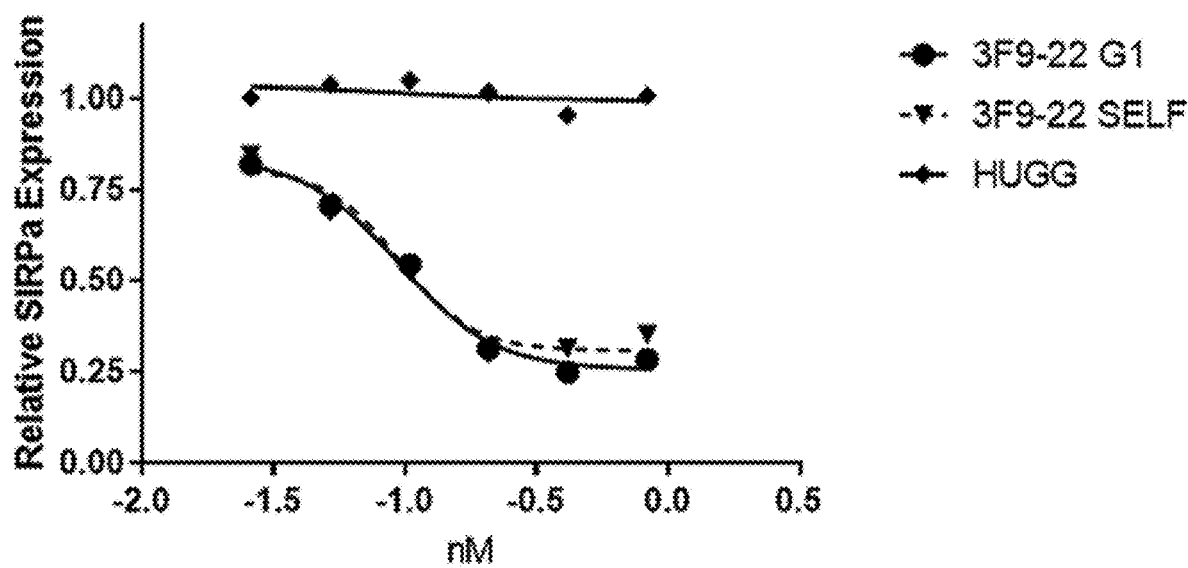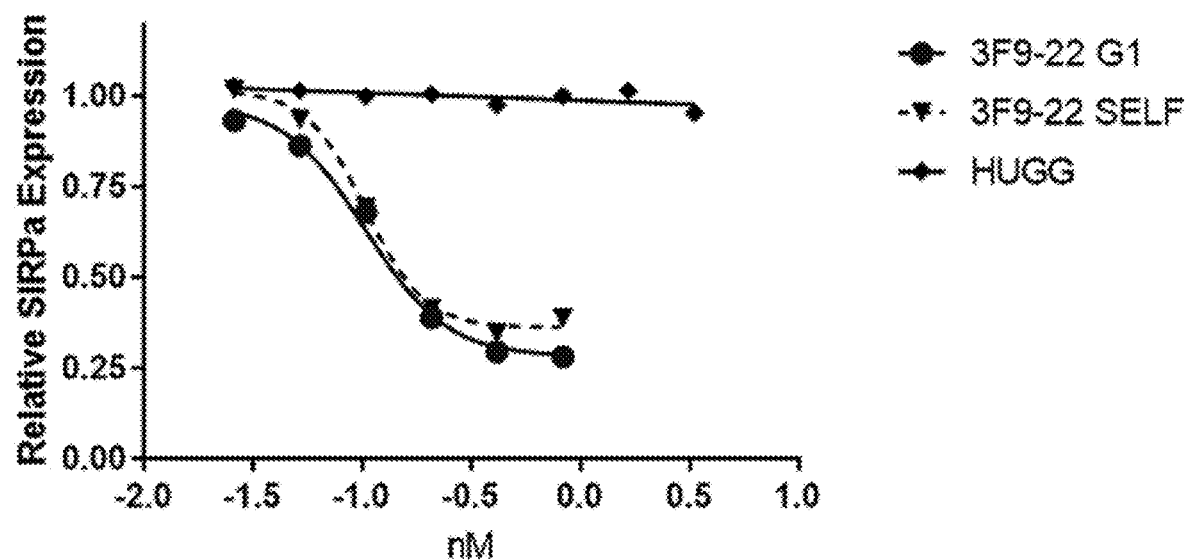
Fig. 8B

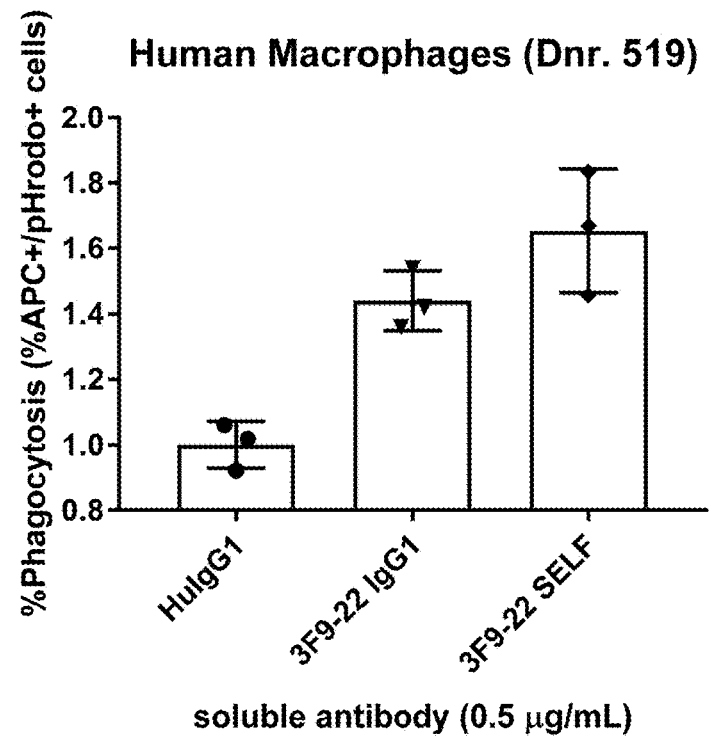
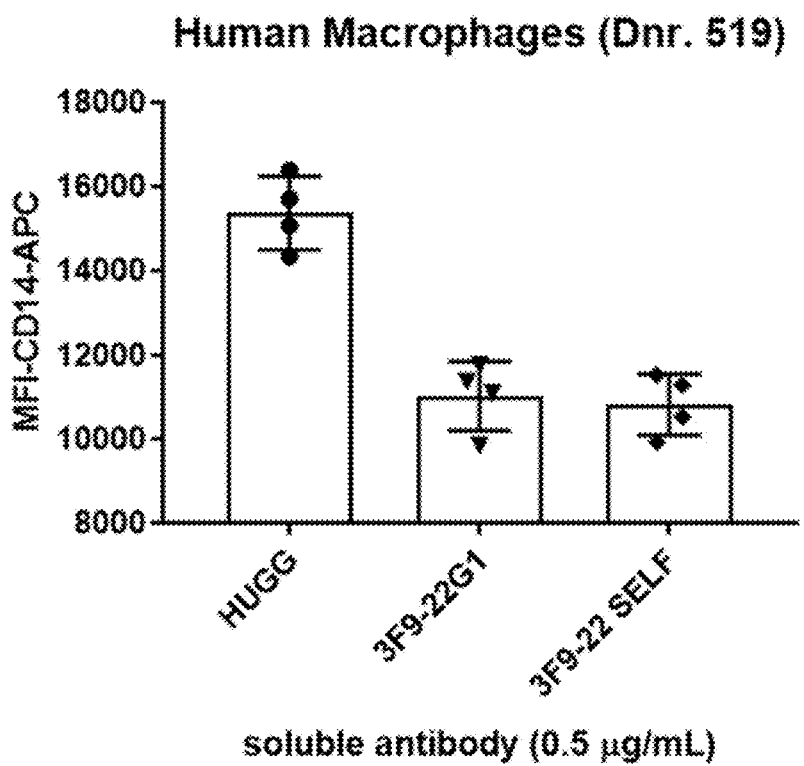
Fig. 10A

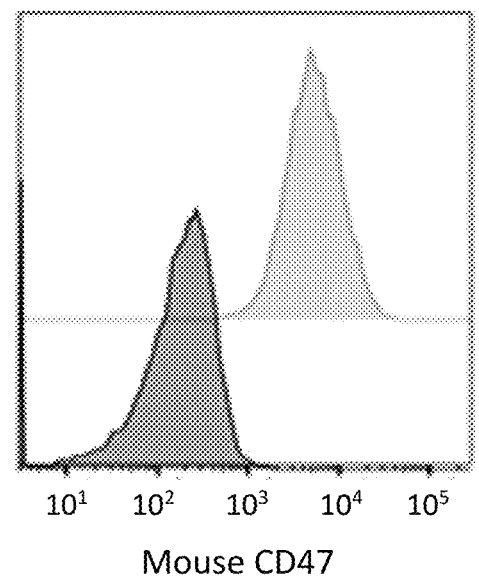
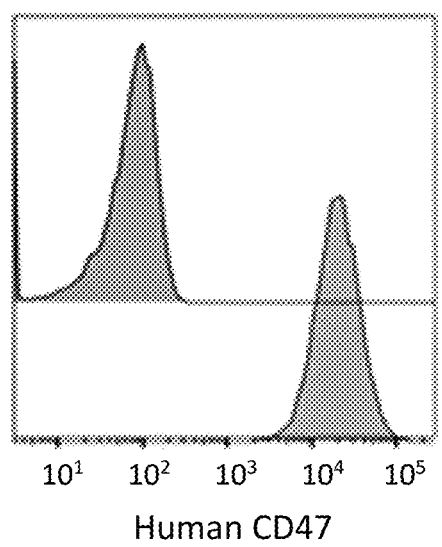
Fig. 17A

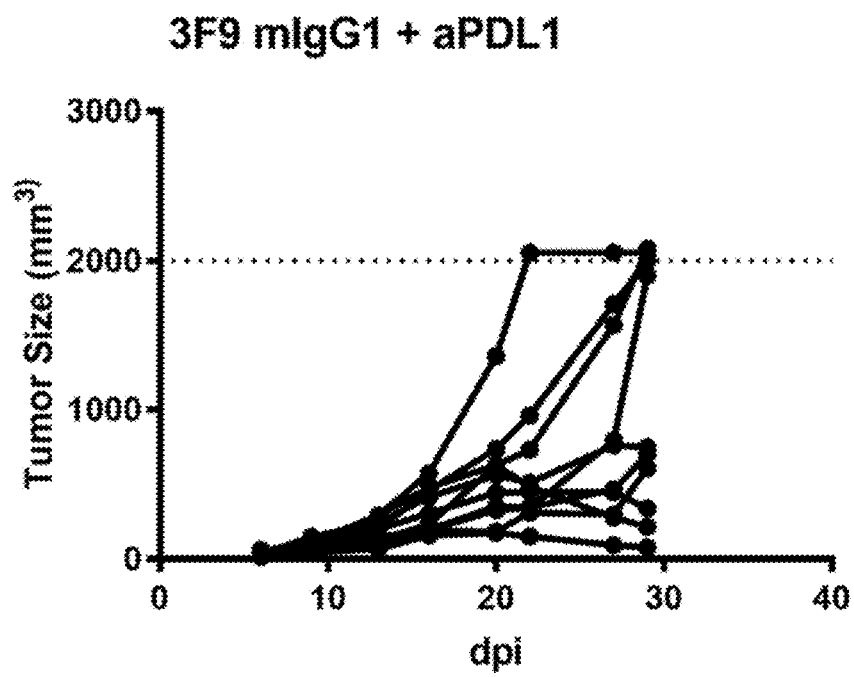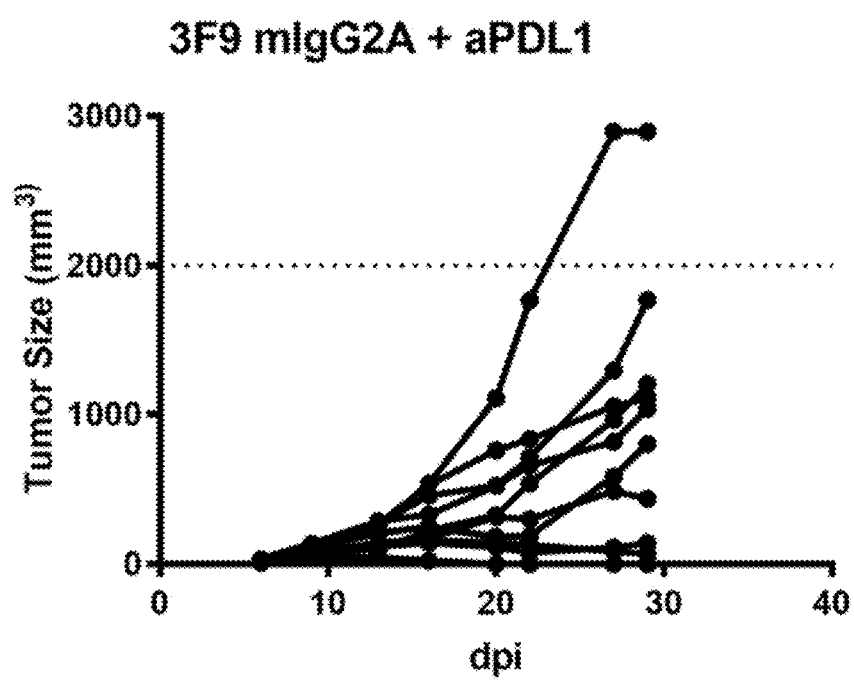
Fig. 17C (cont.)

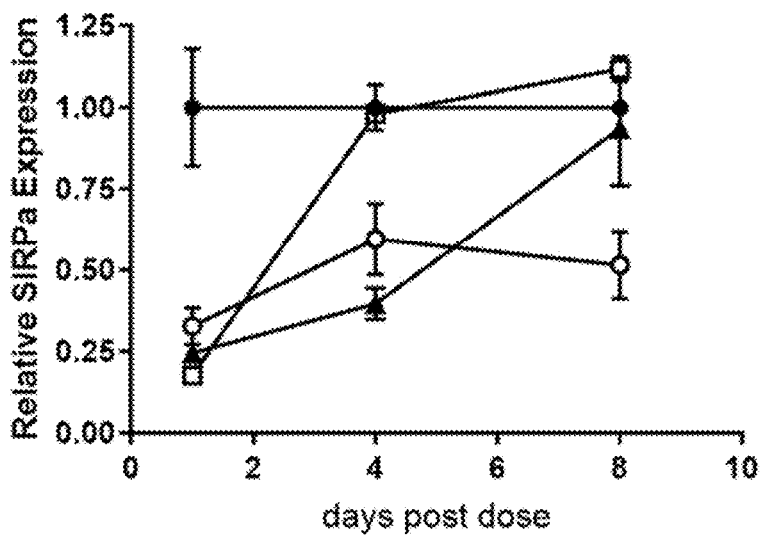
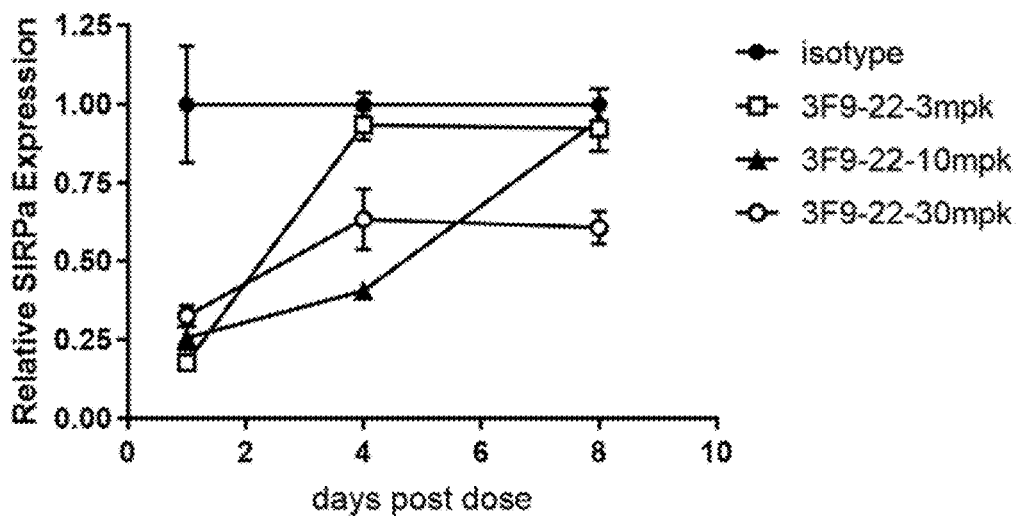
Fig. 18A

| Group | CD34+ HSC Donor A # mice | CD34+ HSC Donor B # mice | Antibody Treatment | Dose | Schedule | Inoculum |
|---|---|---|---|---|---|---|
| 1 | 2 | 9 | huIgG1 | 10 mpk | q3dx2 | 3 million A375 cells |
| 2 | 3 | 10 | 3F9-22 PS | 10 mpk | q3dx2 | 3 million A375 cells |
| 3 | 3 | 10 | 3F9-22 NSLF | 10 mpk | q3dx2 | 3 million A375 cells |

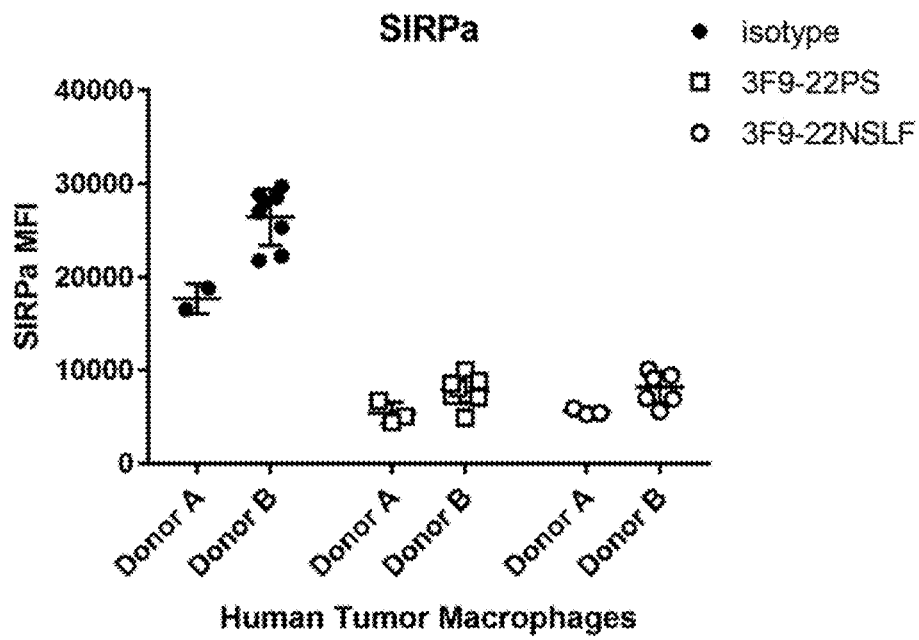
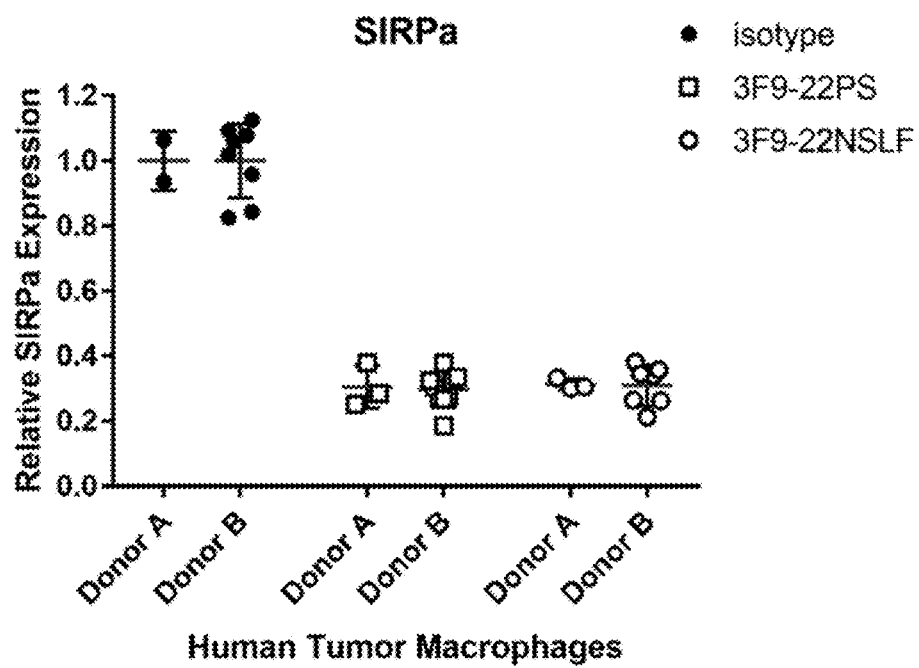
Fig. 19B

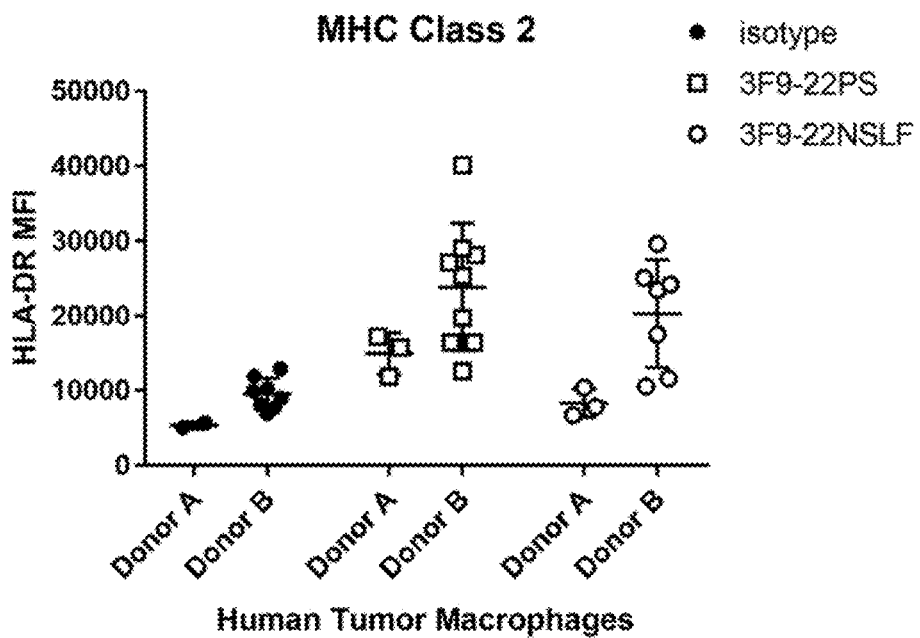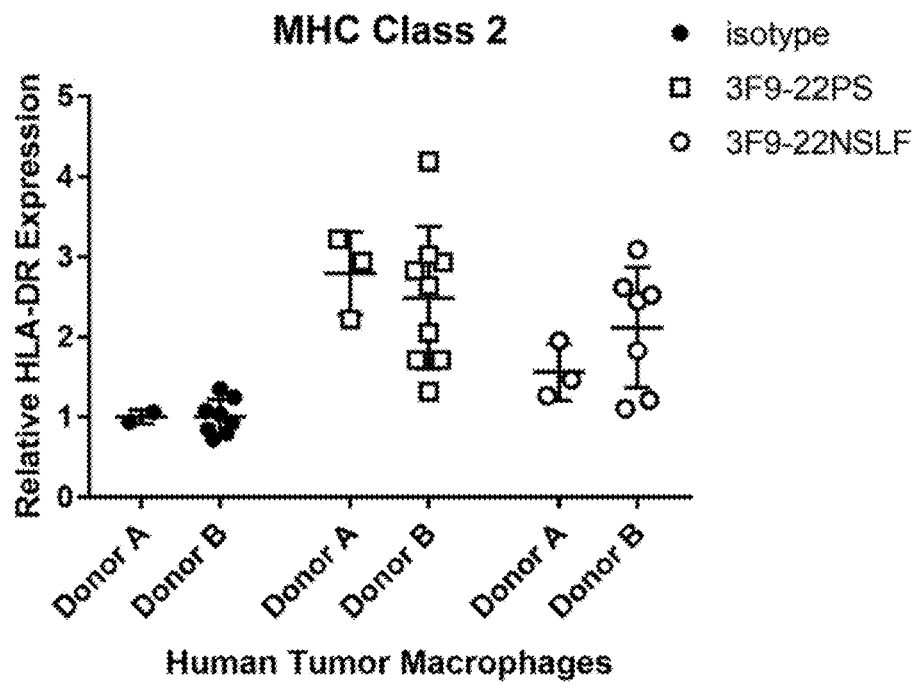
Fig. 20A

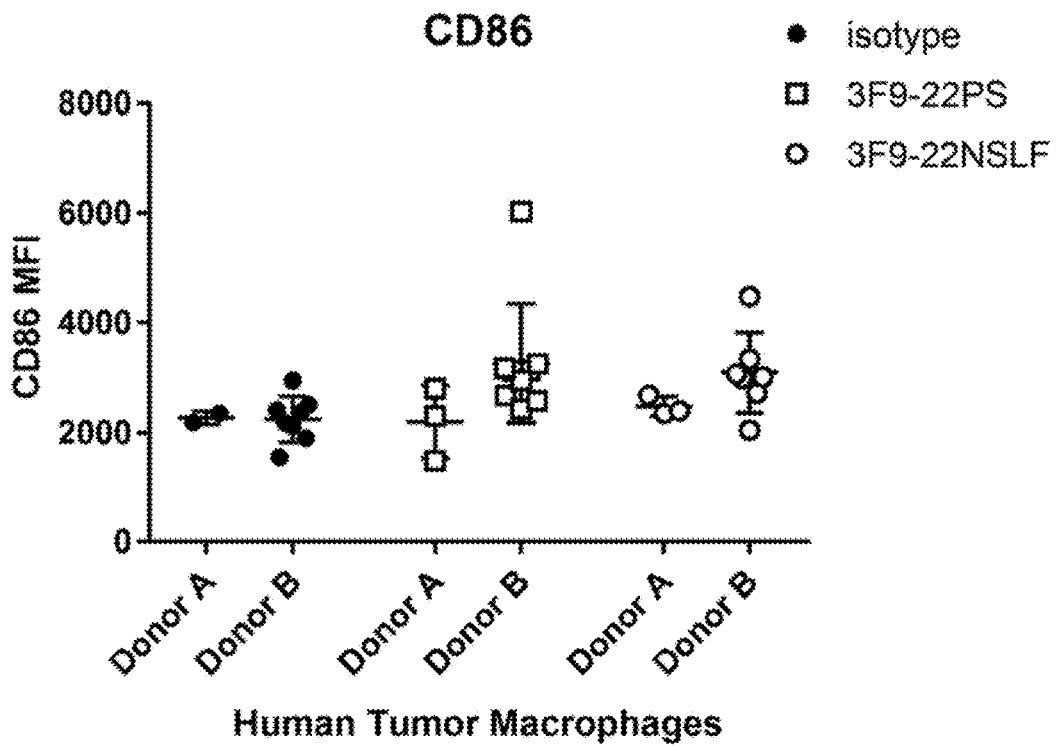
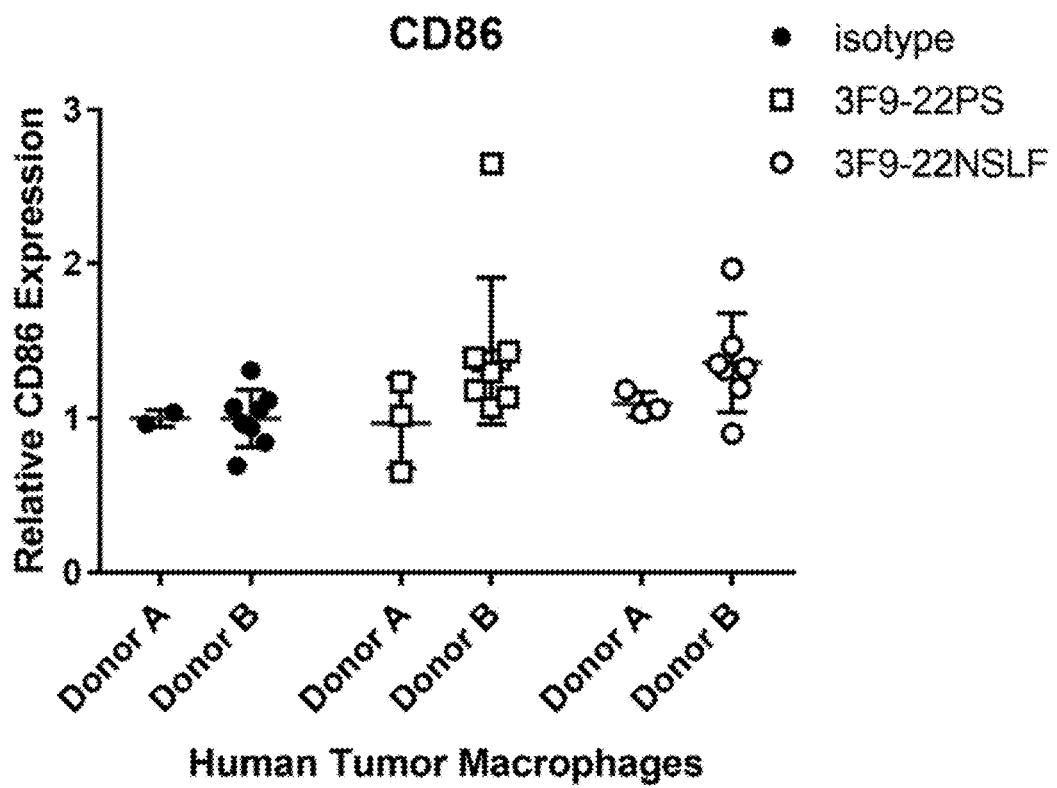
Fig. 20B

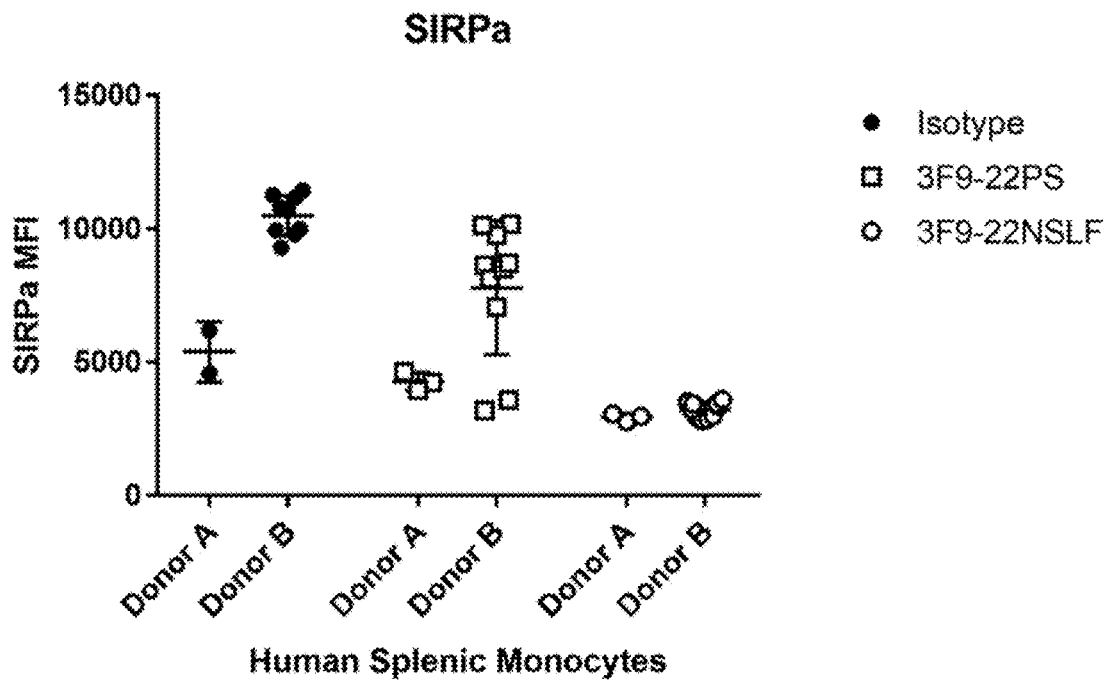
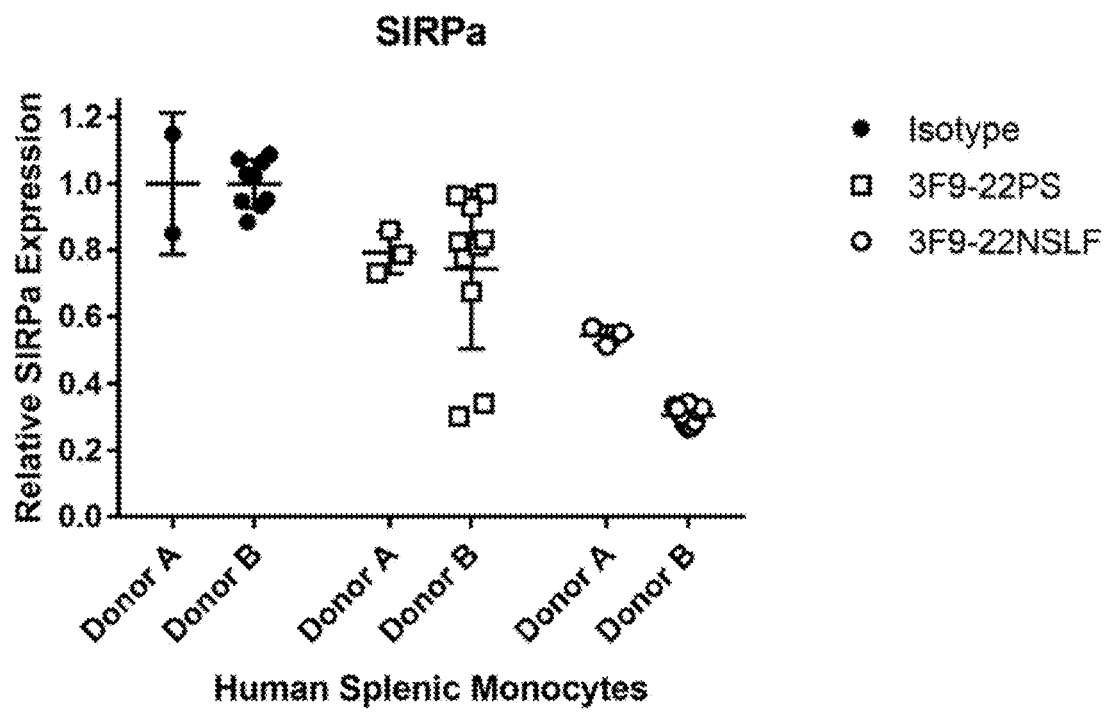
Fig. 21A

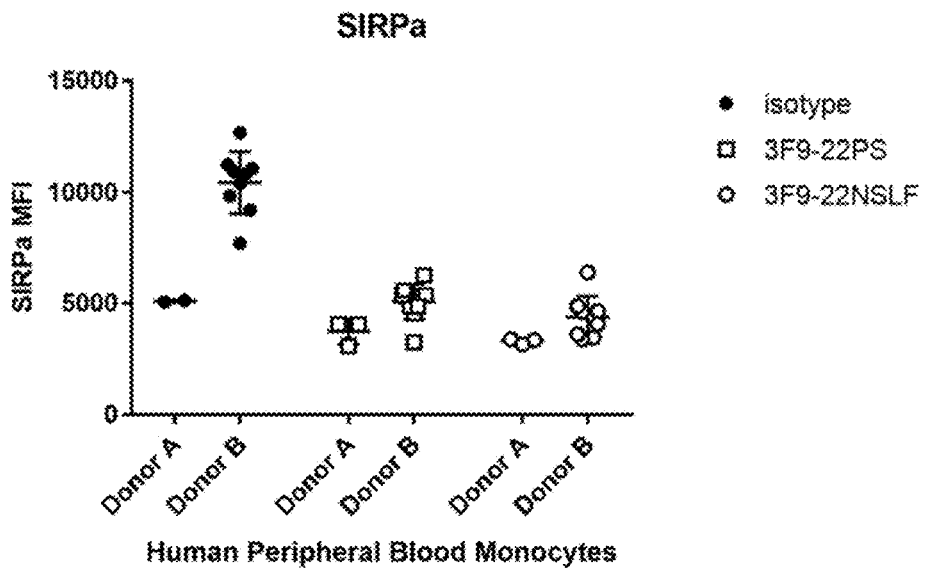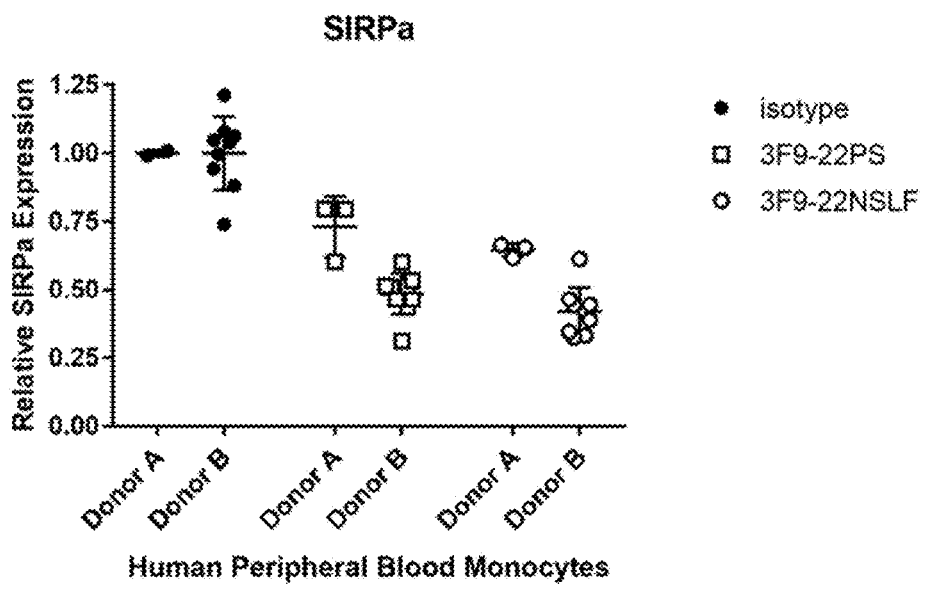
Fig. 21B

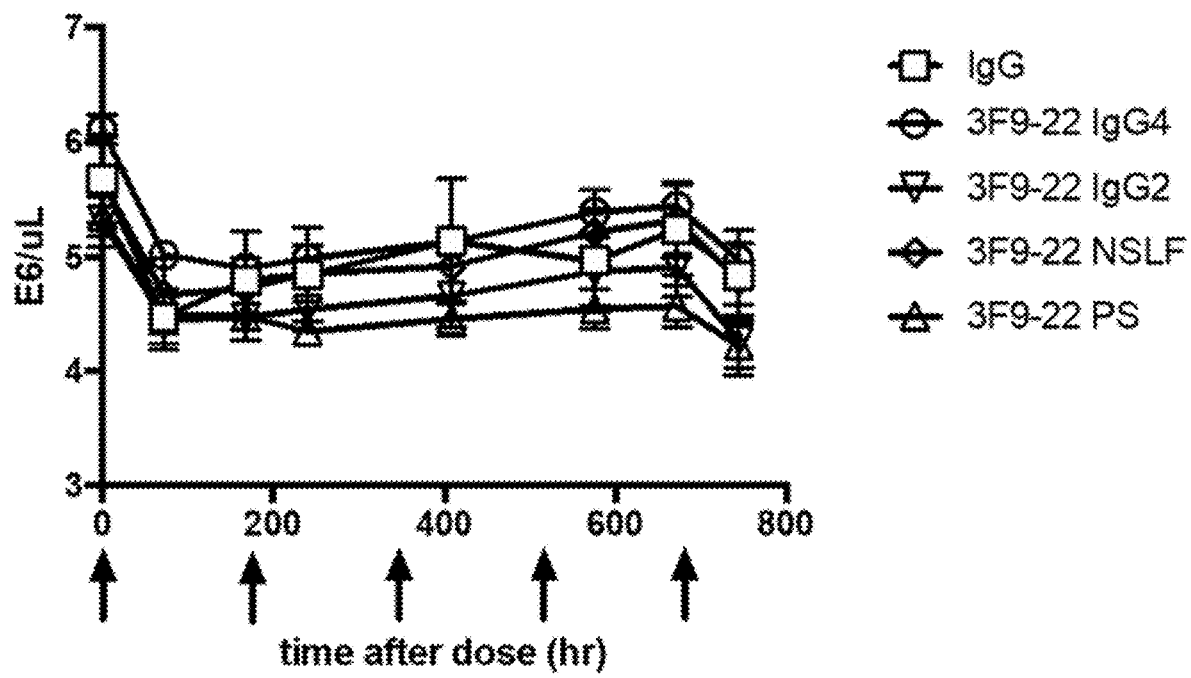
Platelets
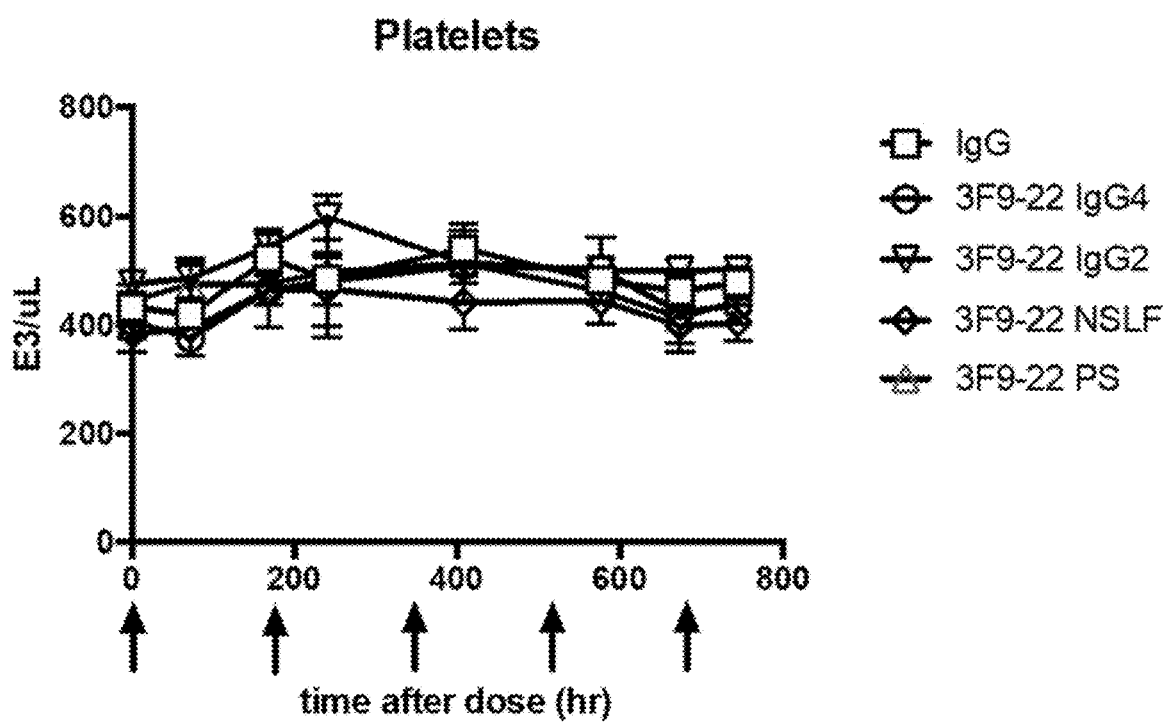
*Fig. 24*

ANTI-SIRPα ANTIBODIES AND METHODS OF USE THEREOF

CROSS-REFERENCE TO RELATED APPLICATIONS

This application is a divisional of U.S. application Ser. No. 17/707,637, filed on Mar. 29, 2022, which is a divisional of U.S. application Ser. No. 16/421,692, filed on May 24, 2019, which claims the benefit of priority of U.S. Provisional Application No. 62/676,813, filed May 25, 2018, each of which are incorporated by reference herein for any purpose.

SEQUENCE LISTING

This application contains a Sequence Listing that has been submitted electronically in XML format and is hereby incorporated by reference in its entirety. Said XML copy, created on Apr. 18, 2024, is named 01209-0004-02SL-ST26-Updated and is 71,560 bytes in size.

FIELD

The present disclosure relates to anti-SIRPA antibodies and therapeutic uses of such antibodies.

BACKGROUND

Phagocytic cells, such as macrophages (MΦ) and dendritic cells (DCs), distinguish healthy from abnormal cells through an intricate array of cell surface receptors that modulate cellular activation status, proliferation, and/or effector functions. Many of these receptors recognize diverse ligands that either mark unwanted cells for removal (so-called "eat-me" signals) or protect normal cells from destruction (so called "don't-eat-me" signals). In recent years, the SIRPα-CD47 axis has emerged as a critical determinant in programmed cell removal by macrophages in various clinical settings ranging from cancer cell survival to successful engraftment of hematopoietic cell transplantation. Therapeutic agents that impact this pathway may meet a relevant medical need to ameliorate disease with particular relevance in many types of human cancers.

SIRPα (signal regulatory protein-α) belongs to the SIRP family of transmembrane receptors, which are primarily expressed within the myeloid cell lineage (including MΦ, DCs, granulocytes, etc.) and characterized by an extracellular region containing 2 membrane-proximal IgC domains and a distal IgV domain. Unique among this family, SIRPα contains an intracellular, cytoplasmic immunoreceptor tyrosine-based inhibitory motif (ITIM). Upon receptor cross-linking, tyrosine-phosphorylated ITIM sites recruit and activate SHP phosphatases to negatively regulate cellular functions, such as phagocytosis or inflammatory cytokine release. CD47 serves as the principal ligand for SIRPα, and its broad expression in most cell types, including endothelial/epithelial cells, leukocytes, and erythrocytes, suggests that it mediates a "don't-eat-me" signal to protect healthy cells from phagocyte-dependent clearance. In support of this view, several studies show that adoptive transfer of red blood cells or leukocytes from CD47-knockout mice into wild-type recipients results in rapid clearance of CD47-deficient cells. Conversely, positional genetic analysis of multiple strains of immune-compromised mice receiving human hematopoietic cells identified the Sirpα allele in NOD mice as the causal factor for successful engraftment in xenotransplantation models. Subsequent studies demonstrated that the allelic variant of SIRPα expressed only in NOD mice retained the ability to bind human CD47 expressed on human hematopoietic stem cells, and thus, suppress macrophage-dependent graft rejection.

Regulated expression of SIRPα and CD47 establishes a homeostatic control mechanism to modulate phagocytic cell activity. For example, apoptotic cells downregulate expression of CD47 to facilitate engulfment by resident macrophages while live cells remain unharmed. Likewise, inflammatory stimuli, such as LPS, decrease SIRPα expression in macrophages and dendritic cells (DCs) to potentiate their activation during inflammation. However, dysregulation of SIRPα and CD47 expression contributes to immune-associated diseases, as seen in cancer. Several tumors significantly augment expression of CD47 relative to non-cancerous cells in order to evade immune surveillance mechanisms that normally eliminate malignant cells. Preclinical studies reveal that genetic knockdown of CD47 in syngeneic tumor models, such as B16F10 melanoma, is sufficient to inhibit tumor growth in immune-competent mice. Similar results have been observed with CD47-knocked down human cancer cell lines transplanted into immune-compromised mice. Alternatively, biologic agents that disrupt SIRPα-CD47 interaction, such as anti-CD47 antibodies, also enhance tumor clearance in mouse models. When combined with commercial anti-tumor antigen antibodies, such as trastuzumab or rituximab, anti-CD47 antibodies facilitate a synergistic increase in the anti-tumor response compared to standard monotherapy. Yet, given the ubiquitous expression of CD47, anti-CD47 antibodies risk severe toxicity burdens due to off-target effects limiting their therapeutic efficacy. Nevertheless, these studies establish a crucial role for the SIRPα-CD47 pathway in regulating myeloid cells with potential applications in cancer immunotherapy.

Anti-SIRPA antibodies have been previously described in, e.g., International Patent Application Publication Nos: WO2018/057669, WO 2018/026600, WO 2017/178653, WO2017/068164, WO2016/063233, WO2016/205042, WO2015/138600, WO2013/0956352, WO2009/091547, WO2009/131453, and WO2009/046541.

Accordingly, there is a need for therapeutic anti-SIRPA antibodies to treat diseases, disorders, and conditions associated with undesired SIRPA activity.

All references cited herein, including patent applications and publications, are hereby incorporated by reference in their entirety.

SUMMARY

The present disclosure is generally directed to compositions that include antibodies, e.g., monoclonal, chimeric, humanized antibodies, antibody fragments, etc., that specifically bind human SIRPA, and to methods of using such compositions.

Certain aspects of the present disclosure are based, at least in part, on the identification of anti-SIRPA antibodies with improved and/or enhanced functional characteristics (e.g., relative to an anti-SIRPA antibody with a heavy chain variable region comprising the amino acid sequence of SEQ ID NO:2 and a light chain variable region comprising the amino acid sequence of SEQ ID NO:5, including, for example, improved and/or enhanced capabilities of decreasing cell surface levels of SIRPA on cells, and/or have improved and/or enhanced binding kinetics, and/or have improved and/or enhanced KD, and/or have improved and/or enhanced EC50 values. In some embodiments, anti- SIRPA antibodies of the present disclosure have a KD for human SIRPA that is at least 2-fold, at least 3-fold, at least 4-fold, at least 5-fold, at least 6-fold, at least 7-fold, at least 8-fold, at least 9-fold, or at least 10-fold lower than an anti-SIRPA antibody having a heavy chain variable region comprising the amino acid sequence of SEQ ID NO:2 and a light chain variable region comprising the amino acid sequence of SEQ ID NO:5. In some embodiments, an anti-SIRPA antibody of the present disclosure has a KD for human SIRPA of less than 6 nM, less than 5 nM, less than 4 nM, less than 3 nM, less than 2 nM, less than 1 nM, less than 0.9 nM, less than 0.8 nM, less than 0.7 nM, less than 0.6 nm, or less than 0.5 nM.

In some embodiments, anti-SIRPA antibodies of the present disclosure reduce cell surface expression levels of SIRPA in vitro with an EC50 that is at least about 20%, at least about 30%, at least about 40%, or at least about 50% lower than an anti-SIRPA antibody having a heavy chain variable region comprising the amino acid sequence of SEQ ID NO:2 and a light chain variable region comprising the amino acid sequence of SEQ ID NO:5. Advantageously, an anti-SIRPA antibody of the present disclosure decreases cellular levels of SIRPA in vitro with a half-maximal effective concentration (EC50) that ranges from about 0.4 nM to about 0.5 nM. Advantageously, an anti-SIRPA antibody of the present disclosure has a dissociation constant (KD) for human SIRPA that ranges from about 0.6 nM to 0.7 nM.

In some embodiments, which may be combined with any of the embodiments herein, an anti-SIRPA antibody of the present disclosure binds human SIRPA v1. In some embodiments, which may be combined with any of the embodiments herein, an anti-SIRPA antibody of the present disclosure binds human SIRPA v2. In some embodiments, which may be combined with any of the embodiments herein, an anti-SIRPA antibody of the present disclosure binds human SIRPB (SIRPbeta) v3. In some embodiments, which may be combined with any of the embodiments herein, an anti-SIRPA antibody of the present disclosure does not bind human SIRPB v1. In some embodiments, which may be combined with any of the embodiments herein, an anti-SIRPA antibody of the present disclosure does not bind murine SIRPA. In some embodiments, which may be combined with any of the embodiments herein, an anti-SIRPA antibody of the present disclosure does not bind human SIRPγ. In some embodiments, which may be combined with any of the embodiments herein, an anti-SIRPA antibody of the present disclosure binds cynoSIRPA. In some embodiments, which may be combined with any of the embodiments herein, an anti-SIRPA antibody of the present disclosure does not bind cynoSIRPB1. In In some embodiments, which may be combined with any of the embodiments herein, an anti-SIRPA antibody of the present disclosure binds marmoset SIRPA.

In some embodiments, which may be combined with any of the embodiments herein, the present disclosure provides an isolated antibody that binds to human SIRPA, wherein the antibody binds human SIRPA, human SIRPA v1, human SIRPA v2, cyno SIRPA, marmoset SIRPA, and human SIRPβ3.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises: an HVR—H1 comprising the amino acid sequence of SEQ ID NO:20; an HVR—H2 comprising the amino acid sequence of SEQ ID NO:21; and an HVR—H3 comprising an amino acid sequence selected from SEQ ID NOs: 22, 23, and 24.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises: an HVR-L1 comprising the amino acid sequence of SEQ ID NO:9; an HVR-L2 comprising the amino acid sequence of SEQ ID NO: 10; and an HVR-L3 comprising an amino acid sequence selected from SEQ ID NOs: 11, 12, 13, 14, 15, 16, 17, 18, and 19.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises: an HVR—H1 comprising the amino acid sequence of SEQ ID NO:20; an HVR—H2 comprising the amino acid sequence of SEQ ID NO:21; an HVR—H3 comprising an amino acid sequence selected from SEQ ID NOs: 22, 23, and 24; an HVR-L1 comprising the amino acid sequence of SEQ ID NO:9; an HVR-L2 comprising the amino acid sequence of SEQ ID NO:10; and an HVR-L3 comprising an amino acid sequence selected from SEQ ID NOs: 11, 12, 13, 14, 15, 16, 17, 18, and 19.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises an amino acid sequence at least 90% or at least 95% or at least 99% identical to an amino acid sequence selected from SEQ ID NOs: 33, 34, and 35.

In some embodiments, which may be combined with any of the embodiments herein, the present disclosure provides an isolated antibody that binds to human SIRPA, wherein the antibody comprises a heavy chain variable region and a light chain variable region, wherein the light chain variable region comprises an amino acid sequence at least 90% or at least 95% or at least 99% identical to an amino acid sequence selected from SEQ ID NOs: 36, 37, 38, 39, 40, 41, 42, 43, and 44.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises one, two, three or four frame work regions selected from VH FR1 comprising the amino acid sequence of SEQ ID NO:25, VH FR2 comprising the amino acid sequence of SEQ ID NO:26, VH FR3 comprising the amino acid sequence of SEQ ID NO:27, and VH FR4 comprising the amino acid sequence of SEQ ID NO:28.

In some embodiments, which may be combined with any of the embodiments herein, the present disclosure provides an isolated antibody that binds to human SIRPA, wherein the antibody comprises a heavy chain variable region and a light chain variable region, wherein the light chain variable region comprises one, two, three or four frame work regions selected from VL FR1 comprising the amino acid sequence of SEQ ID NO:29, VL FR2 comprising the amino acid sequence of SEQ ID NO:30, VL FR3 comprising the amino acid sequence of SEQ ID NO:31, and VL FR4 comprising the amino acid sequence of SEQ ID NO:32.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises one, two, three or four frame work regions selected from VH FR1 comprising the amino acid sequence of SEQ ID NO:25, VH FR2 comprising the amino acid sequence of SEQ ID NO:26, VH FR3 comprising the amino acid sequence of SEQ ID NO:27, and VH FR4 comprising the amino acid sequence of SEQ ID NO:28; and wherein the light chain variable region comprises one, two, three or four frame work regions selected from VL FR1 comprising the amino acid sequence of SEQ ID NO:29, VL FR2 comprising the amino acid sequence of SEQ ID NO:30, VL FR3 comprising the amino acid sequence of SEQ ID NO:31, and VL FR4 comprising the amino acid sequence of SEQ ID NO:32.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises an amino acid sequence selected from SEQ ID NOs:33, 34, and 35.

In some embodiments, which may be combined with any of the embodiments herein, the present disclosure provides an isolated antibody that binds to human SIRPA, wherein the antibody comprises a heavy chain variable region and a light chain variable region, wherein the light chain variable region comprises an amino acid sequence selected from SEQ ID NOs: 36, 37, 38, 39, 40, 41, 42, 43, and 44.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises an amino acid sequence selected from SEQ ID NOs:33, 34, and 35, and wherein the light chain variable region comprises an amino acid sequence selected from SEQ ID NOs: 36, 37, 38, 39, 40, 41, 42, 43, and 44.

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises the HVR—H1, HVR—H2, and HVR—H3 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25 (as shown in Table 8).

In some embodiments, which may be combined with any of the embodiments herein, the present disclosure provides an isolated antibody that binds to human SIRPA, wherein the antibody comprises a heavy chain variable region and a light chain variable region, wherein the light chain variable region comprises the HVR-L1, HVR-L2, and HVR-L3 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25 (as shown in Table 7).

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises the HVR—H1, HVR—H2, and HVR—H3 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25 (as shown in Table 8); and wherein the light chain variable region comprises the HVR-L1, HVR-L2, and HVR-L3 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25 (as shown in Table 7).

In some embodiments, which may be combined with any of the embodiments herein, the present disclosure provides an isolated antibody that binds to human SIRPA, wherein the antibody comprises a heavy chain variable region comprising an HVR—H1, HVR—H2, and HVR—H3 and a light chain variable region comprising an HVR-L1, HVR-L2, and HVR-L3, wherein the antibody comprises the HVR—H1, HVR—H2, HVR—H3, HVR-L1, HVR-L2, and HVR-L3 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25 (as shown in Tables 7 and 8).

In some embodiments, which may be combined with any of the embodiments herein, the present disclosure provides an isolated antibody that binds to human SIRPA, wherein the antibody comprises a heavy chain variable region and a light chain variable region, wherein the heavy chain variable region comprises one, two, three, or four framework regions selected from VH FR1, VH FR2, VH, Fr3, and $V_H$ FR4, wherein: VH FR1 comprises the amino acid sequence of SEQ ID NO:25; VH FR2 comprises the amino acid sequence of SEQ ID NO:26; VH FR3 comprises the amino acid sequence of SEQ ID NO:27; and VH FR4 comprises the amino acid sequence of SEQ ID NO:28; and/or the light chain variable region comprises one, two, three, or four framework regions selected VL FR1, VL FR2, VL FR3, and VL FR4, wherein VL FR1 comprises the amino acid sequence of SEQ ID NO:29; VL FR2 comprises the amino acid sequence of SEQ ID NO:30; VL FR3 comprises the amino acid sequence of SEQ ID NO:31; and VL FR4 comprises the amino acid sequence of SEQ ID NO:32.

In some embodiments, which may be combined with any of the embodiments herein, the present disclosure provides an isolated antibody that binds to human SIRPA, wherein the antibody comprises a heavy chain and a light chain, wherein the heavy chain comprises the amino acid sequence of SEQ ID NO:49 and the light chain comprises the amino acid sequence of SEQ ID NO:50.

In some embodiments, which may be combined with any of the embodiments herein, the present invention provides an isolated anti-SIRPA antibody that binds to human SIRPA, wherein the antibody comprises a heavy chain and a light chain, wherein the heavy chain comprises the amino acid sequence of SEQ ID NO:47 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:48 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:49 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:53 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:54 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:51 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:52 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:55 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:56 and the light chain comprises the amino acid sequence of SEQ ID NO:50.

In some embodiments, which may be combined with any of the embodiments herein, the present invention provides an isolated anti-SIRPA antibody, wherein the antibody comprises a heavy chain and a light chain, wherein the heavy chain comprises the amino acid sequence of SEQ ID NO:57 and the light chain comprises the amino acid sequence of SEQ ID NO:50.

In some embodiments, which may be combined with any of the embodiments herein, the present disclosure provides an isolated antibody that binds to human SIRPA, wherein the antibody is a monoclonal antibody.

In some embodiments, which may be combined with any of the embodiments herein, the present disclosure provides an isolated antibody that binds to human SIRPA wherein the antibody is a humanized antibody.

In some embodiments, which may be combined with any of the embodiments herein, the present disclosure provides an isolated antibody that binds to human SIRPA, wherein the antibody is a Fab, Fab', Fab'-SH, F(ab')$_2$, Fv, or scFv fragment.

In some embodiments, which may be combined with any of the embodiments herein, the present disclosure provides an isolated antibody that binds to human SIRPA, wherein the antibody is a multivalent antibody.

In some embodiments, which may be combined with any of the embodiments herein, the present disclosure provides an isolated antibody that binds to human SIRPA, wherein the antibody is of the IgG class, the IgM class, or the IgA class.

In some embodiments, which may be combined with any of the embodiments herein, the present disclosure provides an isolated antibody that binds to human SIRPA wherein the antibody is of the IgG class and as an IgG1, IgG2, IgG3, or IgG4 isotype.

In some embodiments, which may be combined with any of the embodiments herein, the present disclosure provides an isolated antibody that binds to human SIRPA, wherein the antibody binds to an inhibitory Fc receptor. In some embodiments, which may be combined with any of the embodiments herein, the inhibitory Fc receptor is inhibitory Fc-gamma receptor IIB (FcγRIIB).

In some embodiments, which may be combined with any of the embodiments herein, the present disclosure provides an isolated antibody that binds to human SIRPA, wherein the antibody decreases cellular levels of FcγRIIB.

In some embodiments, which may be combined with any of the embodiments herein, the present disclosure provides an isolated antibody that binds to human SIRPA, wherein the anti-SIRPA antibody has a human or mouse IgG1 isotype and comprises one or more amino acid substitutions in the Fc region at an amino acid residue selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236.

In some embodiments, which may be combined with any of the embodiments herein, the present disclosure provides an isolated antibody that binds to human SIRPA, wherein the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the amino acid residues is according to EU numbering.

In some embodiments, which may be combined with any of the embodiments herein, the present disclosure provides an isolated antibody that binds to human SIRPA, wherein the anti-SIRPA antibody decreases cell surface levels of SIRPA, decreases intracellular levels of SIRPA, decreases total cellular levels of SIRPA, or any combination thereof.

In some embodiments, which may be combined with any of the embodiments herein, the present disclosure provides an isolated antibody that binds to human SIRPA, wherein the anti-SIRPA antibody induces SIRPA degradation, induces SIRPA cleavage, induces SIRPA internalization, induces SIRPA shedding, induces downregulation of SIRPA expression, or any combination thereof.

In some embodiments, which may be combined with any of the embodiments herein, the present disclosure provides an isolated antibody that binds to human SIRPA, wherein the antibody reduces cell surface levels of SIRPA in vitro.

In some embodiments, which may be combined with any of the embodiments herein, the present disclosure provides an isolated antibody that binds to human SIRPA, wherein the antibody reduces cell surface levels of SIRPA in vivo.

In some embodiments, which may be combined with any of the embodiments herein, the present disclosure provides an isolated antibody that binds to human SIRPA, wherein the anti-SIRPA antibody down-regulates expression of SIRPA in human monocytes.

In some embodiments, which may be combined with any of the embodiments herein, the present disclosure provides an isolated antibody that binds to human SIRPA, wherein the anti-SIRPA antibody down-regulates expression of SIRPA in human macrophages.

In some embodiments, which may be combined with any of the embodiments herein, the present disclosure provides an isolated antibody that binds to human SIRPA, wherein the anti-SIRPA antibody down-regulates expression of SIRPA in human macrophages by about 70-95%.

In some embodiments, which may be combined with any of the embodiments herein, the present disclosure provides an isolated antibody that binds to human SIRPA, wherein the antibody has an affinity (KD) to human SIRPA of less than 6 nM, less than 5 nM, less than 4 nM, less than 3 nM, less than 2 nM, or less than 1 nM.

In some embodiments, which may be combined with any of the embodiments herein, the present disclosure provides an isolated antibody that binds to human SIRPA, wherein the antibody has an affinity (KD) to human SIRPA of about 0.1 nM to 2 nM.

In some embodiments, which may be combined with any of the embodiments herein, the present disclosure provides an isolated antibody that binds to human SIRPA, wherein the antibody has an affinity to human SIRPA with a KD that is at least 2-fold, at least 3-fold, at least 4-fold, at least 5-fold, at least 6-fold, at least 7-fold, at least 8-fold, at least 9-fold, or at least 10-fold lower than the affinity to human SIRPA of an anti-SIRPA antibody comprising a heavy chain variable region comprising the amino acid sequence of SEQ ID NO:2 and a light chain variable region comprising the amino acid sequence of SEQ ID NO:5.

In some embodiments, which may be combined with any of the embodiments herein, the present disclosure provides an isolated antibody that binds to human SIRPA, wherein the antibody reduces cell surface levels of SIRPA v1 in vitro with a half maximal effective concentration (EC50) of about 0.05 nM to 2 nM or about 0.4 nM about 0.5 nM as measured by flow cytometry.

In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) of about 0.05 to 0.20 nM for human SIRPA v1, of about 0.05 to 0.10 nM for human SIRPA v2, and/or of about 0.05 to 1 nM for cyno SIRPA as measured by flow cytometry.

In some embodiments, which may be combined with any of the embodiments herein, the present disclosure provides an isolated antibody that binds to human SIRPA, wherein the antibody binds to the D3 domain of human SIRPA v1 of SEQ ID NO:1.

In some embodiments, which may be combined with any of the embodiments herein, the present disclosure provides an isolated antibody that binds to human SIRPA, wherein the antibody binds to amino acid residues R282, Q284, and G337 of human SIRPA v1 of SEQ ID NO: 1.

In some embodiments, which may be combined with any of the embodiments herein, the present disclosure provides an isolated antibody that binds to human SIRPA, wherein the anti-SIRPA antibody increases tumor cell phagocytosis in macrophages, increases tumor cell phagocytosis in M1 macrophages, increases tumor cell phagocytosis in M2 macrophages, down-regulates CD14 expression in macrophages, and/or any combination thereof.

In some embodiments, which may be combined with any of the embodiments herein, the present disclosure provides an isolated antibody that binds to human SIRPA, wherein the anti-SIRPA antibody enhances T cell proliferation.

In some embodiments, which may be combined with any of the embodiments herein, the present disclosure provides an isolated antibody that binds to human SIRPA, wherein the anti-SIRPA antibody blocks the interaction or binding of SIRPA with surfactant protein D (SP-D).

In some embodiments, which may be combined with any of the embodiments herein, the present disclosure provides an isolated antibody that binds to human SIRPA, wherein the anti-SIRPA antibody does not block the interaction or binding of SIRPA to CD47.

In some embodiments, which may be combined with any of the embodiments herein, the present disclosure provides an isolated antibody that binds to human SIRPA, wherein the anti-SIRPA antibody down-regulates cell surface expression of CD32A/B.

In some embodiments, which may be combined with any of the embodiments herein, the present disclosure provides an isolated antibody that binds to human SIRPA, wherein the anti-SIRPA antibody down-regulates cell surface expression of CD14.

In some embodiments, which may be combined with any of the embodiments herein, the present disclosure provides an isolated antibody that binds to human SIRPA, wherein the anti-SIRPA antibody enhances T cell proliferation without blocking the interaction of SIRPγ and CD47.

In some embodiments, which may be combined with any of the embodiments herein, the present disclosure provides an isolated antibody that binds to human SIRPA, wherein the anti-SIRPA antibody stimulates ROS production in monocytes and/or increases IL-8 expression in monocytes.

In some embodiments, which may be combined with any of the embodiments herein, the present disclosure provides an isolated antibody that binds to human SIRPA, wherein the anti-SIRPA antibody inhibits tumor growth in vivo.

In some embodiments, which may be combined with any of the embodiments herein, the present disclosure provides an isolated antibody that binds to human SIRPA, wherein the anti-SIRPA antibody reduces the number of $CD14^+$ myeloid cells in peripheral blood and/or increases the number of CD14+ myeloid cells in a tumor.

In some embodiments, which may be combined with any of the embodiments herein, the present disclosure provides an isolated antibody that binds to human SIRPA, wherein the antibody binds human SIRPA but does not substantially block binding of CD47 to SIRPA.

In some embodiments, which may be combined with any of the embodiments herein, the present disclosure provides an isolated antibody that binds to human SIRPA, wherein the antibody recognizes a first and a second antigen, wherein the first antigen is SIRPA and the second antigen is:
  (a) an antigen facilitating transport across the blood-brain-barrier;
  (b) an antigen facilitating transport across the blood-brain-barrier selected from transferrin receptor (TR), insulin receptor (HIR), insulin-like growth factor receptor (IGFR), low-density lipoprotein receptor related proteins 1 and 2 (LPR-1 and 2), and diphtheria toxin receptor;

(c) a disease-causing agent selected from disease-causing peptides or proteins, disease-causing nucleic acids, wherein the disease-causing nucleic acids are antisense GGCCCC (G2C4) repeat-expansion RNA, the disease-causing proteins are selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; and (d) ligands and/or proteins expressed on immune cells, wherein the ligands and/or proteins selected from PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, CD73, and phosphatidylserine; and a protein, lipid, polysaccharide, or glycolipid expressed on one or more tumor cells.

In some embodiments, which may be combined with any of the embodiments herein, the present disclosure provides an isolated antibody that binds to human SIRPA, wherein the anti-SIRPA antibody is conjugated to a peptide that facilitates transport across the blood-brain-barrier. In some embodiments, the peptide is selected from CRM197, a protein transduction domain, TAT, Syn-B, penetratin, a poly-arginine peptide, an angiopep peptide, and ANG1005.

In some embodiments, which may be combined with any of the embodiments herein, the present disclosure provides an isolated antibody that binds to human SIRPA, wherein the anti-SIRPA antibody is an opsonizing antibody.

In some embodiments, which may be combined with any of the embodiments herein, the present disclosure provides an isolated antibody that binds to human SIRPA, wherein the anti-SIRPA antibody is a conjugated antibody.

In some embodiments, which may be combined with any of the embodiments herein, the present disclosure provides an isolated antibody that binds to human SIRPA, wherein the anti-SIRPA antibody is conjugated to a detectable marker, a toxin, or a therapeutic agent.

In some embodiments, which may be combined with any of the embodiments herein, the present disclosure provides an isolated antibody that binds to human SIRPA, wherein the anti-SIRPA antibody is conjugated to a toxin selected from ricin, ricin A chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, Pseudomonas exotoxin (PE) A, PE40, abrin, abrin A chain, modeccin A chain, alpha sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

In some embodiments, which may be combined with any of the embodiments herein, the present disclosure provides an isolated antibody that binds to human SIRPA, wherein the anti-SIRPA antibody is used in combination with one or more antibodies that specifically bind a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: PD1/PDL1, CD40, OX40, ICOS, CD28, CD137/4-1BB, CD27, GITR, PD-L1, CTLA4, PD-L2, PD-1, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, CD73, TREM1, TREM2, CD33, Siglec-5, Siglec-7, Siglec-9, Siglec-11, phosphatidylserine, disease-causing nucleic acids, antisense GGCCCC (G2C4) repeat-expansion RNA, and any combination thereof.

In some embodiments, which may be combined with any of the embodiments herein, the present disclosure provides a method of preventing, reducing risk, or treating cancer, wherein the method comprises administering to an individual in need thereof a therapeutically effective amount of an anti-SIRPA antibody of the present disclosure, thereby treating cancer. In some embodiments, which may be combined with any of the embodiments herein, the present invention provides a method of preventing, reducing risk, or treating an individual having a disease, disorder, or injury, wherein the disease, disorder, or injury is cancer, the method comprising administering to the individual a therapeutically effective amount of an anti-SIRPA antibody of the present disclosure, thereby preventing, reducing risk, or treating the individual.

In some embodiments, which may be combined with any of the embodiments herein, the present disclosure provides a method of treating cancer, wherein the method comprises administering to an individual in need thereof a therapeutically effective amount of an anti-SIRPA antibody of the present disclosure, wherein the cancer is selected from sarcoma, bladder cancer, brain cancer, breast cancer, colon cancer, rectal cancer, endometrial cancer, kidney cancer, renal pelvis cancer, leukemia, lung cancer, small cell lung cancer, melanoma, lymphoma, pancreatic cancer, prostate cancer, ovarian cancer, and fibrosarcoma, glioblastoma multiforme; renal clear cell carcinoma; adrenocortical carcinoma; bladder urothelial carcinoma, diffuse large B-cell lymphoma, lung adenocarcinoma; pancreatic adenocarcinoma, renal cell cancer, Hodgkin's lymphoma, non-Hodgkin's lymphoma, indolent B cell lymphoma, aggressive B cell lymphoma, T cell lymphoma, acute lymphoblastic leukemia (ALL), acute myeloid leukemia (AML), chronic lymphocytic leukemia (CLL), chronic myeloid leukemia (CML), multiple myeloma, myelodysplastic syndromes, myeloproliferative neoplasms, breast invasive carcinoma, cervical squamous cell carcinoma, endocervical adenocarcinoma, cholangiocarcinoma, colon adenocarcinoma, diffuse large B-cell lymphoma, esophageal carcinoma, head and neck squamous cell carcinoma, kidney chromophobe, renal papillary cell carcinoma, lower grade glioma, hepatocellular carcinoma, lung squamous cell carcinoma, mesothelioma, ovarian serous cystadenocarcinoma, pancreatic adenocarcinoma, pheochromocytoma and paraganglioma, prostate adenocarcinoma, rectal adenocarcinoma, cutaneous melanoma, stomach adenocarcinoma, testicular germ cell tumors, thyroid carcinoma, thymoma, uterine corpus endometrial carcinoma, uterine carcinosarcoma, and uveal melanoma.

In some embodiments, which may be combined with any of the embodiments herein, the present disclosure provides a method of treating cancer, wherein the method comprises administering to an individual in need thereof a therapeutically effective amount of an anti-SIRPA antibody of the present disclosure, the method further comprises administering a therapeutic agent that inhibits PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments that may be combined with any of the embodiments herein, the therapeutic agent is an antibody that inhibits PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73.

In some embodiments, which may be combined with any of the embodiments herein, the present disclosure provides a method of treating cancer, wherein the method comprises administering to an individual in need thereof a therapeutically effective amount of an anti-SIRPA antibody of the present disclosure, the method comprising administering to the individual at least one antibody that specifically binds to an inhibitory checkpoint molecule, and/or one or more standard or investigational anti-cancer therapies. In some embodiments, which may be combined with any of the embodiments herein, the at least one antibody that specifically binds to an inhibitory checkpoint molecule is administered in combination with the anti-SIRPA antibody. In some embodiments, which may be combined with any of the embodiments herein, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM-1 antibody, an anti-TIM3 antibody, an anti-TIM-4 antibody, an anti-A2AR antibody, an anti-CD39 antibody, an anti-CD73 antibody, an anti-LAG-3 antibody, an anti-phosphatidylserine antibody, an anti-CD27 antibody, an anti-CD30 antibody, an anti-TNFα antibody, an anti-CD33 antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, an anti-TIGIT antibody, an anti-VISTA antibody, an anti-CD2 antibody, an anti-CD5 antibody, and any combination thereof.

In some embodiments, which may be combined with any of the embodiments herein, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, which may be combined with any of the embodiments herein, the present disclosure provides a method of treating cancer, wherein the method comprises administering to an individual in need thereof a therapeutically effective amount of an anti-SIRPA antibody of the present disclosure, wherein the method further comprises administering to the individual at least one antibody that specifically binds to an inhibitory cytokine. In some embodiments, which may be combined with any of the embodiments herein, the at least one antibody that specifically binds to an inhibitory cytokine is administered in combination with the anti-SIRPA antibody. In some embodiments, which may be combined with any of the embodiments herein, the at least one antibody that specifically binds to an inhibitory cytokine is selected from an anti-CCL2 antibody, an anti-CSF-1 antibody, an anti-IL-2 antibody, and any combination thereof.

In some embodiments, which may be combined with any of the embodiments herein, the present disclosure provides a method of treating cancer, wherein the method comprises administering to an individual in need thereof a therapeutically effective amount of an anti-SIRPA antibody of the present disclosure, wherein the method further comprises administering to the individual at least one agonistic antibody that specifically binds to a stimulatory checkpoint protein. In some embodiments, which may be combined with any of the embodiments herein, the at least one agonistic antibody that specifically binds to a stimulatory checkpoint protein is administered in combination with the anti-SIRPA antibody.

In some embodiments, which may be combined with any of the embodiments herein, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, an agonist anti-CD30 antibody, an agonist anti-BTLA antibody, an agonist anti-HVEM antibody, an agonist anti-CD2 antibody, an agonist anti-CD5 antibody, and any combination thereof.

In some embodiments, which may be combined with any of the embodiments herein, the present disclosure provides a method of treating cancer, wherein the method comprises administering to an individual in need thereof a therapeutically effective amount of an anti-SIRPA antibody of the present disclosure, the method further comprising administering to the individual at least one stimulatory cytokine. In some embodiments, the at least one stimulatory cytokine is selected from IFN-α4, IFN-β, IL-1β, TNF-α, IL-6, IL-8, CRP, IL-20 family members, LIF, IFN-γ, OSM, CNTF, GM-CSF, IL-11, IL-12, IL-15, IL-17, IL-18, IL-23, CXCL10, IL-33, MCP-1, MIP-1-beta, and any combination thereof.

In some embodiments, the present invention provides an isolated nucleic acid comprising a nucleic acid sequence encoding an anti-SIRPA antibody of the present disclosure.

In some embodiments, the present invention provides a vector comprising an isolated nucleic acid comprising a nucleic acid sequence encoding an anti-SIRPA antibody of the present disclosure. In some embodiments, the present invention provides an isolated host cell comprising a vector comprising an isolated nucleic acid comprising a nucleic acid sequence encoding an anti-SIRPA antibody of the present disclosure.

In some embodiments, the present invention provides a method of producing an antibody that binds to human SIRPA, wherein the method comprises culturing a host cell comprising a vector comprising an isolated nucleic acid comprising a nucleic acid sequence encoding an anti-SIRPA antibody of the present disclosure so that the antibody is produced. The present invention further provides for recovering the antibody produced by the cell.

In some embodiments, the present invention provides a pharmaceutical composition comprising an anti-SIRPA antibody of the present disclosure and a pharmaceutically acceptable carrier.

BRIEF DESCRIPTION OF THE DRAWINGS

FIG. 1 shows the amino acid sequence alignment of the extracellular domains of human SIRPA variant 1 and SIRPA proteins from various species. The percent identity recorded demonstrates high homology within the extracellular region. Accession numbers are P78324 (human SIRPA variant 1), XP015313153 (cynomolgus), JAB51896 (marmoset), G1U0I5 (rabbit), and XP005634938 (dog). FIG. 1 discloses SEQ ID NOS 59-63, respectively, in order of appearance.

FIG. 2A lists potential humanized sequences of the heavy chain variable domain of anti-SIRPA antibody 3F9. Humanized sequence is based on IGHV3-23*01 acceptor framework and IGHJ4*01 joining region. FIG. 2A discloses SEQ ID NOS 64-65, 2, 64, and 3-4, respectively, in order of appearance. FIG. 2B lists potential humanized sequences of the light chain variable domain of anti-SIRPA antibody 3F9. FIG. 2B discloses SEQ ID NOS 66-67, 5, 66, and 68-70, respectively, in order of appearance.

FIG. 4A sets forth data showing antibody-mediated receptor downregulation depends on the N-linked Fc glycan.

FIG. 5A sets forth data showing humanized anti-SIRPA 3F9 IgG4 antibody variants failed to induce tumor cell phagocytosis. FIG. 5B sets forth data showing humanized anti-SIRPA 3F9 IgG4 antibody variants fail to downregulate CD14 expression on macrophages.

FIG. 6B shows that anti-SIRPA antibody 3F9 treatment downregulates CD32A and CD32B expression on primary human macrophages.

FIG. 7A sets forth data showing CD32A/B blockade inhibits anti-SIRPA antibody 3F9-mediated SIRPA downregulation on primary human macrophages. FIG. 7B sets forth data showing CD32A/B blockade inhibits anti-SIRPA antibody 3F9-mediated enhancement of tumor cell phagocytosis.

FIG. 8A-8B sets forth data showing CD32A allotype affected anti-SIRPA antibody 3F9-mediated SIRPA downregulation. FIG. 8A shows donors 507 and 508 were CD32A-R/H131 heterozygous; FIG. 8B shows donors 516 and 517 donor CD32A-H/H131 homozygous.

In FIG. 9A, 5 µg, 10 µg, and 20 µg of whole cell lysate was loaded onto SDS-PAGE and immunoblotted with anti-SIRPA cytoplasmic domain (a-SIRPAct). In FIG. 9B, 20 µg of whole cell lysate was loaded onto SDS-PAGE and probed with a-SIRPAct and anti-SHP2.

FIG. 10A-10B sets forth data comparing the enhancement of phagocytic activity of different Fc variants of anti-SIRPA antibody 3F9-22. In FIG. 10A, primary human macrophages were treated with anti-SIRPA 3F9-22 antibody on a wild type human IgG1 backbone or on a human IgG1 bearing S267E/L328F Fc mutations or an isotype control antibody. In FIG. 10B, primary human macrophages were treated with anti-SIRPA 3F9-22 antibody on a human IgG1 backbone bearing S267E/L328F or A330S/P331S Fc mutations or an isotype control antibody.

FIG. 17A-17C sets forth data showing the effect of anti-SIRPA antibody 3F9-22 on tumor growth inhibition in combination with anti-PD-L1 antibody in a syngeneic mouse colon carcinoma model. FIG. 17A sets forth FACS histograms showing the expression of mouse CD47 (top panel) and human CD47 (bottom panel) in wild-type and engineered MC38 cell lines. FIG. 17B sets forth data showing the average tumor growth curves of huSIRPA/huCD47 BAC transgenic mice implanted subcutaneously with MC38 cells engineered to lack mouse CD47 expression and that overexpress human CD47 (MC38-mCD47KO/huCD47+). FIG. 17C sets forth spaghetti plots of each individual animal in each treatment group of FIG. 17B.

FIG. 18A-18B sets forth data showing kinetics of antibody-mediated downregulation of SIRPA in myeloid cells of tumor-bearing BAC transgenic mice treated with increasing doses of anti-SIRPA antibody of the present disclosure. FIG. 18A sets forth data showing the relative change in SIRPA expression over time on tumor-infiltrating myeloid cells. FIG. 18B sets forth data showing the relative change in SIRPA expression over time on splenic myeloid cells.

FIG. 19A shows treatment conditions of anti-SIRPA antibody-mediated downregulation of SIRPA study in humanized NOG-EXL mice bearing A375 tumors. FIG. 19B sets forth data showing the expression level of SIRPA on human tumor macrophages as MFI values (left panel) or normalized values (right panel) associated with treatment with anti-SIRPA antibodies of the present disclosure.

FIG. 20A-20B shows expression levels of M1 macrophage markers HLA-DR/MHC class 2 (FIG. 20A) and CD86 (FIG. 20B) on human tumor macrophages isolated from humanized NOG-EXL mice bearing A375 tumors following treatment with anti-SIRPA antibodies of the present invention. FIG. 20A and FIG. 20B set forth data showing the expression of HLA-DR/MHC class 2 and CD86, respectively, as MFI values (left panels) or as normalized values (right panels).

FIG. 21A-21B shows downregulation of human SIRPA in splenic monocytes (FIG. 21A) and peripheral blood monocytes (FIG. 21B) isolated from humanized NOG-EXL mice bearing A375 tumors associated with administration of anti-SIRPA antibodies of the present invention. FIG. 21A and FIG. 21B set forth data showing the expression of human SIRPA as MFI values (left panels) or as normalized values (right panels).

FIG. 24 sets forth data showing red blood cell and platelet counts in cynomolgus monkeys administered control IgG antibody, anti-SIRPA antibody 3F9-22 PS, anti-SIRPA antibody 3F9-22 IgG4, anti-SIRPA antibody 3F9-IgG2, and anti-SIRPA antibody 3F9-22 NSLF.

Figure 3:
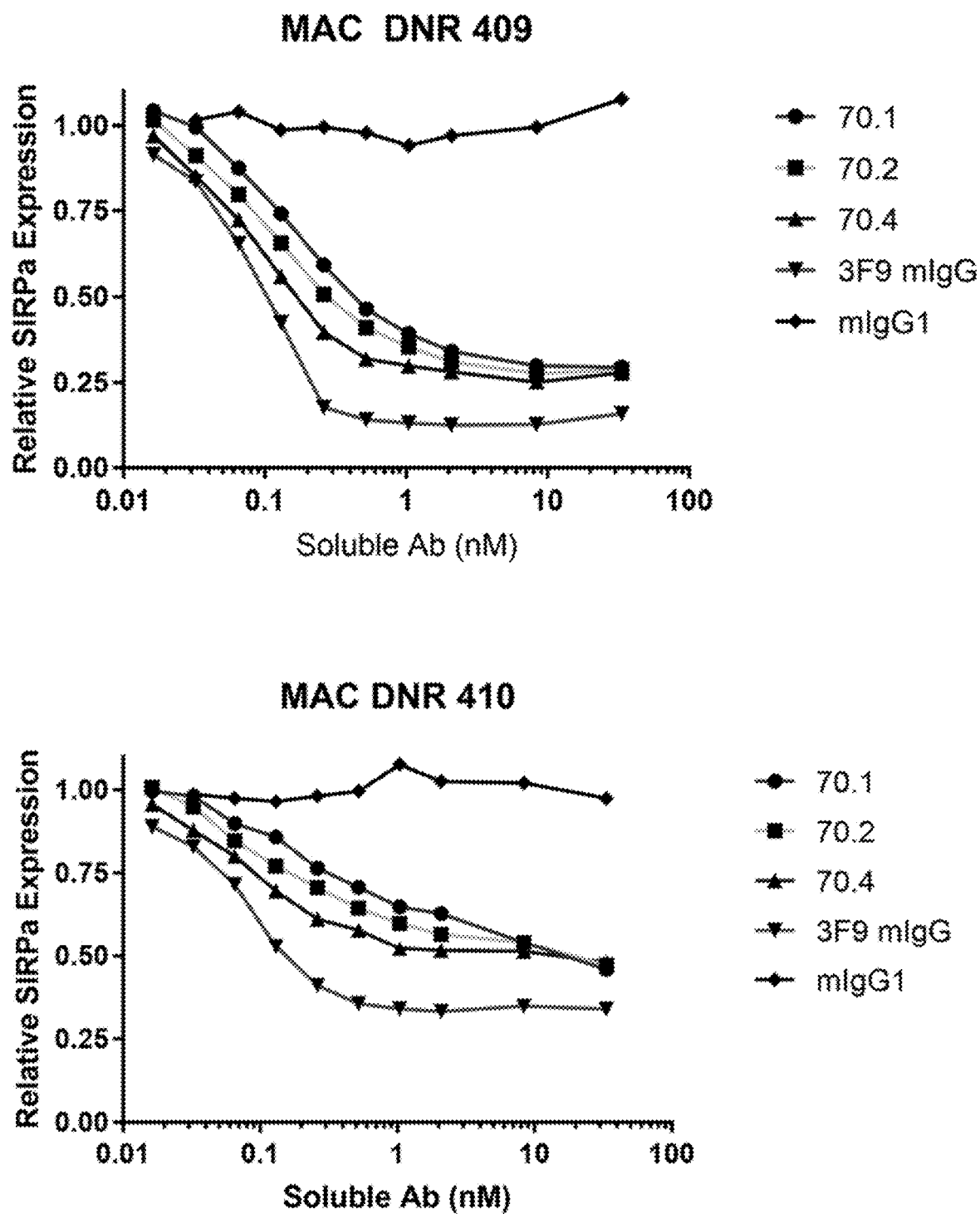
FIG. 3 sets forth data showing antibody-mediated SIRPA downregulation on primary human macrophages by murine and humanized anti-SIRPA 3F9 antibodies.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

The present disclosure relates to anti-SIRPA antibodies (e.g., monoclonal antibodies); methods of making and using such antibodies; pharmaceutical compositions comprising such antibodies; nucleic acids encoding such antibodies; and host cells comprising nucleic acids encoding such antibodies.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

I. Definitions

The terms "SIRPα" or "SIRPα polypeptide" or "SIRPA" or "SIRPA polypeptide" are used interchangeably herein refer herein to any native SIRPA from any vertebrate source, including mammals such as primates (e.g., humans and cynos) and rodents (e.g., mice and rats), unless otherwise indicated. In some embodiments, the term encompasses both wild-type sequences and naturally occurring variant sequences, e.g., splice variants or allelic variants. In some embodiments, the term encompasses "full-length," unprocessed SIRPA as well as any form of SIRPA that results from processing in the cell. In some embodiments, the SIRPA is human SIRPA. In some embodiments, the amino acid sequence of an exemplary SIRPA is Uniprot Accession No. P78324 as of 25 Apr. 2018. In some embodiments, the amino acid sequence of an exemplary human SIRPA v1 is SEQ ID NO: 1. In some embodiments, the amino acid sequence of an exemplary human SIRPA v2 is GenBank CAA71403.

The terms "anti-SIRPA antibody," an "antibody that binds to SIRPA," and "antibody that specifically binds SIRPA" refer to an antibody that is capable of binding SIRPA with sufficient affinity such that the antibody is useful as a diagnostic and/or therapeutic agent in targeting SIRPA. In one embodiment, the extent of binding of an anti-SIRPA antibody to an unrelated, non-SIRPA polypeptide is less than about 10% of the binding of the antibody to SIRPA as measured, e.g., by a radioimmunoassay (RIA). In certain embodiments, an antibody that binds to SIRPA has a dissociation constant (KD) of <1 μM, <100 nM, <10 nM, <1 nM, <0.1 nM, <0.01 nM, or <0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-SIRPA antibody binds to an epitope of SIRPA that is conserved among SIRPA from different species.

With regard to the binding of an antibody to a target molecule, the term "specific binding" or "specifically binds" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a KD for the target of about any of $10^{-4}$ M or lower, $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, $10^{-12}$ M or lower or a KD in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and KD values are inversely related. A high affinity for an antigen is measured by a low KD value. In one embodiment, the term "specific binding" refers to binding where a molecule binds to a particular polypeptide or epitope on a particular polypeptide without substantially binding to any other polypeptide or polypeptide epitope.

The term "immunoglobulin" (Ig) is used interchangeably with "antibody" herein. The term "antibody" herein is used in the broadest sense and specially covers monoclonal antibodies, polyclonal antibodies, multispecific antibodies (e.g., bispecific antibodies) including those formed from at least two intact antibodies, and antibody fragments so long as they exhibit the desired biological activity.

"Native antibodies" are usually heterotetrameric glycoproteins of about 150,000 Daltons, composed of two identical Light ("L") chains and two identical heavy ("H") chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, C T, 1994, page 71 and Chapter 6.

The light chain from any vertebrate species can be assigned to one of two clearly distinct types, called kappa ("κ") and lambda ("λ"), based on the amino acid sequences of their constant domains.

Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ"), and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three-dimensional configurations of different classes of immunoglobulins are well known and described generally in, for example, Abbas et al., Cellular and Molecular Immunology, 4$^{th}$ ed. (W.B. Saunders Co., 2000).

The "variable region" or "variable domain" of an antibody, such as an anti-SIRPA antibody of the present disclosure, refers to the amino-terminal domains of the heavy or light chain of the antibody. The variable domains of the heavy chain and light chain may be referred to as "$V_H$" and "$V_L$" respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-SIRPA antibodies of the present disclosure. The variable domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Immunological Interest*, Fifth Edition, National Institute of Health, Bethesda, MD (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as a monoclonal anti-SIRPA antibody of the present disclosure, obtained from a population of substantially homogeneous antibodies, i.e., the individual antibodies comprising the population are identical except for possible naturally occurring mutations and/or post-translation modifications (e.g., isomerizations, amidations, etc.) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including, for example, the hybridoma method, recombinant DNA methods, and technologies for producing human or human-like antibodies in animals that have parts or all of the human immunoglobulin loci or genes encoding human immunoglobulin sequences. For example, the monoclonal antibodies to be used in accordance with the present disclosure may be made by a variety of techniques, including, for example, phage-display technologies (see, e.g., Clackson et al., Nature, 352:624-628 (1991); Marks et al., J. Mol. Biol. 222:581-597 (1992); Sidhu et al., J. Mol. Biol. 338(2): 299-310 (2004); Lee et al., J. Mol. Biol. 340(5):1073-1093 (2004); Fellouse, Proc. Nat'l Acad. Sci. USA 101(34):12467-472 (2004); and Lee et al., J. Immunol. Methods 284(1-2):119-132 (2004), the hybridoma method (e.g., Kohler and Milstein., Nature, 256: 495-97 (1975); Hongo et al., Hybridoma, 14 (3):253-260 (1995), Harlow et al., Antibodies: A Laboratory Manual, (Cold Spring Harbor Laboratory Press, 2d ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), yeast presentation technologies (see, e.g., WO2009/036379A2; WO2010105256; WO2012009568, and Xu et al., Protein Eng. Des. Sel., 26(10): 663-70 (2013), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc. Nat'l Acad. Sci. USA 90:2551 (1993); Jakobovits et al., Nature 362:255-258 (1993); Bruggemann et al., Year in Immunol. 7:33 (1993); U.S. Pat. Nos. 5,545,807; 5,545,806; 5,569,825; 5,625,126; 5,633,425; and 5,661,016; Marks et al., Bio/Technology 10:779-783 (1992); Lonberg et al., Nature 368:856-859 (1994); Morrison, Nature 368:812-813 (1994); Fishwild et al., Nature Biotechnol. 14:845-851 (1996); Neuberger, Nature Biotechnol. 14:826 (1996); and Lonberg and Huszar, Intern. Rev. Immunol. 13:65-93 (1995).

The terms "full-length antibody," "intact antibody" or "whole antibody" are used interchangeably to refer to an antibody, such as an anti-SIRPA antibody of the present disclosure, in its substantially intact form, as opposed to an antibody fragment. Specifically, whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" refers to a molecule other than an intact antibody that comprises a portion of an intact antibody that binds the antigen to which the intact antibody binds. Examples of antibody fragments include Fab, Fab', F(ab')$_2$ and Fv fragments; diabodies; linear antibodies (see U.S. Pat. 5641870, Example 2; Zapata et al., *Protein Eng.* 8(10):1057-1062 (1995)); single-chain antibody molecules and multispecific antibodies formed from antibody fragments.

Papain digestion of antibodies, such as anti-SIRPA antibodies of the present disclosure, produces two identical antigen-binding fragments, called "Fab" fragments, and a residual "Fc" fragment, a designation reflecting the ability to crystallize readily. The Fab fragment consists of an entire light chain along with the variable region domain of the heavy chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both heavy chains held together by disulfides. The effector functions of antibodies are determined by sequences in the Fc region, the region which is also recognized by Fc receptors (FcR) found on certain types of cells.

"Functional fragments" of antibodies, such as anti-SIRPA antibodies of the present disclosure, comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the variable domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains.

As used herein, a "chimeric antibody" refers to an antibody (immunoglobulin), such as a chimeric anti-SIRPA antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity. Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as humanized forms of anti-SIRPA antibodies of the present disclosure, are chimeric antibodies comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "human antibody" is one that possesses an amino-acid sequence corresponding to that of an antibody, such as an anti-SIRPA antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries and yeast-display libraries. Human antibodies can be prepared by administering the antigen to a transgenic animal that has been modified to produce such antibodies in response to antigenic challenge, but whose endogenous loci have been disabled, e.g., immunized xenomice as well as generated via a human B-cell hybridoma technology. Human antibodies can be produced using various techniques known in the art, including phage-display libraries. Hoogenboom and Winter, J. Mol. Biol., 227:381 (1991); Marks et al., J. Mol. Biol., 222:581 (1991). Also available for the preparation of human monoclonal antibodies are methods described in Cole et al., Monoclonal Antibodies and Cancer Therapy, Alan R. Liss, p. 77 (1985); Boerner et al., J. Immunol., 147(1):86-95 (1991). See also van Dijk and van de Winkel, Curr. Opin. Pharmacol. 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., Proc. Nat'l Acad. Sci. USA, 103:3557-3562 (2006) regarding human antibodies generated via a human B-cell hybridoma technology. Alternatively, human antibodies can also be prepared by employing yeast libraries and methods as disclosed in, for example, WO2009/036379A2; WO2010105256; WO2012009568; and Xu et al., Protein Eng. Des. Sel., 26(10): 663-70 (2013).

The term "hypervariable region," "HVR," or "HV," when used herein refers to the regions of an antibody-variable domain, such as that of an anti-SIRPA antibody of the present disclosure, that are hypervariable in sequence and/or form structurally defined loops. Generally, antibodies comprise six HVRs; three in the $V_H$ (H1, H2, H3), and three in the $V_L$ (L1, L2, L3). In native antibodies, H3 and L3 display the most diversity of the six HVRs, and H3 in particular is believed to play a unique role in conferring fine specificity to antibodies. Naturally occurring camelid antibodies consisting of a heavy chain only are functional and stable in the absence of light chain.

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk J. Mol. Biol. 196: 901-917 (1987)). In some embodiments, the HVRs may be AbM HVRs. The AbM HVRs represent a compromise between the Kabat CDRs and Chothia structural loops and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

"Framework" or "FR" residues are those variable-domain residues other than the HVR residues as herein defined.

The phrase "variable-domain residue-numbering as in EU or Kabat" or [0076] "amino-acid-position numbering as in EU or Kabat," and variations thereof, refers to the numbering system used for heavy-chain variable domains or light-chain variable domains of the compilation of antibodies in EU or Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc, according to Kabat) after heavy-chain FR residue 82. The EU or Kabat numbering of residues may be determined for a given antibody by alignment at regions of homology of the sequence of the antibody with a "standard" Kabat numbered sequence.

The EU or Kabat numbering system is generally used when referring to a residue in the [0077] variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or Kabat numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU or Kabat numbering system (e.g., see United States Patent Publication No. 2010-280227).

An "acceptor humanframework" as used herein is a framework comprising the amino acid sequence of a $V_L$ or $V_H$ framework derived from a human immunoglobulin framework or a human consensus framework. An acceptor human framework "derived from" a human immunoglobulin framework or a human consensus framework may comprise the same amino acid sequence thereof, or it may comprise pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the $V_L$ human immunoglobulin framework sequence or human consensus framework sequence.

A "human consensus framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of*

*Proteins of Immunological Interest*, 5th Ed. Public Health Service, National Institutes of Health, Bethesda, MD (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al., supra.

An "amino-acid modification" at a specified position, e.g., of an anti-SIRPA antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an affinity matured anti-SIRPA antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al. *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155: 1994-2004 (1995); Jackson et al. *J. Immunol.* 154(7):3310-9 (1995); and Hawkins et al, *J. Mol. Biol.* 226:889-896 (1992).

"Fv" is the minimum antibody fragment which comprises a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains, which enables the sFv to form the desired structure for antigen binding.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain. Inhibiting receptor FcγRIIB contains an immunoreceptor tyrosine-based inhibition motif ("ITIM") in its cytoplasmic domain. Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., J. Biol. Chem. 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full-length of the sequences being compared.

The term "compete" when used in the context of antibodies (e.g., neutralizing antibodies) that compete for the same epitope means competition between antibody as determined by an assay in which the antibody being tested prevents or inhibits (e.g., reduces) specific binding of a reference molecule (e.g., a ligand, or a reference antibody) to a common antigen (e.g., SIRPA or a fragment thereof).

Numerous types of competitive binding assays can be used to determine if antibody competes with another, for example: solid phase direct or indirect radioimmunoassay (RIA), solid phase direct or indirect enzyme immunoassay (EIA), sandwich competition assay (see, e.g., Stahli et al., 1983, Methods in Enzymology 9:242-253); solid phase direct biotin-avidin EIA (see, e.g., Kirkland et al., 1986, J. Immunol. 137:3614-3619) solid phase direct labeled assay, solid phase direct labeled sandwich assay (see, e.g., Harlow and Lane, 1988, Antibodies, A Laboratory Manual, Cold Spring Harbor Press); solid phase direct label RIA using 1-125 label (see, e.g., Morel et al., 1988, Molec. Immunol. 25:7-15); solid phase direct biotin-avidin EIA (see, e.g., Cheung, et al., 1990, Virology 176:546-552); and direct labeled RIA (Moldenhauer et al., 1990, Scand. J. Immunol. 32:77-82). Typically, such an assay involves the use of purified antigen bound to a solid surface or cells bearing either of these, an unlabelled test antibody and a labeled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided herein. Usually, when a competing antibody is present in excess, it will inhibit (e.g., reduce) specific binding of a reference antibody to a common antigen by at least 20%, 30%, 40%, 50%, 60%, 70%, 80%, 85%, 90%, 95%, 97.5%, and/or near 100%.

As used herein, an "interaction" between a SIRPA polypeptide and a second polypeptide encompasses, without limitation, protein-protein interaction, a physical interaction, a chemical interaction, binding, covalent binding, and ionic binding. As used herein, an antibody "inhibits interaction" between two polypeptides when the antibody disrupts, reduces, or completely eliminates an interaction between the two polypeptides. An antibody of the present disclosure, thereof, "inhibits interaction" between two polypeptides when the antibody thereof binds to one of the two polypeptides. In some embodiments, the interaction can be inhibited by at least about any of 20%, 30%, 40%, 50%, 60%, 70%, 80%, 85%, 90%, 95%, 97.5%, and/or near 100%.

The term "epitope" includes any determinant capable of being bound by an antibody. An epitope is a region of an antigen that is bound by an antibody that targets that antigen, and when the antigen is a polypeptide, includes specific amino acids that directly contact the antibody. Most often, epitopes reside on polypeptides, but in some instances, can reside on other kinds of molecules, such as nucleic acids. Epitope determinants can include chemically active surface groupings of molecules such as amino acids, sugar side chains, phosphoryl or sulfonyl groups, and can have specific three-dimensional structural characteristics, and/or specific charge characteristics. Generally, antibodies specific for a particular target antigen will preferentially recognize an epitope on the target antigen in a complex mixture of polypeptides and/or macromolecules.

An "agonist" antibody or an "activating" antibody is an antibody that induces (e.g., increases) one or more activities or functions of the antigen after the antibody binds the antigen.

An "antagonist" antibody or a "blocking" antibody or an "inhibitory" antibody is an antibody that reduces, inhibits, and/or eliminates (e.g., decreases) antigen binding to one or more ligand after the antibody binds the antigen, and/or that reduces, inhibits, and/or eliminates (e.g., decreases) one or more activities or functions of the antigen after the antibody binds the antigen. In some embodiments, antagonist antibodies, or blocking antibodies, or inhibitory antibodies substantially or completely inhibit antigen binding to one or more ligand and/or one or more activities or functions of the antigen.

An "isolated" antibody, such as an isolated anti-SIRPA antibody of the present disclosure, is one that has been identified, separated and/or recovered from a component of its production environment (e.g., naturally or recombinantly). Preferably, the isolated antibody is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the antibody will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T-cells since at least one component of the antibody's natural environment will not be present. Ordinarily, however, an isolated polypeptide or antibody will be prepared by at least one purification step.

An "isolated" nucleic acid molecule encoding an antibody, such as an anti-SIRPA antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. In some embodiments, the individual is human.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration. In some embodiments, administration in conjunction is administration as a part of the same treatment regimen.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Anti-SIRPA Antibodies
Anti-SIRPA Antibody-Binding Regions

In some embodiments, anti-SIRPA antibodies of the present disclosure may bind a conformational epitope. In some embodiments, anti-SIRPA antibodies of the present disclosure may bind a discontinuous SIRPA epitope. In some embodiments, the discontinuous SIRPA epitope comprises two or more peptides, three or more peptides, four or more peptides, five or more peptides, six or more peptides, seven or more peptides, eight or more peptides, nine or more peptides, or 10 or more peptides. In some embodiments, anti-SIRPA antibodies of the present disclosure may bind a SIRPA epitope comprising one or more peptides. As disclosed herein, SIRPA epitopes may comprise one or more peptides comprising five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO: 1, or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian SIRPA protein corresponding to the amino acid sequence of SEQ ID NO: 1.

In some embodiments, anti-SIRPA antibodies of the present disclosure bind to an epitope of human SIRPA that is the same as or overlaps with the SIRPA epitope bound by an anti-SIRPA antibody comprising a heavy chain variable region comprising the amino acid sequence of SEQ ID NO:2 and a light chain variable region comprising the amino acid sequence of SEQ ID NO:5, an anti-SIRPA antibody comprising a heavy chain variable region comprising the amino acid sequence of SEQ ID NO:3 and a light chain variable region comprising the amino acid sequence of SEQ ID NO:6, an anti-SIRPA antibody comprising a heavy chain variable region comprising the amino acid sequence of SEQ ID NO:3 and a light chain variable region comprising the amino acid sequence of SEQ ID NO:7, an anti-SIRPA antibody comprising a heavy chain variable region comprising the amino acid sequence of SEQ ID NO:3 and a light chain variable region comprising the amino acid sequence of SEQ ID NO:8, an anti-SIRPA antibody comprising a heavy chain variable region comprising the amino acid sequence of SEQ ID NO:4 and a light chain variable region comprising the amino acid sequence of SEQ ID NO:6, an anti-SIRPA antibody comprising a heavy chain variable region comprising the amino acid sequence of SEQ ID NO:4 and a light chain variable region comprising the amino acid sequence of SEQ ID NO:7, or an anti-SIRPA antibody comprising a heavy chain variable region comprising the amino acid sequence of SEQ ID NO:4 and a light chain variable region comprising the amino acid sequence of SEQ ID NO:8. In some embodiments, anti-SIRPA antibodies of the present disclosure bind essentially the same SIRPA epitope bound by an anti-SIRPA antibody comprising a heavy chain variable region comprising the amino acid sequence of SEQ ID NO:2 and a light chain variable region comprising the amino acid sequence of SEQ ID NO:5, an anti-SIRPA antibody comprising a heavy chain variable region comprising the amino acid sequence of SEQ ID NO:3 and a light chain variable region comprising the amino acid sequence of SEQ ID NO:6, an anti-SIRPA antibody comprising a heavy chain variable region comprising the amino acid sequence of SEQ ID NO:3 and a light chain variable region comprising the amino acid sequence of SEQ ID NO:7, an anti-SIRPA antibody comprising a heavy chain variable region comprising the amino acid sequence of SEQ ID NO:3 and a light chain variable region comprising the amino acid sequence of SEQ ID NO:8, an anti-SIRPA antibody comprising a heavy chain variable region comprising the amino acid sequence of SEQ ID NO:4 and a light chain variable region comprising the amino acid sequence of SEQ ID NO:6, an anti-SIRPA antibody comprising a heavy chain variable region comprising the amino acid sequence of SEQ ID NO:4 and a light chain variable region comprising the amino acid sequence of SEQ ID NO:7, or an anti-SIRPA antibody comprising a heavy chain variable region comprising the amino acid sequence of SEQ ID NO:4 and a light chain variable region comprising the amino acid sequence of SEQ ID NO:8.

In some embodiments, anti-SIRPA antibodies of the present disclosure competitively inhibit binding of an anti-SIRPA antibody comprising a heavy chain variable region comprising the amino acid sequence of SEQ ID NO:2 and a light chain variable region comprising the amino acid sequence of SEQ ID NO:5, an anti-SIRPA antibody comprising a heavy chain variable region comprising the amino acid sequence of SEQ ID NO:3 and a light chain variable region comprising the amino acid sequence of SEQ ID NO:6, an anti-SIRPA antibody comprising a heavy chain variable region comprising the amino acid sequence of SEQ ID NO:3 and a light chain variable region comprising the amino acid sequence of SEQ ID NO:7, an anti-SIRPA antibody comprising a heavy chain variable region comprising the amino acid sequence of SEQ ID NO:3 and a light chain variable region comprising the amino acid sequence of SEQ ID NO:8, an anti-SIRPA antibody comprising a heavy chain variable region comprising the amino acid sequence of SEQ ID NO:4 and a light chain variable region comprising the amino acid sequence of SEQ ID NO:6, an anti-SIRPA antibody comprising a heavy chain variable region comprising the amino acid sequence of SEQ ID NO:4 and a light chain variable region comprising the amino acid sequence of SEQ ID NO:7, or an anti-SIRPA antibody comprising a heavy chain variable region comprising the amino acid sequence of SEQ ID NO:4 and a light chain variable region comprising the amino acid sequence of SEQ ID NO:8. In some embodiments, anti-SIRPA antibodies of the present disclosure compete with an anti-SIRPA antibody comprising a heavy chain variable region comprising the amino acid sequence of SEQ ID NO:2 and a light chain variable region comprising the amino acid sequence of SEQ ID NO:5, an anti-SIRPA antibody comprising a heavy chain variable region comprising the amino acid sequence of SEQ ID NO:3 and a light chain variable region comprising the amino acid sequence of SEQ ID NO:6, an anti-SIRPA antibody comprising a heavy chain variable region comprising the amino acid sequence of SEQ ID NO:3 and a light chain variable region comprising the amino acid sequence of SEQ ID NO:7, an anti-SIRPA antibody comprising a heavy chain variable region comprising the amino acid sequence of SEQ ID NO:3 and a light chain variable region comprising the amino acid sequence of SEQ ID NO:8, an anti-SIRPA antibody comprising a heavy chain variable region comprising the amino acid sequence of SEQ ID NO:4 and a light chain variable region comprising the amino acid sequence of SEQ ID NO:6, an anti-SIRPA antibody comprising a heavy chain variable region comprising the amino acid sequence of SEQ ID NO:4 and a light chain variable region comprising the amino acid sequence of SEQ ID NO:7, or an anti-SIRPA antibody comprising a heavy chain variable region comprising the amino acid sequence of SEQ ID NO:4 and a light chain variable region comprising the amino acid sequence of SEQ ID NO:8 for binding to SIRPA.

In some embodiments, anti-SIRPA antibodies of the present disclosure competitively inhibit binding of at least one antibody selected from any of the antibodies listed in Tables 4, 5, 7, 8 and 10. In some embodiments, anti-SIRPA antibodies of the present disclosure competitively inhibit binding of at least one antibody selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof. In some embodiments, an anti-SIRPA antibody of the present disclosure competes with one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof, for binding to SIRPA when the anti-SIRPA antibody reduces the binding of one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9- 6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof to SIRPA by an amount the ranges from about 50% to 100%, as compared to binding to SIRPA in the absence of the anti-SIRPA antibody. In some embodiments, an anti-SIRPA antibody of the present disclosure competes with one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof for binding to SIRPA when the anti-SIRPA antibody reduces the binding of one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof to SIRPA by at least 50%, at least 55%, by at least 60%, at least 65%, at least 70%, at least 75%, at least 80%, at least 85%, at least 90%, at least 95%, or 100%, as compared to binding to SIRPA in the absence of the anti-SIRPA antibody. In some embodiments, an anti-SIRPA antibody of the present disclosure that reduces the binding of one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof to SIRPA by 100% indicates that the anti-SIRPA antibody essential completely blocks the binding of one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9- 16, 3F9-17, 3F9-18, 3F9-19, 3F9-20, 3F9-21, 3F9-22, 3F9-23, 3F9-24, 3F9-25, and any combination thereof to SIRPA. In some embodiments, the anti-SIRPA antibody and the one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001 ratio of anti-SIRPA antibody to one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof. In some embodiments, the anti-SIRPA antibody is present in excess by an amount that ranges from about 1.5-fold to 100-fold, or greater than 100-fold compared to the amount of the one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9- 6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof. In some embodiments, the anti-SIRPA antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof.

In some embodiments, anti-SIRPA antibodies of the present disclosure bind to an epitope of human SIRPA that is the same as or overlaps with the SIRPA epitope bound by at least one antibody selected from any of the antibodies listed in Tables 4, 5, 7, 8, and 10. In some embodiments, anti-SIRPA antibodies of the present disclosure bind to an epitope of human SIRPA that is the same as or overlaps with the SIRPA epitope bound by at least one antibody selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25.

In some embodiments, anti-SIRPA antibodies of the present disclosure bind essentially the same SIRPA epitope bound by at least one antibody selected from any of the antibodies listed in Tables 4, 5, 7, 8, and 10. In some embodiments, anti-SIRPA antibodies of the present disclosure bind essentially the same SIRPA epitope bound by at least one antibody selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In some embodiments, anti-SIRPA antibodies of the present disclosure compete with one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, 3F9-25, and any combination thereof for binding to SIRPA.

Any suitable competition assay or SIRPA binding assay known in the art, such as BIAcore analysis, ELISA assays, or flow cytometry, may be utilized to determine whether an anti-SIRPA antibody competes with one or more antibodies selected from m3F9, h3F9 H1/L1 (14.70.1), h3F9 H1/L2 (14.70.2), h3F9 H1/L3, h3F9 H2/L1 (14.70.4), h3F9 H2/L2, h3F9 H2/L3, 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9- 16, 3F9-17, 3F9-18, 3F9-19, 3F9-20, 3F9-21, 3F9-22, 3F9-23, 3F9-24, 3F9-25, and any combination thereof for binding to SIRPA. In an exemplary competition assay, immobilized SIRPA or cells expressing SIRPA on the cell surface are incubated in a solution comprising a first labeled antibody that binds to SIRPA (e.g., human or non-human primate) and a second unlabeled antibody that is being tested for its ability to compete with the first antibody for binding to SIRPA. The second antibody may be present in a hybridoma supernatant. As a control, immobilized SIRPA or cells expressing SIRPA is incubated in a solution comprising the first labeled antibody but not the second unlabeled antibody. After incubation under conditions permissive for binding of the first antibody to SIRPA, excess unbound antibody is removed, and the amount of label associated with immobilized SIRPA or cells expressing SIRPA is measured. If the amount of label associated with immobilized SIRPA or cells expressing SIRPA is substantially reduced in the test sample relative to the control sample, then that indicates that the second antibody is competing with the first antibody for binding to SIRPA. See, Harlow and Lane (1988) *Antibodies: A Laboratory Manual* ch. 14 (Cold Spring Harbor Laboratory, Cold Spring Harbor, NY).

In some embodiments, provided herein are anti-SIRPA antibodies comprising at least one, two, three, four, five, or six HVRs selected from (a) HVR—H1 comprising the amino acid sequence of SEQ ID NO:20; (b) HVR—H2 comprising the amino acid sequence of SEQ ID NO:21; (c) HVR—H3 comprising an amino acid sequence selected from SEQ ID NOs:22, 23, and 24; (d) HVR-L1 comprising the amino acid sequence of SEQ ID NO:9; (e) HVR-L2 comprising the amino acid sequence of SEQ ID NO: 10; and (f) HVR-L3 comprising an amino acid sequence selected from SEQ ID NOs:11, 12, 13, 14, 15, 16, 17, 18, and 19.

In some embodiments, provided herein are anti-SIRPA antibodies comprising at least one, two, three, four, five, or six HVRs selected from: (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 11; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 12; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO:10; and (f) HVR-L3 comprising the amino acid sequence of SEQ ID NO: 13; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 14; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 15; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 16; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 17; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e)

HVR-L2 comprising the amino acid sequence of SEQ ID NO: 10; and (f) HVR-L3 comprising the amino acid sequence of SEQ ID NO: 18; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:22; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 19; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 11; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 13; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 14; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 15; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 16; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 17; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 16; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 17; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 18; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:23; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 19; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 11; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 13; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 14; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 15; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 16; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 17; (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 18; and (a) HVR—H1 comprising the amino acid sequence of SEQ ID NO:20; (b) HVR—H2 comprising the amino acid sequence of SEQ ID NO:21; (c) HVR—H3 comprising the amino acid sequence of SEQ ID NO:24; (d) HVR-L1 comprising the amino acid sequence of SEQ ID NO:9; (e) HVR-L2 comprising the amino acid sequence of SEQ ID NO: 10; and (f) HVR-L3 comprising the amino acid sequence of SEQ ID NO: 19.

In some embodiments, provided herein are anti-SIRPA antibodies comprising at least one, at least two, or all three $V_H$ HVR sequences selected from (a) HVR—H1 comprising the amino acid sequence of SEQ ID NO:20; (b) HVR—H2 comprising the amino acid sequence of SEQ ID NO:21; and (c) HVR—H3 comprising an amino acid sequence selected from SEQ ID NOs:22, 23, and 24.

In some embodiments, provided herein are anti-SIRPA antibodies comprising at least one, at least two, or all three $V_L$ HVR sequences selected from (a) HVR-L1 comprising the amino acid sequence of SEQ ID NO:9; (b) HVR-L2 comprising the amino acid sequence of SEQ ID NO: 10; and (c) HVR-L3 comprising an amino acid sequence selected from SEQ ID NOs:11, 12, 13, 14, 15, 16, 17, 18, and 19.

In some embodiments, provided herein are anti-SIRPA antibodies comprising (a) a $V_H$ domain comprising at least one, at least two, or all three $V_H$ HVR sequences selected from (i) HVR—H1 comprising the amino acid sequence of SEQ ID NO:20, (ii) HVR—H2 comprising the amino acid sequence of SEQ ID NO:21, and (iii) HVR—H3 comprising an amino acid sequence selected from SEQ ID NOs:22, 23, and 24, and (b) a $V_L$ domain comprising at least one, at least two, or all three $V_L$ HVR sequences selected from (i) HVR-L1 comprising the amino acid sequence of SEQ ID NO:9, (ii) HVR-L2 comprising the amino acid sequence of SEQ ID NO: 10, and (c) HVR-L3 comprising an amino acid sequence selected from SEQ ID NOs:11, 12, 13, 14, 15, 16, 17, 18, and 19.

In some embodiments, provided herein are anti-SIRPA antibodies comprising (a) a $V_H$ domain comprising (i) HVR—H1 comprising the amino acid sequence of SEQ ID NO:20, (ii) HVR—H2 comprising the amino acid sequence of SEQ ID NO:21, and (iii) HVR—H3 comprising an amino acid sequence selected from SEQ ID NOs:22, 23, and 24, and (b) a $V_L$ domain comprising (i) HVR-L1 comprising the amino acid sequence of SEQ ID NO:9, (ii) HVR-L2 comprising the amino acid sequence of SEQ ID NO: 10, and (c) HVR-L3 comprising an amino acid sequence of selected from SEQ ID NOs:11, 12, 13, 14, 15, 16, 17, 18, and 19.

In another aspect, an anti-SIRPA antibody comprises a heavy chain variable domain ($V_H$) sequence having at least 90%, 91%, 92%, 93%, 94%, 95%, 96%, 97%, 98%, 99%, or 100% sequence identity to an amino acid sequence elected from SEQ ID NOs:33, 34, and 35. In certain embodiments, a $V_H$ sequence having at least 90%, 91%, 92%, 93%, 94%, 95%, 96%, 97%, 98%, or 99% identity to an amino acid sequence selected from SEQ ID NOs:33, 34, and 35 contains substitutions (e.g., conservative substitutions), insertions, or deletions relative to the reference sequence, but an anti-SIRPA antibody comprising that sequence retains the ability to bind to SIRPA. In certain embodiments, a total of 1 to 10 amino acids have been substituted, inserted, and/or deleted in SEQ ID NO:33, SEQ ID NO:34, or SEQ ID NO:35. In certain embodiments, a total of 1 to 5 amino acids have been substituted, inserted and/or deleted in SEQ ID NO: 33, SEQ ID NO:34, or SEQ ID NO:35. In certain embodiments, substitutions, insertions, or deletions occur in regions outside the HVRs (i.e., in the FRs). Optionally, the anti-SIRPA antibody comprises the $V_H$ sequence of SEQ ID NO:33, SEQ ID NO:34, or SEQ ID NO:35, including post-translational modifications of that sequence. In a particular embodiment, the $V_H$ comprises one, two or three HVRs selected from: (a) HVR—H1 comprising the amino acid sequence of SEQ ID NO:20, (b) HVR—H2 comprising the amino acid sequence of SEQ ID NO:21, and (c) HVR—H3 comprising an amino acid sequence selected from SEQ ID NOs:22, 23, and 24.

In another aspect, an anti-SIRPA antibody is provided, wherein the antibody comprises a light chain variable domain ($V_L$) having at least 90%, 91%, 92%, 93%, 94%, 95%, 96%, 97%, 98%, 99%, or 100% sequence identity to an amino acid sequence selected from SEQ ID NOs:36, 37, 38, 39, 40, 41, 42, 43, and 44. In certain embodiments, a $V_L$ sequence having at least 90%, 91%, 92%, 93%, 94%, 95%, 96%, 97%, 98%, or 99% identity to an amino acid sequence selected from SEQ ID NOs: 36, 37, 38, 39, 40, 41, 42, 43, and 44 contains substitutions (e.g., conservative substitutions), insertions, or deletions relative to the reference sequence, but an anti-SIRPA antibody comprising that sequence retains the ability to bind to SIRPA. In some embodiments, a total of 1 to 10 amino acids have been substituted, inserted and/or deleted in SEQ ID NO:36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44. In certain embodiments, a total of 1 to 5 amino acids have been substituted, inserted and/or deleted in SEQ ID NO: 36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44. In certain embodiments, the substitutions, insertions, or deletions occur in regions outside the HVRs (i.e. in the FRs). Optionally, the anti-SIRPA antibody comprises the $V_L$ sequence of SEQ ID NO: 36, SEQ ID NO:37, SEQ ID NO:38, SEQ ID NO:39, SEQ ID NO:40, SEQ ID NO:41, SEQ ID NO:42, SEQ ID NO:43, or SEQ ID NO:44, including post-translational modifications of that sequence. In a particular embodiment, the $V_L$ comprises one, two or three HVRs selected from (a) HVR-L1 comprising the amino acid sequence of SEQ ID NO:9, (b) HVR-L2 comprising the amino acid sequence of SEQ ID NO: 10, and (c) HVR-L3 comprising an amino acid sequence selected from SEQ ID NOs:11, 12, 13, 14, 15, 16, 17, 18, and 19.

In some embodiments, the anti-SIRPA antibody is provided, wherein the antibody comprises a $V_H$ as in any of the embodiments provided above, and a $V_L$ as in any of the embodiments provided above. In some embodiments, provided herein are anti-SIRPA antibodies, wherein the antibody comprises a $V_H$ as in any of the embodiments provided above, and a $V_L$ as in any of the embodiments provided above. In one embodiment, the antibody comprises the $V_H$ and $V_L$ sequences in SEQ ID NOs:33, 34, or 35 and SEQ ID NOs:36, 37, 38, 39, 40, 41, 42, 43, or 44, respectively, including post-translational modifications of those sequences.

In some embodiments, provided herein are anti-SIRPA antibodies comprising a heavy chain variable domain ($V_H$) and a light chain variable domain ($V_L$), wherein the $V_H$ and $V_L$ are selected from the group consisting of: $V_H$ comprising the amino acid sequence of SEQ ID NO:33 and $V_L$ comprising the amino acid sequence of SEQ ID NO:36; $V_H$ comprising the amino acid sequence of SEQ ID NO:33 and $V_L$ comprising the amino acid sequence of SEQ ID NO:37; $V_H$ comprising the amino acid sequence of SEQ ID NO:33 and $V_L$ comprising the amino acid sequence of SEQ ID NO:38; $V_H$ comprising the amino acid sequence of SEQ ID NO:33 and $V_L$ comprising the amino acid sequence of SEQ ID NO:39; $V_H$ comprising the amino acid sequence of SEQ ID NO:33 and $V_L$ comprising the amino acid sequence of SEQ ID NO:40; $V_H$ comprising the amino acid sequence of SEQ ID NO:33 and $V_L$ comprising the amino acid sequence of SEQ ID NO:41; $V_H$ comprising the amino acid sequence of SEQ ID NO:33 and $V_L$ comprising the amino acid sequence of SEQ ID NO:42; $V_H$ comprising the amino acid sequence of SEQ ID NO:33 and $V_L$ comprising the amino acid sequence of SEQ ID NO:43; $V_H$ comprising the amino acid sequence of SEQ ID NO:33 and $V_L$ comprising the amino acid sequence of SEQ ID NO:44; $V_H$ comprising the amino acid sequence of SEQ ID NO:34 and $V_L$ comprising the amino acid sequence of SEQ ID NO:36; $V_H$ comprising the amino acid sequence of SEQ ID NO:34 and $V_L$ comprising the amino acid sequence of SEQ ID NO:38; $V_H$ comprising the amino acid sequence of SEQ ID NO:34 and $V_L$ comprising the amino acid sequence of SEQ ID NO:39; $V_H$ comprising the amino acid sequence of SEQ ID NO:34 and $V_L$ comprising the amino acid sequence of SEQ ID NO:40; $V_H$ comprising the amino acid sequence of SEQ ID NO:34 and $V_L$ comprising the amino acid sequence of SEQ ID NO:41; $V_H$ comprising the amino acid sequence of SEQ ID NO:34 and $V_L$ comprising the amino acid sequence of SEQ ID NO:42; $V_H$ comprising the amino acid sequence of SEQ ID NO:34 and $V_L$ comprising the amino acid sequence of SEQ ID NO:43; $V_H$ comprising the amino acid sequence of SEQ ID NO:34 and $V_L$ comprising the amino acid sequence of SEQ ID NO:44; $V_H$ comprising the amino acid sequence of SEQ ID NO:35 and $V_L$ comprising the amino acid sequence of SEQ ID NO:36; $V_H$ comprising the amino acid sequence of SEQ ID NO:35 and $V_L$ comprising the amino acid sequence of SEQ ID NO:38; $V_H$ comprising the amino acid sequence of SEQ ID NO:35 and $V_L$ comprising the amino acid sequence of SEQ ID NO:39; $V_H$ comprising the amino acid sequence of SEQ ID NO:35 and $V_L$ comprising the amino acid sequence of SEQ ID NO:40; $V_H$ comprising the amino acid sequence of SEQ ID NO:35 and $V_L$ comprising the amino acid sequence of SEQ ID NO:41; $V_H$ comprising the amino acid sequence of SEQ ID NO:35 and $V_L$ comprising the amino acid sequence of SEQ ID NO:42; $V_H$ comprising the amino acid sequence of SEQ ID NO:35 and $V_L$ comprising the amino acid sequence of SEQ ID NO:43; and $V_H$ comprising the amino acid sequence of SEQ ID NO:35 and $V_L$ comprising the amino acid sequence of SEQ ID NO:44.

Further provided herein are anti-SIRPA antibodies which competitively inhibit binding of and/or competes for binding with an anti-SIRPA antibody comprising (a) a $V_H$ domain comprising (i) HVR—H1 comprising the amino acid sequence of SEQ ID NO:20, (ii) HVR—H2 comprising the amino acid sequence of SEQ ID NO:21, and (iii) HVR—H3 comprising an amino acid sequence selected from SEQ ID NOs:22, 23, and 24, and (b) a $V_L$ domain comprising (i) HVR-L1 comprising the amino acid sequence of SEQ ID NO:9, (ii) HVR-L2 comprising the amino acid sequence of SEQ ID NO: 10, and (c) HVR-L3 comprising an amino acid sequence of selected from SEQ ID NOs:11, 12, 13, 14, 15, 16, 17, 18, and 19. In some embodiments, the antibody comprises the VH and VL sequences in SEQ ID NOs:33, 34, or 35, and SEQ ID NOs:36, 37, 38, 39, 40, 41, 42, 43, or 44, respectively.

Provided herein are anti-SIRPA antibodies which bind to an epitope of human SIRPA that is the same as or overlaps with the epitope bound by an anti-SIRPA antibody comprising (a) a $V_H$ domain comprising (i) HVR—H1 comprising the amino acid sequence of SEQ ID NO:20, (ii) HVR—H2 comprising the amino acid sequence of SEQ ID NO:21, and (iii) HVR—H3 comprising an amino acid sequence selected from SEQ ID NOs:22, 23, and 24, and (b) a VL domain comprising (i) HVR-L1 comprising the amino acid sequence of SEQ ID NO:9, (ii) HVR-L2 comprising the amino acid sequence of SEQ ID NO: 10, and (c) HVR-L3 comprising an amino acid sequence selected from SEQ ID NOs: 11, 12, 13, 14, 15, 16, 17, 18, and 19. In some embodiments, the antibody comprises the $V_H$ and $V_L$ sequences in SEQ ID NOs:33, 34, or 35, and SEQ ID NOs:36, 37, 38, 39, 40, 41, 42, 43, and 44, respectively. In some embodiments, the epitope of human SIRPA is the same epitope as bound by an anti-SIRPA antibody.

In some embodiments, the anti-SIRPA antibody according to any of the above embodiments is a monoclonal antibody, including a humanized and/or human antibody. In some embodiments, the anti-SIRPA antibody is an antibody fragment, e.g., a Fv, Fab, Fab', scFv, diabody, or F(ab')2 fragment. In some embodiments, the anti-SIRPA antibody is a substantially full-length antibody, e.g., an IgG1 antibody, IgG2a antibody or other antibody class or isotype as defined herein.

In some embodiments, an anti-SIRPA antibody according to any of the above embodiments may incorporate any of the features, singly or in combination, as described herein.

Provided herein are anti-SIRPA antibodies. Antibodies provided are useful, e.g., for the diagnosis or treatment of SIRPA mediated disorders.

The present disclosure relates, in part, to anti-SIRPA antibodies that exhibit one or more improved and/or enhanced functional characteristics (e.g., relative to an anti-SIRPA antibody having a heavy chain variable region comprising the amino acid sequence of SEQ ID NO: 2 and a light chain variable region comprising the amino acid sequence of SEQ ID NO:5), including, for example, anti-SIRPA antibodies capable of decreasing cellular levels of SIRPA, anti-SIRPA antibodies capable of decreasing cell surface levels of SIRPA, anti-SIRPA antibodies capable of degrading SIRPA, anti-SIRPA antibodies capable of decreasing cellular levels of CD32A/B, anti-SIRPA antibodies capable of increasing or enhancing phagocytosis, anti-SIRPA antibodies capable increasing or enhancing tumor cell phagocytosis by macrophages, anti-SIRPA antibodies capable of increasing or enhancing anti-tumor activity of anti-cancer therapies, anti-SIRPA antibodies capable of increasing or enhancing T cell proliferation, anti-SIRPA antibodies capable of increasing or enhancing pro-inflammatory cytokine release from macrophages, and/or anti-SIRPA antibodies capable of binding human SIRPA with improved/enhanced kinetics; methods of making and using such anti-SIRPA antibodies; pharmaceutical compositions containing such anti-SIRPA antibodies; nucleic acids encoding such anti-SIRPA antibodies; and host cells containing nucleic acids encoding such anti-SIRPA antibodies.

In some embodiments, the anti-SIRPA antibodies of the present disclosure may have one or more activities that are due, at least in part, to the ability of the antibodies to reduce cellular expression (e.g., cell surface expression) of SIRPA by inducing degradation, down regulation, cleavage, receptor desensitization, and/or lysosomal targeting of SIRPA. In some embodiments, an anti-SIRPA antibody of the present disclosure that decreases cellular levels of SIRPA is an antibody that exhibits one or more of the following characteristics: (1) inhibits or reduces one or more SIRPA activities; (2) the ability to reduce SIRPA expression (such as at the mRNA level and/or at protein level) in SIRPA-expressing cells; (3) the ability to interact, bind, or recognize a SIRPA protein; (4) the ability to specifically interact with or bind to a SIRPA protein; and (5) the ability to treat, ameliorate, or prevent any aspect of a disease or disorder described or contemplated herein.

In some embodiments, the anti-SIRPA antibodies exhibit one or more of the following properties: a) have a dissociation constant (KD) for human SIRPA that is lower than that of an anti-SIRPA antibody having a heavy chain variable region comprising the amino acid sequence of SEQ ID NO:2 and a light chain variable region comprising the amino acid sequence of SEQ ID NO:5; b) binds to human cells, such as human monocytes and macrophages; c) decrease cell surface levels of SIRPA (e.g., decrease cell surface levels of SIRPA on human macrophages cells in vitro with a half-maximal effective concentration (EC50) that is lower than that of an anti-SIRPA antibody having a heavy chain variable region comprising the amino acid sequence of SEQ ID NO:2 and a light chain variable region comprising the amino acid sequence of SEQ ID NO:5; d) have a dissociation constant (KD) for human SIRPA that may range from about 0.6 nM to about 0.7 nM; and/or e) decreases cell surface levels of SIRPA (e.g., decreases cell surface levels of SIRPA on human macrophages in vitro with a half-maximal effective concentration (EC50) that may range from about 0.4 nM to about 0.5 nM. As disclosed herein half-maximal effective concentration (EC50) refers to the concentration at which an anti-SIRPA antibody of the present disclosure reduces cellular levels of SIRPA on a cell or in a cell to half that of untreated cells, or the concentration at which the antibody achieves half-maximal binding to SIRPA on a cell.

In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) to human SIRPA v1 of about 0.40 nM about 0.5 nM as measured by flow cytometry. In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) to human SIRPA v1 of about 5 nM, of about 4 nM, of about 3 nM, of about 2 nM, of about 1 nM, of about 0.9 nM, of about 0.8 nM, of about 0.7 nM, of about 0.6 nM, of about 0.5 nM, of about 0.4 nM, of about 0.3 nM, of about 0.2 nM, or of about 0.1 nM as measured by flow cytometry. In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) to human SIRPA v1 in the range of about 5 nM to 1 nM, of about 1 nM to 0.9 nM, of about 1 nM to 0.8 nM, of about 1 nM to 0.7 nM, of about 1 nM to 0.6 nM, of about 1 nM to 0.5 nM, of about 1 nM to 0.4 nM, of about 1 nM to 0.3 nM, of about 1 nM to 0.2 nM, of about 1 nM to 0.1 nM, of about 0.9 nM to 0.8 nM, of about 0.9 nM to 0.7 nM, of about 0.9 nM to 0.6 nM, of about 0.9 nM to 0.5 nM, of about 0.9 nM to 0.4 nM, of about 0.9 nM to 0.3 nM, of about 0.9 nM to 0.2 nM, of about 0.9 nM to 0.1 nM, of about 0.8 nM to 0.6 nM, of about 0.8 nM to 0.5 nM, of about 0.8 nM to 0.4 nM, of about 0.8 nM to 0.3 nM, of about 0.8 nM to 0.2 nM, of about 0.8 nM to 0.1 nM, of about 0.7 nM to 0.5 nM, of about 0.7 nM to 0.4 nM, of about 0.7 nM to 0.3 nM, of about 0.7 nM to 0.2 nM, of about 0.7 nM to 0.1 nM, of about 0.6 nM to 0.4 nM, of about 0.6 nM to 0.3 nM, of about 0.6 nM to 0.2 nM, of about 0.6 nM to 0.1 nM, of about 0.5 nM to 0.3 nM, of about 0.5 nM to 0.2 nM, of about 0.5 nM to 0.1 nM, of about 0.4 nM to 0.2 nM, of about 0.4 nM to 0.1 nM, or of about 0.3 nM to 0.1 nM as measured by flow cytometry.

In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) to human SIRPA v1 of about 0.093 nM, to human SIRPA v2 of about 0.080 nM, and/or to cyno SIRPA of about 0.879 nM as measured by flow cytometry. In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) to human SIRPA v1 or to human SIRPA v2 in the range of about 2 nM to 0.05 nM, of about 1 nM to 0.05 nM, of about 0.9 nM to 0.05 nM, of about 0.8 nM to 0.05 nM, of about 0.7 nM to 0.05 nM, of about 0.6 nM to 0.05 nM, of about 0.5 nM to 0.05 nM, of about 0.4 nM to 0.05 nM, of about 0.3 nM to 0.05 nM, of about 0.20 nM to 0.05 nM, of about 0.15 nM to 0.05 nM, of about 0.10 nM to 0.05 nM, of about 0.09 nM to 0.05 nM, of about 0.08 nM to 0.05 nM, of about 0.07 nM to 0.05 nM, of about 0.06 nM to 0.05 nM, of about 0.20 nM to 0.06 nM, of about 0.15 nM to 0.06 nM, of about 0.10 nM to 0.06 nM, of about 0.09 nM to 0.06 nM, of about 0.08 nM to about 0.06 nM, of about 0.07 nM to 0.06 nM, of about 0.20 nM to 0.07 nM, of about 0.15 nM to 0.07 nM, of about 0.10 nM to about 0.07 nM, of about 0.09 nM to 0.07 nM, of about 0.08 nM to 0.7 nM, of about 0.20 nM to 0.08 nM, of about 0.15 nM to 0.08 nM, of about 0.10 nM to 0.08 nM, of about 0.09 nM to 0.08 nM, of about 0.20 nM to 0.09 nM, of about 0.15 nM to 0.09 nM, or of about 0.10 nM to 0.9 nM as measured by flow cytometry.

In some embodiments, which may be combined with any of the embodiments herein, the present disclosure provides an isolated antibody that binds to human SIRPA, wherein the antibody reduces cell surface levels of SIRPA in vitro with a half maximal effective concentration (EC50) to human SIRPA v1 of about 0.107 nM, to human SIRPA v2 of about 0.082 nM, and/or to cyno SIRPA of about 0.107 nM as measured by flow cytometry.

Advantageously, anti-SIRPA antibodies of the present disclosure reduce cell surface expression of SIRPA more potently (e.g., with a lower EC50) as compared to a control anti-SIRPA antibody (e.g., a control anti-SIRPA antibody having a heavy chain variable region comprising the amino acid sequence of SEQ ID NO:2 and a light chain variable region comprising the amino acid sequence of SEQ ID NO:5). Moreover, advantageously, anti-SIRPA antibodies of the present disclosure have a higher affinity (e.g., up to approximately 100-fold higher affinity) for SIRPA (e.g., a lower KD value as measured by surface plasmon resonance) as compared to a control anti-SIRPA antibody (e.g., a control anti-SIRPA antibody having a heavy chain variable region comprising the amino acid sequence of SEQ ID NO:2 and a light chain variable region comprising the amino acid sequence of SEQ ID NO:5.

Certain aspects of the present disclosure are based, at least in part, on the identification of anti-SIRPA antibodies that exhibit one or more improved and/or enhanced functional characteristics (e.g., relative to an anti-SIRPA antibody having a heavy chain variable region comprising the amino acid sequence of SEQ ID NO:2 and a light chain variable region of comprising the amino acid sequence of SEQ ID NO:5), including, an improved/enhanced ability to decrease cell surface levels of SIRPA on cells, resulting in the reduction, neutralization, prevention, or curbing of one or more SIRPA activities, including, without limitation, reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; reducing proliferation of monocytes, macrophages, T cells, dendritic cells, neutrophils, and/or microglia; reducing the overall functionality of monocytes, macrophages, T cells, dendritic cells, neutrophils, and/or microglia; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, and multiple sclerosis; binding to SIRPA ligand on tumor cells; binding to SIRPA ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; enhancing infiltration of one or more of immunosuppressor dendritic cells, immunosuppressor macrophages, myeloid derived suppressor cells, tumor-associated macrophages, immunosuppressor neutrophils, and regulatory T cells into tumors; increasing number of tumor-promoting myeloid/granulocytic immune-suppressive cells in a tumor, in peripheral blood, or other lymphoid organ; enhancing tumor-promoting activity of myeloid-derived suppressor cells; decreasing activation of tumor-specific T lymphocytes with tumor killing potential; decreasing infiltration of tumor-specific T lymphocytes with tumor killing potential; increasing tumor growth rate; increasing rate of tumor recurrence; decreasing efficacy of one or more immune-therapies that modulate anti-tumor T cell responses, optionally wherein the one or more immune-therapies are immune-therapies that target one or more proteins selected from CD40, OX40, ICOS, CD28, CD137/4-1BB, CD27, GITR, PD-L1, CTLA4, PD-L2, PD-1, B7-H3, B7-H4, HVEM, LIGHT, BTLA, VISTA, KIR, GAL9, TIM1, TIM3, TIM4, A2AR, LAG3, DR-5, CD39, CD70, TREM1, TREM2, Siglec-5, Siglec-7, Siglec-9, Siglec-11, SirpA, CD447, CSF-1 receptor, and any combination thereof, or of one or chemotherapy agents and/or more cancer vaccines.

In some embodiments, treatment of cancer with anti-SIRPA antibodies as described herein may: (i) increase the number of tumor infiltrating $CD3^+$ T cells; (ii) decrease cellular levels of SIRPA in non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (iii) reduce the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (iv) d reduce PD-L1, PD-L2, B7-H7, B7-H3, CD200R, CD163, and/or CD206 levels in one or more cells, optionally wherein the one or more cells are non-tumorigenic myeloid-derived suppressor cells (MDSC); (v) decrease tumor growth rate of solid tumors; (vi) reduce tumor volume; (vii) increase efficacy of one or more PD-1 inhibitors; (viii) increase efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (ix) increase efficacy of one or more chemotherapy agents, optionally wherein the one or more of the chemotherapy agents are gemcitabine, capecitabine, anthracyclines, doxorubicin (Adriamycin@), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (x) increase proliferation of T cells in the presence of non-tumorigenic myeloid-derived suppressor cells (MDSC); (xi) inhibit differentiation, survival, and/or one or more functions of non-tumorigenic myeloid-derived suppressor cells (MDSC); and (xii) kill CD33-expressing immunosuppressor non-tumorigenic myeloid cells and/or non-tumorigenic CD14-expressing cells in solid tumors and associated blood vessels when conjugated to a chemical or radioactive toxin.

In some embodiments, myeloid cells of the present disclosure include, without limitation, CD45+CD14+ myeloid cells, CD14+ myeloid cells, and myeloid-derived suppressor cells (MDSC). In some embodiments, myeloid cells of the present disclosure are non-tumorigenic myeloid cells. Immunosuppressor cells are sometimes also referred to as myeloid-derived suppressor cells (MDSC). In humans, MDSCs can be defined by one of the following combination of markers: (1) CD14+ HLA-DRlow/-, (2) CD14+IL4Ra+, (3) CD14+ HLA-DR−IL4Rα+, (4) CD34+CD14+CD11b+ CD33+, (5) CD11b+CD14+CD33+, (6) CD33+ HLA-DR−, (7) Lin-HLA-DR−, (8) Lin−HLA-DR−CD33+, (9) Lin− HLA-DR−CD33+CD11b+, (10) Lin−CD33+CD11b+ CD15+, (11) Lin−HLA-DR−CD33+CD11b+CD14−CD15+, (12) CD11b+CD14−CD33+, (13) CD11b+CD14−HLA-DR−CD33+CD15+, (14) CD33+ HLA-DR−CD15+, (15) CD15+IL4Ra+, (16) CD11b+CD15+CD66b+, (17) CD15+ FSClow SSChigh, (18) CD15high CD33+, (19) CD11b+ CD14−CD15+, (20) CD66b+ SSChigh, and (21) CD11b+ CD15+(see also Solito S et al. Annals of the NY Academy of Sciences, 2014). In mice, MDSCs can be defined by the expression of the surface markers CD45+, CD11b+, Gr1+, and/or Il4Ra+. Additional exemplary immunosuppressive monocytic lineages are CD45+, CD11b+, Gr1low; and CD45+, CD11c+.

In some embodiments, an anti-SIRPA antibody of the present disclosure decreases cell surface levels of SIRPA, decreases intracellular levels of SIRPA, decreases total cellular levels of SIRPA, or any combination thereof, only in the presence of SIRPA natural ligands or binding partners.

In some embodiments, an anti-SIRPA antibody of the present disclosure prevents, reduces, or inhibits SIRPA-mediated activity of a SIRPA ligand or binding partner, including for example, the SIRPA ligand or binding partner CD47, surfactant protein A, and/or surfactant protein D.

In some embodiments, an anti-SIRPA antibody of the present disclosure selectively binds to human SIRPA, including human allelic variants, also revered to herein as "polymorphic" variants, including human SIRPA v1 and human SIRPA v2, binds human SIRPβ, binds cyno SIRPA, and binds marmoset SIRPA. In some embodiments, an anti-SIRPA antibody of the present disclosure does not bind mouse/murine SIRPA, does not bind to SIRPB v1 (SIRPβ1), does not bind rabbit SIRPA, and does not bind rat SIRPA.

In some embodiments, an anti-SIRPA antibody of the present disclosure selectively binds to human SIRPA. In some embodiments, an anti-SIRPA antibody of the present disclosure selectively binds to human SIRPA and cyno SIRPA. In some embodiments, an anti-SIRPA antibody of the present disclosure binds to human SIRPA v1, human SIRPA v2, and cyno SIRPA. In some embodiments, an anti-SIRPA antibody of the present disclosure binds to human SIRPA v1, human SIRPA v2, and cyno SIRPA, but does not bind to murine SIRPA. In some embodiments, an anti-SIRPA antibody of the present disclosure binds to human SIRPA v1, human SIRPA v2, and cyno SIRPA, but does not bind to SIRPβ1. In some embodiments, an anti-SIRPA antibody of the present disclosure binds to human SIRPA v1, human SIRPA v2, and cyno SIRPA, but does not bind to murine SIRPA and does not bind to human SIRPβ 1. In some embodiments, an anti-SIRPA antibody of the present disclosure binds to human SIRPA v1, human SIRPA v2, cyno SIRPA, and human SIRPAβ3, but does not bind murine SIRPA and does not bind human SIRPβ1. In any combination of the above embodiments, an anti-SIRPA antibody of the present invention does not block the binding or interaction of SIRPA and CD47.

Certain aspects of the present disclosure relate to anti-SIRPA antibodies that down-regulate, i.e., decrease cellular levels of SIRPA. In some embodiments, the anti-SIRPA antibody decreases cellular levels of SIRPA without inhibiting, blocking, or reducing the interaction (e.g., binding) between SIRPA and one or more SIRPA ligands, e.g., CD47.

In some embodiments, the anti-SIRPA antibodies of the present disclosure may have one or more activities that are due, at least in part, to the ability of the antibodies to reduce cellular levels (e.g., cell surface expression) of SIRPA by inducing degradation, down regulation, cleavage, receptor desensitization, and/or lysosomal targeting of SIRPA.

In some embodiments, an anti-SIRPA antibody of the present disclosure down-regulates SIRPA expression in cells. In some embodiments, down-regulation of SIRPA expression in cells is reduced SIRPA cell surface expression. In some embodiments, an anti-SIRPA antibody of the present disclosure down-regulates SIRPA expression in monocytes (e.g., human monocytes). In some embodiments, an anti-SIRPA antibody of the present disclosure down-regulates SIRPA expression in macrophages (e.g., human macrophages). In some embodiments, an anti-SIRPA antibody of the present invention down-regulates macrophage cell surface expression of SIRPA by greater than 70%, by greater than 75%, by greater than 80%, by greater than 85%, or by greater than 95% compared to the level of SIRPA cell surface expression in macrophages not treated with an anti-SIRPA antibody of the present disclosure. In some embodiments, an anti-SIRPA antibody of the present disclosure down-regulates macrophage cell surface expression of SIRPA by about 70-90%, by about 70-85%, by about 70-80%, but about 70-75%, by about 75-90%, by about 75-85%, by about 75-80% by about 80-90%, by about 80-85%, or by about 85-95% compared to the level of SIRPA cell surface expression in macrophages not treated with an anti-SIRPA antibody of the present disclosure. In some embodiments, the macrophages are human macrophages, including but not limited to human M1 macrophages and human M2 macrophages.

Cellular levels of SIRPA may refer to, without limitation, cell surface levels of SIRPA, intracellular levels of SIRPA, and total levels of SIRPA. In some embodiments, a decrease in cellular levels of SIRPA comprises decrease in cell surface levels of SIRPA. As used herein, an anti-SIRPA antibody decreases cell surface levels of SIRPA if it induces a decrease of 25% or more in cell surface levels of SIRPA as measured by any in vitro cell-based assays or suitable in vivo model described herein or known in the art, for example utilizing flow cytometry, such as fluorescence-activated cell sorting (FACS), to measure cell surface levels of SIRPA. In some embodiments, a decrease in cellular levels of SIRPA comprises a decrease in intracellular levels of SIRPA. As used herein, an anti-SIRPA antibody decreases intracellular levels of Siglec-9 if it induces a decrease of 25% or more in intracellular levels of SIRPA as measured by any in vitro cell-based assays or suitable in vivo model described herein or known in the art, for example immunostaining, Western blot analysis, co-immunoprecipitation, and cell cytometry. In some embodiments, a decrease in cellular levels of SIRPA comprises a decrease in total levels of SIRPA. As used herein, an anti-SIRPA antibody decreases total levels of SIRPA if it induces a decrease of 25% or more in total levels of SIRPA as measured by any in vitro cell-based assays or suitable in vivo model described herein or known in the art, for example immunostaining, Western blot analysis, co-immunoprecipitation, and cell cytometry. In some embodiments, the anti-SIRPA antibodies induce SIRPA degradation, SIRPA cleavage, SIRPA internalization, SIRPA shedding, downregulation of SIRPA expression, or any combination thereof. In some embodiments, cellular levels of SIRPA are measured on primary cells (e.g., dendritic cells, bone marrow-derived dendritic cells, monocytes, microglia, and macrophages) or on cell lines utilizing an SIRPA cell assay.

In some embodiments, a downregulating anti-SIRPA antibody has an $IC_{50}$ of 200 nM of less, typically 100 nM or less (50% of SIRPA expressed on the cell surface is downregulated), after 4 hours of exposure of human macrophages to the antibody at 37° C. In some embodiments, SIRPA remains down-regulated for at least 24 hours of exposure to an antibody of the present invention. Cells may be analyzed for SIRPA surface expression using any technology, e.g., flow cytometry.

In some embodiments, anti-SIRPA antibodies of the present disclosure decrease cellular levels of SIRPA by at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more as compared to cellular levels of SIRPA in the absence of the anti-SIRPA antibody.

In some embodiments, which may be combined with any of the down-regulation activities summarized in the preceding paragraphs, an anti-SIRPA antibody of the present disclosure inhibits cell surface clustering of SIRPA.

In some embodiments, an anti-SIRPA antibody of the present disclosure down-regulates SIRPA, but does not block, inhibit, or reduce binding of a SIRPA ligand, e.g., CD47, to SIRPA. In the context of the present invention, an antibody directed against SIRPA that does not block binding of CD47 to SIRPA refers to an antibody that does not result in a significant decrease in CD47 binding to SIRPA when the antibody is incubated with CD47 and cells expressing SIRPA. A "significant decrease" in the context of CD47 binding to SIRPA refers to a decrease in binding of 30% or less, typically at least 25%, at least 20%, at least 15%, or at least 10% or less compared to CD47 binding to SIRPA in the presence of an isotype-matched control antibody that does not bind SIRPA. An illustrative assay for assessing blocking activity is set forth in the examples herein. For example, cells that express human SIRPA, e.g., human macrophages or cells such as CHO cells that are modified to recombinantly express human SIRPA, are plated at $10^5$ cells/well in a 96-well plate, washed, and incubated in 100 μl buffer for fluorescent activate cell sorting containing 1.0 μg/ml of monoclonal antibody or isotype control. Cells are then washed and incubated in with soluble human CD47 for 30 minutes on ice. Cells are then analyzed for surface-bound CD47.

In some embodiments, an anti-SIRPA antibody of the present invention down-regulates CD32A/B expression in cells (i.e., FcγRIIA/FcγRIIB). In some embodiments, downregulation of CD32A/B (i.e., FcγRIIA/FcγRIIB) expression in cells is reduced CD32A/B (i.e., FcγRIIA/FcγRIIB) cell surface expression. In some embodiments, an anti-SIRPA antibody of the present disclosure down-regulates CD32A/B expression in macrophages (e.g., human macrophages). In some embodiments, an anti-SIRP antibody of the present disclosure down-regulates CD32A (i.e., FcγRIIA) expression in macrophages (e.g., human macrophages). In some embodiments, an anti-SIRPA antibody of the present invention down-regulates CD32B (i.e., FcγRIIB) expression in macrophages (e.g., human macrophages). In some embodiments, an anti-SIRPA antibody of the present disclosure down-regulates cell surface expression of CD32A (i.e., FcγRIIA) in human macrophages by about 75%, by about 80%, or by about 85% compared to the level of CD32A cell surface expression in human macrophages not treated with an anti-SIRPA antibody of the present invention. In some embodiments, an anti-SIRPA antibody of the present disclosure down-regulates cell surface expression of CD32A in human macrophages by about 70-85% compared to the level of CD32A cell surface expression in human macrophages not treated with an anti-SIRPA antibody of the present invention. In some embodiments, an anti-SIRPA antibody of the present disclosure down-regulates cell surface expression of CD32B (i.e., FcγRIIB) in human macrophages to undetectable levels.

In one aspect, the present disclosure provides antibodies, such as isolated (e.g., monoclonal) antibodies, that interact with or otherwise bind to a region, such as an epitope, within a SIRPA protein of the present disclosure. In some embodiments, the antibodies interact with or otherwise bind to a region, such as an epitope, within a SIRPA protein of the present disclosure with improved/enhanced kinetics (e.g., relative to an anti-SIRPA antibody having a heavy chain variable region comprising the amino acid sequence of SEQ ID NO:2 and a light chain variable region comprising the amino acid sequence of SEQ ID NO:5). In some embodiments, the antibodies interact with or otherwise bind to a region, such as an epitope, within a SIRPA protein on human cells, such as dendritic cells, myeloid cells, monocytes, macrophages, etc. with a half-maximal effective concentration ($EC_{50}$) that is lower than that of a control antibody (e.g., relative to an anti-SIRPA antibody having a heavy chain variable region comprising the amino acid sequence of SEQ ID NO:2 and a light chain variable region comprising the amino acid sequence of SEQ ID NO:5). In some embodiments, anti-SIRPA antibodies of the present disclosure bind to a SIRPA protein and modulate one or more SIRPA activities after binding to the SIRPA protein, for example, an activity associated with SIRPA expression on a cell. SIRPA proteins of the present disclosure include, without limitation, a mammalian SIRPA protein, human SIRPA protein, mouse SIRPA protein, cyno SIRPA protein, and rat SIRPA protein.

In some embodiments, antibodies of the present disclosure may bind SIRPA in a pH dependent manner. In some embodiments, antibodies of the present disclosure can bind to SIRPA at a neutral pH and be internalized without dissociating from the SIRPA protein. Alternatively, at an acidic pH, antibodies of the present disclosure may dissociate from SIRPA once they are internalized and are then degraded by endosome/lysosome pathway. In certain embodiments, an anti-SIRPA antibody binds SIRPA at a pH that ranges from 5.5 to 8.0, from 5.5 to 7.5, from 5.5 to 7.0, from 5.5 to 6.5, from 5.5 to 6.0, from 6.0 to 8.0, from 6.5 to 8.0, from 7.0 to 8.0, from 7.5 to 8.0, from 6.0 to 7.5, from 6.0 to 7.0, from 6.5 to 7.5. In certain embodiments, an anti-SIRPA antibody dissociates from SIRPA at a pH of less than 6.0, less than 5.5, less than 5.0, less than 4.5, less than 4.0, less than 3.5, less than 3.0, less than 2.5, or less than 2.0.

SIRPA is a single-pass type I membrane protein. Within the amino acid sequence of human SIRPA (SEQ ID NO: 1), an extracellular domain is located at amino acid residues 31-373; a transmembrane domain is located at amino acid residues 374-394; and an intracellular domain is located at amino acid residues 395-504. Human SIRPA comprises a single V-set and two C1-sets of Ig super family (IgSF) domains, referred to as the D1 domain, the D2 domain, and the D3 domain, respectively. The D1 domain comprises amino acid residues 32-137 of human SIRPA; the D2 domain comprises amino acid residues 148-247 of human SIRPA; and the D3 domain comprises amino acid residues 254-348 of human SIRPA. As one of skill in the art will appreciate, the beginning and ending residues of the domains of the present disclosure may vary depending upon the computer modeling program used or the method used for determining the domain In some embodiments, an anti-SIRPA antibody of the present disclosure binds to the D3 domain of SIRPA. In some embodiments, an anti-SIRPA antibody of the present disclosure binds to the D3 domain of human SIRPA comprising amino acid residues 254-348 of the human SIRPA amino acid sequence of SEQ ID NO:1. In some embodiments, an anti-SIRPA antibody of the present disclosure binds to an epitope within the D3 domain of human SIRPA. In some embodiments, an anti-SIRPA antibody of the present disclosure binds to an epitope within the D3 domain of human SIRPA, wherein the epitope comprises an amino acid sequence selected from amino acid residues 254-348, amino acid residues 254-274, amino acid residues 264-279, amino acid residues 274-289, amino acid residues 273-331, amino acid residues 281-315, amino acid residues 281-337, amino acid residues 284-299, amino acid residues 294-309, amino acid residues 304-319, amino acid residues 314-329, amino acid residues 324-339, and amino acid residues 334-348 of the human SIRPA amino acid sequence of SEQ ID NO: 1. In some embodiments, an anti-SIRPA antibody of the present disclosure binds to an epitope within the D3 domain of human SIRPA, wherein the epitope includes amino acid residues R282, Q284, and G337 of the human SIRPA v1 amino acid sequence (SEQ ID NO: 1). In some embodiments, an anti-SIRPA antibody of the present disclosure binds to an epitope within the D3 domain of human SIRPA, wherein the epitope includes amino acid residues Q281, R282, Q284, L285, W287, R295, E297, V302, and W315 of the human SIRPA v1 amino acid sequence (SEQ ID NO: 1).

In some embodiments, the antibody binds to the D3 domain of SIRPA, e.g., human SIRPA. In some embodiments, an anti-SIRPA antibody of the present disclosure binds to the same SIRPA epitope or part of the SIRPA epitope bound by an antibody having the CDRs of the antibody designated as m3F9 as described herein. Accordingly, in some embodiments, an antibody of the present disclosure binds to the same SIRPA epitope or part of the SIRPA epitope bound by an antibody having the CDRs of the antibody designated as m3F9 as described herein.

Certain aspects of the present disclosure are based, at least in part, on the identification of anti-SIRPA antibodies that exhibit one or more improved and/or enhanced functional characteristics (e.g., relative to an anti-SIRPA antibody having a heavy chain variable region comprising the amino acid sequence of SEQ ID NO:2 and a light chain variable region comprising the amino acid sequence of SEQ ID NO:5), including, an improved/enhanced ability to decrease cell surface levels of SIRPA on cells, resulting in the reduction, neutralization, prevention, or curbing of one or more SIRPA activities, including, without limitation, reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; decreasing survival of neutrophils, dendritic cells, bone marrow-derived dendritic cells, macrophages, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, microglia, M1 microglia, activated M1 microglia, and/or M2 microglia; decreasing or reducing proliferation of neutrophils, dendritic cells, bone marrow-derived dendritic cells, macrophages, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, microglia, M1 microglia, activated M1 microglia, and/or M2 microglia; decreasing or inhibiting one or more functions of neutrophils, dendritic cells, bone marrow-derived dendritic cells, macrophages, NK cells, M1 macrophages, M1 neutrophils, M1 NK cells, activated M1 macrophages, activated M1 neutrophils, activated M1 NK cells, M2 macrophages, M2 neutrophils, M2 NK cells, monocytes, osteoclasts, T cells, T helper cells, cytotoxic T cells, granulocytes, microglia, M1 microglia, activated M1 microglia, and/or M2 microglia; reducing proliferation of monocytes, macrophages, T cells, dendritic cells, neutrophils, and/or microglia; reducing the overall functionality of monocytes, macrophages, T cells, dendritic cells, neutrophils, and/or microglia; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, tauopathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, and multiple sclerosis; binding to SIRPA ligand on tumor cells; binding to SIRPA ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; enhancing infiltration of one or more of immunosuppressor dendritic cells, immunosuppressor macrophages, myeloid derived suppressor cells, tumor-associated macrophages, immunosuppressor neutrophils, and regulatory T cells into tumors; promoting or rescuing functionality of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, and regulatory T cells; increasing infiltration of one or more of immunosuppressor dendritic cells, immunosuppressor macrophages, immunosuppressor neutrophils, immunosuppressor NK cells, myeloid-derived suppressor cells, tumor-associated macrophages, tumor-associated neutrophils, tumor-associated NK cells, non-tumorigenic CD45+CD14$^+$ myeloid cells, and regulatory T cells into tumors; increasing number of tumor-promoting myeloid/granulocytic immune-suppressive cells in a tumor, in peripheral blood, or other lymphoid organ; enhancing tumor-promoting activity of myeloid-derived suppressor cells; decreasing activation of tumor-specific T lymphocytes with tumor killing potential; enhancing survival of non-tumorigenic myeloid-derived suppressor cells and/or non-tumorigenic CD45+CD14$^+$ myeloid cells; decreasing infiltration and/or activation of tumor-specific T lymphocytes with tumor killing potential; increasing tumor growth rate; increasing rate of tumor recurrence; decreasing efficacy of one or more immune-therapies that modulate anti-tumor T cell responses, optionally wherein the one or more immune-therapies are immune-therapies that target one or more proteins selected from CD40, OX40, ICOS, CD28, CD137/4-1BB, CD27, GITR, PD-L1, CTLA4, PD-L2, PD-1, B7-H3, B7-H4, HVEM, LIGHT, BTLA, VISTA, KIR, GAL9, TIM1, TIM3, TIM4, A2AR, LAG3, DR-5, CD39, CD70, TREM1, TREM2, Siglec-5, Siglec-7, Siglec-9, Siglec-11, SIRPA, CD447, CSF-1 receptor, and any combination thereof, or of one or chemotherapy agents and/or more cancer vaccines.

In some embodiments, which may be combined with any of the other embodiments above, an anti-SIRPA antibody of the present disclosure induces, enhances, or increases one or more activities, including: (i) increasing the number of tumor infiltrating CD3$^+$ T cells; (ii) decreasing cellular levels of SIRPA in non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (iii) reducing the number of non-tumorigenic CD14$^+$ myeloid cells, optionally wherein the non-tumorigenic CD14$^+$ myeloid cells are tumor infiltrating cells or optionally wherein the non-tumorigenic CD14$^+$ myeloid cells are present in blood; (iv) reducing PD-L1, PD-L2, B7-H2, B7-H3, CD200R, CD163, and/or CD206 levels in one or more cells, optionally wherein the one or more cells are non-tumorigenic myeloid-derived suppressor cells (MDSC); (v) decreasing tumor growth rate of solid tumors; (vi) reducing tumor volume; (vii) increasing efficacy of one or more PD-1 inhibitors; (viii) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (ix) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (x) i increasing proliferation of T cells in the presence of non-tumorigenic myeloid-derived suppressor cells (MDSC); (xi) inhibiting differentiation, survival, and/or one or more functions of non-tumorigenic myeloid-derived suppressor cells (MDSC); and (xii) killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, an anti-SIRPA antibody of the present disclosure decreases the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML).

In some embodiments, an anti-SIRPA antibody of the present disclosure induces or promotes the survival, maturation, functionality, migration, or proliferation of one or more immune cells, e.g., one or more immune cells are selected from dendritic cells, macrophages, neutrophils, NK cells, microglia, T cells, T helper cells, cytotoxic T cells, and any combination thereof in an individual.

Anti-SIRPA Antibody Binding Affinity

In some embodiments of any of the antibodies provided herein, the antibody has a dissociation constant (Kd) of <1 µM, <100 nM, <10 nM, <1 nM, <0.1 nM, <0.01 nM, or <0.001 nM (e.g., $10^{-8}$ M or less, e.g., from $10^{-8}$ M to $10^{-13}$ M, e.g. from $10^{-9}$ M to $10^{-13}$ M). Dissociation constants may be determined through any analytical technique, including any biochemical or biophysical technique such as ELISA, surface plasmon resonance (SPR), bio-layer interferometry (see, e.g., Octet System by ForteBio), isothermal titration calorimetry (ITC), differential scanning calorimetry (DSC), circular dichroism (CD), stopped-flow analysis, and colorimetric or fluorescent protein melting analyses. In one embodiment, Kd is measured by a radiolabeled antigen binding assay (RIA). In some embodiment, an RIA is performed with the Fab version of an antibody of interest and its antigen, for example as described in Chen et al. J. Mol. Biol. 293:865-881(1999)). In some embodiments, Kd is measured using a BIACORE surface plasmon resonance assay, for example, an assay using a BIACORE-2000 or a BIACORE-3000 (BIAcore, Inc., Piscataway, NJ) is performed at 25° C. with immobilized antigen CM5 chips at ~10 response units (RU). In some embodiments, the $K_D$ is determined using a monovalent antibody (e.g., a Fab) or a full-length antibody. In some embodiments, the $K_D$ is determined using a full-length antibody in a monovalent form.

Antibody Fragments

In some embodiments of any of the antibodies provided herein, the antibody antibodies is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP404097; WO 1993/01161; Hudson et al. *Nat. Med.* 9:129-134 (2003). Triabodies and tetrabodies are also described in Hudson et al. *Nat. Med.* 9:129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (see, e.g., U.S. Pat. No. 6,248,516).

Antibody fragments can be made by various techniques, including but not limited to proteolytic digestion of an intact antibody as well as production by recombinant host cells (e.g., *E. coli* or phage), as described herein.

Chimeric and Humanized Antibodies

In some embodiments of any of the antibodies provided herein, the antibody is a chimeric antibody. Certain chimeric antibodies are described, e.g., in U.S. Pat. No. 4,816,567. In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In some embodiments of any of the antibodies provided herein, the antibody is a humanized antibody. Typically, a non-human antibody is humanized to reduce immunogenicity to humans, while retaining the specificity and affinity of the parental non-human antibody. In certain embodiments, a humanized antibody is substantially non-immunogenic in humans. In certain embodiments, a humanized antibody has substantially the same affinity for a target as an antibody from another species from which the humanized antibody is derived. See, e.g., U.S. Pat. Nos. 5,530,101, 5,693,761; 5,693,762; and 5,585,089. In certain embodiments, amino acids of an antibody variable domain that can be modified without diminishing the native affinity of the antigen binding domain while reducing its immunogenicity are identified. See, e.g., U.S. Pat. Nos. 5,766,886 and 5,869,619. Generally, a humanized antibody comprises one or more variable domains in which HVRs (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), for example, to restore or improve antibody specificity or affinity.

Humanized antibodies and methods of making them are reviewed, for example, in Almagro et al. *Front. Biosci.* 13:161 9-1633 (2008), and are further described, e.g., in U.S. Pat. Nos. 5,821,337, 7,527,791, 6,982,321, and 7,087, 409. Human framework regions that may be used for humanization include but are not limited to: framework regions selected using the "best-fit" method (see, e.g., Sims et al. *J Immunol.* 151:2296 (1993)); framework regions derived from the consensus sequence of human antibodies of a particular subgroup of light or heavy chain variable regions (see, e.g., Carter et al. *Proc. Natl. Acad. Sci. USA* 89:4285 (1992); and Presta et al., *J Immunol.* 151:2623 (1993)); human mature (somatically mutated) framework regions or human germline framework regions (see, e.g., Almagro and Fransson *Front. Biosci.* 13:1619-1633 (2008)); and framework regions derived from screening FR libraries (see, e.g., Baca et al. *J. Biol. Chem.* 272:10678-10684 (1997) and Rosok et al. *J. Biol. Chem.* 271:22611-22618 (1996)).

Human Antibodies

In some embodiments of any of the antibodies provided herein, the antibody is a human antibody. Human antibodies can be produced using various techniques known in the art. Human antibodies are described generally in van Dijk et al. *Curr. Opin. Pharmacol.* 5:368-74 (2001) and Lonberg *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. One can engineer mouse strains deficient in mouse antibody production with large fragments of the human Ig loci in anticipation that such mice would produce human antibodies in the absence of mouse antibodies. Large human Ig fragments can preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains can yield high affinity fully human antibodies against any antigen of interest, including human antigens. Using the hybridoma technology, antigen-specific human mAbs with the desired specificity can be produced and selected. Certain exemplary methods are described in U.S. Pat. No. 5,545,807, EP 546073, and EP 546073. See also, for example, U.S. Pat. Nos. 6,075,181 and 6,150,584 describing XENOMOUSE™ technology; U.S. Pat. No. 5,770,429 describing HUMAB@ technology; U.S. Pat. No. 7,041,870 describing K-M MOUSE® technology, and U.S. Patent Application Publication No. US 2007/ 0061900, describing VELOCIMOUSE@ technology. Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.* 133:3001 (1984) and Boemer et al. *J. Immunol.* 147:86 (1991)). Human antibodies generated via human B-cell hybridoma technology are also described in Li et al. *Proc. Natl. Acad. Sci. USA,* 1 03:3557-3562 (2006). Additional methods include those described, for example, in U.S. Pat. No. 7,189,826 (describing production of monoclonal human IgM antibodies from hybridoma cell lines). Human hybridoma technology (Trioma technology) is also described in Vollmers et al. *Histology and Histopathology*

20(3):927-937 (2005) and Vollmers et al. *Methods and Findings in Experimental and Clinical Pharmacology* 27(3): 185-91 (2005). Human antibodies may also be generated by isolating Fv clone variable domain sequences selected from human-derived phage display libraries. Such variable domain sequences may then be combined with a desired human constant domain.

Techniques for selecting human antibodies from antibody libraries are described below.

In some embodiments of any of the antibodies provided herein, the antibody is a human antibody isolated by in vitro methods and/or screening combinatorial libraries for antibodies with the desired activity or activities. Suitable examples include but are not limited to phage display (CAT, Morphosys, Dyax, Biosite/Medarex, Xoma, Symphogen, Alexion (formerly Proliferon), Affimed) ribosome display (CAT), yeast display (Adimab), and the like. In certain phage display methods, repertoires of VH and VL genes are separately cloned by polymerase chain reaction (PCR) and recombined randomly in phage libraries, which can then be screened for antigen-binding phage as described in Winter et al. *Ann. Rev. Immunol.* 12: 433-455 (1994). For example, a variety of methods are known in the art for generating phage display libraries and screening such libraries for antibodies possessing the desired binding characteristics. See also Sidhu et al. *J. Mol. Biol.* 338(2): 299-310, 2004; Lee et al. *J. Mol. Biol.* 340(5): 1073-1093, 2004; Fellouse *Proc. Natd. Acad. Sci. USA* 101(34):12467-12472 (2004); and Lee et al. *J. Immunol. Methods* 284(-2):1 19-132 (2004). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al. *EMBO J.* 12: 725-734 (1993). Finally, naive libraries can also be made synthetically by cloning unrearranged V-gene segments from stem cells, and using PCR primers comprising random sequence to encode the highly variable HVR3 regions and to accomplish rearrangement in vitro, as described by Hoogenboom et al. *J. Mol. Biol.*, 227: 381-388, 1992. Patent publications describing human antibody phage libraries include, for example: U.S. Pat. No. 5,750,373, and US Patent Publication Nos. 2007/0292936 and 2009/0002360. Antibodies isolated from human antibody libraries are considered human antibodies or human antibody fragments herein.

Constant Regions Including Fc Regions

In some embodiments of any of the anti-SIRPA antibodies provided herein, the antibody comprises an Fc. In some embodiments, the Fc is a human IgG1, IgG2, IgG3, and/or IgG4 isotype. In some embodiments, the antibody is of the IgG class, the IgM class, or the IgA class.

In certain embodiments of any of the anti-SIRPA antibodies provided herein, the antibody has an IgG2 isotype. In some embodiments, the anti-SIRPA antibody contains a human IgG2 constant region. In some embodiments, the human IgG2 constant region includes an Fc region. In some embodiments, the anti-SIRPA antibody induces the one or more SIRPA activities or independently of binding to an Fc receptor. In some embodiments, the anti-SIRPA antibody binds an inhibitory Fc receptor. In certain embodiments, the inhibitory Fc receptor is inhibitory Fc-gamma receptor IIB (FcγIIB).

In certain embodiments of any of the antibodies provided herein, the antibody has an IgG1 isotype. In some embodiments, the anti-SIRPA antibody contains a mouse IgG1 constant region. In some embodiments, the anti-SIRPA antibody contains a human IgG1 constant region. In some embodiments, the human IgG1 constant region includes an Fc region. In some embodiments, the anti-SIRPA antibody binds an inhibitory Fc receptor. In certain embodiments, the inhibitory Fc receptor is inhibitory Fe-gamma receptor IIB (FcγIIB).

In certain embodiments of any of the anti-SIRPA antibodies provided herein, the antibody has an IgG4 isotype. In some embodiments, the anti-SIRPA antibody contains a human IgG4 constant region. In some embodiments, the human IgG4 constant region includes an Fc region. In some embodiments, the anti-SIRPA antibody binds an inhibitory Fc receptor. In certain embodiments, the inhibitory Fc receptor is inhibitory Fe-gamma receptor IIB (FcγIIB).

In certain embodiments of any of the anti-SIRPA antibodies provided herein, the antibody has a hybrid IgG2/4 isotype. In some embodiments, the anti-SIRPA antibody includes an amino acid sequence comprising amino acids 118 to 260 according to EU numbering of human IgG2 and amino acids 261-447 according to EU numbering of human IgG4 (WO 1997/11971; WO 2007/106585).

In some embodiments, the Fc region increases clustering without activating complement as compared to a corresponding antibody comprising an Fc region that does not comprise the amino acid substitutions. In some embodiments, the antibody induces one or more activities of a target specifically bound by the antibody. In some embodiments, the antibody binds to SIRPA.

It may also be desirable to modify an anti-SIRPA antibody of the present disclosure to modify effector function and/or to increase serum half-life of the antibody. For example, the Fc receptor binding site on the constant region may be modified or mutated to remove or reduce binding affinity to certain Fe receptors, such as FcγRI, FcγRII, and/or FcγRIII to reduce antibody-dependent cell-mediated cytotoxicity. In some embodiments, the effector function is impaired by removing N-glycosylation of the Fc region (e.g., in the $C_H2$ domain of IgG) of the antibody. In some embodiments, the effector function is impaired by modifying regions such as 233-236, 297, and/or 327-331 of human IgG as described in WO 99/58572 and Armour et al. *Molecular Immunology* 40: 585-593 (2003); Reddy et al. *J. Immunology* 164:1925-1933 (2000). In other embodiments, it may also be desirable to modify an anti-SIRPA antibody of the present disclosure to modify effector function to increase finding selectivity toward the ITIM-containing FcgRIIb (CD32b) to increase clustering of SIRPA antibodies on adjacent cells without activating humoral responses including Antibody-dependent cell-mediated cytotoxicity and antibody-dependent cellular phagocytosis.

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fe region of an IgG molecule (e.g., $IgG_1$, $IgG_2$, $IgG_3$, or $IgG_4$) that is responsible for increasing the in vivo serum half-life of the IgG molecule.

Multispecific Antibodies

Multispecific are antibodies that have binding specificities for at least two different epitopes, including those on the same or another polypeptide (e.g., one or more SIRPA polypeptides of the present disclosure). In some embodiments, the multispecific antibody can be a bispecific antibody. In some embodiments, the multispecific antibody can be a trispecific antibody. In some embodiments, the multispecific antibody can be a tetraspecific antibody. Such antibodies can be derived from full-length antibodies or antibody fragments (e.g., F(ab')$_2$ bispecific antibodies). In some embodiments, the multispecific antibody comprises a first antigen binding region which binds to first site on SIRPA and comprises a second antigen binding region which binds to a second site on SIRPA. In some embodiment, the multispecific antibodies comprises a first antigen binding region which binds to SIRPA and a second antigen binding region that binds to a second polypeptide.

Provided herein are multispecific antibodies comprises a first antigen binding region, wherein the first antigen binding region comprises the six HVRs of an antibody described herein, which binds to SIRPA and a second antigen binding region that binds to a second polypeptide. In some embodiments, the first antigen binding region comprises the $V_H$ or $V_L$ of an antibody described herein.

In some embodiments of any of the multispecific antibodies, the second polypeptide is an antigen facilitating transport across the blood-brain-barrier. Numerous antigens and peptides are known in the art that facilitate transport across the blood-brain barrier (see, e.g., Gabathuler R. *Neurobiol. Dis.* 37:48-57 (2010)). Such second antigens and peptides include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, including CRM197 (a non-toxic mutant of diphtheria toxin), TMEM 30(A) (Flippase), protein transduction domains such as TAT, Syn-B, or penetratin, poly-arginine or generally positively charged peptides, Angiopep peptides such as ANG1005 (see, e.g., Gabathuler, 2010), and other cell surface proteins that are enriched on blood-brain barrier endothelial cells (see, e.g., Daneman et al. *PLoS One* 5(10): e13741 (2010)).

In some embodiments of any of the multispecific antibodies, the second polypeptide is a disease-causing protein selected from amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; (d) ligands and/or proteins expressed on immune cells, wherein the ligands and/or proteins selected from CD40, OX40, ICOS, CD28, CD137/4-1BB, CD27, GITR, PD-L1, CTLA-4, PD-L2, PD-1, B7-H3, B7-H4, HVEM, BTLA, KIR, GAL9, TIM3, A2AR, LAG-3, and phosphatidylserine; and/or (e) a protein, lipid, polysaccharide, or glycolipid expressed on one or more tumor cells and any combination thereof.

The multivalent antibodies may recognize the SIRPA antigen as well as, without limitation, additional antigens, such as an A3 peptide antigen, an α-synuclein protein antigen, Tau protein antigen, TDP-43 protein antigen, prion protein antigen, huntingtin protein antigen, RAN translation products antigen (including the DiPeptide Repeats, (DPRs peptides) composed of glycine-alanine (GA), glycine-proline (GP), glycine-arginine (GR), proline-alanine (PA), or proline-arginine (PR)), insulin receptor, insulin like growth factor receptor, or transferrin receptor or any other antigen that facilitate antibody transfer across the blood brain barrier. In some embodiments, the second polypeptide is transferrin. In some embodiments, the second polypeptide is Tau. In some embodiments, the second polypeptide is α-synuclein. In some embodiments, the second polypeptide is TREM2. In some embodiments, the second polypeptide is α-synuclein.

The multivalent antibody contains at least one polypeptide chain (and preferably two polypeptide chains), wherein the polypeptide chain or chains comprise two or more variable domains. For instance, the polypeptide chain or chains may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$—$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Techniques for making multispecific antibodies include, but are not limited to, recombinant co-expression of two immunoglobulin heavy chain-light chain pairs having different specificities (see Milstein and Cuello *Nature* 305: 537 (1983), WO 93/08829, and Traunecker et al. *EMBO J.* 10:3655 (1991)), and "knob-in-hole" engineering (see, e.g., U.S. Pat. No. 5,731,168). See also WO 2013/026833 (CrossMab). Multi-specific antibodies may also be made by engineering electrostatic steering effects for making antibody Fc-heterodimeric molecules (WO 2009/089004A1); cross-linking two or more antibodies (see, e.g., U.S. Pat. No. 4,676,980); using leucine; using "diabody" technology for making bispecific antibody fragments (see, e.g., Hollinger et al. *Proc. Natd. Acad. Sci. USA* 90:6444-6448 (1993)); and using single-chain Fv (scFv) dimers (see, e.g., Gruber et al. *J. Immunol.* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576). The antibody herein also includes a "Dual Acting FAb" or "DAF" comprising an antigen binding site that binds to multiple SIRPA (see, US 2008/0069820, for example).

Antibody Variants

In some embodiments of any of the antibodies provided herein, amino acid sequence variants of the antibodies are contemplated. For example, it may be desirable to improve the binding affinity and/or other biological properties of the antibody.

Substitution, Insertion, and Deletion Variants

In some embodiments of any of the antibodies provided herein, antibody variants having one or more amino acid substitutions are provided. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody.

TABLE 1

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro; and
(6) aromatic: Trp, Tyr, Phe.

For example, non-conservative substitutions can involve the exchange of a member of one of these classes for a member from another class. Such substituted residues can be introduced, for example, into regions of a human antibody that are homologous with non-human antibodies, or into the non-homologous regions of the molecule.

In making changes to the polypeptide or antibody described herein, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al. *J. Mol. Biol.*, 157:105-131 (1982). It is known that certain amino acids can be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those which are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0±1); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those which are within ±1 are included, and in certain embodiments, those within ±0.5 are included. One can also identify epitopes from primary amino acid sequences on the basis of hydrophilicity. These regions are also referred to as "epitopic core regions".

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

Amino acid sequence insertions include amino- and/or carboxyl-terminal fusions ranging in length from one residue to polypeptides comprising a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment, such as an Fv fragment).

Glycosylation Variants

In some embodiments of any of the antibodies provided herein, the antibody is altered to increase or decrease the extent to which the antibody is glycosylated. Addition or deletion of glycosylation sites to an antibody may be conveniently accomplished by altering the amino acid sequence such that one or more glycosylation sites is created or removed.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. Native antibodies produced by mammalian cells typically comprise a branched, biantennary oligosaccharide that is generally attached by an N-linkage to Asn297 according to Kabat numbering of the $C_H2$ domain of the Fc region. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. See, e.g., US Patent Publication Nos. 2003/0157108 and 2004/0093621. Examples of publications related to "defucosylated" or "fucose-deficient" antibody variants include: US 2003/0157108; US 2003/0115614; US 2002/0164328; US 2004/0093621; US 2004/0132140; US 2004/0110704; US 2004/0110282; US 2004/0109865; Okazaki et al. *J. Mol. Biol.* 336:1239-1249 (2004); Yamane-Ohnuki et al. *Biotech. Bioeng.* 87:614 (2004). Examples of cell lines capable of producing defucosylated antibodies include Led 3 CHO cells deficient in protein fucosylation (Ripka et al. *Arch. Biochem. Biophys.* 249:533-545 (1986); US 2003/0157108), and knockout cell lines, such as alpha-1,6-fucosyltransferase gene, FUT8, knockout CHO cells (see, e.g., Yamane-Ohnuki et al. *Biotech. Bioeng.* 87: 614 (2004) and Kanda et al. *Biotechnol. Bioeng.* 94(4):680-688 (2006)).

Modified Constant Regions

In some embodiments of any of the anti-SIRPA antibodies provided herein, the antibody Fc is an antibody Fc isotypes and/or modifications. In some embodiments, the antibody Fc isotype and/or modification is capable of binding to Fc gamma receptor.

Exemplary antibody Fc isotypes and modifications are provided in Table 2 below. In some embodiments, an anti-SIRPA antibody of the present disclosure is capable of binding an Fc gamma receptor has an Fc isotype listed in Table 2 below.

TABLE 2

Exemplary anti-SIRPA antibody Fc isotypes that are capable of binding Fc gamma receptor

| Fc Isotype | Mutation (EU numbering scheme) |
|---|---|
| IgG1 | N297A |
| IgG1 | D265A and N297A |
| IgG1 | D270A |
| IgG1 | L234A and L235A |
| | L234A and G237A |
| | L234A and L235A and G237A |
| IgG1 | D270A, and/or P238D, and/or L328E, and/or E233D, and/or G237D and/or H268D, and/or P271G, and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |
| IgG1 | P238D and S267E and L328F and G237D and H268D and P271G and A330R |
| IgG2 | V234A and G237A |
| IgG4 | L235A and G237A and E318A |
| IgG4 | S228P and L236E |
| IgG2/4 hybrid | IgG2 aa 118 to 260 and IgG4 aa 261 to 447 |
| | H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E and L328F |
| | S267E alone |
| IgG2 | S267E and L328F |
| IgG4 | S267E and L328F |
| IgG2 | WT HC with Kappa (light chain) LC |
| | HC C127S with Kappa LC |
| | Kappa LC C214S |
| | Kappa LC C214S and HC C233S |
| | Kappa LC C214S and HC C232S |
| | Any of the above listed mutations together with P330S and P331S mutations |
| | F(ab')2 fragment of WT IgG1 and any of the above listed mutations |
| IgG1 | Substitute the Constant Heavy 1 (CH1) and hinge region of IgG1 With CH1 and hinge region of IGg2 ASTKGPSVFP LAPCSRSTSE STAALGCLVK DYFPEPVTVS WNSGALTSGV HTFPAVLQSS GLYSLSSVVT VPSSNFGTQT YTCNVDHKPS NTKVDKTVER KCCVECPPCP (SEQ ID NO: 58) With a Kappa LC |
| IgG1 | Any of the above listed mutations together with A330L/A330S and/or L234F and/or L235E and/or P331S |
| IgG1, IgG2, or IgG4 | Any of the above listed mutations together with M252Y and/or S254T and/or T256E |
| Mouse IgG1, mouse IgG2a, mouse IgG2b | For mouse disease models |
| IgG4 | WT |
| IgG1 | Any of the above listed mutation together with E430G, E430S, E430F, E430T, E345K, E345Q, E345R, E345Y, S440Y, S440W and/or any combination thereof. |
| IgG2 | Any of the above listed mutation together with E430G, E430S, E430F, E430T, E345K, E345Q, E345R, E345Y, S440Y, S440W and/or any combination thereof. |

In addition to the isotypes described in Table 2, and without wishing to be bound to theory, it is thought that antibodies with human $IgG_1$ or $IgG_3$ isotypes and mutants thereof (e.g. Strohl (2009) Current Opinion in Biotechnology 2009, 20:685-691) that bind the Fcg Receptors I, IIA, IIC, IIIA, IIIB in human and/or Fcg Receptors I, III and IV in mouse, may also act as transient agonist antibodies.

In some embodiments, the Fc gamma receptor-binding antibody is of the IgG class, the IgM class, or the IgA class. In some embodiments, the Fc gamma receptor-binding antibody has an $IgG_1$, $IgG_2$, $IgG_3$, or $IgG_4$ isotype. In some embodiments, the antibody comprises one or more (e.g., one or more, two or more, three or more, four or more, five or more, six or more, seven or more, eight or more, nine or more, 10 or more, ii or more, 12 or more, or all thirteen) amino acid substitutions in the Fc region at a residue position selected from the group consisting of: C127S, L234A, L234F, L235A, L235E, S267E, K322A, L328F, A330S, P331S, E345R, E430G, S440Y in any combination (residue position according to EU or Kabat numbering). In some embodiments, the Fc region comprises an amino acid substitution at position E430G. In some embodiments, the Fc region comprises an amino acid substitution at positions L243A, L235A, and P331A. In some embodiments, the Fc region comprises an amino acid substitution at positions L243A, L235A, P331A. In some embodiments, the Fc region comprises an amino acid substitution at positions K322A and E430G. In some embodiments, the Fc region comprises an amino acid substitution at positions P331S and E430G. In some embodiments, the Fc region comprises an amino acid substitution at positions A330S, P331S, and E430G. In some embodiments, the Fc region comprises an amino acid substitution at positions K322A, A330S, and P331S. In some embodiments, the Fc region comprises an amino acid substitution at positions K322A, P331S, and E430G. In some embodiments, the Fc region comprises an amino acid substitution at positions A330S, P331S, and E430G. In some embodiments, the Fc region comprises an amino acid substitution at positions S267E and L328F. In some embodiments, the Fc region comprises an amino acid substitution at position C127S. In some embodiments, the Fc region comprises an amino acid substitution at positions E345R, E430G and S440Y In certain embodiments, the Fc gamma receptor-binding antibody has an IgG2 isotype. In some embodiments, the Fc gamma receptor-binding antibody contains a human IgG2 constant region. In some embodiments, the human IgG2 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) *Transplantation* 57:1537-1543. 31; Xu et al., (2000) *Cell Immunol*, 200:16-26), G237A (Cole et al. (1999) *Transplantation*, 68:563-571), H268Q, V309L, A330S, P331S (US 2007/0148167; Armour et al. (1999) *Eur J Immunol* 29: 2613-2624; Armour et al. (2000) *The Haematology Journal* 1 (Suppl. 1):27; Armour et al. (2000) *The Haematology Journal* 1 (Suppl. 1):27), C232S, and/or C233S (White et al. (2015) *Cancer Cell* 27, 138-148), S267E, L328F (Chu et al., (2008) *Mol Immunol*, 45:3926-3933), M252Y, S254T, and/or T256E, where the amino acid position is according to the EU or Kabat numbering convention.

In some embodiments, the Fc gamma receptor-binding antibody has an IgG2 isotype with a heavy chain constant domain that contains a C127S amino acid substitution, where the amino acid position is according to the EU or Kabat numbering convention (White et al., (2015) *Cancer Cell* 27, 138-148; Lightle et al., (2010) *PROTEIN SCIENCE* 19:753-762; and WO2008079246).

In some embodiments, the Fc gamma receptor-binding antibody has an IgG2 isotype with a Kappa light chain constant domain that contains a C214S amino acid substitution, where the amino acid position is according to the EU or Kabat numbering convention (White et al., (2015) *Cancer Cell* 27, 138-148; Lightle et al., (2010) *PROTEIN SCIENCE* 19:753-762; and WO2008079246).

In certain embodiments, the Fc gamma receptor-binding antibody has an IgG1 isotype. In some embodiments, the Fc gamma receptor-binding antibody contains a mouse IgG1 constant region. In some embodiments, the Fc gamma receptor-binding antibody contains a human IgG1 constant region. In some embodiments, the human IgG1 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) *Eur J Immunol* 23:403-411), D265A (Shields et al. (2001) *R. J. Biol. Chem.* 276, 6591-6604), D270A, L234A, L235A (Hutchins et al. (1995) *Proc Natl Acad Sci USA*, 92:11980-11984; Alegre et al., (1994) *Transplantation* 57:1537-1543. 31; Xu et al., (2000) *Cell Immunol*, 200:16-26), G237A (Alegre et al. (1994) *Transplantation* 57:1537-1543. 31; Xu et al. (2000) *Cell Immunol*, 200:16-26), P238D, L328E, E233D, G237D, H268D, P271G, A330R, C226S, C229S, E233P, L234V, L234F, L235E (McEarchern et al., (2007) *Blood*, 109:1185-1192), P331S (Sazinsky et al., (2008) *Proc Natl Acad Sci USA* 2008, 105:20167-20172), S267E, L328F, A330L, M252Y, S254T, T256E, N297Q, P238S, P238A, A327Q, A327G, P329A, K322A, and/or T394D, where the amino acid position is according to the EU or Kabat numbering convention.

In some embodiments, the antibody includes an IgG2 isotype heavy chain constant domain 1($C_H$1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYFPEPVTVSWNS-GALTSGVHTFPAVLQSSGLYSL SSVVTVPSSNFG-TQTYTCNVDHKPSNTKVDKTVERKCCVECPPCP (SEQ ID NO:58). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In certain embodiments, the Fc gamma receptor-binding antibody has an IgG4 isotype. In some embodiments, the Fc gamma receptor-binding antibody contains a human IgG4 constant region. In some embodiments, the human IgG4 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) *J Immunol*, 164:1925-1933), S267E, E318A, L328F, M252Y, S254T, and/or T256E, where the amino acid position is according to the EU or Kabat numbering convention.

In certain embodiments, the Fc gamma receptor-binding antibody has a hybrid IgG2/4 isotype. In some embodiments, the Fc gamma receptor-binding antibody includes an amino acid sequence containing amino acids 118 to 260 according to EU or, Kabat numbering of human IgG2 and amino acids 261-447 according to EU or, Kabat numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from A330L, L234F; L235E, and P331S according to EU or, Kabat numbering; and any combination thereof.

In certain embodiments, the antibody contains one or more amino acid substitutions in the Fc region at a residue position selected from C127S, L234A, L234F, L235A, L235E, S267E, K322A, L328F, A330S, P331S, E345R, E430G, S440Y, and any combination thereof, where the numbering of the residues is according to EU or Kabat numbering. In some embodiments, the Fc region contains an amino acid substitution at positions E430G, L243A, L235A, and P331S, where the numbering of the residue position is according to EU numbering. In some embodiments, the Fc region contains an amino acid substitution at positions E430G and P331S, where the numbering of the residue position is according to EU numbering. In some embodiments, the Fc region contains an amino acid substitution at positions E430G and K322A, where the numbering of the residue position is according to EU numbering. In some embodiments, the Fc region contains an amino acid substitution at positions E430G, A330S, and P331S, where the numbering of the residue position is according to EU numbering. In some embodiments, the Fc region contains an amino acid substitution at positions E430G, K322A, A330S, and P331S, where the numbering of the residue position is according to EU numbering. In some embodiments, the Fc region contains an amino acid substitution at positions E430G, K322A, and A330S, where the numbering of the residue position is according to EU numbering. In some embodiments, the Fc region contains an amino acid substitution at positions E430G, K322A, and P331S, where the numbering of the residue position is according to EU numbering. In some embodiments, the Fc region contains an amino acid substitution at positions S267E and L328F, where the numbering of the residue position is according to EU numbering. In some embodiments, the Fc region contains an amino acid substitution at position C127S, where the numbering of the residue position is according to EU numbering. In some embodiments, the Fc region contains an amino acid substitution at positions E345R, E430G and S440Y, where the numbering of the residue position is according to EU numbering.

In some embodiments, antibodies that bind a SIRPA protein may include antibodies that reduce cellular levels of SIRPA (e.g., cell surface levels of SIRPA), inhibit interaction (e.g., binding) between SIRPA and/or one or more SIRPA ligands, and inhibit one or more activities of a SIRPA protein. Such antibodies inhibit one or more activities of a SIRPA protein either by preventing interaction (e.g., binding) between SIRPA and one or more SIRPA ligands or by preventing signal transduction from the extracellular domain of SIRPA into the cell cytoplasm in the presence of one or more SIRPA ligands. Antibodies also can inhibit one or more activities of a SIRPA protein by decreasing cell surface levels of SIRPA by inducing SIRPA degradation, SIRPA desensitization, SIRPA cleavage, SIRPA internalization, SIRPA shedding, downregulation of SIRPA expression, and/or lysosomal degradation of SIRPA. In some embodiments, such anti-SIRPA antibodies may not transiently activate SIRPA.

In some embodiments, anti-SIRPA antibodies of the present disclosure may have the epitope specificity of a transient agonist anti-SIRPA antibody of the present disclosure but have an Fc domain that is not capable of binding Fcg receptors and thus is unable to, for example, transiently clustering and activating SIRPA.

In some embodiments, anti-SIRPA antibodies of the present disclosure have, without limitation, one or more of the following activities: the ability to decrease binding of a SIRPA protein to one or more SIRPA ligands, such as sialic acid-containing glycolipid s or sialic acid-containing glycoproteins, the ability to decrease the binding of a suppressor of cytokine signaling (SOCS) protein (e.g., SOCS3 protein) to a SIRPA protein, the ability to increase the proteasomal degradation of a SIRPA protein, the ability to reduce functional expression of SIRPA on the surface of circulating dendritic cells, macrophages, monocytes, T cells, and/or microglia, the ability to decrease phosphorylation of Tyr-340 and Tyr-358 by a Src family tyrosine kinase such as LCK and FYN, the ability to decrease recruitment of and binding to the tyrosine-specific protein phosphatases SHP1 and SHP2, the ability to decrease recruitment of and binding to PLC-g 1, which acts as a guanine nucleotide, exchange factor for Dynamin-1, the ability to decrease recruitment of and binding to Crk1, the ability to decrease recruitment of and binding to the Spleen tyrosine kinase Syk, the ability to decrease recruitment of and binding to SH3-SH2-SH3 growth factor receptor-bound protein 2 (Grb2), the ability to decrease recruitment of and binding to multiple SH2 containing proteins, the ability to increase intracellular calcium mobilization, the ability to modulate production of pro-inflammatory cytokines IL-1β, IL-8, and TNF-α, the ability to decrease activation of phosphoinositide 3-kinase, the ability to increase the growth of monocytes, macrophages, dendritic cells, T cells, and/or microglia, the ability to increase the survival of monocytes, macrophages, dendritic cells, T cells, and/or microglia, the ability to increase tyrosine phosphorylation on multiple cellular proteins, the ability to increase phagocytic activity of monocytes, macrophages, dendritic cells and/or microglia, the ability to increase cell proliferation of monocytes, macrophages, dendritic cells, T cells, and/or microglia, the ability to increase phosphorylation of signaling molecules that mediates ITAM signaling, the ability to increase the function of pattern recognition receptors, the ability to increase the function of Toll-like receptors, the ability to increases the function of damage-associated molecular pattern (DAMP) receptors, the ability to modulate expression of C—C chemokine receptor 7 (CCR7), and the ability to increase of clearance of cellular and protein debris.

In some embodiments, anti-SIRPA antibodies of the present disclosure have an Fc region that displays reduced binding to one or more Fcγ Receptor. Examples of such Fc regions and modifications are provided in Table 3 below. In some embodiments, the antibody has an Fc isotype listed in Table 3 below.

In some embodiments, anti-SIRPA antibodies of the present disclosure with reduced binding to Fc gamma receptors have an Fc isotype listed in Table 3 below.

TABLE 3

Exemplary anti-SIRPA antibody Fc isotypes with reduced binding to Fc gamma receptor

| Fc Isotype | Mutation (EU numbering scheme) |
|---|---|
| IgG1 | N297A or N297Q and/or D270A |
| IgG1 | D265A, D270A, and/or N297A |
| IgG1 | L234A and L235A |
| IgG2 | V234A and G237A |
| IgG4 | F235A and G237A and E318A |
|  | E233P and/or F234V |
|  | N297A or N297Q |
| IgG4 | S228P and L236E |
|  | S241P |
|  | S241P and L248E |
|  | S228P and F234A and L235A |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
|  | P238A |
|  | D265A |
|  | N297A |
|  | A327Q or A327G |
|  | P329A |
| IgG1 | K322A and L234A and L235A |
| IgG1 | L234F and L235E and P331S |
| IgG1 or IgG4 | T394D |
| IgG2 | C232S or C233S |
|  | N297A or N297Q |
| IgG2 | V234A and G237A and P238S and H268A and V309L and A330S and P331S |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-SIRPA antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A, N297Q (Bolt S et al. (1993) Eur J Immunol 23:403-411), D265A, D270A, L234A, L235A (McEarchem et al., (2007) Blood, 109:1185-1192), C226S, C229S (McEarchem et al., (2007) Blood, 109:1185-1192), P238S (Davis et al., (2007) J Rheumatol, 34:2204-2210), E233P, L234V (McEarchem et al., (2007) Blood, 109:1185-1192), P238A, A327Q, A327G, P329A (Shields R L, et al., (2001) J Biol Chem. 276(9):6591-604), K322A, L234F, L235E (Hezareh, et al., (2001) J Virol 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the anti-SIRPA antibody has an IgG1 isotype with a heavy chain constant region that contains a C220S amino acid substitution according to the EU or Kabat numbering convention. In some embodiments, the Fc region further contains one or more additional amino acid substitutions selected from A330L, L234F; L235E, and/or P331S according to EU or Kabat numbering convention. In certain embodiments, the anti-SIRPA antibody has an IgG2 isotype. In some embodiments, the anti-SIRPA antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297Q, V309L, A330S, P331S, C232S, C233S, M252Y, S254T, and/or T256E, where the amino acid position is according to the EU or Kabat numbering convention (Vafa O. et al., (2014) Methods 65:114-126).

In certain embodiments, the anti-SIRPA antibody has an IgG4 isotype. In some embodiments, the anti-SIRPA antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) Proc Natl Acad Sci USA, 92:11980-11984), S228P, L234A/F234A, L236E, S241P, L248E (Reddy et al., (2000) J Immunol, 164:1925-1933; Angal et al., (1993) Mol Immunol. 30(1):105-8; U.S. Pat. No. 8,614,299 B2; Vafa O. et al., (2014) Methods 65:114-126), T394D, M252Y, S254T, T256E, N297A, and/or N297Q, where the amino acid position is according to the EU or Kabat numbering convention. In some embodiments the antibody has an IgG4 isotype, and comprises an S228P amino acid substitution at residue position 228, an F234A amino acid substitution at residue position 234, and an L235A amino acid substitution at residue position 235 (residue position according to EU numbering).

In some embodiments, the Fc region further contains one or more additional amino acid substitutions selected from a M252Y, S254T, and/or T256E, where the amino acid position is according to the EU or Kabat numbering convention.

In some embodiments of any of the antibodies provided herein, the modified antibody Fc is an IgG1 modified Fc. In some embodiments, the IgG1 modified Fc comprises one or more modifications. For example, in some embodiments, the IgG1 modified Fc comprises one or more amino acid substitutions (e.g., relative to a wild-type Fc region of the same isotype). In some embodiments, the one or more amino acid substitutions are selected from N297A (Bolt S et al. (1993) Eur J Immunol 23:403-411), D265A (Shields et al. (2001) R. J. Biol. Chem. 276, 6591-6604), L234A, L235A (Hutchins et al. (1995) Proc Natl Acad Sci USA, 92:11980-11984; Alegre et al., (1994) Transplantation 57:1537-1543. 31; Xu et al., (2000) Cell Immunol, 200:16-26), G237A (Alegre et al. (1994) Transplantation 57:1537-1543. 31; Xu et al. (2000) Cell Immunol, 200:16-26), C226S, C229S, E233P, L234V, L234F, L235E (McEarchem et al., (2007) Blood, 109:1185-1192), P331S (Sazinsky et al., (2008) Proc Natl Acad Sci USA 2008, 105:20167-20172), S267E, L328F, A330L, M252Y, S254T, and/or T256E, where the amino acid position is according to the EU numbering convention.

In some embodiments of any of the IgG1 modified Fc, the Fc comprises N297A mutation according to EU numbering. In some embodiments of any of the IgG1 modified Fc, the Fc comprises D265A and N297A mutations according to EU numbering. In some embodiments of any of the IgG1 modified Fc, the Fc comprises D270A mutations according to EU numbering. In some embodiments, the IgG1 modified Fc comprises L234A and L235A mutations according to EU numbering. In some embodiments of any of the IgG1 modified Fc, the Fc comprises L234A and G237A mutations according to EU numbering. In some embodiments of any of the IgG1 modified Fc, the Fc comprises L234A, L235A and G237A mutations according to EU numbering. In some embodiments of any of the IgG1 modified Fc, the Fc comprises one or more (including all) of P238D, L328E, E233, G237D, H268D, P271G and A330R mutations according to EU numbering. In some embodiments of any of the IgG1 modified Fc, the Fc comprises one or more of S267E/L328F mutations according to EU numbering. In some embodiments of any of the IgG1 modified Fc, the Fc comprises P238D, L328E, E233D, G237D, H268D, P271G and A330R mutations according to EU numbering. In some embodiments of any of the IgG1 modified Fc, the Fc comprises P238D, L328E, G237D, H268D, P271G and A330R mutations according to EU numbering. In some embodiments of any of the IgG1 modified Fc, the Fc comprises P238D, S267E, L328E, E233D, G237D, H268D, P271G and A330R mutations according to EU numbering. In some embodiments of any of the IgG1 modified Fc, the Fc comprises P238D, S267E, L328E, G237D, H268D, P271G and A330R mutations according to EU numbering. In some embodiments of any of the IgG1 modified Fc, the Fc comprises C226S, C229S, E233P, L234V, and L235A mutations according to EU numbering. In some embodiments of any of the IgG1 modified Fc, the Fc comprises L234F, L235E, and P331S mutations according to EU numbering. In some embodiments of any of the IgG1 modified Fc, the Fc comprises S267E and L328F mutations according to EU numbering. In some embodiments of any of the IgG1 modified Fc, the Fc comprises S267E mutations according to EU numbering. In some embodiments of any of the IgG1 modified Fc, the Fc comprises a substitute of the constant heavy 1 (CH1) and hinge region of IgG1 with CH1 and hinge region of IgG2 (amino acids 118-230 of IgG2 according to EU numbering) with a Kappa light chain.

In some embodiments of any of the IgG1 modified Fc, the Fc includes two or more amino acid substitutions that increase antibody clustering without activating complement as compared to a corresponding antibody having an Fc region that does not include the two or more amino acid substitutions. Accordingly, in some embodiments of any of the IgG1 modified Fc, the IgG1 modified Fc is an antibody comprising an Fc region, where the antibody comprises an amino acid substitution at position E430G and one or more amino acid substitutions in the Fc region at a residue position selected from: L234F, L235A, L235E, S267E, K322A, L328F, A330S, P331S, and any combination thereof according to EU numbering. In some embodiments, the IgG1 modified Fc comprises an amino acid substitution at positions E430G, L243A, L235A, and P331S according to EU numbering. In some embodiments, the IgG1 modified Fc comprises an amino acid substitution at positions E430G and P331S according to EU numbering. In some embodiments, the IgG1 modified Fc comprises an amino acid substitution at positions E430G and K322A according to EU numbering. In some embodiments, the IgG1 modified Fc comprises an amino acid substitution at positions E430G, A330S, and P331S according to EU numbering. In some embodiments, the IgG1 modified Fc comprises an amino acid substitution at positions E430G, K322A, A330S, and P331S according to EU numbering. In some embodiments, the IgG1 modified Fc comprises an amino acid substitution at positions E430G, K322A, and A330S according to EU numbering. In some embodiments, the IgG1 modified Fc comprises an amino acid substitution at positions E430G, K322A, and P331S according to EU numbering.

In some embodiments of any of the IgG1 modified Fc, the IgG1 modified Fc may further comprise herein may be combined with an A330L mutation (Lazar et al. *Proc Natl Acad Sci USA*, 103:4005-4010 (2006)), or one or more of L234F, L235E, and/or P331S mutations (Sazinsky et al. *Proc Natl Acad Sci USA*, 105:20167-20172 (2008)), according to the EU numbering convention, to eliminate complement activation. In some embodiments of any of the IgG1 modified Fc, the IgG1 modified Fc may further comprise one or more of A330L, A330S, L234F, L235E, and/or P331S according to EU numbering. In some embodiments of any of the IgG1 modified Fc, the IgG1 modified Fc may further comprise one or more mutations to enhance the antibody half-life in human serum (e.g., one or more (including all) of M252Y, S254T, and T256E mutations according to the EU numbering convention). In some embodiments of any of the IgG1 modified Fc, the IgG1 modified Fc may further comprise one or more of E430G, E430S, E430F, E430T, E345K, E345Q, E345R, E345Y, S440Y, and/or S440W according to EU numbering.

Other aspects of the present disclosure relate to antibodies having modified constant regions (i.e., Fc regions). An antibody dependent on binding to FcgR receptor to activate targeted receptors may lose its agonist activity if engineered to eliminate FcgR binding (see, e.g., Wilson et al. *Cancer Cell* 19:101-113 (2011); Armour at al. *Immunology* 40:585-593 (2003); and White et al. *Cancer Cell* 27:138-148 (2015)). As such, it is thought that an anti-SIRPA antibody of the present disclosure with the correct epitope specificity can activate the target antigen, with minimal adverse effects, when the antibody has an Fc domain from a human IgG2 isotype (CH1 and hinge region) or another type of Fc domain that is capable of preferentially binding the inhibitory FcgRIIB r receptors, or a variation thereof.

In some embodiments of any of the antibodies provided herein, the modified antibody Fc is an IgG2 modified Fc. In some embodiments, the IgG2 modified Fc comprises one or more modifications. For example, in some embodiments, the IgG2 modified Fc comprises one or more amino acid substitutions (e.g., relative to a wild-type Fc region of the same isotype). In some embodiments of any of the IgG2 modified Fc, the one or more amino acid substitutions are selected from V234A (Alegre et al. *Transplantation* 57:1537-1543 (1994); Xu et al. *Cell Immunol*, 200:16-26 (2000)); G237A (Cole et al. *Transplantation*, 68:563-571 (1999)); H268Q, V309L, A330S, P331S (US 2007/0148167; Armour et al. *Eur J Immunol* 29: 2613-2624 (1999); Armour et al. *The Haematology Journal* 1 (Suppl. 1):27 (2000); Armour et al. *The Haematology Journal* 1 (Suppl. 1):27 (2000)), C219S, and/or C220S (White et al. *Cancer Cell* 27, 138-148 (2015)); S267E, L328F (Chu et al. *Mol Immunol*, 45:3926-3933 (2008)); and M252Y, S254T, and/or T256E according to the EU numbering convention. In some embodiments of any of the IgG2 modified Fc, the Fc comprises an amino acid substitution at positions V234A and G237A according to EU numbering. In some embodiments of any of the IgG2 modified Fc, the Fc comprises an amino acid substitution at positions C219S or C220S according to EU numbering. In some embodiments of any of the IgG2 modified Fc, the Fc comprises an amino acid substitution at positions A330S and P331S according to EU numbering. In some embodiments of any of the IgG2 modified Fc, the Fc comprises an amino acid substitution at positions S267E and L328F according to EU numbering.

In some embodiments of any of the IgG2 modified Fc, the Fc comprises a C127S amino acid substitution according to the EU numbering convention (White et al., (2015) *Cancer Cell* 27, 138-148; Lightle et al. *Protein Sci.* 19:753-762 (2010); and WO 2008/079246). In some embodiments of any of the IgG2 modified Fc, the antibody has an IgG2 isotype with a Kappa light chain constant domain that comprises a C214S amino acid substitution according to the EU numbering convention (White et al. *Cancer Cell* 27:138-148 (2015); Lightle et al. *Protein Sci.* 19:753-762 (2010); and WO 2008/079246).

In some embodiments of any of the IgG2 modified Fc, the Fc comprises a C220S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc comprises a C219S amino acid substitution according to the EU numbering convention. In some embodiments of any of the IgG2 modified Fc, the antibody has an IgG2 isotype with a Kappa light chain constant domain that comprises a C214S amino acid substitution according to the EU numbering convention.

In some embodiments of any of the IgG2 modified Fc, the Fc includes an IgG2 isotype heavy chain constant domain 1($C_H1$) and hinge region (White et al. *Cancer Cell* 27:138-148 (2015)). In certain embodiments of any of the IgG2 modified Fc, the IgG2 isotype CH1 and hinge region comprise the amino acid sequence of 118-230 according to EU numbering. In some embodiments of any of the IgG2 modified Fc, the antibody Fc region comprises a S267E amino acid substitution, a L328F amino acid substitution, or both, and/or a N297A or N297Q amino acid substitution according to the EU numbering convention.

In some embodiments of any of the IgG2 modified Fc, the Fc further comprises one or more amino acid substitution at positions E430G, E430S, E430F, E430T, E345K, E345Q, E345R, E345Y, S440Y, and S440W according to EU numbering. In some embodiments of any of the IgG2 modified Fc, the Fc may further comprise one or more mutations to enhance the antibody half-life in human serum (e.g., one or more (including all) of M252Y, S254T, and T256E mutations according to the EU numbering convention). In some embodiments of any of the IgG2 modified Fc, the Fc may further comprise A330S and P331S.

In some embodiments of any of the IgG2 modified Fc, the Fc is an IgG2/4 hybrid Fc. In some embodiments, the IgG2/4 hybrid Fc comprises IgG2 aa 118 to 260 and IgG4 aa 261 to 447. In some embodiments of any IgG2 modified Fc, the Fc comprises one or more amino acid substitutions at positions H268Q, V309L, A330S, and P331S according to EU numbering.

In some embodiments of any of the IgG1 and/or IgG2 modified Fc, the Fc comprises one or more additional amino acid substitutions selected from A330L, L234F; L235E, or P331S according to EU numbering; and any combination thereof.

In certain embodiments of any of the IgG1 and/or IgG2 modified Fc, the Fc comprises one or more amino acid substitutions at a residue position selected from C127S, L234A, L234F, L235A, L235E, S267E, K322A, L328F, A330S, P331S, E345R, E430G, S440Y, and any combination thereof according to EU numbering. In some embodiments of any of the IgG1 and/or IgG2 modified Fc, the Fc comprises an amino acid substitution at positions E430G, L243A, L235A, and P331S according to EU numbering. In some embodiments of any of the IgG1 and/or IgG2 modified Fc, the Fc comprises an amino acid substitution at positions E430G and P331S according to EU numbering. In some embodiments of any of the IgG1 and/or IgG2 modified Fc, the Fc comprises an amino acid substitution at positions E430G and K322A according to EU numbering. In some embodiments of any of the IgG1 and/or IgG2 modified Fc, the Fc comprises an amino acid substitution at positions E430G, A330S, and P331S according to EU numbering. In some embodiments of any of the IgG1 and/or IgG2 modified Fc, the Fc comprises an amino acid substitution at positions E430G, K322A, A330S, and P331S according to EU numbering. In some embodiments of any of the IgG1 and/or IgG2 modified Fc, the Fc comprises an amino acid substitution at positions E430G, K322A, and A330S according to EU numbering. In some embodiments of any of the IgG1 and/or IgG2 modified Fc, the Fc comprises an amino acid substitution at positions E430G, K322A, and P331S according to EU numbering. In some embodiments of any of the IgG1 and/or IgG2 modified Fc, the Fc comprises an amino acid substitution at positions S267E and L328F according to EU numbering. In some embodiments of any of the IgG1 and/or IgG2 modified Fc, the Fc comprises an amino acid substitution at position C127S according to EU numbering. In some embodiments of any of the IgG1 and/or IgG2 modified Fc, the Fc comprises an amino acid substitution at positions E345R, E430G and S440Y according to EU numbering.

In some embodiments of any of the antibodies provided herein, the modified antibody Fc is an IgG4 modified Fc. In some embodiments, the IgG4 modified Fc comprises one or more modifications. For example, in some embodiments, the IgG4 modified Fc comprises one or more amino acid substitutions (e.g., relative to a wild-type Fc region of the same isotype). In some embodiments of any of the IgG4 modified Fc, the one or more amino acid substitutions are selected from L235A, G237A, S229P, L236E (Reddy et al. *J Immunol* 164:1925-1933(2000)), S267E, E318A, L328F, M252Y, S254T, and/or T256E according to the EU numbering convention. In some embodiments of any of the IgG4 modified Fc, the Fc may further comprise L235A, G237A, and E318A according to the EU numbering convention. In some embodiments of any of the IgG4 modified Fc, the Fc may further comprise S228P and L235E according to the EU numbering convention. In some embodiments of any of the IgG4 modified Fc, the IgG4 modified Fc may further comprise S267E and L328F according to the EU numbering convention.

In some embodiments of any of the IgG4 modified Fc, the IgG4 modified Fc comprises may be combined with an S228P mutation according to the EU numbering convention (Angal et al. *Mol Immunol.* 30:105-108 (1993)) and/or with one or more mutations described in (Peters et al. *J Biol Chem.* 287(29):24525-33 (2012)) to enhance antibody stabilization.

In some embodiments of any of the IgG4 modified Fc, the IgG4 modified Fc may further comprise one or more mutations to enhance the antibody half-life in human serum (e.g., one or more (including all) of M252Y, S254T, and T256E mutations according to the EU numbering convention).

In some embodiments of any of the IgG4 modified Fc, the Fc comprises L235E according to EU numbering. In certain embodiments of any of the IgG4 modified Fc, the Fc comprises one or more amino acid substitutions at a residue position selected from C127S, F234A, L235A, L235E, S267E, K322A, L328F, E345R, E430G, S440Y, and any combination thereof, according to EU numbering. In some embodiments of any of the IgG4 modified Fc, the Fc comprises an amino acid substitution at positions E430G, L243A, L235A, and P331S according to EU numbering. In some embodiments of any of the IgG4 modified Fc, the Fc comprises an amino acid substitution at positions E430G and P331S according to EU numbering. In some embodiments of any of the IgG4 modified Fc, the Fc comprises an amino acid substitution at positions E430G and K322A according to EU numbering. In some embodiments of any of the IgG4 modified Fc, the Fc comprises an amino acid substitution at position E430 according to EU numbering. In some embodiments of any of the IgG4 modified Fc, the Fc region comprises an amino acid substitution at positions E430G and K322A according to EU numbering. In some embodiments of any of the IgG4 modified Fc, the Fc comprises an amino acid substitution at positions S267E and L328F according to EU numbering. In some embodiments of any of the IgG4 modified Fc, the Fc comprises an amino acid substitution at position C127S according to EU numbering. In some embodiments of any of the IgG4 modified Fc, the Fc comprises an amino acid substitution at positions E345R, E430G and S440Y according to EU numbering.

Other Antibody Modifications

In some embodiments of any of the antibodies, the antibody is a derivative. The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen binding protein can have a greater circulating half-life than an antigen binding protein that is not chemically modified. In certain embodiments, a chemically modified antigen binding protein can have improved targeting capacity for desired cells, tissues, and/or organs. In some embodiments, a derivative antigen binding protein is covalently modified to include one or more water soluble polymer attachments, including, but not limited to, polyethylene glycol, polyoxyethylene glycol, or polypropylene glycol. See, e.g., U.S. Pat. Nos. 4,640,835, 4,496,689, 4,301,144, 4,670,417, 4,791,192 and 4,179,337. In certain embodiments, a derivative antigen binding protein comprises one or more polymer, including, but not limited to, monomethoxy-polyethylene glycol, dextran, cellulose, copolymers of ethylene glycol/propylene glycol, carboxymethylcellulose, polyvinyl pyrrolidone, poly-1, 3-dioxolane, poly-1,3,6-trioxane, ethylene/maleic anhydride copolymer, polyaminoacids (either homopolymers or random copolymers), poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of such polymers.

In certain embodiments, a derivative is covalently modified with polyethylene glycol (PEG) subunits. In certain embodiments, one or more water-soluble polymer is bonded at one or more specific position, for example at the amino terminus, of a derivative. In certain embodiments, one or more water-soluble polymer is randomly attached to one or more side chains of a derivative. In certain embodiments, PEG is used to improve the therapeutic capacity for an antigen binding protein. In certain embodiments, PEG is used to improve the therapeutic capacity for a humanized antibody. Certain such methods are discussed, for example, in U.S. Pat. No. 6,133,426, which is hereby incorporated by reference for any purpose.

Peptide analogs are commonly used in the pharmaceutical industry as non-peptide drugs with properties analogous to those of the template peptide. These types of non-peptide compound are termed "peptide mimetics" or "peptidomimetics." Fauchere, *J. Adv. Drug Res.*, 15:29 (1986); and Evans et al. *J. Med. Chem.*, 30:1229 (1987), which are incorporated herein by reference for any purpose. Such compounds are often developed with the aid of computerized molecular modeling. Peptide mimetics that are structurally similar to therapeutically useful peptides can be used to produce a similar therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from: —$CH_2NH$—, —$CH_2S$—, —$CH_2$—$CH_2$—, —CH=CH- (cis and trans), —$COCH_2$—, —$CH(OH)CH_2$—, and —$CH_2SO$—, by methods well known in the art. Systematic substitution of one or more amino acids of a consensus sequence with a D-amino acid of the same type (e.g., D-lysine in place of L-lysine) can be used in certain embodiments to generate more stable peptides. In addition, constrained peptides comprising a consensus sequence or a substantially identical consensus sequence variation can be generated by methods known in the art (Rizo and Gierasch *Ann. Rev. Biochem.*, 61:387 (1992), incorporated herein by reference for any purpose); for example, by adding internal cysteine residues capable of forming intramolecular disulfide bridges which cyclize the peptide.

Drug conjugation involves coupling of a biological active cytotoxic (anticancer) payload or drug to an antibody that specifically targets a certain tumor marker (e.g, a polypeptide that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue OncLive Jul. 5, 2012; ADC Review on antibody-drug conjugates; and Ducry et al. *Bioconjugate Chemistry* 21 (1):5-13 (2010).

Antibody Frameworks

Any of the anti-SIRPA antibodies described herein further include a framework (FR). In some embodiments, the framework is a human immunoglobulin framework. For example, in some embodiments, an antibody (e.g., an anti-SIRPA antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

In some embodiments, an anti-SIRPA antibody of the present disclosure comprises a heavy chain variable region comprising one or more (e.g., one or more, two or more, three or more, or all four) framework regions selected from VH FR1, VH FR2, VH FR3, and VH FR4 (as shown in Table 9). In some embodiments, an anti-SIRPA antibody of the present disclosure comprises a heavy chain variable region comprising a VH FR1, wherein the VH FR1 comprises the amino acid sequence of SEQ ID NO:25. In some embodiments, and anti-SIRPA antibody of the present disclosure comprises a heavy chain variable region comprising a VH FR2, wherein the VH FR2 comprises the amino acid sequence of SEQ ID NO: 26. In some embodiments, an anti-SIRPA antibody of the present disclosure comprises a heavy chain variable region comprising a VH FR3, wherein the VH FR3 comprises the amino acid sequence of SEQ ID NO:27. In some embodiments, an anti-SIRPA antibody of the present disclosure comprises a heavy chain variable region comprising a VH FR4, wherein the VH FR4 comprises the amino acid sequence of SEQ ID NO:28. In some embodiments, an anti-SIRPA antibody of the present disclosure comprises a heavy chain variable region comprising a VH FR1 comprising the amino acid sequence of SEQ ID NO:25, a VH FR2 comprising the amino acid sequence of SEQ ID NO:26, a $V_H$ FR3 comprising the amino acid sequence of SEQ ID NO:27, and a VH FR4 comprising the amino acid sequence of SEQ ID NO:28.

In some embodiments, an anti-SIRPA antibody of the present disclosure comprise a heavy chain variable region comprising a VH FR1, a VH FR2, a VH FR3, and VH FR4 of anti-SIRPA antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25.

In some embodiments, an anti-SIRPA antibody of the present disclosure comprises a light chain variable region comprising one or more (e.g., one or more, two or more, three or more, or all four) framework regions selected from VL FR1, VL FR2, VL FR3, and VL FR4 (as shown in Table 9). In some embodiments, an anti-SIRPA antibody of the present disclosure comprises a light chain variable region comprising a VL FR1, wherein the VL FR1 comprises the amino acid sequence of SEQ ID NO:29. In some embodiments, an anti-SIRPA antibody of the present disclosure comprises a light chain variable region comprising a VL FR2, wherein the VL FR2 comprises the amino acid sequence of SEQ ID NO:30. In some embodiments, an anti-SIRPA antibody of the present disclosure comprises a light chain variable region comprising a VL FR3, wherein the VL FR3 comprises the amino acid sequence of SEQ ID NO:31. In some embodiments, an anti-SIRPA antibody of the present disclosure comprises a light chain variable region comprising a VL FR4, wherein the VL FR4 comprises the amino acid sequence of SEQ ID NO:32. In some embodiments, an anti-SIRPA antibody of the present disclosure comprises a light chain variable region comprising a VL FR1 comprising the amino acid sequence of SEQ ID NO:29, a VL FR2 comprising the amino acid sequence of SEQ ID NO:30, a VL FR3 comprising the amino acid sequence of SEQ ID NO:31, and a VL FR4 comprising the amino acid sequence of SEQ ID NO:32.

In some embodiments, an anti-SIRPA antibody of the present disclosure comprise a light chain variable region comprising a VL FR1, a VL FR2, a VL FR3, and VL FR4 of anti-SIRPA antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25.

In some embodiments, an anti-SIRPA antibody of the present disclosure comprise a heavy chain variable region comprising a VH FR1 comprising the amino acid sequence of SEQ ID NO:25, a VH FR2 comprising the amino acid sequence of SEQ ID NO:26, a VH FR3 comprising the amino acid sequence of SEQ ID NO:27, and a VH FR4 comprising the amino acid sequence of SEQ ID NO:28, and a light chain variable region comprising a VL FR1 comprising the amino acid sequence of SEQ ID NO:29, a VL FR2 comprising the amino acid sequence of SEQ ID NO:30, a VL FR3 comprising the amino acid sequence of SEQ ID NO:31, and a VL FR4 comprising the amino acid sequence of SEQ ID NO:32. In some embodiments, an anti-SIRPA antibody of the present disclosure comprise a heavy chain variable region comprising a VH FR1, a VH FR2, a VH FR3, and a VH FR4 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25, and a light chain variable region comprising a VL FR1, a VL FR2, a VL FR3, and a VL FR4 of antibody 3F9-1, 3F9-2, 3F9-3, 3F9-4, 3F9-5, 3F9-6, 3F9-7, 3F9-8, 3F9-9, 3F9-10, 3F9-11, 3F9-12, 3F9-13, 3F9-14, 3F9-15, 3F9-16, 3F9-17, 3F9-18, 3F9-19, 3F9-20, 3F9-21, 3F9-22, 3F9-23, 3F9-24, or 3F9-25.

In some embodiments, the present invention provides an anti-SIRPA antibody, wherein the antibody comprises a heavy chain and a light chain, wherein the heavy chain comprises the amino acid sequence of SEQ ID NO:47 and the light chain comprises the amino acid sequence of SEQ ID NO:50.

In some embodiments, the present invention provides an anti-SIRPA antibody, wherein the antibody comprises a heavy chain and a light chain, wherein the heavy chain comprises the amino acid sequence of SEQ ID NO:48 and the light chain comprises the amino acid sequence of SEQ ID NO:50.

In some embodiments, the present invention provides an anti-SIRPA antibody, wherein the antibody comprises a heavy chain and a light chain, wherein the heavy chain comprises the amino acid sequence of SEQ ID NO:49 and the light chain comprises the amino acid sequence of SEQ ID NO:50.

In some embodiments, the present invention provides an anti-SIRPA antibody, wherein the antibody comprises a heavy chain and a light chain, wherein the heavy chain comprises the amino acid sequence of SEQ ID NO:51 and the light chain comprises the amino acid sequence of SEQ ID NO:50.

In some embodiments, the present invention provides an anti-SIRPA antibody, wherein the antibody comprises a heavy chain and a light chain, wherein the heavy chain comprises the amino acid sequence of SEQ ID NO:52 and the light chain comprises the amino acid sequence of SEQ ID NO:50.

Nucleic Acids, Vectors, and Host Cells

Anti-SIRPA antibodies of the present disclosure may be produced using recombinant methods and compositions, e.g., as described in U.S. Pat. No. 4,816,567. In some embodiments, isolated nucleic acids having a nucleotide sequence encoding any of the anti-SIRPA antibodies of the present disclosure are provided. Such nucleic acids may encode an amino acid sequence comprising the $V_L$ and/or an amino acid sequence comprising the $V_H$ of the anti-SIRPA antibody (e.g., the light and/or heavy chains of the antibody). In some embodiments, one or more vectors (e.g., expression vectors) comprising such nucleic acids are provided. In some embodiments, a host cell comprising such nucleic acid is also provided. In some embodiments, the host cell comprises (e.g., has been transduced with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, the host cell is eukaryotic, e.g., a Chinese Hamster Ovary (CHO) cell or lymphoid cell (e.g., Y0, NS0, Sp20 cell). Host cells of the present disclosure also include, without limitation, isolated cells, in vitro cultured cells, and ex vivo cultured cells.

Methods of making an anti-SIRPA antibody of the present disclosure are provided. In some embodiments, the method includes culturing a host cell of the present disclosure comprising a nucleic acid encoding the anti-SIRPA antibody, under conditions suitable for expression of the antibody. In some embodiments, the antibody is subsequently recovered from the host cell (or host cell culture medium).

For recombinant production of an anti-SIRPA antibody of the present disclosure, a nucleic acid encoding the anti-SIRPA antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors comprising a nucleic acid sequence encoding any of the anti-SIRPA antibodies of the present disclosure, or cell-surface expressed fragments or polypeptides thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones comprising the vector. Suitable examples include plasmids and bacterial viruses, e.g., pUC18, pUC19, Bluescript (e.g., pBS SK+) and its derivatives, mp18, mp19, pBR322, µMB9, ColE1, pCR1, RP4, phage DNAs, and shuttle vectors such as pSA3 and pAT28. These and many other cloning vectors are available from commercial vendors such as BioRad, Strategene, and Invitrogen.

Suitable host cells for cloning or expression of antibody-encoding vectors include prokaryotic or eukaryotic cells. For example, anti-SIRPA antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523. After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross *Nat. Biotech.* 22:1409-1414 (2004); and Li et al. *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK); buffalo rat liver cells (BRL 3A); human lung cells (W138); human liver cells (Hep G2); mouse mammary tumor (MMT 060562); TRI cells, as described, e.g., in Mather et al. *Annals N. Y. Acad. Sci.* 383:44-68 (1982); MRC 5 cells; and FS4 cells. Other useful mammalian host cell lines include Chinese hamster ovary (CHO) cells, including DHFR—CHO cells (Urlaub et al. *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, NJ), pp. 255-268 (2003).

Pharmaceutical Compositions/Formulations

Provided herein are pharmaceutical compositions and/or pharmaceutical formulations comprising the anti-SIRPA antibodies of the present disclosure and a pharmaceutically acceptable carrier.

In some embodiments, pharmaceutically acceptable carrier preferably are nontoxic to recipients at the dosages and concentrations employed. The antibodies described herein may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutically acceptable carriers can include, depending on the formulation desired, pharmaceutically-acceptable, non-toxic carriers of diluents, which are vehicles commonly used to formulate pharmaceutical compositions for animal or human administration. In certain embodiments, the pharmaceutical composition can comprise formulation materials for modifying, maintaining or preserving, for example, the pH, osmolarity, viscosity, clarity, color, isotonicity, odor, sterility, stability, rate of dissolution or release, adsorption or penetration of the composition.

In certain embodiments, pharmaceutically acceptable carriers include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. Further examples of formulations that are suitable for various types of administration can be found in Remington: The Science and Practice of Pharmacy, Pharmaceutical Press 22nd ed. (2013). For a brief review of methods for drug delivery, see, Langer, Science 249:1527-1533 (1990).

Formulations suitable for parenteral administration include aqueous and non-aqueous, isotonic sterile injection solutions, which can comprise antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the antibody, such as an anti-SIRPA antibody of the present disclosure, in a biodegradable or bioerodible implant. The rate of release of the therapeutically active agent is controlled by the rate of transport through the polymeric matrix, and the biodegradation of the implant. Implants may be particles, sheets, patches, plaques, fibers, microcapsules and the like and may be of any size or shape compatible with the selected site of insertion. Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the subject invention. Hydrogels are typically a copolymer material, characterized by the ability to imbibe a liquid.

Therapeutic Uses

As disclosed herein, anti-SIRPA antibodies of the present disclosure may be used for preventing, reducing risk, or treating diseases and disorders.

In one aspect of the invention, an agent that down-regulates SIRPA, e.g., an anti-SIRPA antibody, is used as a therapeutic agent. Such agents are administered to treat, alleviate, and/or prevent a disease or pathology associated with SIRPA expression, activity and/or signaling in a subject. A therapeutic regimen is carried out by identifying a subject, e.g., a human patient suffering from (or at risk of developing) a disease or disorder associated with SIRPA expression, activity and/or signaling, e.g., a cancer or other neoplastic disorder, using standard methods. In some embodiments, cells having the pathology associated with SIRPA expression, activity, and/or signaling, express a SIRPA ligand, e.g., CD47. In some embodiments, cells having the pathology associated with SIRPA expression, activity, and/or signaling, express SIRPA.

As further detailed below an agent that down-regulates SIRPA, e.g., an anti-SIRPA antibody can be used in combination with an additional therapeutic agent that is used to treat the disease or pathology associated with SIRPA expression, activity, or signaling. The terms "in combination" and "in conjunction" are used interchangeably in the present disclosure. The additional therapeutic agent being administered in combination with an anti-SIRPA antibody may be administered before, after, or concurrently with the agent that down-regulates SIRPA, e.g., an anti-SIRPA antibody.

In one aspect of the present disclosure, an anti-SIRPA antibody preparation, e.g., comprising an anti-SIRPA antibody that decreases expression of SIRPA on the cell surface, but does not substantially block binding of ligand, e.g., CD47, to SIRPA, is administered to a human subject. Administration of the antibody may abrogate or inhibit or interfere with the expression, activity and/or signaling function of SIRPA that is mediated by ligand binding, e.g., CD47 binding.

In one embodiment the disease or disorder associated with SIRPA expression is cancer. In some embodiments, an anti-SIRPA antibody is administered to a patient that has a cancer, such as a hematological proliferative disorder of myeloid cells, that express SIRPA. In typical embodiments, an anti-SIRPA antibody is administered to a patient that has a cancer that expresses CD47.

In certain embodiments, a cancer to be prevented or treated by the methods of the present disclosure includes, without limitation, squamous cell carcinoma (e.g., epithelial squamous cell carcinoma), lung cancer, small-cell lung cancer, non-small cell lung cancer, squamous non-small cell lung cancer (NSCLC), adenocarcinoma of the lung, squamous carcinoma of the lung, non-squamous NSCLC, glioma, cancer of the peritoneum, hepatocellular cancer, gastrointestinal cancer, gastric or stomach cancer including gastrointestinal cancer and gastrointestinal stromal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, myelodysplastic syndromes, colorectal neoplasms, solid tumors, tumor angiogenesis, spinal axis tumor, brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages and mast cells) or lymphoid cell line (which produces B, T, NK and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (M0), myeloblastic leukemia (M1), myeloblastic leukemia (M2; with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), indolent lymphoma, large B cell diffuse lymphoma, B cell hematologic malignancy, e.g., B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angioimmunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma (DLBCL) (including DLBCL patients who are primary refractory, Rituximab refractory, refractory to Rituximab/CHOP (cyclophosphamide, doxorubicin, vincristine, and prednisone), relapsed or refractory (R/R) DLBCL, and/or CAR-T ineligible DLBCL patients), Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytic lymphoma (LPL) with Waldenstrom's macroglobulinemia; myelomas, such as IgG myeloma, light chain myeloma, nonsecretory myeloma, smoldering myeloma (also called indolent myeloma), solitary plasmacytoma, and multiple myelomas, chronic lymphocytic leukemia (CLL), hairy cell lymphoma; hematopoietic tumors of myeloid lineage, tumors of mesenchymal origin, including fibrosarcoma and rhabdomyosarcoma; seminoma, teratocarcinoma, tumors of the central and peripheral nervous, including astrocytoma, schwannomas; tumors of mesenchymal origin, including fibrosarcoma, rhabdomyosarcoma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL heptasyllabic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. An anti-SIRPA antibody of the present disclosure may also be used to treat metastatic cancer.

In some embodiments, the cancer is selected from sarcoma, bladder cancer, brain cancer, breast cancer, colon cancer, rectal cancer, endometrial cancer, kidney cancer, renal pelvis cancer, leukemia, lung cancer, melanoma, lymphoma, pancreatic cancer, prostate cancer, ovarian cancer, and fibrosarcoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, the cancer is selected from glioblastoma multiforme; renal clear cell carcinoma; adrenocortical carcinoma; bladder urothelial carcinoma; diffuse large B-cell lymphoma; lung adenocarcinoma; pancreatic adenocarcinoma, renal cell cancer, non-Hodgkin's lymphoma, acute lymphoblastic leukemia (ALL), acute myeloid leukemia (AML), chronic lymphocytic leukemia (CLL), chronic myeloid leukemia (CML), multiple myeloma, breast invasive carcinoma, cervical squamous cell carcinoma, endocervical adenocarcinoma, cholangiocarcinoma, colon adenocarcinoma, diffuse large B-cell lymphoma, esophageal carcinoma, head and neck squamous cell carcinoma, kidney chromophobe, renal papillary cell carcinoma, lower grade glioma, hepatocellular carcinoma, lung squamous cell carcinoma, mesothelioma, ovarian serous cystadenocarcinoma, pancreatic adenocarcinoma, pheochromocytoma and paraganglioma, prostate adenocarcinoma, rectal adenocarcinoma, cutaneous melanoma, stomach adenocarcinoma, testicular germ cell tumors, thyroid carcinoma, thymoma, uterine corpus endometrial carcinoma, uterine carcinosarcoma, and uveal melanoma.

In some embodiments, the present disclosure provides methods of preventing, reducing risk, or treating an individual having cancer, wherein the individual is refractory to checkpoint inhibitor therapy, by administering to the individual a therapeutically effective amount of an anti-SIRPA antibody of the present disclosure.

In some embodiments, the present disclosure provides methods of preventing, reducing risk, or treating an individual having cancer, by administering to the individual a therapeutically effective amount of an anti-SIRPA antibody of the present disclosure.

In some embodiments, an anti-SIRPA antibody of the present disclosure may be administered in conjunction with a therapeutic agent that acts as a checkpoint inhibitor. In some embodiments, the method further includes administering to the individual at least one antibody that specifically binds to an inhibitory immune checkpoint molecule, and/or another standard or investigational anti-cancer therapy. In some embodiments, the inhibitory checkpoint molecule is selected from PD1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, and CD73. In typical embodiments, the therapeutic agent is an antibody to a checkpoint inhibitor selected from D1, PDL1, CD40, OX40, ICOS, CD28, CD137/4-1BB, CD27, GITR, CTLA4, PD-L2, B7-H3, B7-H4, HVEM, LIGHT, BTLA, CD30, TIGIT, VISTA, KIR, GAL9, TIM1, TIM3, TIM4, A2AR, LAG3, DR-5, CD2, CD5, CD39, or CD73. In some embodiments, the at least one antibody that specifically binds to an inhibitory checkpoint molecule is administered in combination with the anti-SIRPA antibody of the present disclosure. In some embodiments, a combination of antibodies to directed against checkpoint inhibitors is administered in conjunction with an anti-SIRPA antibody of the present invention.

In some embodiments, an anti-SIRPA antibody of the present disclosure may be administered in conjunction with at least one agonistic antibody that specifically binds to a stimulatory checkpoint protein, e.g., an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, an agonist anti-CD30 antibody, an agonist anti-BTLA antibody, an agonist anti-HVEM antibody, an agonist anti-CD2 antibody, an agonist anti-CD5 antibody, and any combination thereof.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the anti-SIRPA antibody of the present disclosure. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-B- and T-lymphocyte attenuator (BTLA) antibody, an anti-Killer inhibitory receptor (KIR) antibody, an anti-GAL9 antibody, an anti-TIM3 antibody, an anti-A2AR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy. In some embodiments, the method further includes administering to the individual at least one antibody that specifically binds to an inhibitory cytokine. In some embodiments, the at least one antibody that specifically binds to an inhibitory cytokine is administered in combination with the anti-SIRPA antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the anti-SIRPA antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, an anti-SIRPA antibody of the present invention is administered in combination with radiation therapy and/or a chemotherapeutic agent. Chemotherapeutic agents include, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (methotrexate, pemetrexed, mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones, eribulin and navelbine; epipidophyllotoxins (etoposide, teniposide); DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); DNA methyltransferase inhibitors (azacytidine); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkylsulfonates (busulfan), nitrosoureas (carmustine (BCNU) and analogs, streptozocin), triazenes (dacarbazine (DTIC)); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein, pomalidomide) and growth factor inhibitors (vascular endothelial growth factor (VEGF) inhibitors, such as ziv-aflibercept; fibroblast growth factor (FGF) inhibitors); inhibitors of apoptosis protein (IAP) antagonists (birinapant); histone deacetylase (HDAC) inhibitors (vorinostat, romidepsin, chidamide, panobinostat, mocetinostat, abexinostat, belinostat, entinostat, resminostat, givinostat, quisinostat, SB939); proteasome inhibitors (ixazomib); angiotensin receptor blocker; nitric oxide donors; anti-sense oligonucleotides; antibodies (trastuzumab, panitumumab, pertuzumab, cetuximab, adalimumab, golimumab, infliximab, rituximab, ocrelizumab, ofatumumab, obinutuzumab, alemtuzumab, abciximab, atlizumab, daclizumab, denosumab, efalizumab, elotuzumab, rovelizumab, ruplizumab, ustekinumab, visilizumab, gemtuzumab ozogamicin, brentuximb vedotin); chimeric antigen receptors; cell cycle inhibitors (flavopiridol, roscovitine, bryostatin-1) and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); PARP inhibitors (niraparib, olaparib); focal adhesion kinase (FAK) inhibitors (defactinib (VS-6063), VS-4718, VS-6062, GSK2256098); growth factor signal transduction kinase inhibitors (cediranib, galunisertib, rociletinib, vandetanib, afatinib, EGF816, AZD4547); c-Met inhibitors (capmatinib, INC280); ALK inhibitors (ceritinib, crizotinib); mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. In some embodiments, a chemotherapeutic agent is a B-Raf inhibitor, a MEK inhibitor, a VEGF inhibitor, a VEGFR inhibitor, a tyrosine kinase inhibitor, an anti-mitotic agent, or any combination thereof.

In some embodiments, an anti-SIRPA antibody of the present disclosure is administered in combination with adoptive cell transfer (ACT) therapy, chimeric antigen receptor T cell transfer (CAR-T) therapy, vaccine therapy, and/or cytokine therapy.

In some embodiments, an anti-SIRPA antibody of the present disclosure is administered in combination with at least one antibody that specifically binds to an inhibitory cytokine, e.g., an inhibitory cytokine such as an anti-CCL2 antibody, an anti-CSF-1 antibody, or an anti-IL-2 antibody.

In some embodiments, an anti-SIRPA antibody of the present disclosure is administered in combination with at least one stimulatory cytokine. In some embodiments that may be combined with any of the embodiments herein, the at least one stimulatory cytokine is selected from IFN-α4, IFN-β, IL-1p, TNF-α, IL-6, IL-8, CRP, IL-20 family members, LIF, IFN-γ, OSM, CNTF, GM-CSF, IL-11, IL-12, IL-15, IL-17, IL-18, IL-23, CXCL10, IL-33, MCP-1, MIP-1-beta, and any combination thereof.

In some embodiments, an agent that down-regulates SIRPA, e.g., an anti-SIRPA antibody, is administered to a patient that has a neurological disorder, or is administered to reduce risk, slow onset, or prevent a neurological disorder. In some embodiments, the neurological disorder is dementia, including dementia, frontotemporal dementia, Alzheimer's disease, vascular dementia, mild cognitive impairment, Parkinson's disease, Amyotrophic lateral sclerosis (ALS), Huntington's disease, Taupathy disease, or multiple sclerosis.

In some embodiments, an agent that down-regulates SIRPA, e.g., an anti-SIRPA antibody, is administered to a patient that has Parkinson's disease, amyotrophic lateral sclerosis, Huntington's disease, Taupathy diseases, or multiple sclerosis. In some embodiments, the agent is administered to a patient that has Creutzfeldt-Jakob disease, normal pressure hydrocephalus, Nasu-Hakola disease, stroke, an infection, traumatic brain injury, progressive supranuclear palsy, dementia pugilistica (chronic traumatic encephalopathy), Parkinsonism linked to chromosome 17, Lytico-Bodig disease (Parkinson-dementia complex of Guam), tangle-predominant dementia, ganglioglioma and gangliocytoma, meningioangiomatosis, subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), frontotemporal lobar degeneration, dementia with Lewy bodies, multiple system atrophy, Shy-Drager syndrome, progressive supranuclear palsy, or cortical basal ganglionic degeneration.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-SIRPA antibody of the present disclosure can prevent, reduce the risk, and/or treat dementia. In some embodiments, an anti-SIRPA antibody may modulate one or more SIRPA activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

In some embodiments, administering an anti-SIRPA antibody of the present disclosure, can prevent, reduce the risk, and/or treat FTD. In some embodiments, administering an anti-SIRPA antibody, may modulate one or more SIRPA activities in an individual having FTD.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier. Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering an anti-SIRPA antibody of the present disclosure can prevent, reduce the risk, and/or treat Alzheimer's disease. In some embodiments, administering an anti-SIRPA antibody may modulate one or more SIRPA activities in an individual having Alzheimer's disease.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-SIRPA antibody of the present disclosure can prevent, reduce the risk, and/or treat Parkinson's disease. In some embodiments, administering an anti-SIRPA antibody may modulate one or more SIRPA activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J[0343] Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p 75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering an anti-SIRPA antibody of the present disclosure can prevent, reduce the risk, and/or treat ALS. In some embodiments, administering an anti-SIRPA antibody may modulate one or more SIRPA activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering as an anti-SIRPA antibody of the present disclosure can prevent, reduce the risk, and/or treat Huntington's disease (HD). In some embodiments, administering an anti-SIRPA antibody may modulate one or more SIRPA activities in an individual having Huntington's disease.

Tauopathy Disease

Taupathy diseases, or Tauopathies, are a class of neurodegenerative disease caused by aggregation of the microtubule-associated protein tau within the brain. Alzheimer's disease (AD) is the most well-known tauopathy disease and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering an anti-SIRPA antibody of the present disclosure, can prevent, reduce the risk, and/or treat taupathy disease. In some embodiments, administering an anti-SIRPA antibody may modulate one or more SIRPA activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women.

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoff's phenomenon, which is an exacerbation of extant symptoms due to an exposure to higher than usual ambient temperatures; and Lhermitte's sign, which is an electrical sensation that runs down the back when bending the neck.

In some embodiments, administering an anti-SIRPA antibody of the present disclosure can prevent, reduce the risk, and/or treat multiple sclerosis. In some embodiments, administering an anti-SIRPA antibody may modulate one or more SIRPA activities in an individual having multiple sclerosis.

In some embodiments, a subject or individual is a mammal. Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

An antibody provided herein (and any additional therapeutic agent) can be administered by any suitable means, including parenteral, intrapulmonary, intranasal, intralesional administration, intracerobrospinal, intracranial, intraspinal, intrasynovial, intrathecal, oral, topical, or inhalation routes. Parenteral infusions include intramuscular, intravenous administration as a bolus or by continuous infusion over a period of time, intraarterial, intra-articular, intraperitoneal, or subcutaneous administration. In some embodiments, the administration is intravenous administration. In some embodiments, the administration is subcutaneous. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies provided herein would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g., every week or every three weeks (e.g., such that the patient receives from about two to about twenty, or e.g., about six doses of the antibody). In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. An initial higher loading dose, followed by one or more lower doses may be administered. However, other dosage regimens may be useful. The progress of this therapy is easily monitored by conventional techniques and assays.

Diagnostic Uses

In some embodiments of any of the antibodies, any of the anti-SIRPA antibodies provided herein is useful for detecting the presence of SIRPA in a sample or an individual. The term "detecting" as used herein encompasses quantitative or qualitative detection. Provided herein are methods of using the antibodies of this disclosure for diagnostic purposes, such as the detection of SIRPA in an individual or in tissue samples derived from an individual. In some embodiments, the individual is a human.

The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}$F and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

Articles of Manufacture

Provided herein are articles of manufacture (e.g., kit) comprising an anti-SIRPA antibody described herein. Article of manufacture may include one or more containers comprising an antibody described herein. Containers may be any suitable packaging including, but is not limited to, vials, bottles, jars, flexible packaging (e.g., sealed Mylar or plastic bags), and the like. The containers may be unit doses, bulk packages (e.g., multi-dose packages) or sub-unit doses.

In some embodiments, the kits may further include a second agent. In some embodiments, the second agent is a pharmaceutically-acceptable buffer or diluting agent including, but not limited to, such as bacteriostatic water for injection (BWFI), phosphate-buffered saline, Ringer's solution and dextrose solution. In some embodiments, the second agent is a pharmaceutically active agent as described above.

In some embodiments of any of the articles of manufacture, the article of manufactures further includes instructions for use in accordance with the methods of this disclosure. The instructions generally include information as to dosage, dosing schedule, and route of administration for the intended treatment. In some embodiments, these instructions comprise a description of administration of the isolated anti-SIRPA antibody of the present disclosure (e.g., an anti-SIRPA antibody described herein) to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express SIRPA, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria* meningitidis infection, type I HIV, and *Haemophilus* influenza, according to any methods of this disclosure. In some embodiments, the instructions include instructions for use of the anti-SIRPA antibody and the second agent (e.g., second pharmaceutically active agent).

The present disclosure will be more fully understood by reference to the following Examples. They should not, however, be construed as limiting the scope of the present disclosure. All citations throughout the disclosure are hereby expressly incorporated by reference.

EXAMPLES

The following examples are provided by way of illustration only and not by way of limitation. Those of skill in the art will readily recognize a variety of parameters that could be changed or modified to yield essentially similar results.

Example 1: Production of Anti-SIRPA Antibodies

The amino acid sequence of the human SIRPA protein is set forth below in SEQ ID NO: 1.

Human SIRPA contains a signal peptide located at amino residues 1-30 of SEQ ID NO: 1. Human SIRPA contains an extracellular immunoglobulin-like variable-type (IgV) domain located at amino residues 32-137 of SEQ ID NO: 1; additional extracellular immunoglobulin-like constant-type (IgC) domain sequences located at amino residues 148-247 and 254-348 of SEQ ID NO: 1; a transmembrane domain located at amino residues 374-394 of SEQ ID NO: 1; and an intracellular domain located at amino residues 395-504 of SEQ ID NO: 1.

```
Human SIRPA v1 amino acid sequence (SEQ ID NO: 1):
         10         20         30         40
MEPAGPAPGR LGPLLCLLLA ASCAWSGVAG EEELQVIQPD 50         60         70         80
KSVLVAAGET ATLRCTATSL IPVGPIQWFR GAGPGRELIY 90        100        110        120
NQKEGHFPRV TTVSDLTKRN NMDFSIRIGN ITPADAGTYY 130        140        150        160
CVKFRKGSPD DVEFKSGAGT ELSVRAKPSA PVVSGPAARA 170        180        190        200
TPQHTVSFTC ESHGFSPRDI TLKWFKNGNE LSDFQTNVDP 210        220        230        240
VGESVSYSIH STAKVVLTRE DVHSQVICEV AHVTLQGDPL 250        260        270        280
RGTANLSETI RVPPTLEVTQ QPVRAENQVN VTCQVRKFYP 290        300        310        320
QRLQLTWLEN GNVSRTETAS TVTENKDGTY NWMSWLLVNV
```

-continued

| Human SIRPA v1 amino acid sequence (SEQ ID NO: 1): |
|---|
| 330 340 350 360<br>SAHRDDVKLT CQVEHDGQPA VSKSHDLKVS AHPKEQGSNT |
| 370 380 390 400<br>AAENTGSNER NIYIVVGVVC TLLVALLMAA LYLVRIRQKK |
| 410 420 430 440<br>AQGSTSSTRL HEPEKNAREI TQDTNDITYA DLNLPKGKKP |
| 450 460 470 480<br>APQAAEPNNH TEYASIQTSP QPASEDTLTY ADLDMVHLNR |
| 490 500<br>TPKQPAPKPE PSFSEYASVQ VPRK |

Crystal structure analyses of SIRPA-CD47 complexes resolve the ligand binding site to the variable loops that link the β-sheet strands in the IgV domain of SIRPA. The CD47-binding interface consists of amino acid residues S59-P65, L96-F104, and K123-D130 of SIRPA.

Multiple polymorphisms of SIRPA have been identified in humans. Since most variations in sequence lie beyond the CD47 ligand binding site, most SIRPA variants examined appear to bind CD47 with similar affinities. Another member of the SIRP family, SIRPB1, shares high sequence homology with SIRPA but fails to bind CD47. A single A57M substitution is sufficient to rearrange the S59-P65 ligand-binding interface to prevent SIRPB1 binding to CD47. Furthermore, the SIRPA-CD47 interaction is highly species-specific. Human SIRPA fails to bind mouse or rat or cow CD47 (among species tested) and human CD47 only recognizes a single allelic variant of mouse SIRPA expressed by NOD mouse strain.

Protein BLAST analysis of SIRPA sequences from multiple species shows significant degree of identity with human SIRPA (FIG. 1). The high sequence homology within the SIRP family presents a significant challenge in generating SIRPA-specific antibodies while still maintaining cross-reactivity to non-human SIRPA antigens.

Example 2: Characterization of Humanized Anti-SIRPA Antibody

The mouse SIRPA antibody m3F9 discussed herein, which contains a heavy chain variable region comprising the amino acid sequence of SEQ ID NO:2 and a light chain variable region comprising the amino acid sequence of SEQ ID NO:5.

Tables 4 and 5 below lists hybridoma-derived heavy chain variable region and light chain variable region amino acid sequences of murine anti-SIRPA antibody, m3F9, as well as corresponding humanized sequences (referred to as "h3F9"). The first humanized antibody sequence for anti-SIRPA antibody 3F9 heavy chain variable domain (h3F9-H1) is a "CDR-swap" with no changes to the human framework sequence.

The subsequent humanized heavy chain variable region sequence (h3F9-H2) has altered framework residues at certain CDR junctions. (See FIG. 2A.) FIG. 2A lists potential humanized sequences of the heavy chain variable domain of anti-SIRPA antibody 3F9. Humanized sequence is based on IGHV3-23*01 acceptor framework and IGHJ4*01 joining region.

The first humanized sequence for anti-SIRPA antibody 3F9 light chain variable domain (h3F9-L1) is a "CDR-swap" of the light chain variable domain with no changes to human framework sequence. The subsequent humanized light chain variable region sequences alter certain framework amino acid residues (h3F9-L2 and h3F9-L3). (See FIG. 2B.) FIG. 2B lists potential humanized sequences of the light chain variable domain of anti-SIRPA antibody 3F9.

Humanized sequence is based on IGKV3-11*01 acceptor framework and IGKJ2*01 Joining region. CDR sequences noted in bold. CDR definitions are AbM from website www.bioinf.org.uk/abs/. "b" notes buried sidechain; "p" notes partially buried; "i" notes sidechain at interface between $V_H$ and VL domains. Sequence differences between human and murine germlines noted by asterisk (*). Potential additional mutations in frameworks are noted below sequence. Potential changes in CDR sequences noted below each CDR sequence. These may prevent asparagine (N) deamidation. All six different humanized versions of anti-SIR-PA antibody 3F9 (based on the following combinations of heavy chain and light chain variable regions: h3F9-H1/L1; h3F9-H1/L2; h3F9-H1/L3; h3F9-H2/L1; h3F9-H2/L2; and h3F9-H2/L3) were grafted onto a human IgG4 backbone, recombinantly produced in CHO-Ki cells, and characterized further as described below.

TABLE 4

| Antibody | Heavy chain variable region sequences | SEQ ID NO: |
|---|---|---|
| m3F9 VH | EVKLVESGGGLVKPGGSLKLSCAASGFTFSSYAMS WVRQTPEKRLEWVATISDYGGSYTYYPDSVKGRFT ISRDNAKYTLYLQMSSLRSEDTALYYCARPPYDDY YGGFAYWGQGTLVTVSA | 2 |
| h3F9-H1 | EVQLLESGGGLVQPGGSLRLSCAASGFTFSSYAMS WVRQAPGKGLEWVSTISDYGGSYTYYADSVKGRFT ISRDNSKNTLYLQMNSLRAEDTAVYYCAKPPYDDY YGGFAYWGQGTLVTVSS | 3 |
| h3F9-H2 | EVQLLESGGGLVQPGGSLRLSCAASGFTFSSYAMS WVRQAPGKGLEWVATISDYGGSYTYYADSVKGRFT ISRDNSKNTLYLQMNSLRAEDTAVYYCARPPYDDY YGGFAYWGQGTLVTVSS | 4 |

TABLE 5

| Antibody | Light chain variable region sequences | SEQ ID NO: |
|---|---|---|
| m3F9 VL | DIVLTQSPASLAVSLGQRATISCRASKSVSSSGYSYM HWYQQKPGQPPKLLIYLASNLESGVPARFSGSGSGTD FTLNIHPVEEEDAATYYCQHNRELPCTFGGGTKLEIK | 5 |
| h3F9-L1 | DIQMTQSPSSLSASVGDRVTITCRASKSVSSSGYSYM HWYQQKPGKAPKLLIYLASNLESGVPSRFSGSGSGTD FTLTISSLQPEDFATYYCQHNRELPCTFGQGTKLEIK | 6 |
| h3F9-L2 | DIQLTQSPSSLSASVGDRVTITCRASKSVSSSGYSYM HWYQQKPGKAPKLLIYLASNLESGVPSRFSGSGSGTD FTLTISSVQPEDFATYYCQHNRELPCTFGQGTKLEIK | 7 |
| h3F9-L3 | DIQLTQSPSSLSVSVGDRATITCRASKSVSSSGYSYM HWYQQKPGKAPKLLIYLASNLESGVPSRFSGSGSGTD FTLTISSVQPEDFATYYCQHNRELPCTFGQGTKLEIK | 8 |

Affinity measurements for the anti-SIRPA antibodies were performed as follows. Bio-layer interferometry (BLI) data were collected on a Pall ForteBio Octet RED96 instrument. Data analysis was performed using ForteBio Data Analysis Software, version 9.0. Standard kinetic buffer (PBS, 0.100 BSA, 0.02% Tween-20, pH 7.2) was used for the assay and for preparing reagents. After sensor equilibration in buffer, each of the humanized 3F9 anti-SIRPA antibodies (2.5 µg/mL, 300 s loading time) was captured on Anti-Human IgG Fc Capture Dip and Read Biosensors (Pall ForteBio, Menlo Park, CA). Varying concentrations (0-200 nM) of histidine-tagged human SIRPA (Sino Biological, Beijing, China) were then bound to the captured anti-SIRPA surface (300 s association time, 600 s dissociation time). The resulting BLI signal was obtained as the difference in response from the reference (2.5 µg/mL IgG+0 nM SIRPA) sensor. A zero-ligand control (0 µg/mL IgG+200 nM SIRPA) showed no measurable non-specific binding of SIRPA to the sensor tip surface. Measurements of the affinity for the parental m3F9 antibody were performed using a similar method, except with antibody captured on Anti-Mouse IgG Fc biosensors. Multi-concentration kinetic analysis was performed using a 1:1 interaction model to extract association and dissociation rate constants (ka and kd, respectively) for each antibody. Binding affinity constants (KD) were calculated from the ratio kd/ka.

Immobilized anti-mouse IgG Fc or anti-human IgG Fc antibodies captured murine anti-SIRPA antibody 3F9 and humanized anti-SIRPA antibody 3F9 on biosensors, respectively. Increasing concentrations of histidine-tagged huSIRPA isoform 1 ($10^{-500}$ nM) flowed over captured anti-SIRPA antibody 3F9 to record traces. Best-fit traces from the resulting sensorgrams were analyzed to calculate association rate, dissociation rate, and affinity values. The three humanized anti-SIRPA antibody 3F9 variants tested were mAb 14.70.1 (heavy chain variable sequence of SEQ ID NO:3 and light chain variable sequence of SEQ ID NO:6), mAb 14.70.2 (heavy chain variable sequence of SEQ ID NO:3 and light chain variable sequence of SEQ ID NO:7), and mAb 14.70.4 (heavy chain variable sequence of SEQ ID NO:4 and light chain variable sequence of SEQ ID NO:6). The measured binding kinetics of the humanized anti-SIRPA 3F9 antibodies are summarized in Table 6 below, as extracted ka, kd, and KD values. Of the six h3F9 variants produced, 3 anti-SIRPA antibodies (mAb 14.70.1: H1/L1; mAb 14.70.2: H1/L2; mAb 14.70.4: H2/L1) exhibited similar affinities to soluble SIRPA antigen as the parental m3F9 anti-SIRPA antibody (heavy chain variable sequence of SEQ ID NO:2 and light chain variable sequence of SEQ ID NO:5).

TABLE 6

| 3F9 Antibody Clone | Kon (M-1 s-1) | Koff (s-1) | KD (nM) |
| --- | --- | --- | --- |
| Parental m3F9 IgG1 | 5.08E+04 | 1.00E-03 | 18 |
| mAb 14.70.1 | 1.10E+05 | 2.00E-03 | 19 |
| mAb 14.70.2 | 1.10E+05 | 2.20E-03 | 20 |
| mAb 14.70.4 | 8.60E+04 | 9.40E-04 | 11 |

In addition to binding soluble antigen, cell-based affinity measurements were also performed to ascertain the apparent affinities of h3F9 anti-SIRPA antibodies relative to m3F9 anti-SIRPA antibody to membrane-bound SIRPA vi antigen. EC50 values assign relative affinity by adding increasing concentrations of anti-SIRPA 3F9 antibodies to BWZ cells overexpressing human SIRPA. Receptor bound antibodies were detected by staining cells with anti-mouse IgG Fc APC or anti-human IgG PE secondary antibody. Serial dilutions of the monoclonal antibodies were added to $10^5$ BWZ cells overexpressing huSIRPA (BWZ-huSIRPA) and allowed to achieve binding equilibrium at 4° C. After addition of fluorescently labeled secondary antibody and brief washing steps, mean fluorescent intensity (MFI) values as a function of titrated antibody concentration was recorded via FACS analysis. Curves were fit using nonlinear regression analysis with Graphpad Prism 6 software. Cell-based titration experiments with h3F9 anti-SIRPA antibodies mAb 14.70.1, mAb 14.70.2, and mAb 14.70.4 yielded EC50 values of 1.065 nM, 0.9682 nM, and 1.607 nM, respectively. The humanized 3F9 anti-SIRPA antibodies yielded lower EC50 values than m3F9 anti-SIRPA antibody (EC50=2.1 nM), showing improved binding affinity of the humanized antibodies relative to that determined for the murine 3F9 anti-SIRPA antibody.

A competition-based assay was also performed to calculate IC50 values of the anti-SIRPA antibodies, where increasing concentrations of humanized and murine 3F9 anti-SIRPA antibodies were added to BWZ-huSIRPA v1 cells to displace a fluorophore-labelled reference antibody. IC50 values provide another comparison of relative affinity. In a competition-based assay, increasing concentrations of anti-SIRPA 3F9 antibodies were added to huSIRPA-expressing cells to displace a fluorophore-labelled reference antibody. The IC50 values were determined to be as follows: m3F9=11.54 nM; mAb 14.70.1=3.303 nM; mAb 14.70.2=2.185 nM; mAb 14.70.4=4.606 nM). These results demonstrated that the humanized anti-SIRPA antibodies of the present disclosure were more effective competitors against reference m3F9 anti-SIRPA antibody binding to SIRPA.

The ability of h3F9 anti-SIRPA antibodies to reduce cell surface expression of SIRPA was evaluated on primary human macrophages (huMacs). Human monocytes were isolated from peripheral blood of healthy donors and differentiated into macrophages in vitro by supplementing growth media with human M-CSF. Following differentiation, huMacs were harvested and seeded onto 96-well tissue culture plates with increasing concentration of isotype control or soluble anti-SIRPA antibodies and incubated overnight at 37° C. Cells were analyzed by flow cytometry for SIRPA surface expression using a DyLight650-conjugated anti-human SIRPA antibody (clone SA56) belonging to a separate epitope bin than anti-SIRPA antibody 3F9. As shown in FIG. 3, h3F9 anti-SIRPA antibody variants (mAb 14.70.1 (70.1), mAb 14.70.2 (70.2), and mAb 14.70.4 (70.4)) downregulated SIRPA receptor expression levels in macrophages in a dose-dependent manner. However, the parental m3F9 anti-SIRPA antibody exhibited greater maximal receptor downregulation than the humanized antibodies despite similar antigen binding properties discussed above. These results suggested that anti-SIRPA antibody properties beyond receptor engagement determine the functional activity of anti-SIRPA antibody 3F9 on macrophages.

Example 3: Anti-SIRPA Antibodies Require Fc Gamma Receptors (FcγRs) for Functional Activity A principal difference between human and murine 3F9 anti-SIRPA antibodies is the ability to engage Fc gamma receptors (FcγRs). Humanized anti-SIRPA antibodies were grafted onto a human IgG4 Fc backbone known to possess poor FcγR binding properties. The hybridoma m3F9 anti-SIRPA antibody, despite being a murine IgG1 antibody, still retains binding activity towards certain human FcγRs. To verify that FcγRs modulate the functional activity of anti-SIRPA antibodies, m3F9 anti-SIRPA antibody was treated with EndoS to enzymatically remove the Fc glycan on Asn297, a key determinant mediating IgG-FcγR interaction. Primary human macrophages from 2 healthy donors were treated overnight with increasing concentrations of glycosylated or deglycosylated m3F9 anti-SIRPA antibody. The cells were subsequently stained with a DyLight650-conjugated anti-SIRPA reference antibody (SA56-DyL650) that binds to a distinct epitope bin and analyzed then for SIRPA surface expression by FACS analysis.

As shown in FIG. 4A, both glycoforms of m3F9 anti-SIRPA antibody significantly downregulated cell surface expression of SIRPA. However, in both donors, the deglycosylated m3F9 anti-SIRPA antibody variant exhibited reduced maximal activity compared to that observed for the glycosylated form of the antibody. In particular, glycosylated m3F9 anti-SIRPA antibody downregulated SIRPA expression by as much as 90% and 85% in Donor (Dnr) 413 and Donor 414, respectively; whereas deglycosylated m3F9 anti-SIRPA antibody only achieved 70% and 75% SIRPA receptor downregulation in the same donor macrophages, respectively. This finding suggested that anti-SIRPA antibodies, specifically the antibody m3F9, requires FcγR engagement for enhanced down-regulation of SIRPA cell surface expression. Results in FIG. 4A are presented as percent of reference antibody binding by dividing MFI value of samples treated with anti-SIRPA antibodies by the MFI value of samples treated with the isotype control.

In addition to antibody-mediated receptor downregulation as disclosed above, the role of FcγRs was evaluated in 3F9 anti-SIRPA antibody-mediated enhancement of tumor cell phagocytosis. A tumor cell phagocytosis assay was developed based on pHrodo fluorescence. Primary human macrophages were treated overnight with isotype control antibody (MOPC) or indicated anti-SIRPA 3F9 antibody variants. Raji cells labeled with pHrodo dye were added to macrophages and incubated at 37° C. for 2 hours. Red Avidin (Invitrogen) is a streptavidin molecule conjugated with pHrodo Red dye, a fluorogenic marker that acquires fluorescence in acidic environments, such as the phagosome. For target tumor cell labeling, 500 nM Red Avidin was mixed with 15 nM biotinylated *Lens Culinaris* Agglutinin (LCA; Vector Labs). Red Avidin-LCA complexes were then mixed in a 1:1 volumetric ratio with 400,000 Raji cells in serum-free RPMI media on ice. The sugar-binding properties of LCA links Red Avidin to carbohydrate structures on the tumor cell surface. After brief washing steps, Red Avidin-LCA-labeled Raji cells were mixed with monocyte-derived human macrophages in serum-free RPMI media and incubated at 37° C. for 2 hours. Macrophages were then collected and stained on ice with anti-CD14 APC in FACS buffer containing FcγR-blocking antibodies. Phagocytic activity was measured by counting percent of CD14/pHrodo-double positive macrophages. As a control, unlabeled Raji cells were mixed with macrophages to establish background fluorescence levels. Results in FIG. 4B are presented as the fold increase in percent population of pHrodo/CD14 double-positive macrophages.

Figure 4B:
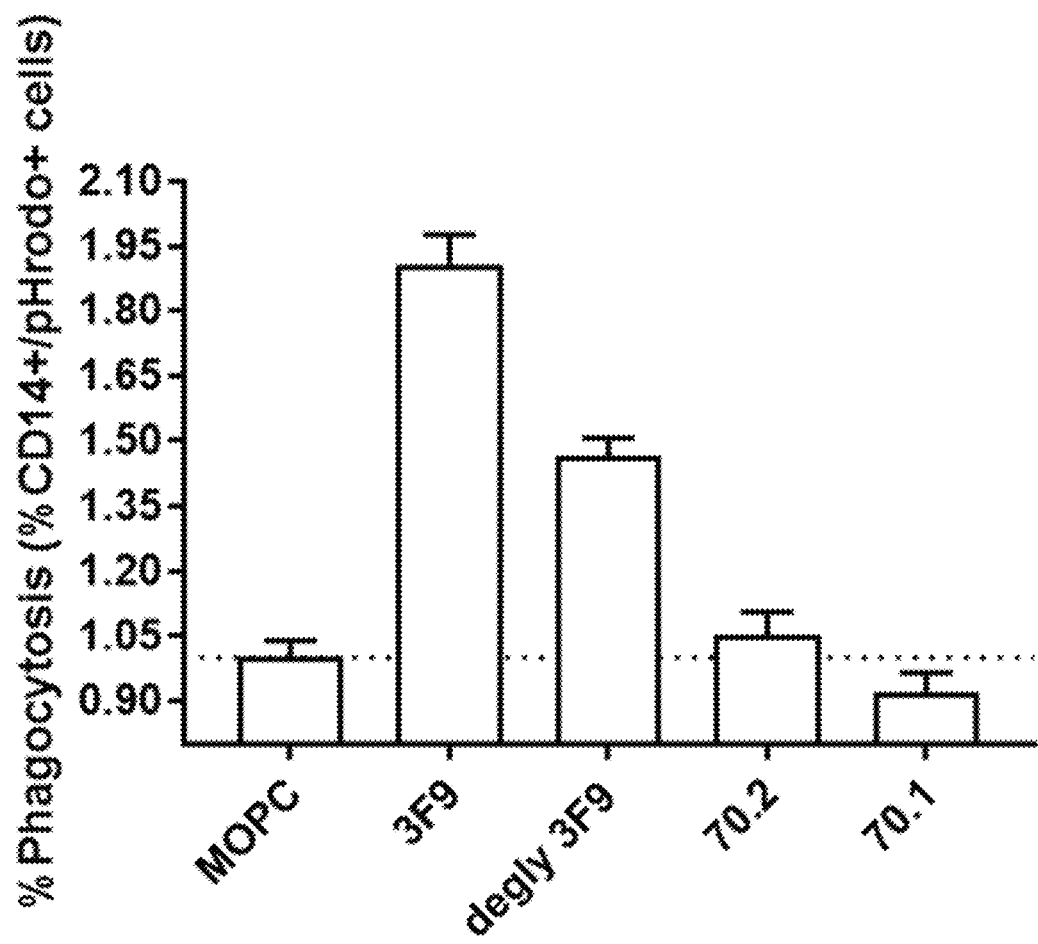
FIG. 4B sets forth data showing antibody-mediated enhancement of tumor cell phagocytosis depends on the N-linked Fc glycan.

As shown in FIG. 4B, macrophages treated overnight with glycosylated m3F9 anti-SIRPA antibody displayed a ~2-fold increase in tumor cell phagocytosis relative to that observed using isotype control antibody-treated macrophages. Macrophages treated with deglycosylated m3F9 anti-SIRPA antibody displayed ~1.5-fold increase in tumor cell phagocytosis relative to isotype control-treated macrophages. This ~1.5-fold increase in tumor cell phagocytosis represents a statistically significant ~50% decrease in activity relative to that observed with glycosylated m3F9 anti-SIRPA antibody. Furthermore, macrophages treated with h3F9 IgG4 (mAb 14.70.1 or mAb 14.70.2) did not display any ability to enhance tumor cell phagocytosis above baseline levels.

Previous studies established a correlation between increased phagocytic activity and CD14 downregulation upon stimulation of macrophages with 3F9 anti-SIRPA antibody. To determine if this correlation also depends, at least in part, on FcγRs, primary human macrophages were treated overnight with either glycosylated m3F9 or h3F9 IgG4 anti-SIRPA antibody variants (mAb 14.70.1, mAb 14.70.2, and mAb 14.70.4) and assayed for tumor cell phagocytosis and CD14 expression. As shown in FIG. 5A, only macrophages treated with m3F9 anti-SIRPA antibody showed enhanced phagocytosis of Raji cells relative to that observed with isotype control antibody-treated macrophages. Results are presented as the fold increase in percent population of pHrodo/CD14 double-positive macrophages. Humanized anti-SIRPA IgG4 antibodies failed to enhance phagocytosis of Raji cells. Likewise, only m3F9 anti-SIRPA antibody stimulation downregulated CD14 expression on macrophages, whereas h3F9 IgG4 anti-SIRPA antibody variants did not alter CD14 expression (FIG. 5B). In addition to supporting a correlation between CD14 expression level and phagocytic activity in macrophages, these results confirmed that functional activity of 3F9 anti-SIRPA antibody is dependent, at least in part, on FcγRs.

Example 4: CD32 Downregulation by Anti-SIRPA Antibodies

In addition to the target antigen of interest, cells of the myeloid lineage also express multiple Fc receptors capable of binding to the Fc domain of therapeutic antibodies. The Fc gamma receptors (FcγR) constitute the best characterized and most potent receptor class to mediate Fc-dependent effector functions. FcγRs consist of both ITAM-associated activating receptors (CD64/FcγRI, CD32A/FcγRIIA, and CD16A/FcγRIIIA) and an ITIM-bearing inhibitory receptor (CD32B/FcγRIIB), and co-expression of activating/inhibitory receptors on the same cell establishes a threshold for cellular activation. In general, ligation of activating FcγRs by immune complexes initiates several signaling cascades that lead to cellular activation and subsequent induction of effector functions. These activities vary between myeloid cell types, but may include antibody-dependent cellular cytotoxicity, antibody-dependent cellular phagocytosis, and upregulation of several pro-inflammatory cytokines and chemokines, etc. In contrast, ligation of the inhibitory receptor, FcγRIIB, by immune complexes counteracts the immune-stimulatory signals of activating FcγRs supporting the maintenance of tissue homeostasis. For example, several studies establish that genetic knockout of FcγRIIB results in enhanced pro-inflammatory macrophage activity in murine models of immune complex-mediated inflammation. Since FcγRIIB is the only FcγR with inhibitory activity, it plays a central role in regulating FcγR-mediated inflammation by myeloid cells. In the context of the tumor microenvironment, FcγRIIB expression levels may determine the polarization state of tumor-associated macrophages and the regulation of macrophage effector function in vivo.

Figure 6A:
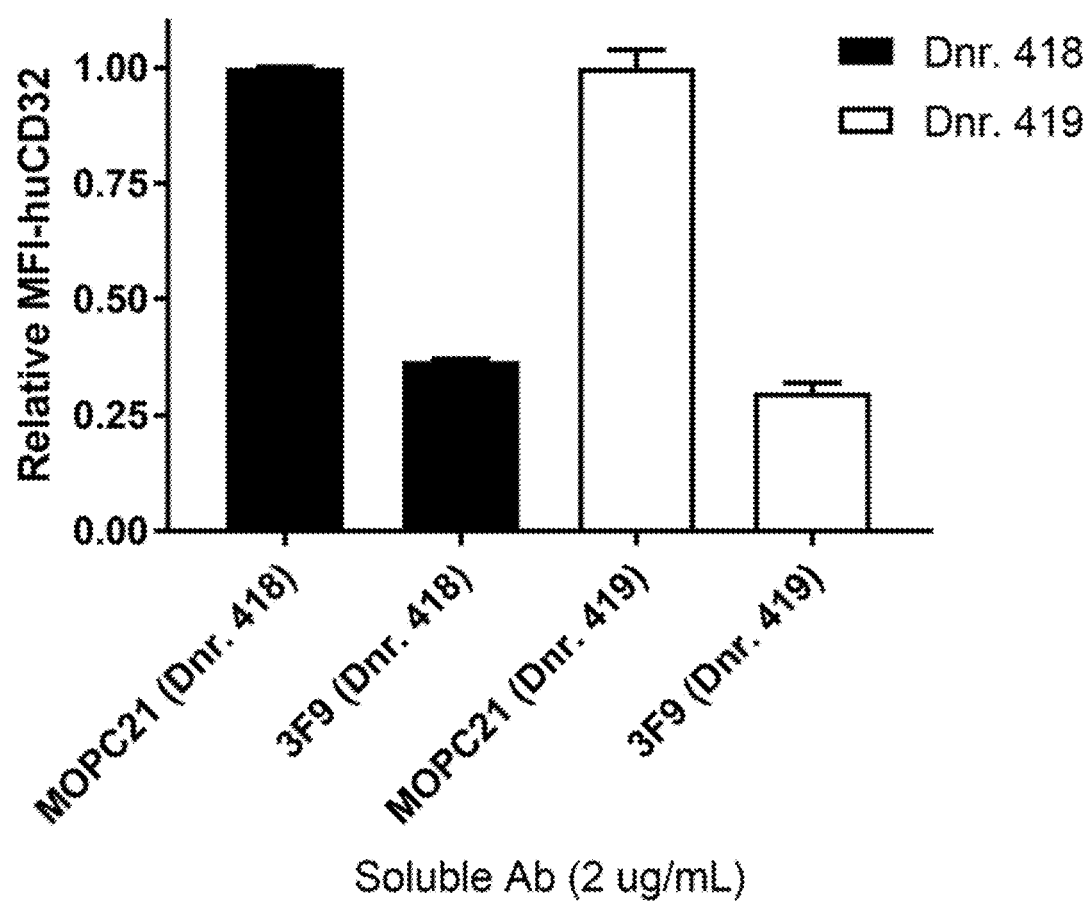
FIG. 6A shows anti-SIRPA antibody 3F9 mIgG1 treatment downregulates CD32A/B expression on primary human macrophages.

To determine which FcγR contributes to the in vitro activity of 3F9 anti-SIRPA antibody, monocyte-derived macrophages obtained from two healthy donors were treated overnight with either isotype control antibody or anti-SIRPA antibody m3F9 and then assessed for surface expression levels of FcγRIIIA (CD16), FcγRI (CD64), and FcγRIIA/B (CD32A/B). As shown in FIG. 6A, m3F9 anti-SIRPA antibody treatment substantially reduced surface expression of CD32A/B relative to that observed in isotype control antibody-treated macrophages. Since the detection antibody used to measure surface levels of FcγRII (clone FUN-2; Biolegend) does not distinguish between the activating receptor FcγRIIA and the inhibitory receptor FcγRIIB, this assay was repeated with receptor-specific antibodies. As previously described, monocyte-derived macrophages obtained from two healthy donors were treated overnight with either isotype control antibody or the indicated variant of 3F9 anti-SIRPA antibody. FIG. 6B shows that anti-SIRPA antibody m3F9 significantly downregulated FcγRIIA in macrophages by ~70-85% relative to that observed in iso-type control antibody-treated cells. This effect was dependent on the Fc domain since both the h3F9 IgG4 variant (mAb 14.70.2) and deglycosylated form of the murine antibody abrogated FcγRIIA downregulation.

When assessing surface expression of FcγRIIB, anti-SIRPA antibody m3F9 treatment reduced expression of the inhibitory receptor to near undetectable levels relative to that observed in isotype control antibody-treated macrophages (FIG. 6B). In contrast, no significant downregulation of FcγRI/CD64 or FcγRIIIA/CD16A was evident on anti-SIRPA antibody 3F9-treated macrophages relative to isotype control-treated cells, indicating that anti-SIRPA 3F9 antibody treatment does not alter CD16 and CD64 expression on primary human macrophages (data not shown).

To confirm that CD32A/B is required for the functional activity of anti-SIRPA antibody m3F9, selective FcγR blockade experiments were performed to assess the role of individual FcγRs on antibody-mediated SIRPA downregulation and tumor cell phagocytosis. In blocking experiments, primary human macrophages from two healthy donors were pre-incubated with anti-CD16 or anti-CD32A/B blocking antibodies for 15 minutes on ice. Subsequently, cells were incubated overnight with either isotype control (MOPC21) or m3F9 anti-SIRPA antibodies. SIRPA expression was detected with DyLight650-conjugated anti-SIRPA reference antibody (SA56-DyL650). Results are presented as percent of reference antibody binding by dividing MFI value of samples treated with anti-SIRPA antibodies by the MFI value of samples treated with the isotype control. As shown in FIG. 7A, CD16 blockade did not disrupt SIRPA downregulation following anti-SIRPA antibody m3F9 treatment relative to that observed in macrophages not treated with FcγR-blocking antibodies. In contrast, m3F9-mediated SIRPA downregulation was significantly impaired in macrophages pre-incubated with anti-CD32A/B blocking antibodies.

To ascertain if CD32A/B blockade also impedes phagocytosis, primary human macrophages were pre-incubated with anti-CD32A/B blocking antibody and treated overnight with isotype control antibody or anti-SIRPA antibody m3F9. Raji cells labeled with pHrodo dye were mixed with macrophages and incubated at 37° C. for 2 hours. Results are presented as the fold increase in percent population of pHrodo/CD14 double-positive macrophages. As shown in FIG. 7B, m3F9-treated macrophages from both donors enhanced phagocytosis of Raji cells ~2-fold relative to that observed in isotype control antibody-treated macrophages. However, CD32A/B blockade either partially or completely blocked m3F9-mediated enhancement of tumor cell phagocytosis. Taken together, these results established that CD32A/B engagement is functionally required for the activity of anti-SIRPA antibody m3F9.

Example 5: Affinity Maturation of h3F9 Anti-SIRPA Antibodies

Affinity maturation of humanized h3F9 anti-SIRPA antibody was performed. Briefly, certain amino acid residues in the heavy or light chain were selectively mutagenized and mutants that improved binding were selected through additional rounds of screening. This process simultaneously improves specificity, species cross-reactivity, and developability profiles, allowing precise tuning of properties involved in the desired mechanism of action, potency in biological assays, and pre-clinical modeling. Characterizations included Forte Bio and MSD affinity measurements, cell binding and several developability assays. After the first round of affinity maturation, antibodies with improved affinity also displayed improved polyspecific reactivity (PSR), which is used to determine nonspecific binding of the antibody. Thus, a second round of affinity maturation was performed to improve affinity without elevating PSR.

Antibody Heavy Chain and Light Chain Variable Domain Sequences

Using standard techniques, the amino acid sequences of the light chain variable domains and the heavy chain variable domains of the affinity matured antibodies described herein were determined. The light chain HVR sequences of the antibodies are set forth in Table 7-8. The light chain HVR sequences of the antibodies are set forth in Table 7. The heavy chain HVR sequences of the antibodies are set forth in Table 8. The light chain and heavy chain framework (FR) sequences of the antibodies are set forth in Table 9. Heavy chain variable region and light chain variable region sequences of the antibodies are set forth below in Table 10.

TABLE 7

Light chain HVR sequences of affinity matured anti-SIRPA antibodies

| | | SEQ ID NO: | MAb ID (3F9-#) |
|---|---|---|---|
| HVR-L1 | RASKSVSSGYSYMH | 9 | 1, 2, 3, 4, 5, 6, 7, 8, 9, 10, 11, 12, 13, 14, 15, 16, 17, 18, 19, 20, 21, 22, 23, 24, and 25 |
| HVR-L2 | LASNLES | 10 | 1, 2, 3, 4, 5, 6, 7, 8, 9, 10, 11, 12, 13, 14, 15, 16, 17, 18, 19, 20, 21, 22, 23, 24, and 25 |
| HVR-L3 | QHNRELPST | 11 | 1, 10, and 18 |
| | QHNRELPCT | 12 | 2 |
| | QHNRELPIT | 13 | 3, 11, and 19 |
| | QHNRELPPT | 14 | 4, 12, and 20 |
| | QHNRELPTT | 15 | 5, 13, and 21 |
| | QHNRELPVT | 16 | 6, 14, and 22 |
| | QHNRELPAT | 17 | 7, 15, and 23 |
| | QHNRELPGT | 18 | 8, 16, and 24 |
| | QHNRELPWT | 19 | 9, 17, and 25 |

TABLE 8

Heavy chain HVR sequences of affinity matured anti-SIRPA antibodies

| | | SEQ ID NO: | mAb ID (3F9-#) |
|---|---|---|---|
| HVR-H1 | GFTFSSYAMS | 20 | 1, 2, 3, 4, 5, 6, 7, 8, 9, 10, 11, 12, 13, 14, 15, 16, 17, 18, 19, 20, 21, 22, 23, 24, and 25 |

TABLE 8-continued

Heavy chain HVR sequences of affinity matured anti-SIRPA antibodies

| | | SEQ ID NO: | mAb ID (3F9-#) |
|---|---|---|---|
| HVR-H2 | TISEYGGSYT YYAESVKG | 21 | 1, 2, 3, 4, 5, 6, 7, 8, 9, 10, 11, 12, 13, 14, 15, 16, 17, 18, 19, 20, 21, 22, 23, 24, and 25 |
| HVR-H3 | PPYDDYYGGF AY | 22 | 1, 2, 3, 4, 5, 6, 7, 8, and 9 |
| | PPYDDYYGGF RY | 23 | 10, 11, 12, 13, 14, 15, 16, and 17 |
| | PPYDDYYGGF QY | 24 | 18, 19, 20, 21, 22, 23, 24, and 25 |

TABLE 9

Heavy and light chain Framework sequences of affinity matured anti-SIRPA antibodies

| FR | VH | SEQ ID NO: | VL | SEQ ID NO: |
|---|---|---|---|---|
| FR 1 | EVQLLESGGGLVQPGG SLRLSCAAS | 25 | DIQLTQSPSSLSASVG DRVTITC | 29 |
| FR 2 | WVRQAPGKGLEWVA | 26 | WYQQKPGKAPKLLIY | 30 |
| FR 3 | RFTISRDNSKNTLYLQ MNSLRAEDTAVYYCAR | 27 | GVPSRFSGSGSGTDFT LTISSVQPEDFATYYC | 31 |
| FR 4 | WGQGTLVTVSS | 28 | FGQGTKLEIK | 32 |

TABLE 10

| | SEQ ID NO:mAb ID (3F9-#) | |
|---|---|---|
| Heavy Chain Variable Region | | |
| EVQLLESGGGLVQPGGSLRLSCAAS GFTFSSYAMSWVRQAPGKGLEWVAT ISEYGGSYTYYAESVKGRFTISRDN SKNTLYLQMNSLRAEDTAVYYCARP PYDDYYGGFAYWGQGTLVTVSS | 33 | 1, 2, 3, 4, 5, 6, 7, 8, and 9 |
| EVQLLESGGGLVQPGGSLRLSCAAS GFTFSSYAMSWVRQAPGKGLEWVAT ISEYGGSYTYYAESVKGRFTISRDN SKNTLYLQMNSLRAEDTAVYYCARP PYDDYYGGFRYWGQGTLVTVSS | 34 | 10, 11, 12, 13, 14, 15, 16, and 17 |
| EVQLLESGGGLVQPGGSLRLSCAAS GFTFSSYAMSWVRQAPGKGLEWVAT ISEYGGSYTYYAESVKGRFTISRDN SKNTLYLQMNSLRAEDTAVYYCARP PYDDYYGGFQYWGQGTLVTVSS | 35 | 18, 19, 20, 21, 22, 23, 24, and 25 |
| Light Chain Variable Region | | |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPS TFGQGTKLEIK | 36 | 1, 10, and 18 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPC TFGQGTKLEIK | 37 | 2 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPI TFGQGTKLEIK | 38 | 3, 11, and 19 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPP TFGQGTKLEIK | 39 | 4, 12, and 20 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPT TFGQGTKLEIK | 40 | 5, 13, and 21 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPV TFGQGTKLEIK | 41 | 6, 14, and 22 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPA TFGQGTKLEIK | 42 | 7, 15, and 23 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPG TFGQGTKLEIK | 43 | 8, 16, and 24 |
| DIQLTQSPSSLSASVGDRVTITCRA SKSVSSGGYSYMHWYQQKPGKAPKL LIYLASNLESGVPSRFSGSGSGTDF TLTISSVQPEDFATYYCQHNRELPW TFGQGTKLEIK | 44 | 9, 17, and 25 |

Example 6: Characterization of Affinity Matured Anti-SIRPA Antibodies

Initial characterization of affinity matured anti-SIRPA antibodies disclosed herein comprised acquiring antigen affinity measurements using bio-layer interferometry (BLI) on a Pall ForteBio Octet RED96 instrument. Immobilized anti-mouse IgG Fc or anti-human IgG Fc antibodies captured murine anti-SIRPA 3F79 antibody and humanized anti-SIRPA 3F79 antibody on biosensors, respectively. Single cycle kinetics were performed with 25 nM huSIRPA [which variant?] or 50 nM huSIRPB 1 flowed over captured antibody 3F79 to record traces. Data analysis was performed using ForteBio Data Analysis Software, version 9.0. Standard kinetic buffer (PBS, 0.100 BSA, 0.02% Tween-20, pH 7.2) was used for the assay and for preparing reagents. After sensor equilibration in buffer, anti-SIRPA antibody h3F9 (2 g/mL, 300 s loading time) or affinity matured variants of anti-SIRPA antibody h3F9 were captured on Anti-Human IgG F Capture Dip and Read Biosensors (Pall ForteBio, Menlo Park, CA). 50 nM of histidine-tagged human SIRPA vi or human SIRPB1 (Novoprotein, Summit, NJ, USA) were then bound to the captured anti-SIRPA antibody coated surface (200 s association time, 900 s dissociation time). The resulting BLI signal was obtained as the difference in response from the reference (2 µg/mL 3F9+0 nM SIRPA) sensor. A zero-ligand control (0 µg/mL 3F9+200 nM SIRPA) showed no measurable non-specific binding of SIRPA to the sensor tip surface. Single-curve kinetic analysis was performed using a 1:1 interaction model to extract association and dissociation rate constants (ka and kd, respectively) for each antibody. Affinity constants (KD) were calculated from the ratio kd/ka. Sensorgrams of 25 anti-SIRPA progeny antibodies and one parental antibody binding to soluble huSIRPA and huSIRPB 1 were obtained, and best-fit traces were used to calculate association rate, dissociation rate, and affinity values. Affinity measurements (ka, kd, and KD) derived from curve fitting analysis of the sensorgrams obtained from these experiments are summarized in Table 11. All affinity matured anti-SIRPA antibodies lacked any measurable cross-reactivity to huSIRPB 1 (data not shown), and six affinity-matured anti-SIRPA antibodies (3F9-18, 3F9-12, 3F9-23, 3F9-14, 3F9-22, and 3F9-20) exhibited ~10-fold increase in affinity towards soluble huSIRPA relative to that observed with the parental anti-SIRPA antibody h3F9.

TABLE 11

Binding Kinetics of Affinity Matured h3F9 Antibodies

| Ab ID (3F9-#) | KD (M) | kon (Ms)−1 | koff (s−1) |
|---|---|---|---|
| 18 | 4.19E−10 | 1.37E+05 | 5.74E−05 |
| 12 | 4.29E−10 | 1.39E+05 | 5.96E−05 |
| 23 | 5.39E−10 | 1.69E+05 | 9.11E−05 |
| 14 | 6.18E−10 | 1.65E+05 | 1.02E−04 |
| 22 | 6.46E−10 | 1.74E+05 | 1.13E−04 |
| 20 | 8.50E−10 | 1.50E+05 | 1.28E−04 |
| 16 | 1.27E−09 | 1.19E+05 | 1.51E−04 |
| 21 | 1.03E−09 | 1.48E+05 | 1.52E−04 |
| 24 | 1.07E−09 | 1.44E+05 | 1.55E−04 |
| 25 | 1.06E−09 | 1.53E+05 | 1.62E−04 |
| 7 | 1.81E−09 | 9.92E+04 | 1.80E−04 |
| 19 | 1.29E−09 | 1.41E+05 | 1.81E−04 |
| 11 | 1.43E−09 | 1.34E+05 | 1.92E−04 |
| 6 | 1.65E−09 | 1.16E+05 | 1.92E−04 |
| 13 | 1.38E−09 | 1.46E+05 | 2.01E−04 |
| 10 | 1.51E−09 | 1.34E+05 | 2.01E−04 |
| 4 | 1.79E−09 | 1.13E+05 | 2.03E−04 |
| 1 | 2.09E−09 | 1.06E+05 | 2.22E−04 |
| 2 | 2.06E−09 | 1.08E+05 | 2.22E−04 |
| 17 | 1.70E−09 | 1.40E+05 | 2.38E−04 |
| 5 | 2.95E−09 | 9.36E+04 | 2.76E−04 |
| 8 | 3.60E−09 | 7.66E+04 | 2.76E−04 |
| 9 | 3.38E−09 | 8.94E+04 | 3.02E−04 |
| 15 | 6.28E−09 | 5.76E+04 | 3.62E−04 |
| 3 | 4.43E−09 | 9.39E+04 | 4.16E−04 |
| h3F9 | 6.48E−09 | 1.84E+05 | 1.19E−03 |

Cell-based affinity measurements were also performed to ascertain the apparent affinities of affinity-matured 3F9 anti-SIRPA antibodies to cell surface-expressed antigen. Serial dilutions of each of the anti-SIRPA monoclonal antibodies were added to 105 BWZ-huSIRPA cells and allowed to achieve binding equilibrium at 4° C. After addition of fluorescently labeled secondary antibody and brief washing steps, MFI values as a function of titrated antibody concentration was recorded via FACS analysis. EC50 values (listed below) assign relative affinity by adding increasing concentrations of 3F9 antibody variants to BWZ cells overexpressing human SIRPA. Receptor bound antibodies were detected by staining cells with anti-human IgG PE secondary antibody. Curves were fit using nonlinear regression analysis with Graphpad Prism 6 software. Cell-based titration experiments with murine 3F9 and humanized affinity matured anti-SIRPA antibodies showed improvement of EC50 values of the humanized affinity matured anti-SIRPA antibodies; two anti-SIRPA antibodies showed significant improvement in EC50 values (mAb 3F9−14=0.42 nM and mAb 3F9−22=0.49 nM) compared to that observed with anti-SIRPA 3F9 mIgG1 antibody (0.72 nM). See Table 12 below.

TABLE 12

| | 3F9-14 | 3F9-17 | 3F9-18 | 3F9-20 | 3F9-21 | 3F9-22 | 3F9-25 | 3F9 mIgG1 |
|---|---|---|---|---|---|---|---|---|
| EC50 (nM) | 0.42 | 0.61 | 0.51 | 0.49 | 0.64 | 0.49 | 0.96 | 0.72 |

Example 7: Cross-Reactivity of Affinity Matured Anti-SIRPA Antibodies to SIRPA Antigenic Variants The CD47-binding domain of human SIRPA is highly polymorphic, which may hinder development of CD47-blocking anti-SIRPA antibodies capable of recognizing all SIRPA allelic variants expressed in human populations. In fact, the two most common alleles of human SIRPA (v1 and v2) are also the most divergent in sequence with 13 residues differing in the IgV domain. Since CD47 competition studies resolved that anti-SIRPA antibody m3F9 binds a region distinct from the CD47 ligand binding site, binding assays were performed to verify cross-reactivity between human SIRPA v1 and v2, as well as cross-species reactivity to determine relevant animal models for toxicology studies.

In an ELISA assay, 96-well Immulon HBX plates were coated with His- or Fc-tagged SIRPA of a given species, as indicated, at 1 µg/mL in PBS overnight at 4C. Plates were blocked in 5% (w/v) bovine serum albumin in PBS for 1 hour, after which they were washed 3 times with PBS/0.05% Tween 20 (PBS/T). Anti-SIRPA antibodies were added to the plate in a dilution series and were incubated at room temperature for 2 hours, after which the unbound antibody was removed by washing with PBS/T. Horseradish peroxidase-conjugated anti-mouse IgG or anti-human kappa light chain (Jackson Immunoresearch) was then added to the wells and incubated for 30 minutes. Unbound antibody was removed by washing with PBS/T, after which bound antibody was detected using tetramethylbenzidine (TMB). The reaction was stopped with 2N $H_2SO_4$, after which the plates were read at A450.

The parental murine 3F9 anti-SIRPA antibody binds both v1 and v2 versions of human SIRPA-Fc with similar EC50 values (0.695 and 0.789 nM, respectively). A partial decrease in apparent affinity is observed with the His-tagged human antigen suggesting greater avid binding to Fc-tagged SIRPA. Additionally, the parental murine 3F9 anti-SIRPA antibody demonstrates weak cross-reactivity to Fc- and His-tagged cynomolgus SIRPA (EC50=1.09 nM). No detectable binding was observed to rat SIRPA.

Following affinity maturation of the parental antibody as described above, two progeny anti-SIRPA antibodies, mAb 3F9-14 and mAb 3F9-22, were screened against the same panel of SIRPA antigens to assess cross-reactivity. As with anti-SIRPA antibody m3F9, both humanized and affinity matured anti-SIRPA antibodies retained binding activity against human SIRPA v1 and v2 but with significantly lower EC50 values, confirming the increase in affinity observed in biosensor measurements and cell binding assays described above. Despite increased affinity towards human SIRPA v1 and v2, anti-SIRPA antibody 3F9-14 exhibited weak cross-reactivity to cynoSIRPA; binding curves yielded EC50 values (EC50=0.879 nM), similar to that observed with anti-SIRPA antibody m3F9. In contrast, anti-SIRPA antibody 3F9-22 demonstrated equivalent binding activity towards cynoSIRPA as with both variants of human SIRPA (EC50=0.107 nM). Neither 3F9-14 nor 3F9-22 antibody bound to rat SIRPA (data not shown). EC50 calculated from binding curves are listed below and establish that all anti-SIRPA antibodies bound both allelic variants of human SIRPA. Only anti-SIRPA antibody hu3F9-22 bound cyno SIRPA with similar affinity to binding to human SIRPA. Table 13 below shows the EC50 values of anti-SIRPA antibodies to various SIRPA proteins (nM).

TABLE 13

| ELISA | huSIPRA v.1 CAA71403.1 | huSIRPA v.2 NP542970.1 | cynoSIRPA XPO15313153.1 |
|---|---|---|---|
| 3F9 mIgG1 | 0.789 | 0.695 | 1.089 |
| 3F9-14 | 0.093 | 0.080 | 0.879 |
| 3F9-22 | 0.108 | 0.082 | 0.107 |

Similar ELISA experiments were performed to determine EC50 values for anti-SIRPA antibody 9C2 (See below for anti-SIRPA antibody 9C2 amino acid sequences) and 3F9 against a panel of different SIRPA and SIRPB proteins. Table 14 below shows the EC50 values of these anti-SIRPA antibodies to various SIRP proteins (nM).

TABLE 14

| | SIRPA v2 | SIRPB1-Fc iso. 1 | SIRPB1-Fc iso. 3 | SIRPB1-His iso. 3 | CynoSIRPA | CynoSIRPB1 |
|---|---|---|---|---|---|---|
| mAb 9C2 | 0.3578 | n.b | 0.3822 | 0.4251 | 7.439 | n.b. |
| mAb 3F9 | 0.3528 | n.b. | 0.3188 | 0.4353 | 0.6582 | n.b. |

Accession Numbers: CAA71403.1 (SIRPA v2); O00241.5 (SIRPB1 iso. 1); Q5TFQ8.1 (SIRPB1 iso. 3); NP_001271679.1 (cyno SIRPA); XP_005568598 (cyno SIRPB1);
n.b. = no binding Given the high sequence similarity between SIRPA proteins from multiple species, as shown in FIG. 1, anti-SIRPA antibody progeny clones were also screened for cross-reactivity against additional SIRPA antigens from various mammalian species. Fc-tagged marmoset SIRPA (accession no. JAB51896) or dog SIRPA (accession no. XP005634938) or rabbit SIRPA (accession no. G1U0I5) were coated onto plates and incubated with increasing concentrations of anti-SIRPA antibody hu3F9-14 and hu3F9-22. Both anti-SIRPA mAb 3F9-14 and mAb 3F9-22 recognized marmoset and dog SIRPA, though with lower affinity than that observed with human SIRPA. For example, EC50 values for 3F9-14 binding marmoset and dog SIRPA were 1.2 nM and 0.64 nM, respectively. Likewise, EC50 values for 3F9-22 binding marmoset and dog SIRPA were 4.3 nM and 0.83 nM, respectively. Neither anti-SIRPA antibody clone 3F9-14 nor 3F9-22 bound rabbit SIRPA.

Example 8: Affinity Matured Anti-SIRPA Antibodies Downregulate SIRPA and CD32A/B Previous experiments established that anti-SIRPA antibody m3F9 non-competitively antagonized CD47 binding to SIRPA by reducing SIRPA surface expression, which resulted in increased ability to stimulate engulfment of tumor cells by macrophages compared to CD47-blocking anti-SIRPA antibodies. Affinity matured anti-SIRPA antibodies were assayed for retention of similar functional properties to the murine antibody.

Since anti-SIRPA antibody m3F9 (on a mouse IgG1 backbone) downregulated SIRPA and CD32A/B in an Fc-dependent manner, chimeric antibodies were produced in which the Fab sequence of the parental anti-SIRPA antibody m3F9 was fused with the Fc domain of wild type human IgG1 (3F9 huIgG1) or human IgG1 Fc bearing S267E/L328F mutations (3F9-SELF) in the heavy chain. Fc SELF mutations enhance binding to human FcγR2B/CD32B >100-fold relative to wild type human IgG1 Fc. Human monocytes were isolated from peripheral blood of healthy donors and differentiated in vitro into macrophages with human M-CSF. Following differentiation, huMacs were harvested and seeded onto 96-well tissue culture plates with increasing concentration of isotype control or soluble anti-SIRPA antibodies and incubated overnight at 37° C. Cells were analyzed by flow cytometry for SIRPA and C32A/B surface expression using a DyLight650-conjugated anti-human SIRPA antibody (clone SA56) and FITC-labeled anti-CD32A/B (FUN-2). Consistent with previous observations, anti-SIRPA antibody 3F9 mIgG1 exhibited robust dose-dependent downregulation of both SIRPA and CD32A/B. However, the chimeric anti-SIRPA 3F9 huIgG1 antibody showed diminished potency in receptor downregulation compared to the murine antibody (data not shown). These results provided further evidence that the Fc domain of the antibody plays an important role in activity. Engineering the SELF mutations onto the Fc domain of chimeric 3F9 (3F9-SELF) restored the ability to downregulate SIRPA and CD32A/B to similar levels observed with anti-SIRPA antibody 3F9 mIgG1. This result confirms that CD32A/B serves as an important co-receptor for m3F9 activity on macrophages.

Earlier experiments revealed that humanized variants of anti-SIRPA antibody 3F9 grafted onto a human IgG4 backbone lost functional activity. Affinity matured anti-SIRPA antibody 3F9 variants were produced on a human IgG1 backbone and evaluated for their ability to downregulate SIRPA and CD32A/B in comparison to parental anti-SIRPA antibody m3F9 and chimeric anti-SIRPA antibody 3F9 huIgG1. SIRPA and CD32A/B expression was detected with anti-SIRPA DyLight650 (clone SA56) and anti-CD32A/B FITC (clone FUN2). The affinity matured antibodies 3F9-14, 3F9-18, 3F9-20, and 3F9-22 downregulated SIRPA to levels similar to that observed with the parental anti-SIRPA m3F9 antibody (data not shown). However, the same affinity matured anti-SIRPA antibodies only minimally improved CD32A/B downregulation compared to that observed with the chimeric anti-SIRPA 3F9 huIgG1 antibody. These results indicated that enhancing affinity of the antibody to the antigen compensates for the Fc-dependence on target receptor (i.e. SIRPA) downregulation but not for Fc-mediated interactions with FcγRs.

To determine if Fc engineering further enhances SIRPA downregulation by affinity matured anti-SIRPA antibodies, the SELF point mutations were introduced into the Fc domain of anti-SIRPA 3F9-22 huIgG1 antibody. Primary human macrophages from 4 healthy donors were treated overnight with increasing concentrations of humanized anti-SIRPA 3F9-22 antibody bearing wild type human IgG1 Fc or human IgG1 S267E/L328F Fc (SELF). SIRPA expression was detected with anti-SIRPA DyLight650 (clone SA56). Blood donors were genotyped for CD32A-R/H131 polymorphism by qPCR. FIGS. 8A and 8B illustrate typical results of these experiments comparing the activity of both Fc variants. Among individuals homozygous for the CD32A-H131 allele (donors 516 and 517 were verified by qPCR), both Fc variants of anti-SIRPA 3F9-22 antibody downregulated SIRPA to similar levels as that observed on human macrophages (FIG. 8B). This result indicated that enhanced binding to FcγR2B fails to enhance antibody-mediated SIRPA downregulation.

Among individuals heterozygous for both CD32A-H131 and -R131 alleles, anti-SIRPA 3F9-22 hIgG1 Fc variant showed greater maximal SIRPA downregulation than that observed with the SELF Fc variant (FIG. 8A). Rather than enhance SIRPA downregulation, SELF Fc may limit this function. Of note, the SELF mutations enhance Fc affinity towards CD32B as well as the CD32A-R131 allele. Given that human macrophages express greater levels of CD32A than CD32B, macrophages from individuals expressing CD32A-R131 may sequester anti-SIRPA antibody 3F9-22 away from either SIRPA or CD32B to limit maximal downregulation activity.

Table 15 below provides a summary of results of antibody-mediated downregulation of SIRPA and CD32 on the human macrophage line U937. In these studies, anti-SIRPA antibodies of the present disclosure were compared to a previously described anti-SIRPA antibody KWAR23 (disclosed in International Patent Application Publication No: WO2015/138600). As shown in Table 15, anti-SIRPA antibodies of the present disclosure down-regulated or reduced cell surface expression of SIRPA in U937 cells, with percent maximum down-regulation of between 68% and 76%. By comparison, anti-SIRPA antibody KWAR23 was only able to down-regulate cell surface expression of SIRPA by 9%.

Table 15 also shows that anti-SIRPA antibodies of the present disclosure were effective at down-regulating or reducing cell surface expression of CD32 in U937 cells. As shown in the table, anti-SIRPA antibodies of the present disclosure down-regulated or reduced CD32 cell surface expression in these cells with percent maximum down-regulation of between 49% and 73%

TABLE 15

| | SIRPA | | CD32 | |
|---|---|---|---|---|
| Antibody | IC50 (nM) | Max % DR | IC50 (nM) | Max % DR |
| 3F9 huIgG1 | 0.804 | 68% | 0.9807 | 49% |
| 3F9 mIgG1 | 0.105 | 75% | 0.005609 | 73% |
| 3F9-14 | 1.17 | 69% | 2.028 | 50% |
| 3F9-18 | 2.19 | 71% | 4.861 | 52% |
| 3F9-20 | 0.152 | 75% | 0.2706 | 58% |
| 3F9-22 | 0.187 | 76% | 0.4305 | 60% |
| KWAR23 | 15.52 | 9% | 0.07118 | 63% |

Example 9: Affinity Matured Anti-SIRPA Antibodies Degrade SIRPA in Macrophages

Figure 9A:
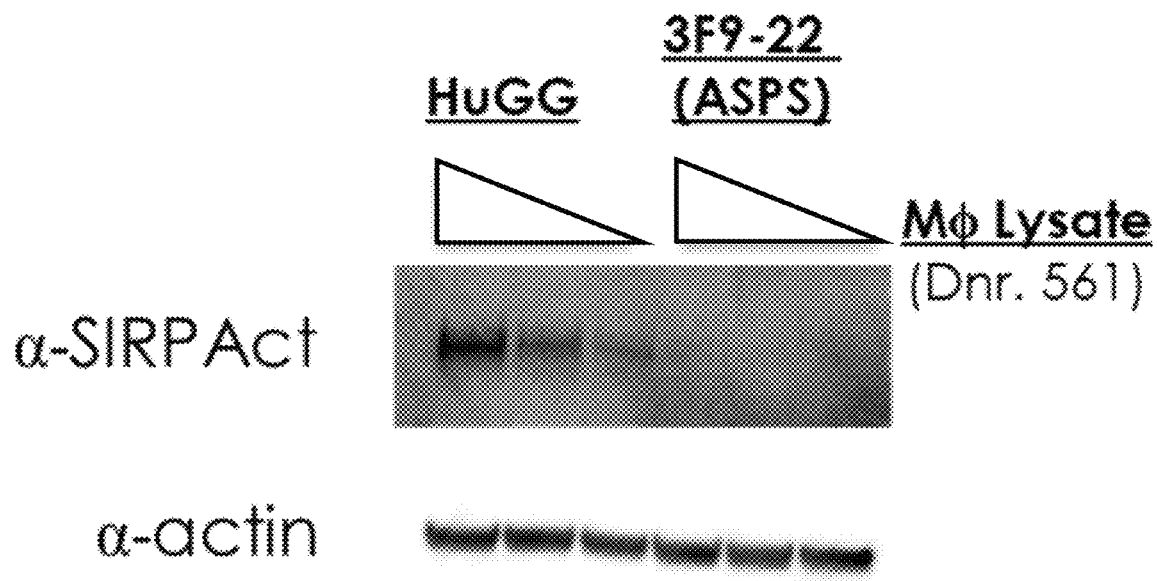
FIG. 9A-9B sets forth data showing antibody-mediated receptor downregulation lead to SIRPA degradation.
Figure 9B:
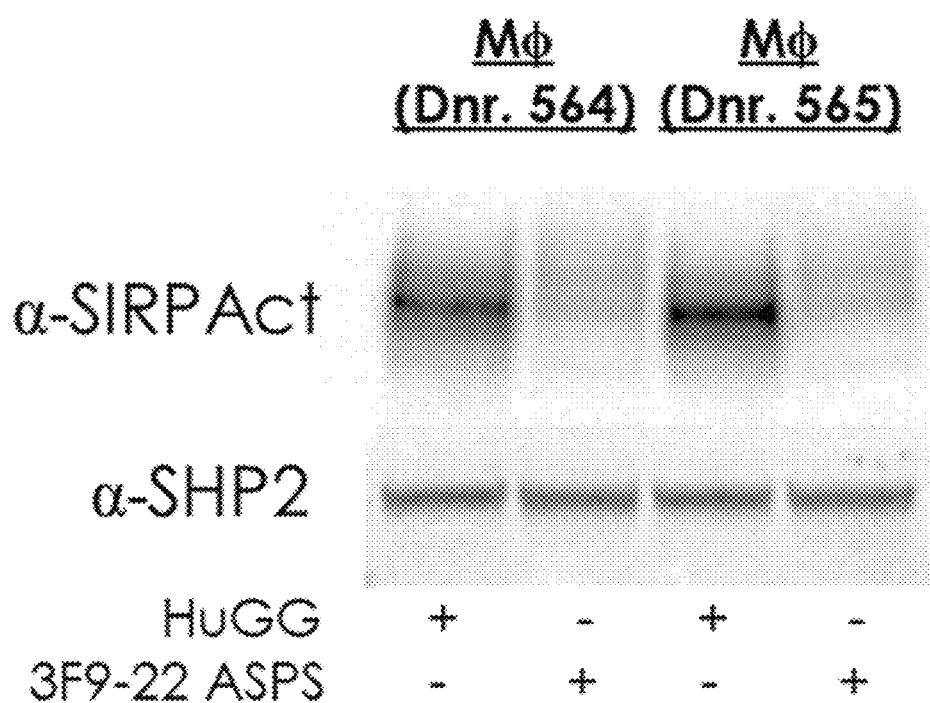

Measuring antibody-mediated receptor downregulation by FACS confirms that target engagement by the anti-SIRPA antibody decreases cell surface expression. To determine whether or not internalized receptors are degraded and not subsequently recycled to the cell surface, human macrophages were assayed for total SIRPA protein levels by western blotting as follows. Monocyte-derived primary human macrophages were treated overnight with 5 μg/ml of either isotype control or anti-SIRPA 3F9-22 A330S/P331S (ASPS) Fc variant. Cells were harvested, washed with cold PBS, and lysed with RIPA buffer supplemented with HALT protease/phosphatase inhibitors on ice for 15 minutes. Lysed cells were centrifuged to pellet membrane fraction and supernatant fraction encompassing total cell lysate was collected. As shown in FIG. 9A, increasing amounts of cell lysate fraction from isotype control antibody or anti-SIRPA antibody 3F9-22 treated macrophages were loaded onto SDS-PAGE and immunoblotted for SIRPA protein with an antigen-specific antibody. In FIG. 9A, 5 μg, 10 μg, and 20 g of whole cell lysate were loaded onto SDS-PAGE and immunoblotted with anti-SIRPA cytoplasmic domain (a-SIRPAct). A band migrating with the predicted molecular weight of SIRPA is detected in isotype control treated macrophages but not observed in anti-SIRPA 3F9-22 antibody treated macrophages. In a similar experiment, cell lysates from isotype control-treated or antibody 3F9-22 ASPS treated macrophages were loaded onto SDS-PAGE and immunoblotted for SIRPA and SHP-2, a tyrosine phosphatase which can associate with SIRPA and other ITIM receptors. In FIG. 9B, 20 μg of whole cell lysate were loaded onto SDS-PAGE and probed with a-SIRPAct and anti-SHP2. Blots demonstrates that SIRPA protein level decrease with mAb 3F9-22 treatment. As shown in FIG. 9B, anti-SIRPA antibody 3F9-22 stimulation leads to degradation of SIRPA but not of SHP2.

Example 10: Affinity Matured Anti-SIRPA Antibodies Stimulate Tumor Cell Phagocytosis in Macrophages Previous experiments verified that affinity matured anti-SIRPA antibodies retained the ability to downregulate SIRPA and CD32A/B, leading to the degradation of SIRPA in human macrophages. Affinity matured antibodies of the present invention were assayed for the ability to induce tumor cell phagocytosis. Primary human macrophages were treated overnight with isotype control or 3F9-22 human IgG1 or 3F9-22 SELF to assess Fc-dependent effect on antibody function. Raji cells labeled with pHrodo were mixed with macrophages and incubated for 2 hours at 37° C.

Phagocytic activity was measured by counting percent of CD14/pHrodo-double positive macrophages. Results are presented as the fold increase in percent population of pHrodo/CD14 double-positive macrophages. Additionally, CD14 expression levels following phagocytosis are shown. As shown in FIG. 10A, both Fc variants of anti-SIRPA antibody 3F9-22 enhanced Raji cell phagocytosis relative to isotype control-treated macrophages. Though antibody 3F9-22 SELF appeared to induce greater phagocytosis compared to antibody 3F9-22 huIgG1, this difference did not reach statistical significance. Additionally, both anti-SIRPA 3F9-22 Fc variants downregulated CD14 expression to similar levels, which indicated similar induction of phagocytic activity and macrophage activation status.

Figure 10B:
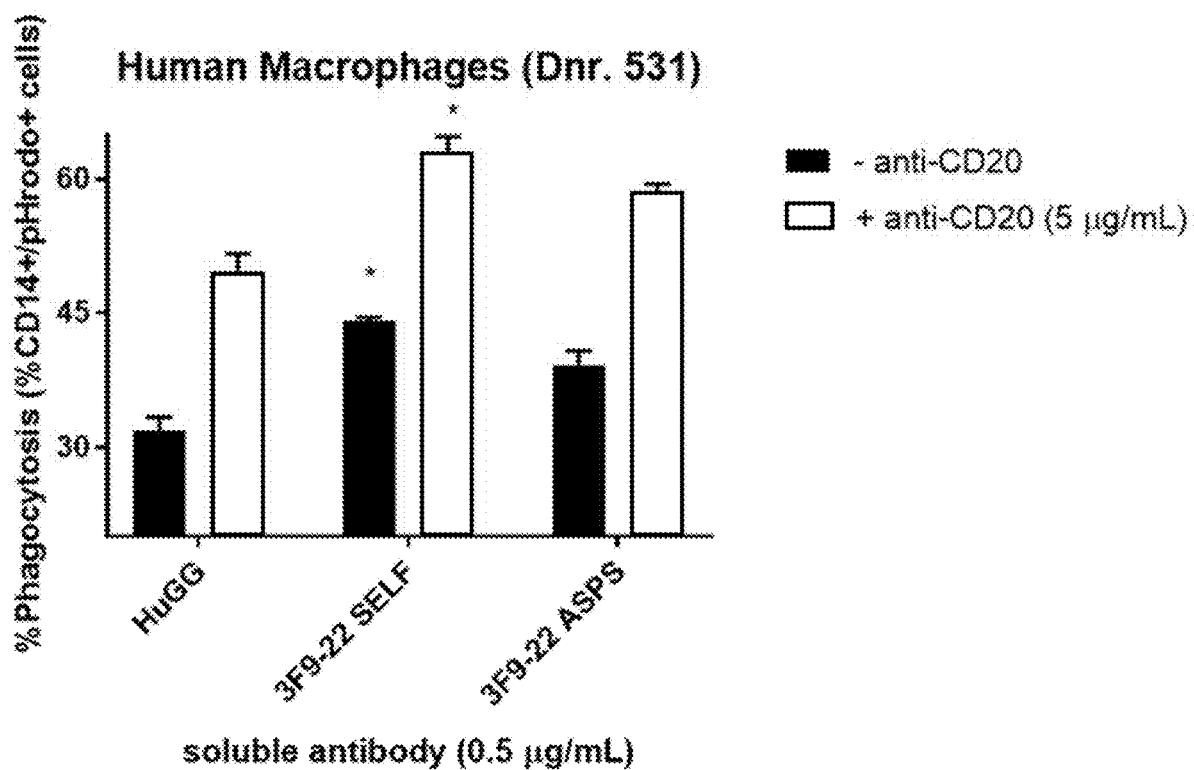

A hallmark of antagonizing the SIRPA-CD47 signaling axis is the enhancement of antibody-dependent phagocytosis of opsonized tumor cells. In FIG. 10B, the phagocytosis of Raji cells with or without the addition of opsonizing anti-CD20 huIgG1 was assessed on anti-SIRPA antibody 3F9-22 treated macrophages. In isotype control-treated macrophages, opsonizing Raji cells with anti-CD20 huIgG1 enhances phagocytosis of tumor cells ~50% compared to non-opsonized Raji cells. Results are presented as the percent population of pHrodo/CD14 double-positive macrophages. As previously shown, macrophages stimulated with either anti-SIRPA antibody 3F9-22 SELF or 3F9-22 ASPS enhanced phagocytosis of non-opsonized Raji cells by ~30-40% relative to isotype control treated macrophages. Similarly, anti-SIRPA antibody 3F9-22 treated macrophages enhanced phagocytosis ~30% relative to control-treated macrophages mixed with anti-CD20 opsonized Raji cells. Adding anti-CD20 opsonized Raji cells to anti-SIRPA antibody 3F9-22 treated macrophages showed an additive effect on phagocytosis with a ~2-fold increase relative to that observed with control-treated macrophages mixed with non-opsonized Raji cells. Though both Fc variants of antibody 3F9-22 induced tumor cell phagocytosis, the SELF Fc variant exhibited statistically significant greater phagocytic activity than the ASPS Fc variant. These results confirmed that affinity matured anti-SIRPA antibodies of the present disclosure enhanced tumor cell phagocytosis in macrophages by antagonizing the SIRPA-CD47 pathway.

Table 16 below provides a summary of IC50 values determined for antibody-mediated downregulation of SIRPA and CD32 in human primary macrophages. Additionally, Table 16 shows the fold-increase in phagocytosis associated with various anti-SIRPA antibodies of the present disclosure in human primary macrophages. In these studies, anti-SIRPA antibodies of the present invention were compared to a previously described anti-SIRPA antibody HEFLB (disclosed in International Patent Application Publication No: WO2017/178653). As shown in Table 16, the anti-SIRPA affinity-matured antibodies of the present disclosure have lower IC50 values compared to that observed with anti-SIRPA 3F9 huIgG1 antibody. Additionally, anti-SIRPA antibodies 3F9-14, 3F9-18, 3F9-20, and 3F9-22 showed lower IC50 values than anti-SIRPA antibody HEFLB. Similarly, anti-SIRPA antibodies of the present disclosure showed better phagocytosis activity compared to anti-SIRPA antibody HEFLB.

TABLE 16

| Antibody | SIRPA IC50 (nM) | SIRPA Max % DR | CD32 IC50 (nM) | CD32 Max % DR | Phagocytosis* |
|---|---|---|---|---|---|
| 3F9 huIgG1 | 0.1722 | 90% | 0.679 | 67% | 1.77 |
| 3F9 mIgG1 | 0.00905 | 89 | 0.0623 | 82% | 1.51 |
| 3F9-14 | 0.0372 | 89% | 0.135 | 62% | 1.56 |
| 3F9-18 | 0.0174 | 90% | 0.0915 | 65% | 1.52 |
| 3F9-20 | 0.0283 | 90% | 0.114 | 66% | 1.62 |
| 3F9-22 | 0.0542 | 91% | 0.133 | 66% | 1.68 |
| OSE HEFLB | 0.0959 | 13% | n.d. | n.d. | 1.05 | n.d. = not determined,
*fold increase over baseline activity

Example 11: Affinity Matured Anti-SIRPA Antibodies Stimulate Tumor Cell Phagocytosis in M1 and M2 Macrophages Macrophages undergo profound phenotypic transformation in response to microenvironmental cues acquiring distinct pro-inflammatory (M1) or anti-inflammatory (M2) phenotypes. Anti-SIRPA antibodies of the present disclosure were evaluated for their ability to induce tumor cell phagocytosis in homeostatic (M2-like) macrophages and inflammatory (M1-like) macrophages. Monocytes were isolated from blood of healthy volunteers using density-gradient centrifugation over Ficoll. M1-like and M2-like macrophages were generated by culturing monocytes in the presence of GM-CSF (800 U/ml; Peprotech) or M-CSF (25 ng/ml; Peprotech) for 6 days. Polarized macrophages were treated overnight with isotype control antibody or anti-SIRPA antibody 3F9-22 Fc variants. Fluorescent-labeled Raji cells with or without opsonizing anti-CD20 huIgG1 were mixed with macrophages for 2 hours at 37° C. Alternatively, Raji cells were opsonized with either anti-CD47 IgG4 (clone hu5F9) alone or with anti-CD47 and anti-CD20 huIgG1 and added to untreated macrophages. Phagocytic activity was measured by counting percent of CD14/pHrodo-double positive macrophages.

Figure 11A:
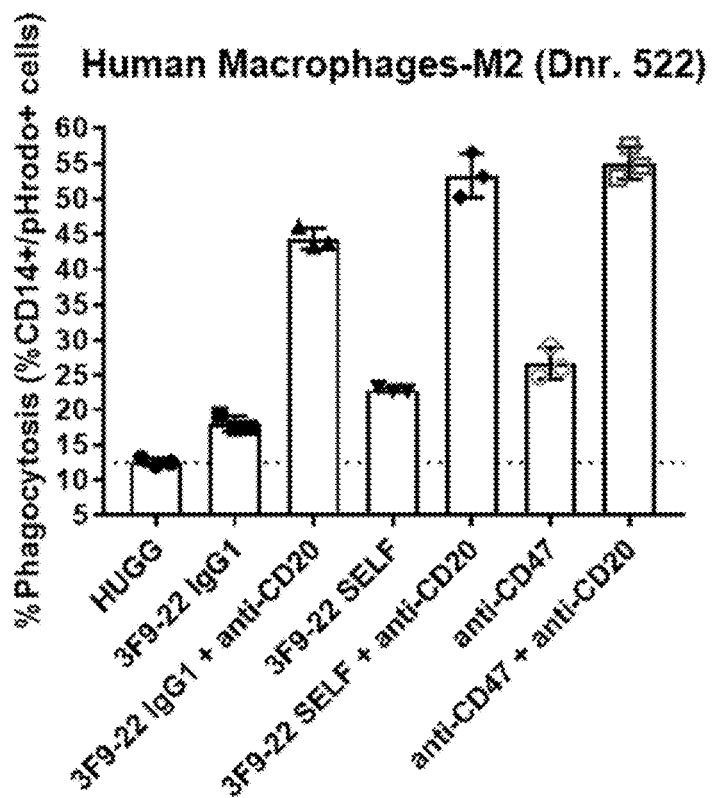
FIG. 11A-11B sets forth data comparing the phagocytic activity of different Fc variants of anti-SIRPA 3F9-22 antibody relative to anti-CD47 on M1 (FIG. 11B) and M2 (FIG. 11A) macrophages.

As shown in FIG. 11A, both Fc variants of antibody 3F9-22-treated M2-like macrophages enhanced tumor cell phagocytosis relative to control-treated macrophages. Consistent with previous observations, the SELF Fc variant antibody showed a statistically significant greater increase in phagocytosis of non-opsonized and opsonized Raji cells compared to antibody 3F9-22 huIgG1. Furthermore, anti-SIRPA antibody 3F9-22 SELF treated M2-like macrophages enhanced phagocytosis of non-opsonized and opsonized Raji cells to a similar extent as anti-CD47 IgG4 treated Raji cells.

Figure 11B:
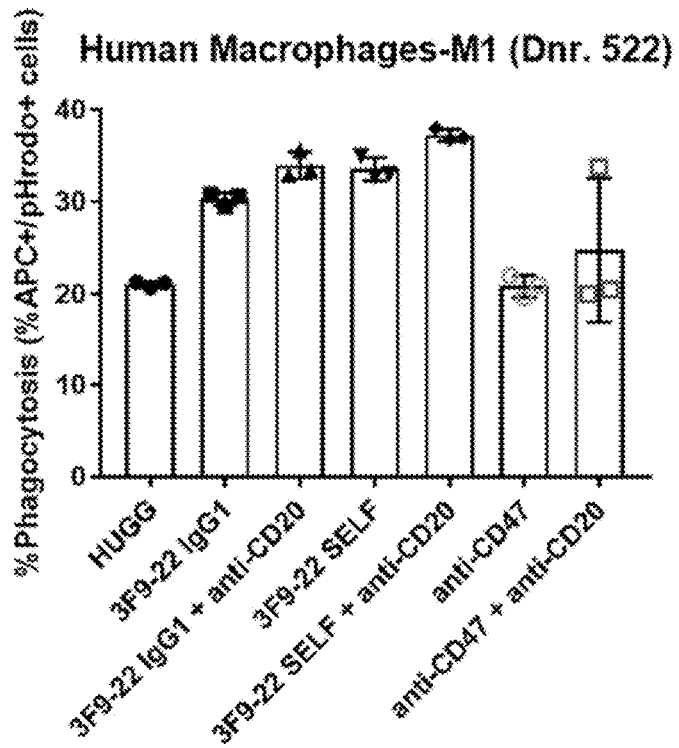

M1-like macrophages differentiated from monocytes cultured in the presence of GM-CSF have different properties than MCSF-derived M2-like macrophages. For example, GM-CSF-derived M1-like macrophages decrease expression of CD14, CD32A/B, and SIRPA. Additionally, M1-like macrophages appear to phagocytose non-opsonized Raji cells at higher rate than M2-like macrophages (FIG. 11B) derived from the same healthy donor. Upon stimulation with either anti-SIRPA antibody 3F9-22 Fc variants, M1-like macrophages increased phagocytosis of non-opsonized Raji cells ~50% relative to control-treated macrophages. Opsonization of Raji cells with anti-CD20 huIgG1 fails to show an additive effect on phagocytosis by antibody 3F9-22 treated M1-like macrophages, which contrasts with observations made with M2-like macrophages. Similarly, Raji cells opsonized with anti-CD47 IgG4 with or without anti-CD20 huIgG1 also failed to increase phagocytosis above baseline levels when added to M1-like macrophages (FIG. 11B). Since GM-CSF-derived macrophages downregulated FcgR expression, these cells may possess a lower potential to mediate antibody-dependent phagocytosis. These results also suggested that anti-SIRPA antibody 3F9-22 functions by antagonizing SIRPA to induce phagocytosis in both M1 and M2 macrophages, whereas anti-CD47 antibodies function primarily as opsonizing agents that require engagement of FcgRs on M2-like macrophages to induce phagocytosis.

Example 12: Combination Therapies Enhance the Anti-Tumor Activity of Affinity Matured Anti-SIRPA Antibodies A small subset of cancer cells, termed tumor-initiating cells (TICs) or cancer stem cells (CSCs), form a reservoir of self-sustaining cancer cells which have the ability to self-renew and maintain the tumor bulk. Evidence suggests that human solid tumor cells and CSCs upregulate CD47 expression to evade immune surveillance mechanisms permitting tumor cell proliferation and metastasis. Tumorsphere cultivation models, in which cancer cells grow as three-dimensional spheroid cell clusters, are widely used to analyze the self-renewal capability of CSCs and to better simulate in vivo cellular growth conditions. Tumorsphere formation is based on culturing cancer cells onto ultralow-attachment plates in serum-free media supplemented with growth factors, such as epidermal growth factor and basic fibroblast growth factor. Co-culturing tumorspheres with primary human macrophages allows for the assessment of anti-SIRPA antibodies on tumor cell viability either as a single agent or in combination with other anti-tumor therapies.

MDA-MB-231 cell line is a well-characterized human triple-negative breast cancer cell line previously shown to form tumorspheres. In order to measure tumor cell viability in co-culture assays, MDA-MB-231 cells were transduced with a lentivirus for the constitutive expression of luciferase and GFP (MB231-Luc). For tumorsphere formation, 10,000 MB231-Luc cells per well were seeded onto 96-well plates in StemXVivo Serum-Free Tumorsphere Media (R&D Systems) supplemented with heparin and hydrocortisone. Tumorsphere media was also supplemented with MCSF to support macrophage viability. MB231-Luc were cultured for 2-3 days either alone or in the presence of 50,000 macrophages/well. Tumor cell viability was quantified by measuring luciferase activity with OneGlo Reagent (Promega) added to each well and incubating the sample for 3 min at room temperature on a plate shaker. The luminescence signal was detected with a BioTek Synergy™ Microplate Reader using GEN5™ 2.04 software.

Figure 12A:
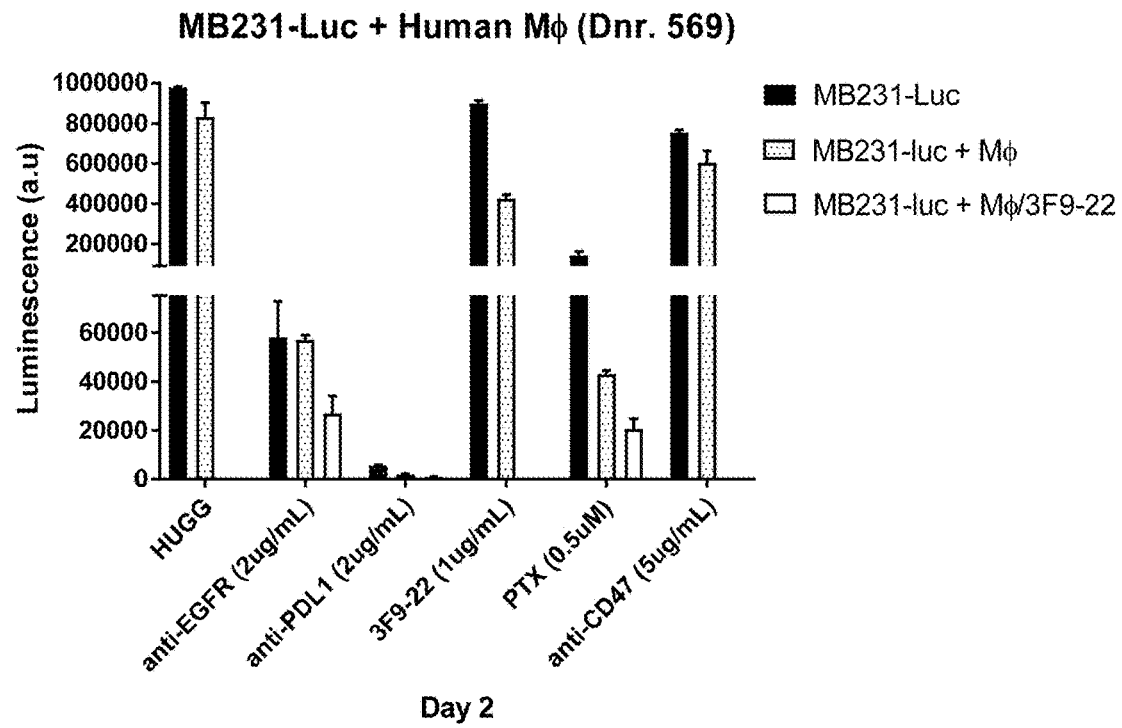
FIG. 12A and FIG. 12B set forth data showing anti-SIRPA antibody 3F9-22-treated macrophages reduced solid tumor cell viability in vitro.

MDA-MB-231 breast cancer cells constitutively expressing luciferase were cultured either alone or in the presence of human macrophages in serum-free tumorsphere media supplemented with MCSF. Cells were treated for 2 days at 37° C. with anti-EGFR (2 µg/mL), anti-PDL1 (2 µg/mL), or paclitaxel (0.5 µM) with or without anti-SIRPA antibody 3F9-22. As a comparison, tumor cells alone or in the presence of macrophages were treated with anti-CD47 IgG4. Tumor cell viability was quantified my measuring luciferase activity with OneGlo substrate reagent. As shown in FIG. 12A, MB231-Luc cells proliferated in culture with or without macrophages based on luminescence values. Anti-SIRPA antibody 3F9-22 only inhibited tumor cell viability when MB231-Luc cells formed tumorspheres in the presence of macrophages. This result demonstrated that macrophages retain tumoricidal potential under cultivation conditions optimized for tumor viability. Under similar conditions, anti-CD47 IgG4 did not significantly inhibit MB231-Luc viability.

After verifying single agent efficacy of anti-SIRPA antibody 3F9-22 in this tumorsphere viability assay, additional studies were performed to show the effect of combinatorial treatment. Since tumor cell viability relies on EGF present in the media, adding anti-EGFR blocking antibody showed profound inhibition of tumor growth when MB231-Luc cells are cultured alone. The anti-tumor activity of anti-EGFR antibody is not enhanced in the presence of untreated macrophages. However, anti-SIRPA antibody 3F9-22-treated macrophages potentiated the anti-tumor activity of anti-EGFR antibody to a statistically significant extent. Under similar culture conditions, the anti-PDL1 antibody revealed an unexpected phenotype by inducing robust tumor cell apoptosis, irrespective of the presence of macrophages. MB231-Luc cell viability was also reduced when exposed to 500 nM of paclitaxel, a microtubule-stabilizing chemotherapeutic agent commonly used to treat multiple cancers. Combining paclitaxel with anti-SIRPA antibody 3F9-22-treated macrophages also shows a statistically significant reduction in tumor cell viability. These results demonstrated that anti-SIRPA antibodies of the present disclosure enhanced the activity of anti-tumor therapies that function by various mechanisms of action beyond tumor cell opsonization.

Figure 12B:
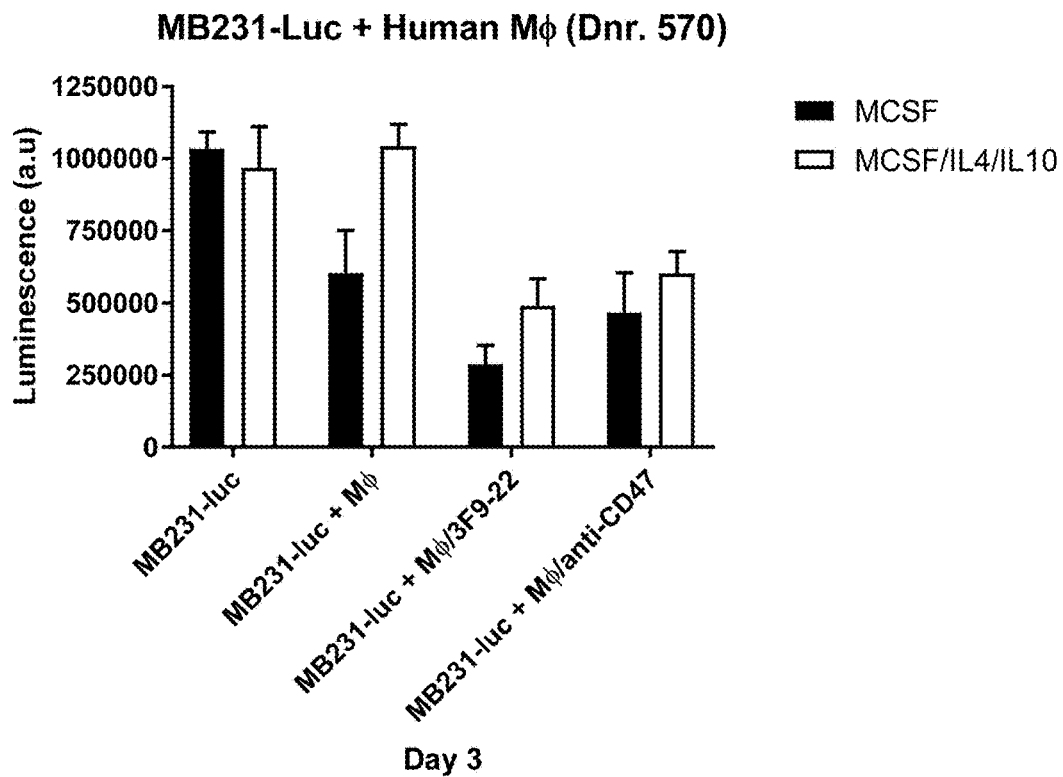

MDA-MB-231 breast cancer cells constitutively expressing luciferase were cultured either alone or in the presence of human macrophages in serum-free tumorsphere media supplemented with MCSF or MCSF+IL-4+IL-10. Where indicated, cells treated with either anti-SIRPA antibody 3F9-22 or anti-CD47 IgG4 for 3 days at 37° C. Tumor cell viability was quantified my measuring luminescence values following the addition with OneGlo reagent containing luciferase substrate. On occasion, monocyte-derived macrophages from healthy volunteers co-cultured with MB231-Luc cells inhibit tumor cell viability without treatment (FIG. 12B). To ensure that macrophages co-cultured with MB231-Luc cells adopt a more tumor-like, immunosuppressive phenotype, the tumorsphere media was supplemented with IL-4 and IL-10. As shown in FIG. 12B, MB231-Luc cells cultured alone proliferated equally well in media supplemented with MCSF or MCSF plus IL-4 and IL-10. However, in media only supplemented with MCSF, macrophages from donor 570 reduced tumor cell viability to a statistically significant extent. This inhibition is reversed by the addition of IL-4 and IL-10 demonstrating that different cultivation strategies polarize macrophages to modulate tumor cell growth. Importantly, anti-SIRPA antibody 3F9-22 treatment of macrophages significantly decreased tumor cell viability under both growth conditions.

Example 13: Affinity Matured Anti-SIRPA Antibodies Enhance T Cell Proliferation

T cells form an immunological synapse with antigen presenting cells (APC) to initiate T cell activation and proliferation. CD47 expression on T cells may counter activation by transmitting an inhibitory signal to APCs through SIRPA. However, T cells also express SIRPG, another member of the SIRP family capable of binding CD47 expressed on APCs. The SIRPG (T cells)-CD47 (APC) interaction has been shown to stabilize the immunological synapse and promote T cell activation and proliferation. Though anti-CD47 antibodies block the inhibitory signal delivered through SIRPA, anti-CD47 antibodies also block the stimulatory effect from SIRPG binding, and thus, may prove deleterious in mounting an effective anti-tumor T cell response. Antagonistic anti-SIRPA antibodies, therefore, avoid this potential drawback by inhibiting SIRPA signaling without disrupting critical interactions in the immunological synapse. To test this hypothesis, anti-SIRPA antibodies were evaluated in one-way and two-way MLR assays.

The principle of an MLR assay is that APC derived from one donor, usually DCs, present peptides on MHC molecules to T cells isolated from a separate donor. A small fraction of T cells will express TCRs capable of recognizing the MHC:peptide complex and proliferate upon costimulation. In this one-way MLR, cells from one donor participate in antigen presentation and cells from another donor respond by proliferating. In a two-way MLR, both donors contribute APCs and T cells to the reaction; thus, two separate T cell populations respond by proliferating.

Figure 13A:
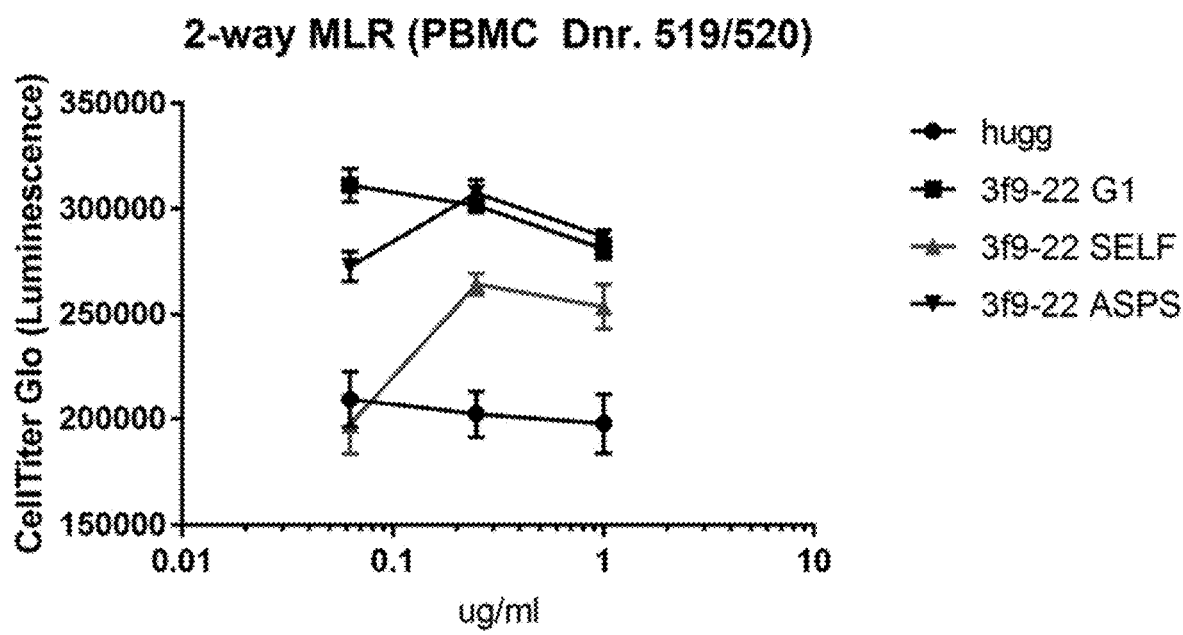
FIG. 13A sets forth data comparing enhancement of T cell proliferation by different Fc variants of anti-SIRPA antibody 3F9-22 in a 2-way MLR assay.

The effect of anti-SIRPA antibodies on T cell proliferation was initially assessed in two-way MLR assays. PBMCs were isolated from healthy donors and co-cultured for 3 days in the presence of increasing concentrations of 3F9-22 Fc variants or isotype control. T cell proliferation was estimated by quantifying the presence of metabolically active cells as an indicator of cell number. Metabolic activity was quantified with CellTiter Glo reagent (Promega), which generates a luminescent signal proportional to the amount of ATP present. As shown in FIG. 13A, anti-SIRPA antibody 3F9-22-treated PBMCs showed ~1.5-fold increase in luminescence relative to isotype-treated PBMCs, which suggested an increase in T cell proliferation. In contrast to the phagocytosis assays described previously, antibody 3F9-22 huIgG1 Fc variant trended to stimulate T cell proliferation more effectively than SELF Fc variant.

Figure 13B:
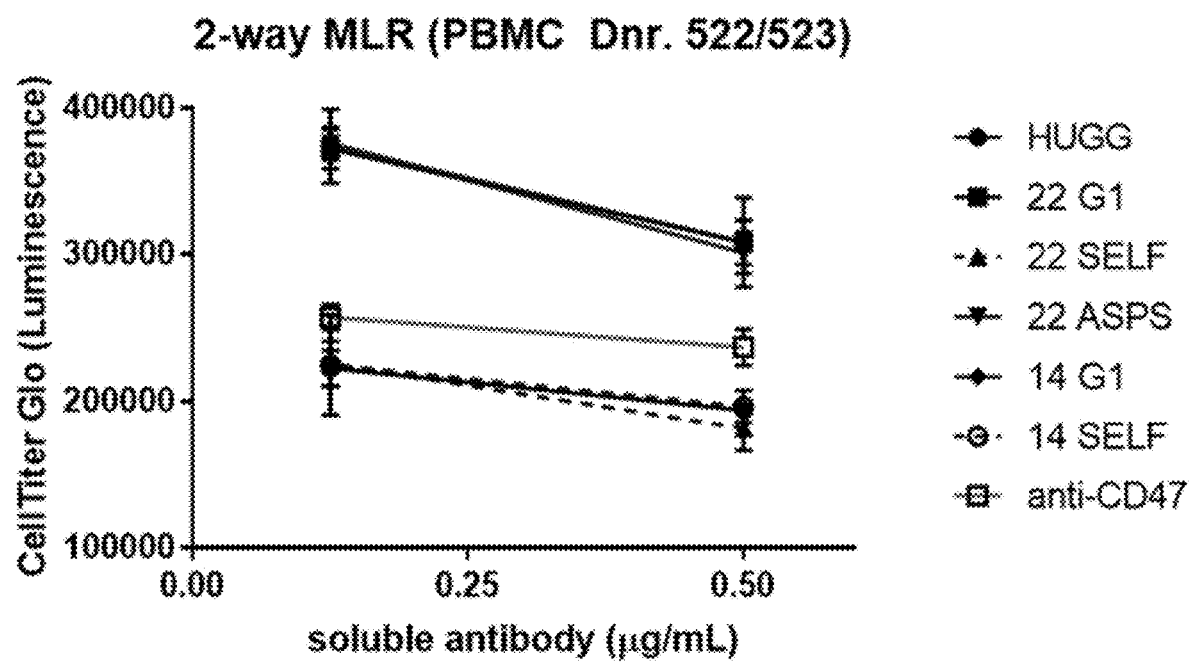
FIG. 13B sets forth data comparing enhancement of T cell proliferation by different Fc variants of anti-SIRPA antibody 3F9-22 and anti-SIRPA antibody 3F9-14 relative to anti-CD47 IgG4 in a 2-way MLR assay.

To determine whether increased luminescence observed with anti-SIRPA antibody 3F9-22 is specific for anti-SIRPA antibodies, the two-way MLR assay was repeated with anti-CD47 antibody. PBMCs from two healthy donors were isolated and 100,000 cells from each donor were mixed together with increasing concentrations of test antibody or isotype control antibody. Cell proliferation was measured with CellTiter Glo reagent after 3 days of co-culture. As shown in FIG. 13B, anti-SIRPA antibodies 3F9-14 and 3F9-22 huIgG1 and ASPS Fc variants increased luminescence signal ~70% relative to that observed with isotype-control antibody treated PBMCs. Anti-SIRPA antibodies on a SELF Fc (3F9-14 SELF and 3F9-22 SELF) failed to increase luminescence signal relative to control under the same conditions establishing another Fc-dependent effect on antibody function. In contrast to antibody 3F9-22 huIgG1, anti-CD47 treatment showed a marginal increase ~10% in luminescence. Taken together, the results from two-way MLR experiments suggested that antagonizing SIRPA with anti-SIRPA antibody 3F9-22 huIgG1 promotes T cell proliferation.

Figure 14A:
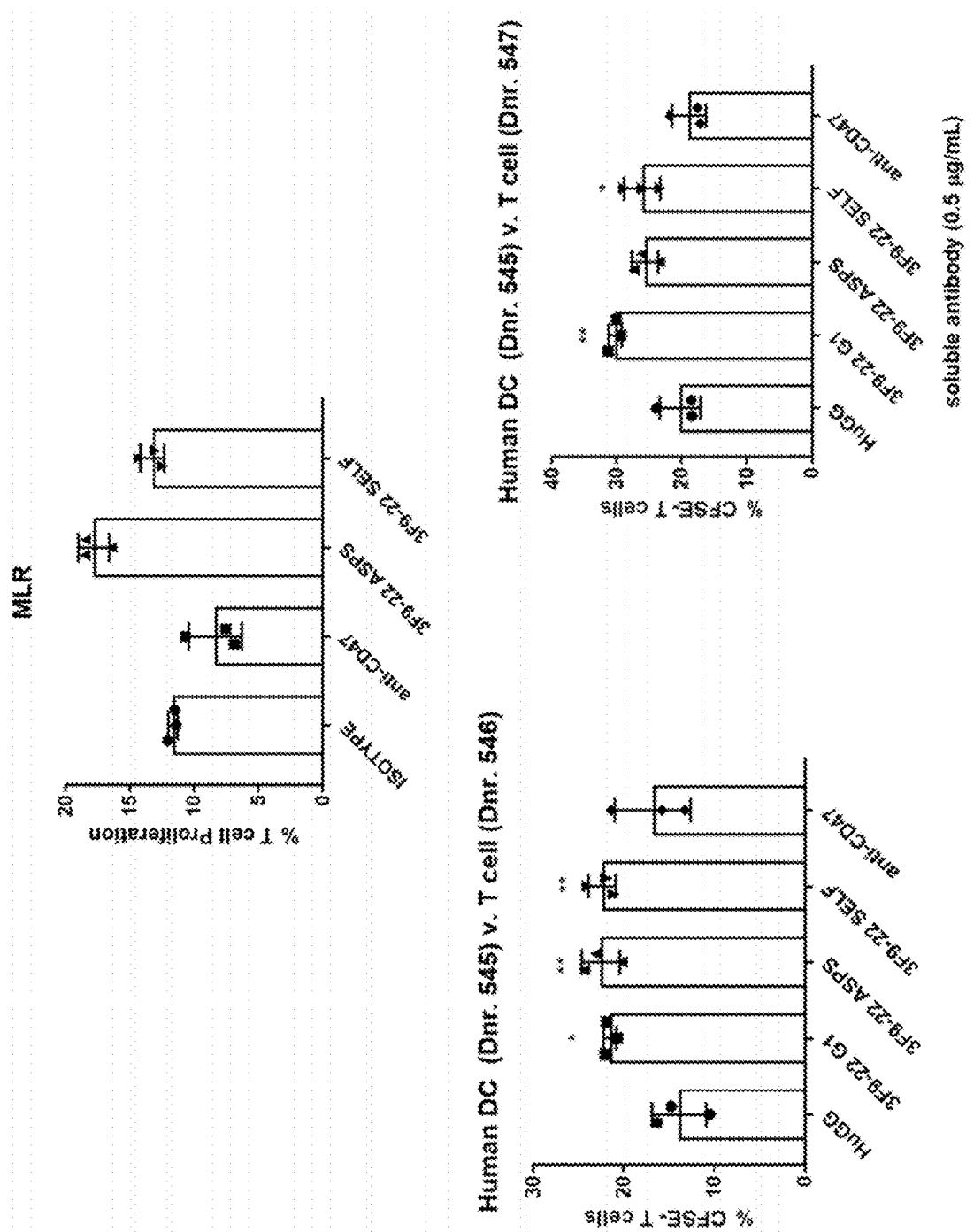
FIG. 14A sets forth data comparing enhancement of T cell proliferation by different Fc variants of anti-SIRPA antibody 3F9-22 relative to anti-CD47 IgG4 in a 1-way MLR assay.
Figure 14B:
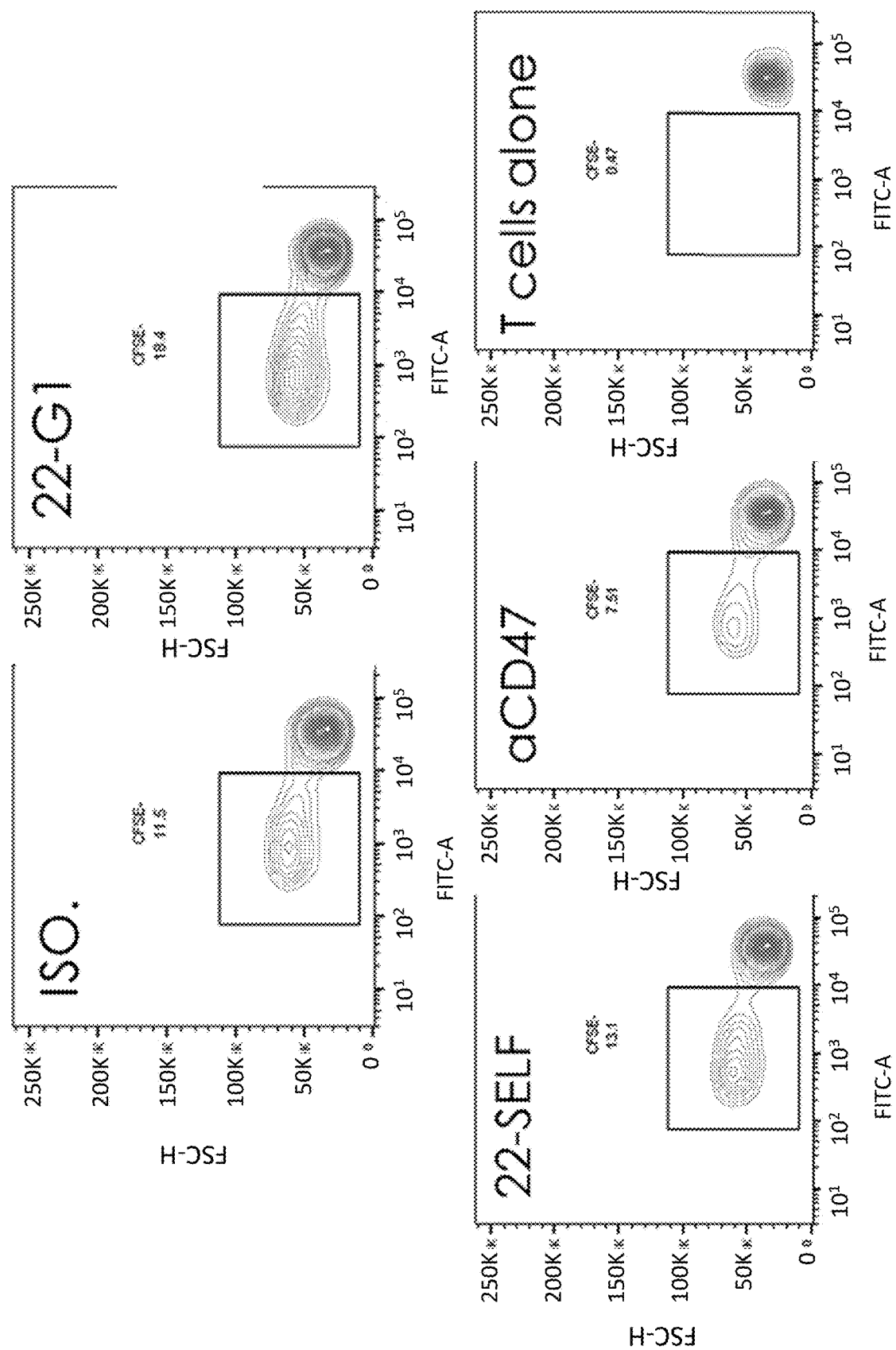
FIG. 14B shows representative FACS plot from 1-way MLR assay.

Since quantifying metabolic activity in two-way MLR is an indirect measurement of T cell proliferation, more traditional one-way MLR assays were performed to confirm the stimulatory effect observed with anti-SIRPA antibody 3F9-22 huIgG1. Primary human dendritic cells (DCs) were derived from monocytes of healthy donors and co-cultured with allogeneic T cells labeled with CFSE dye in a 1:5 ratio. Dendritic cells were treated with either anti-SIRPA antibody 3F9-22 Fc variants or anti-CD47 (hu5F9) or isotype control antibody and incubated at 37° C. for 5 days. T cell proliferation was measured by staining T cells with anti-CD3 APC and gating on CFSE-low population. FIG. 14A shows that DCs from different donors treated with antibody 3F9-22 huIgG1 or ASPS increased T cell proliferation by ~50% relative to either isotype or anti-CD47 treated DCs. This increase in T cell proliferation is proportional to the increase in luminescence observed with antibody 3F9-22 huIgG1 treated PBMCs in the two-way MLR. FIG. 14B shows a representative FACS plot for the data presented in FIG. 14A. The results from one-way and two-way MLR thus suggested that antagonizing SIRPA with anti-SIRPA antibody 3F9-22 huIgG1 without blocking the SIRPG-CD47 interaction can promote T cell proliferation.

Figure 15A:
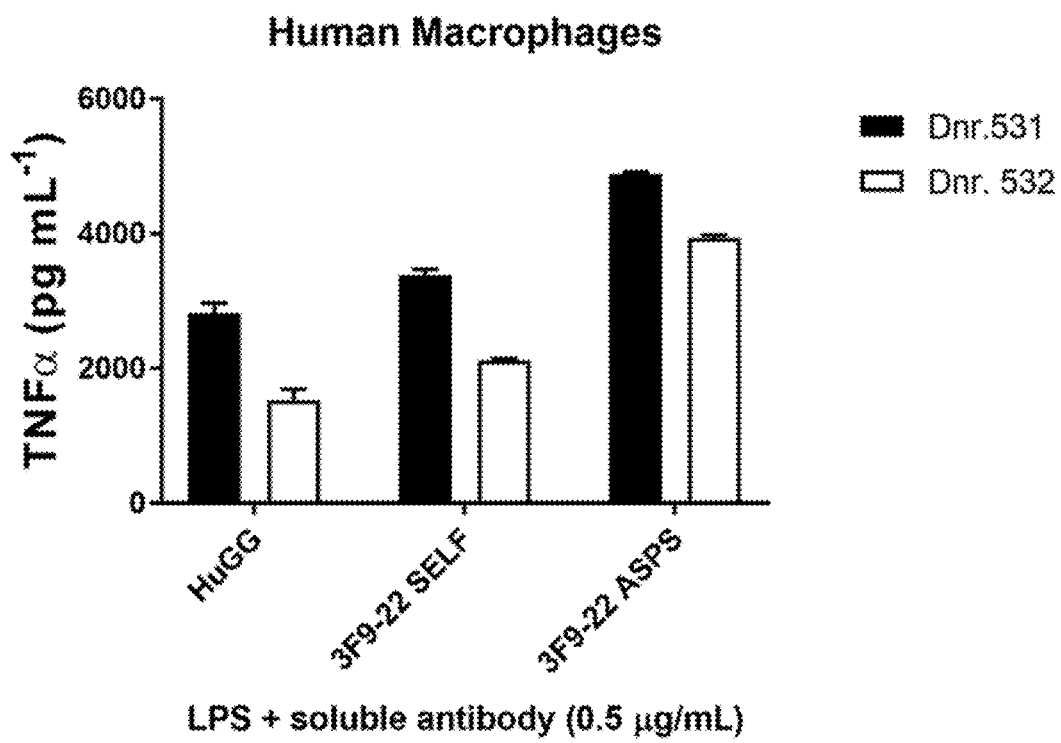
FIG. 15A and FIG. 15B set forth data comparing enhancement of TNF release by different Fc variants of anti-SIRPA antibody 3F9-22 by LPS-primed macrophages.
Figure 15B:
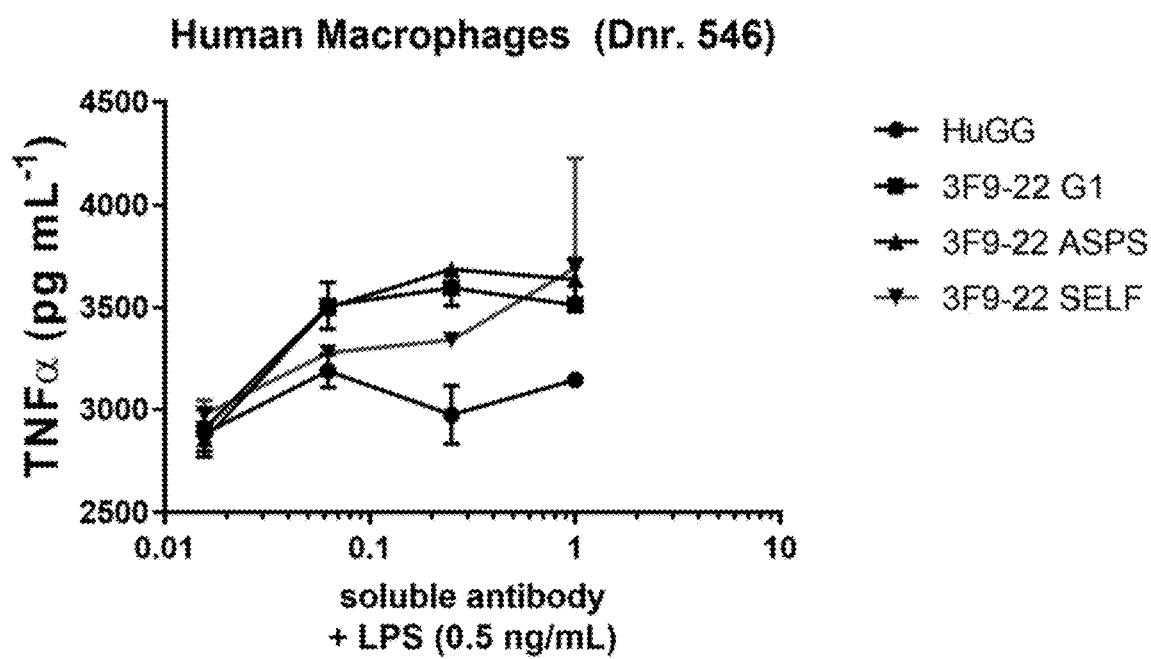

Example 14: Affinity Matured Anti-SIRPA Antibodies Enhance Pro-Inflammatory Cytokine Release To further differentiate the activity of anti-SIRPA antibody 3F9-22 Fc variants, primary human macrophages from two healthy volunteers were stimulated overnight with lose dose LPS in combination with anti-SIRPA antibody 3F9-22 or isotype control antibody. In FIG. 15A, primary human macrophages from 2 healthy donors were stimulated overnight at 37° C. with 0.5 ng/mL of LPS in combination with either anti-SIRPA antibody 3F9-22 Fc variant or isotype control antibody. Supernatant fractions were collected and analyzed for TNFα levels by ELISA. In FIG. 15B, primary human macrophages were stimulated overnight at 37° C. with 0.5 ng/mL of LPS in combination with either increasing concentrations of anti-SIRPA antibody 3F9-22 Fc variant or isotype control antibody. The supernatant fraction was collected and analyzed by ELISA for TNFα release. As shown in FIG. 15A and FIG. 15B, macrophages co-stimulated with antibody 3F9-22 ASPS exhibited a significant increase in TNFα secretion relative to either isotype control antibody or antibody 3F9-22 SELF co-stimulated cells. The antibody 3F9-22 SELF Fc variant showed minimal co-stimulatory activity. Titrating the anti-SIRPA antibodies showed a similar pattern where antibody 3F9-22 huIgG1 and ASPS variants clearly augmented TNFα release in a dose-dependent manner by LPS-primed macrophages, whereas antibody 3F9-22 SELF shows a diminished TNFα response with high variability. These results demonstrated that non-CD47-blocking anti-SIRPA antibodies antagonize SIRPA in an Fc-dependent manner to release the inhibition from ITIM signaling.

Example 15: Epitope Mapping of Anti-SIRPA Antibody Binding Sites

Epitope mapping of anti-SIRPA antibodies was performed using an alanine-scanning library created by shotgun mutagenesis of the human SIRPA cDNA sequence. A SIRPA expression construct encoding a C-terminal V5 epitope tag was subjected to high-throughput alanine scanning mutagenesis (outlined in Davidson and Doranz, 2014 Immunology 143, 13-20) to generate a comprehensive mutation library. Each of the residues representing the SIRPA extracellular domain (amino acids 31-374 of SEQ ID NO:1) was mutated, most to alanine, while alanine codons were mutated to serine.

The SIRPA mutant library clones, arrayed in a 384-well microplate, were transfected individually into HEK-293T cells and allowed to express for 22 hours. Antibodies were digested to generate Fabs, after which cells were incubated with Fabs diluted in 10% normal goat serum (NGS) (Sigma-Aldrich, St. Louis, MO). Prior to library screening, primary Fab concentrations were determined using an independent immunofluorescence titration curve against cells expressing wild type SIRPA to ensure that signals were within the linear range of detection. Fabs were detected using 7.5 µg/ml AlexaFluor488-conjugated secondary antibody (Jackson ImmunoResearch Laboratories, Westgrove, PA) in 10% NGS. Cells were washed twice with PBS and resuspended in Cellstripper (Cellgro, Manassas, VA) with 0.1% BSA (Sigma-Aldrich, St. Louis, MO). In some cases, higher stringency conditions were used, including increased pH, increased temperature, and increased dissociation time. Mean cellular fluorescence was detected using the Intellicyt high throughput flow cytometer (HTFC, Intellicyt, Albuquerque, NM). Fab reactivities against each mutant clone were calculated relative to wild-type SIRPA protein reactivity by subtracting the signal from mock-transfected controls, and normalizing to the signal from wild-type SIRPA transfected controls.

Mutated residues within library clones were identified as "critical" to the Fab binding epitope if they did not support reactivity of the test Fab but did support reactivity of commercially available reference antibody, MAB4546 (R&D Systems), or additional anti-SIRPA Fabs. This counter-screen strategy facilitated the exclusion of SIRPA mutants that were locally misfolded or that had an expression defect.

Anti-SIRPA antibody 9C2 is described in International Patent Application No. PCT/US2017/65366.

```
mAb 9C2: Heavy chain variable domain sequence
                                       (SEQ ID NO: 45)
EFQLQQSGAELVKPGASVKISCKASGYSLTGYNMNWVKQSRGKSLEWIGN

INPHYGSSTYNQNFKDKATLTVDKSSSAAYMQFNSLTSEDSAVYYCAREG

YDGVFDYWGQGTTLTVSS mAb 9C2: Light chain variable domain sequence
                                       (SEQ ID NO: 46)
QIVLSQSPAILSASPGEKVTMTCRASSSVSYMHWYQQKPGSSPKPWIYVT

SNLASGVPTRFSGSGSGTSYSLTISRVEAEDAATYYCQQWSSNPRTFGGG

TKLEIK
```

Figure 16:
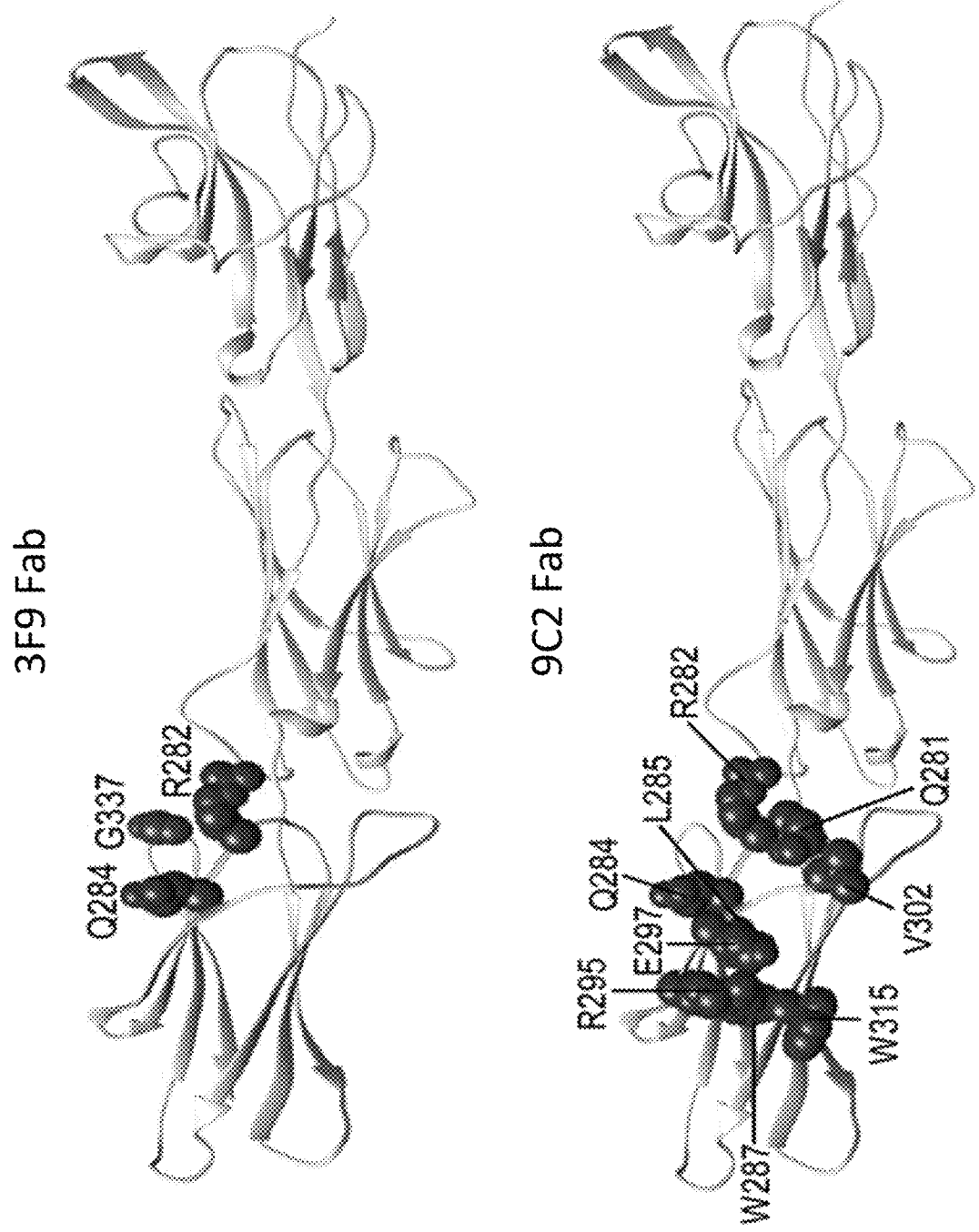
FIG. 16 sets forth data showing the identification and visualization of "critical" residues for anti-SIRPA antibodies in a model of human SIRPA.

Table 17 below depicts the mean binding reactivities and ranges for all residues identified as critical in the screens. Primary critical residues were defined as residues where mutations were negative for test antibody binding (<30% of binding to WT) but positive for the control antibody (>80% WT). FIG. 16 depicts crystal structure models of SIRPA (PDB ID 2WNG; Hatherley et al., 2009, *J Biol Chem*, 284:26613-9) highlighting the critical residues for binding anti-SIRPA antibodies 3F9 and 9C2 as shaded spheres.

As indicated in Table 18, critical SIRPA residues involved in binding by anti-SIRPA antibody 3F9 include amino acid residues R282, Q284, and G337 of the human SIRPA v1 sequence shown above. The critical SIRPA residues involved in binding by antibody 9C2 (as disclosed in International Patent Application No. PCT/US2017/65366) include amino acid residues Q281, R282, Q284, L285, W287, R295, E297, V302, and W315 of the human SIRPA v1 sequence disclosed above. These residues lie within the membrane-proximal Ig domain of SIRPA, referred to in the SIRPA scientific literature as the D3 domain, which correspond to amino acids 254-348 of the human SIRPA v1 sequence. Multiple published reports demonstrate that the D3 domain of human SIRPA binds to pattern recognition molecules in the collectin family, namely surfactant proteins D and A (Sp-D and Sp-A, respectively).

TABLE 17

Critical Residues for Binding of 3F9 and 9C2
Binding Reactivity (% WT)

| Mutation | 3F9 Fab | 9C2 Fab |
| --- | --- | --- |
| Q281A | 151.1 (14) | 14.1 (11) |
| R282A | 3.8 (2) | 4.7 (2) |
| Q284A | 3.3 (1) | 6.5 (5) |
| L285A | 107.0 (12) | 17.9 (1) |
| W287A | 124.8 (12) | 2.4 (2) |
| R295A | 120.9 (10) | 1.8 (2) |
| E297A | 116.9 (14) | 5.3 (0) |
| V302A | 92.3 (29) | 4.9 (0) |
| W315A | 117.3 (10) | 19.0 (6) |
| G337A | 17.9 (9) | 36.3 (68) |

TABLE 18

Residues involved in anti-SIRPA antibody binding

| Antibody | Critical SIRPA residues |
| --- | --- |
| 3F9 | R282, Q284, G337 |
| 9C2 | Q281, R282, Q284, L285, W287, R295, E297, V302, W315 |

Example 16: Anti-SIRPα Antibodies Enhance the Anti-Tumor Activity of Checkpoint Inhibitors in a Syngeneic Tumor Model Therapeutic antibodies targeting the SIRPA-CD47 pathway may rely on xenograft tumor models for proof-of-concept studies in which immune-deficient NOD or NOG mice sustain the growth of implanted human cancer cells. Since the allelic variant of murine SIRPA expressed by NOD mice binds human CD47, this interaction allows engraftment of human cells into a murine host. However, these mice may also exaggerate the role of the pathway because NOD SIRPA binds human CD47 with greater affinity than human SIRPA. Furthermore, Prkdc$^{SCID}$ and IL2Rγ$^{Null}$ mutations in immune-deficient strains of mice eliminate T cells, B cells, and NK cells, thus rendering myeloid cells and the innate immune system as the only effector cells available for inhibiting tumor growth. Tumor xenograft models do not permit the interrogation of therapies that target innate immune cells to prime or enhance an adaptive anti-tumor immune response. Thus, to evaluate human anti-SIRPA antibodies of the present disclosure in the context of immune competent animal hosts, the genes for human SIRPA and human CD47 were introduced into C57BL6/J mouse strain.

Briefly, Bacterial Artificial Chromosomes (BACs) harboring human SIRPA-encoding or human CD47-encoding nucleic acid with flanking sequences to include relevant human gene regulatory elements were identified using the UCSC genome browser and CloneDB from NCBI. One BAC clone (BACRP11-636L228) identified that was predicted to contain the coding sequences for the human SIRPA gene. Another BAC clone (BACRP11-671F8) was identified that was predicted to contain the coding sequences for the human CD47 gene. Mice harboring BAC clones of interest were then generated by injecting the purified BAC DNA into mouse C57BL6/J zygotes using standard pronuclear injection techniques. Zygotes were returned to female mice, and the resulting murine pups were genotyped for the presence of the desired transgene. Founder animals containing the transgene were then bred to non-transgenic animals, and progeny were screened for expression of the transgene by PCR using standard techniques and additionally by FACS staining of peripheral blood cells form the animals. BAC transgenic mice harboring each individual gene of interest were intercrossed in order to produce "humanized" mice expressing both human SIRPA and human CD47.

In addition to engineering mice to express human SIRPA and human CD47 as described above, syngeneic tumor cell lines were also engineered to replace mouse CD47 with human CD47. Briefly, CRISPR-Cas9 technology was utilized to introduce Cas9/guide RNA (gRNA) complexes into the MC38 target cells. Cas9/gRNA mediated indel formation at the targeted region (exon 2 of mouse CD47) resulted in a frameshift and/or premature stop, thus knocking out expression of the endogenous mouse CD47 gene. After transfecting gRNA and Cas9, single cell-derived clones were screened by sequencing and homozygous clones containing the desired mutation were expanded. As shown in FIG. 17A (top panel), FACS analysis of parental MC38 cells and the mouse CD47 knockout cell line (MC38-mCD47KO) stained with an anti-mouse CD47 antibody confirms the loss of mouse CD47 expression in these engineered cells. Subsequently, MC38-mCD47KO cells were transduced with a lentivirus containing the human CD47 gene insert. MC38-mCD47KO-huCD47+ cells were selected with puromycin and expanded. FIG. 17A (bottom panel) shows a FACS histogram verifying the expression of human CD47 in the selected cell population.

The anti-tumor effects of anti-SIRPA antibodies of the present disclosure were evaluated in vivo using a mouse colon carcinoma model with huSIRPA/huCD47 BACtg mice engrafted with MC38-mCD47KO-huCD47+ cells in combination with a T cell checkpoint inhibitor. These mice were injected subcutaneously with 500,000 MC38 cells in the right flank. Antibody therapy commenced when mice were randomized into groups approximately ten days after cell transplant or when tumors achieved an average volume of 80 mm$^3$. Mice received two intraperitoneal (IP) injections per week for 3 weeks of ant-SIRPA antibody 3F9 mIgG1 or anti-SIRPA antibody 3F9 mIgG2A at 10 mg/kg in combination with a suboptimal dose of anti-mouse PDL1 antibody (clone 10F.9G2, Bioxcell) at 5 mg/kg. Animals were sacrificed when tumors reached a volume of ~2000 mm$^3$.

Figure 17B:
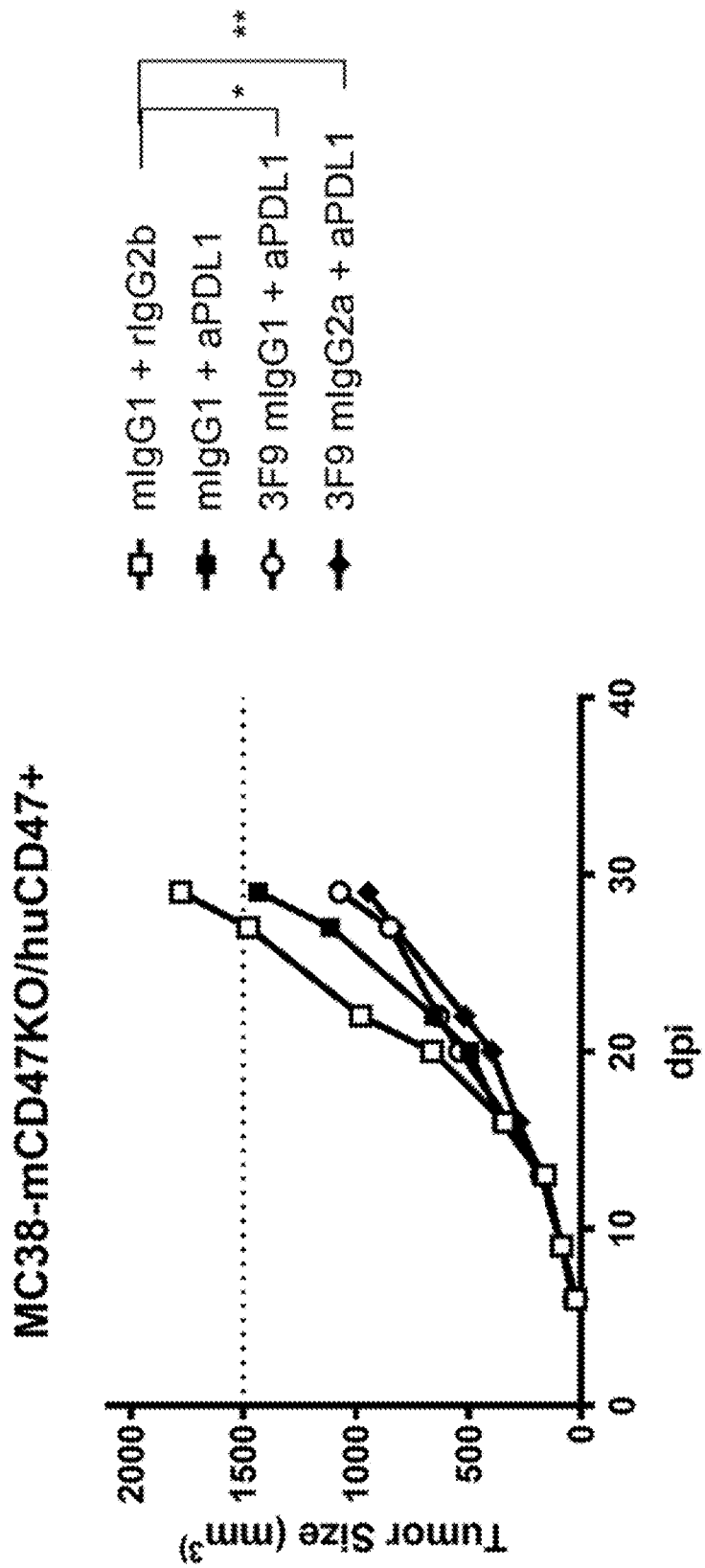
Figure 17C:
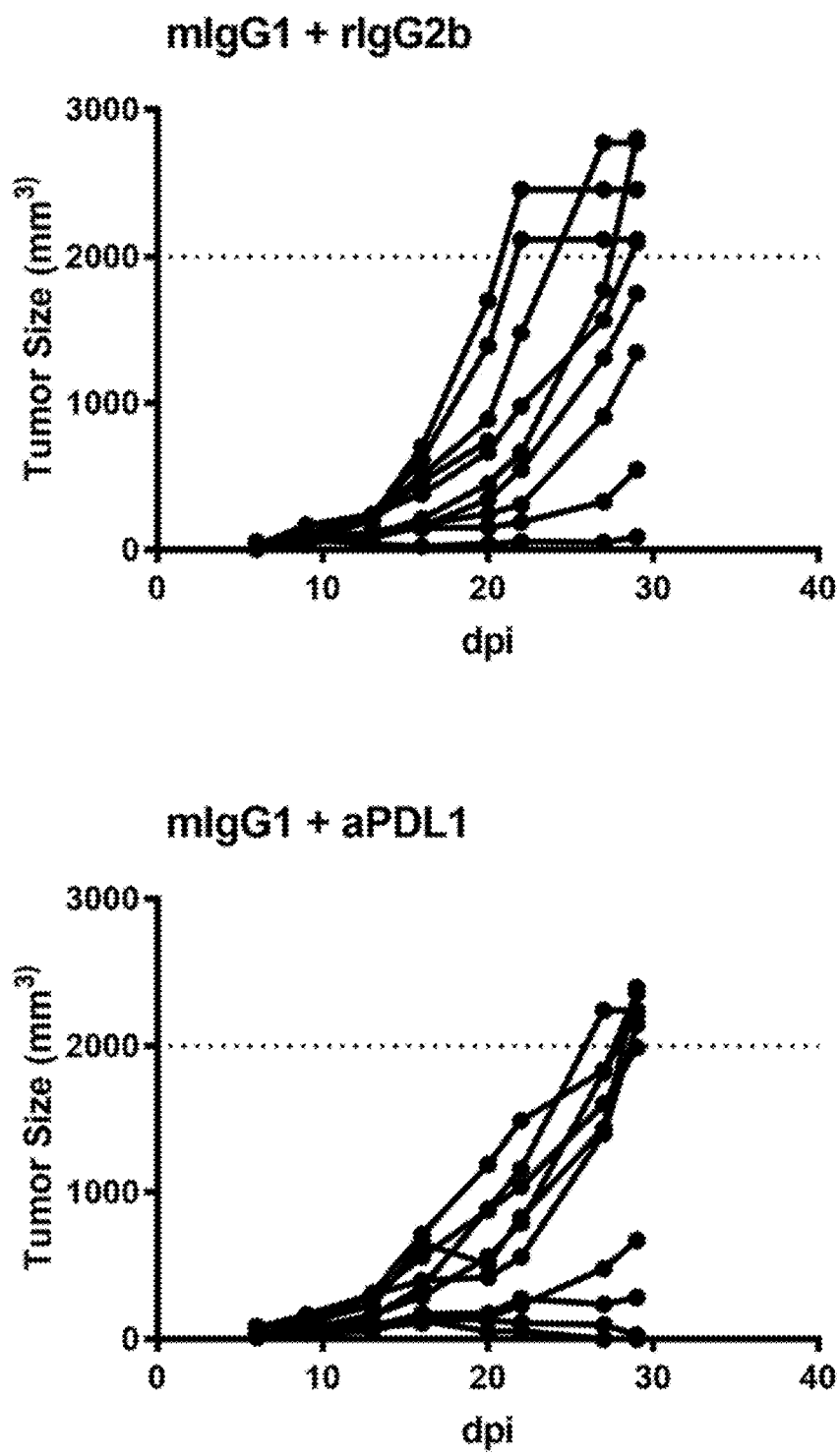

FIG. 17B shows the average tumor growth curves of huSIRPa/huCD47 BAC transgenic mice implanted subcutaneously with MC38 cells engineered to lack mouse CD47 expression and overexpress human CD47 (MC38-mCD47KO/huCD47+). Mice were treated with either isotype control antibody, anti-mouse PDL1 antibody, anti-SIRPA antibody 3F9 mIgG1 plus anti-mouse PDL1 antibody, or anti-SIRPA antibody 3F9 mIgG2A plus anti-mouse PDL1 antibody, as indicated. Treatment was initiated when tumors were an average of 80 mm$^3$. As shown in FIG. 17B, anti-PDL1 antibody treatment inhibited tumor growth by 20% relative to isotype control antibody treated animals, which did not achieve statistical significance. However, combination therapy of anti-PDL1 antibody with either anti-SIRPA antibody 3F9 mIgG1 or ant-SIRPA antibody 3F9 mIgG2A further inhibited tumor growth in these animals by 40% and 47%, respectively. FIG. 17C shows spaghetti plots of tumor volume of each animal within the treatment groups. Except for a few poor responders, tumor volumes did not surpass 1000 mm$^3$ in most animals in the combination therapy treatment groups, whereas tumors in several animals in the isotype control group or anti-PDL1 antibody monotherapy group reached 2000 mm$^3$ limit.

These results demonstrated that anti-SIRPA 3F9 antibodies of the present disclosure are effective at enhancing the anti-tumor activity of checkpoint inhibitors in an immune competent animal model encoding the human SIRPA-CD47 pathway. These results indicated that anti-SIRPA antibodies of the present disclosure are useful for enhancing the anti-tumor activity of checkpoint inhibitors. Accordingly, anti-SIRPA antibodies of the present disclosure are effective at treating cancer when used in combination with a checkpoint inhibitor therapy.

Example 17: Anti-SIRPα Antibodies Downregulate SIRPA Expression on Tumor Infiltrating Myeloid Cells in Mouse Syngeneic Tumors The previous Example demonstrated the anti-tumor activity of anti-SIRPA antibodies of the present disclosure in human SIRPA/CD47 BAC transgenic mice. To verify that anti-tumor activity correlated with antibody-mediated downregulation of SIRPA on tumor macrophages, tumor myeloid cells were characterized following drug administration.

Human SIRPA/huCD47 BAC transgenic mice were implanted subcutaneously in the right flank with 500,000 MC38-mCD47KO/huCD47+ cells. Tumors in the mice grew to an average volume of ~400 mm$^3$ prior to administration of antibodies. Mice received two IP injections of anti-SIRPA antibody 3F9-22 mIgG2A three days apart at 3 mg/kg, 10 mg/kg, or 30 mg/kg. Control mice received 2 IP injections of mIgG2A isotype at 10 mg/kg. Tumor tissue and spleens were harvested from the mice 1 day, 4 days, and 8 days after administration of second dose of antibody. Spleens were processed into single cell suspension by mechanical dissociation through a 70 μm cell strainer. Cells were then washed with PBS and red blood cells lysed with ACK lysis buffer. Subsequently, cells were resuspended in FACS buffer consisting of PBS/2% FBS and prepared for staining. Similarly, tumor tissues were processed into single cell suspensions with enzymatic and mechanical dissociation with the gentleMACS™ Dissociator (Miltenyi Biotec). Tissue homogenate was filtered through a 70 μm cell strainer and resuspended in FACS buffer consisting of PBS/2% FBS for staining. Cells were stained with the following panel:

TABLE 19

| Fluorochrome | Marker | Clone |
|---|---|---|
| AmCyan (BV510) | Live/Dead | |
| PECy7 | mCD45 | 30-F11 |
| Pacific Blue (BV42.1) | mCD11b | M1/70 |
| PerCp/Cy5.5 | mF4/80 | BM8 |
| APC/Cy7 | mLy6G | 1A8 |
| AF488 (FITC) | mLy6C | HK1.4 |
| APC | hSIRPa | SE5A5 |

FIG. 18A shows the relative change in expression of SIRPA over time on tumor infiltrating myeloid cells (monocytes and macrophages). Tumor-associated macrophages were defined as CD45+CD11b+F4/80+Ly6C−Ly6G− cells, whereas tumor-infiltrating monocytes were defined as CD45+CD11 b+F4/80−Ly6C+Ly6G− cells. Compared to animals administered isotype control antibody, animals administered anti-SIRPA antibody showed almost 80% reduction of cell surface SIRPA expression 1-day post antibody administration on both tumor monocytes and tumor macrophages. SIRPA expression returned to baseline levels after 4 days or 8 days in mice administered 3 mg/kg or 10 mg/kg of anti-SIRPA antibody 3F9-22 mIgG2A, respectively. SIRPA expression level stabilized to around 50% below baseline in mice administered 30 mg/kg of anti-SIRPA antibody 3F9-22 mIgG2A.

Figures 18B, 19A:
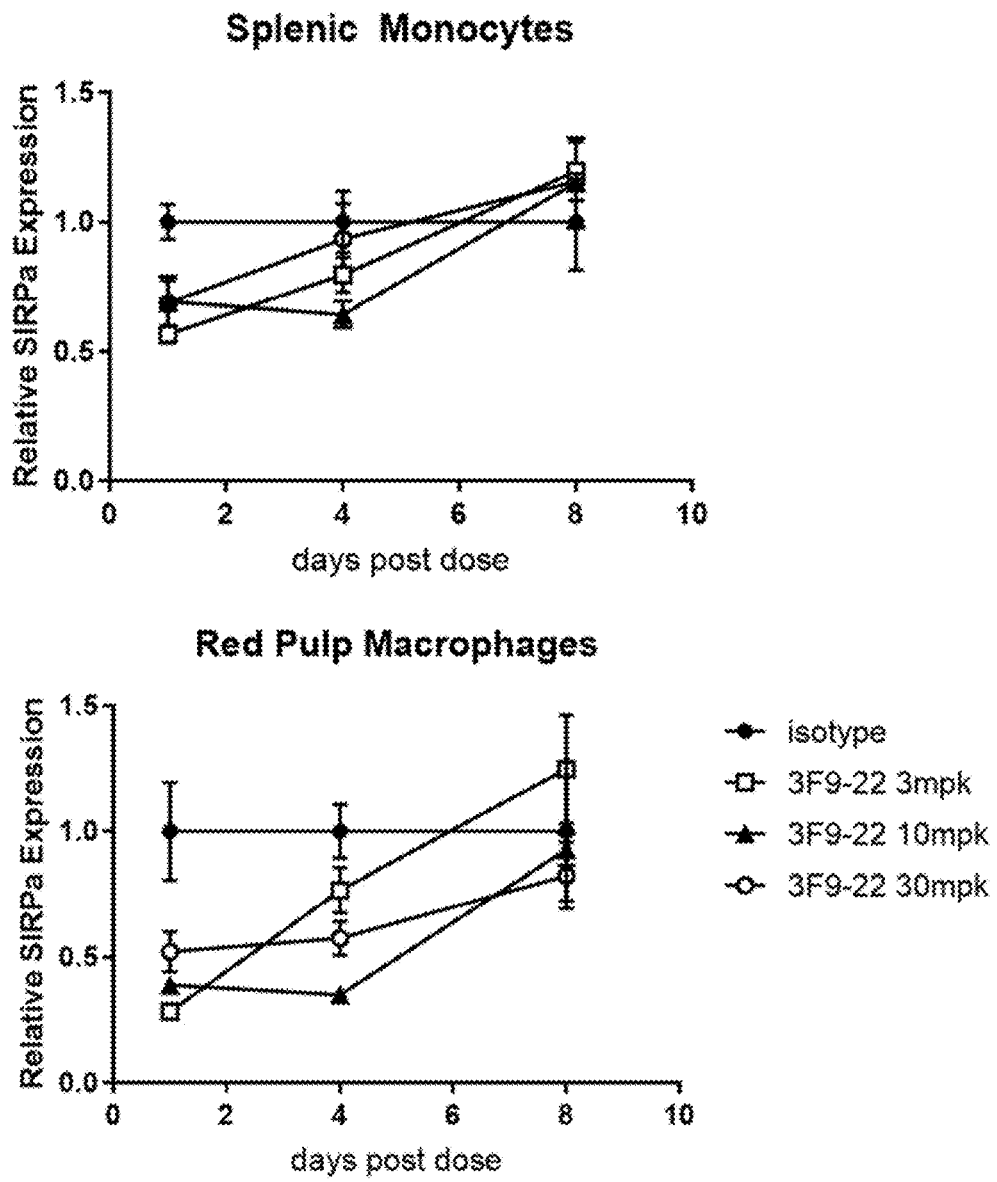

The splenic compartment was also immune profiled to determine if any correlation with the tumor microenvironment could be determined. Splenic monocytes appeared more resistant to antibody-mediated receptor downregulation relative to that observed in tumor monocytes (FIG. 18B). Splenic monocytes were defined as CD45+CD11b+F4/80–Ly6C+Ly6G– cells. Splenic red pulp macrophages were defined as CD45+CD11b–F4/80+Ly6C– cells. Splenic monocytes demonstrated a maximum downregulation of SIRPA of ~40% one-day post antibody administration and rapidly recovered receptor expression at later timepoints. Splenic red pulp macrophages, on the other hand, followed a similar pattern of SIRPA receptor expression as observed with tumor macrophages.

Taken together, these results demonstrated that anti-SIRPA antibodies of the present disclosure are effective at reducing (down-regulating) SIRPA levels on macrophages, in particular tumor-associated macrophages, and the reduction or down-regulation of SIRPA levels on macrophages correlated with anti-tumor activity of the anti-SIRPA antibodies of the present disclosure.

Example 18: Anti-SIRPA Antibodies Downregulate SIRPA Expression on Tumor Infiltrating Myeloid Cells in Human Immune System (HIS) Mice Since the Fc domain of anti-SIRPA antibodies plays a role in receptor downregulation and antibody function, mice reconstituted with a human immune system were employed to compare the activity of different Fc variants with anti-SIRPA antibodies of the present disclosure. HIS mouse models necessitate engraftment of CD34+ human hematopoietic stem cells (hHSCs) obtained from umbilical cord blood into immunodeficient mice (i.e. NOG strain) following their preconditioning with sublethal irradiation. HSCs stably develop extensive cell lineages, especially lymphocyte populations, in peripheral blood, bone marrow, thymus, and spleen (as well as other tissues). NOG mice engineered to express human GM-CSF and human IL-3 (NOG-EXL; Taconic) provide the additional advantage of supporting greater myeloid cell differentiation compared to other mouse strains. HIS mice offer the opportunity to study human tumor-immune system interactions in vivo in mice implanted with human cancer cell lines. Additionally, HIS mice help evaluate mechanisms of action of therapeutic antibody candidates in an in vivo setting.

Mice were inoculated with A375 human melanoma cells subcutaneously in the flank region at a cell density of $3 \times 10^6$ cells per mouse with 50% Matrigel (Cat.354234; Corning). Tumors grew to an average volume of 400 mm$^3$ before mice received 2 IP injections of 3F9-22 huIgG1 P331S (PS), 3F9-22 huIgG1 N325S/L328F (NSLF), or huIgG1 isotype control at 10 mg/kg three days apart. Blood, spleens, and tumor tissues were harvested 1 day after the second injection of antibody. Spleens were processed into single cell suspension by mechanical dissociation through a 70 µm cell strainer. Cells were washed with PBS and red blood cells lysed with ACK lysis buffer. Subsequently, cells were resuspended in FACS buffer consisting of PBS/2% FBS and prepared for staining. Similarly, tumor tissues were processed into single cell suspensions with enzymatic and mechanical dissociation with the gentleMACS™ Dissociator (Miltenyi Biotec). Tissue homogenate was filtered through a 70 µm cell strainer and resuspended in FACS buffer consisting of PBS/2% FBS for staining. Peripheral blood cells were treated with ACK lysis buffer to lyse RBCs and resuspended in FACS buffer consisting of PBS/2% FBS. Cells were stained with the following panel:

TABLE 20

| Fluorochrome | Marker | Clone |
|---|---|---|
| PERCPCY5 | CD3 | SK7 |
| PERCPCY5 | CD19 | HIB19 |
| FITC | CD14 | M5E2 |
| PE-Cy7 | CD11b | ICRF44 |
| Alexa700 | human CD45 | 2D1 |
| AmCyan | Live/DEAD | |
| APC/DyL650 | SIRPA | internal |
| BV421 | CD16 | 3G8 |
| BUV395 | HLA-DR | L243 |
| PE-CF594 | CD163 | GHI/61 |
| PE | CD86 | IT2.2 |
| APC-Cy7 | Mouse CD45 | 30-F11 |

NOG-EXL mice were engrafted with human umbilical cord blood-derived CD34+ hematopoietic stem cells (HSC) from two different donors (donors A and B). All mice were subcutaneously implanted with 3 million cells of A375, a human melanoma cell line. Tumors grew to an average volume of ~400 mm$^3$ prior to antibody administration. Mice received two IP injections of anti-SIRPA antibodies three days apart at 10 mg/kg. Control mice received 2 IP injections of huIgG1 isotype at 10 mg/kg. Tumor tissue was harvested from mice 1 day after administration of the second dose of antibody.

FIG. 19 shows the study design and results of antibody-mediated downregulation of SIRPA in humanized NOG-EXL mice bearing A375 tumors in these studies. FIG. 19A shows that 8 mice were engrafted with CD34+ HSC from donor A and 29 mice were engrafted with CD34+ HSC from donor B. Briefly, 40 mice engrafted with CD34+ HSC from 2 different donors were procured from Taconic, NY. At 10 weeks post engraftment, mice were quality checked prior to shipment for human leukocyte reconstitution by flow cytometry. Most mice (36/40) contained >50% huCD45+ cells in peripheral blood.

Tumor-associated macrophages in NOG-EXL mice were defined as CD45+CD11b+CD14+CD16+CD3–CD19– cells. FIG. 19B shows the expression level of SIRPA on human tumor macrophages depicted as either MFI values (left panel) or normalized values (right panel). Anti-SIRPA antibody treatment resulted in significant downregulation of SIRPA in human tumor macrophages from both donors compared to isotype control group. Normalizing MFI values for each donor reveals ~70% reduction of SIRPA expression, which approximates the extent of downregulation observed in monocyte-derived macrophages in vitro and in tumor macrophages in BAC transgenic mice. No significant difference in activity was observed between anti-SIRPA 3F9-22 PS Fc variant and NSLF Fc variant of the anti-SIRPA antibody in these experiments.

In addition to SIRPA expression, tumor macrophages from these experiments were also profiled to examine expression of M1 markers. Tumor macrophages were defined as huCD45+ huCD11b+CD14+ huCD16+ cells. As shown in FIG. 20A, anti-SIRPA antibodies of the present disclosure upregulated the expression of HLA-DR. Normalizing MFI values for each donor demonstrated that the anti-SIRPA antibody 3F9-22 PS Fc variant increased HLA-DR expression ~3-fold in both donors over that observed with isotype control antibody treatment. In contrast, anti-SIRPA antibody 3F9-22 NSLF Fc variant increased HLA-DR expression ~1.5-2-fold over that observed with isotype control antibody treatment. Only the increase measured on Donor B macrophages reached statistical significance with anti-SIRPA antibody 3F9-22 NSLF Fc variant. Similarly, anti-SIRPA antibodies of the present disclosure increased CD86 expression on tumor macrophages from Donor B only (FIG. 20B). Though both the PS and NSLF Fc variants increased CD86 expression by ~40% relative to isotype control antibody group, only the PS Fc variant achieved statistical significance for increased CD86 expression. These results demonstrated the both PS and NSLF Fc variants of anti-SIRPA antibody 3F9-22 downregulated SIRPA and increased M1 markers on human tumor macrophages; however, the PS variant appears partially more potent than NSLF variant in these experiments.

Antibody-mediated SIRPA downregulation was also assessed in peripheral blood monocytes and splenic monocytes in order to compare the activity of anti-SIRPA antibodies of the present disclosure in tumor and peripheral immune compartments. Human monocyte populations were defined as CD45+CD11b+CD14+CD16−CD3−CD19− cells. Mice received two IP injections of anti-SIRPA antibodies three days apart at 10 mg/kg. Control mice received 2 IP injections of huIgG1 control antibody at 10 mg/kg. Spleens and blood were harvested from mice 1 day after administration of the second dose of antibody. As shown in FIG. 21A, anti-SIRPA antibody 3F9-22 NSLF Fc variant exhibited superior downregulation of SIRPA compared to that observed with anti-SIRPA antibody 3F9-22 PS Fc variant in splenic monocytes. However, in peripheral blood monocytes, both Fc variants displayed similar activity (FIG. 21B). Anti-SIRPA antibodies of the present disclosure showed greater receptor downregulation in monocytes derived from Donor B than Donor A, which may correlate with higher baseline expression of SIRPA on monocytes in Donor B than Donor A.

Taken together, these results demonstrated that anti-SIRPA antibodies of the present disclosure are effective at down-regulating SIRPA levels in both peripheral blood monocytes as well as in splenic monocytes.

Example 19: Anti-SIRPA Antibodies Engineered for Selective FcR Engagement Retain Antibody-Mediated Receptor Downregulation Activity To further evaluate the role of FcRs in the activity of anti-SIRPA antibodies of the present disclosure, the variable domain of anti-SIRPA antibody 3F9-22 was expressed with different Fc domains with distinct FcR binding profiles. FcR affinity measurements for anti-SIRPA antibody Fc variants were obtained using bio-layer interferometry (BLI) on a Pall ForteBio Octet RED96 instrument. Immobilized anti-human Fab-CH1 antibody captured humanized anti-SIRPA antibody 3F9-22 Fc variants on biosensors (10 μg/mL, 300 s loading time). Single cycle kinetics were performed with 100 nM of soluble human FcRs flowed over captured antibody to record traces (300 s association time, 300 s dissociation time). Data analysis was performed using ForteBio Data Analysis Software, version 9.0. Standard kinetic buffer (PBS, 0.1% BSA, 0.02% Tween-20, pH 7.2) was used for the assay and for preparing reagents.

Relative affinity measurements derived from curve fitting analysis of the sensorgrams obtained from these experiments are summarized below in Table 19. Fc variants displayed predicted FcR binding patterns. For example, the LALAPS Fc mutations abrogated binding to all FcRs, except the high-affinity receptor, FcgR1. The N325S/L328F (NSLF) Fc mutations specifically eliminated binding to human FcgR3A. Similarly, the IgG2 and IgG4 isotypes fail to bind FcgR3A and only IgG4 retains binding to FcgR1.

TABLE 19

| | Fc Variant | | | | | |
|---|---|---|---|---|---|---|
| | FcgR1 | FcgR2A H131 | FcgR2A R131 | FcgR2B | FcgR3A F158 | FcgR3A V158 |
| IgG1 LALAPS | + | − | − | − | − | − |
| IgG1 NSLF | ++ | + | ++ | ++ | − | − |
| IgG2 | − | + | + | − | − | − |
| IgG 4 SP | ++ | + | ++ | ++ | − | − |

Anti-SIRPA antibody 3F9-22 Fc variants were subsequently assessed for their ability to downregulate SIRPA expression or levels in human monocyte-derived macrophages. As previously described, human monocytes were isolated from peripheral blood of healthy donors and differentiated into macrophages in vitro by supplementing growth media with human M-CSF. Following differentiation, human macrophages were harvested and seeded onto 96-well tissue culture plates with increasing concentration of control antibody or soluble anti-SIRPA antibodies and incubated overnight at 37° C. Cells were analyzed by flow cytometry for SIRPA cell surface expression using a DyLight650-conjugated anti-human SIRPA antibody belonging to a separate epitope bin than that of anti-SIRPA antibody 3F9-22.

Figure 22:
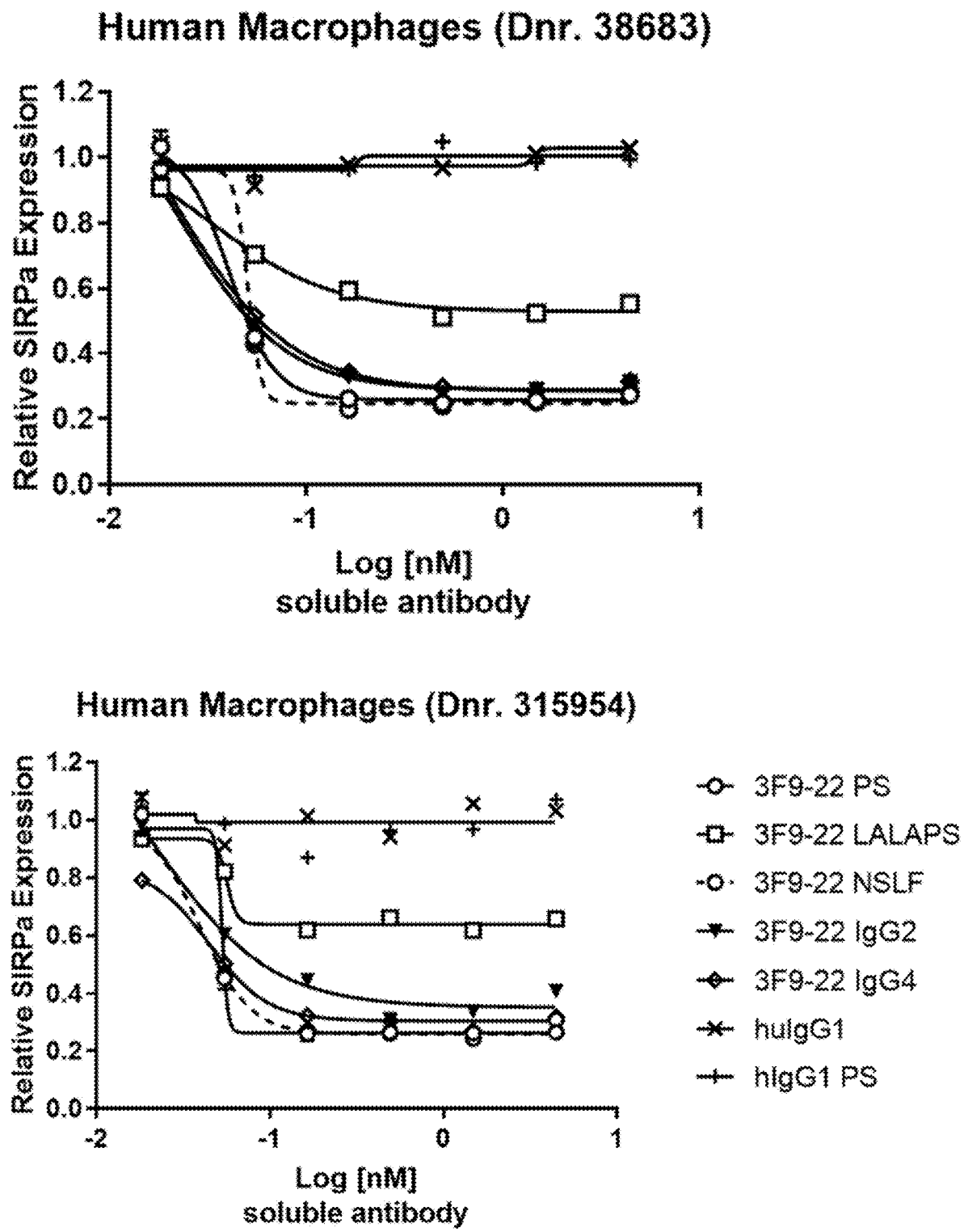
FIG. 22 sets forth data showing antibody-mediated SIRPA downregulation on primary human macrophages by different Fc variants of anti-SIRPA 3F9-22 antibodies.

As shown in FIG. 22 and summarized in Table 20, most Fc variants of anti-SIRPA antibody 3F9-22 maximally downregulated cell surface levels of SIRPA on macrophages with similar IC50 values. However, anti-SIRPA antibody 3F9-22 LALAPS only partially downregulated cell surface levels of SIRPA, confirming that FcR engagement is involved in potentiating this activity of anti-SIRPA antibodies. Additionally, since Fc variants that do not bind FcgR3A demonstrate similar receptor downregulation as anti-SIRPA antibody 3F9-22 PS, which binds all FcRs, suggested that FcgR3A engagement is dispensable for antibody-mediated receptor internalization.

TABLE 20

| Fc Variant | IC50 (nM) | Max % DR |
|---|---|---|
| 3F9-22 PS | 0.04701 | 73.825 |
| 3F9-22 LALAPS | 0.04468 | 41.575 |
| 3F9-22 NSLF | 0.045125 | 74.61 |
| 3F9-22 IgG2 | 0.02185 | 67.955 |
| 3F9-22 IgG4 | 0.032415 | 70.455 |

Example 20: Anti-SIRPA Antibodies Engineered for Selective FcR Engagement Enhance Phagocytosis of Tumor Cells by Macrophages In addition to antibody-mediated receptor downregulation as disclosed above, the role of FcRs was evaluated in anti-SIRPA antibody-mediated enhancement of tumor cell phagocytosis with different Fc variants of anti-SIRPA antibody 3F9-22. Additionally, phagocytic activity for other antibodies that target this pathway were assessed in parallel.

Primary human macrophages were treated overnight with control antibody or the indicated test antibody. Tumor cells were labeled with CFSE dye and added to macrophages at 37° C. overnight. The following day, the macrophages were collected and stained on ice with anti-CD14 APC in FACS buffer containing FcR-blocking antibodies. Phagocytic activity was measured by counting the percent of CD14/CFSE-double positive macrophages.

Figure 23:
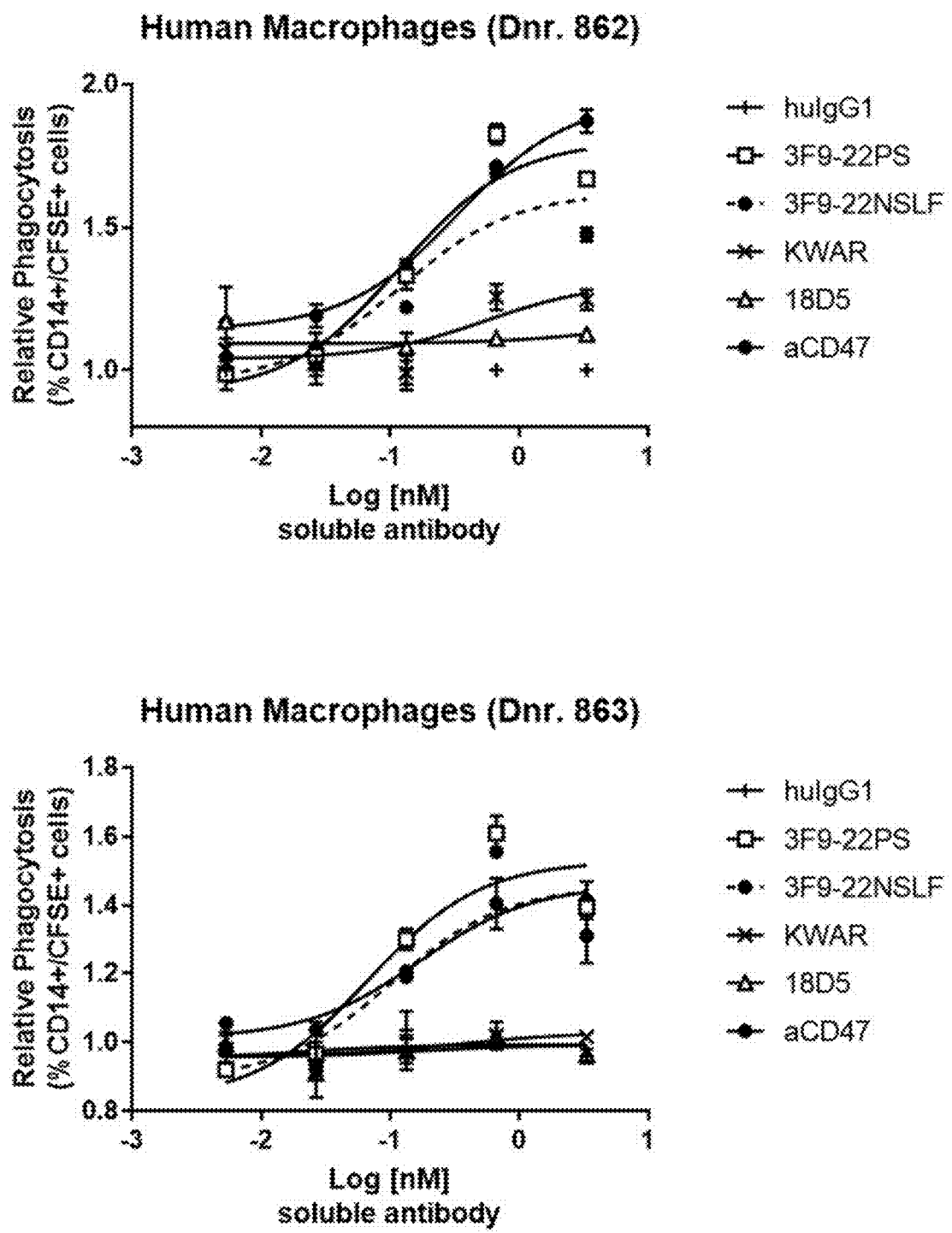
FIG. 23 sets forth data comparing the enhancement of phagocytic activity of different Fc variants of anti-SIRPA antibody 3F9-22 in comparison to anti-CD47-blocking antibodies.

Results of these experiments are shown in FIG. 23 and are presented as the fold increase in percent population of CD14/CFSE double-positive macrophages. As shown in FIG. 23 and summarized below in Table 21, both anti-SIRPA antibody 3F9-22 PS and anti-SIRPA antibody 3F9-22 NSLF variants significantly enhanced phagocytosis of A375 melanoma cells relative to that observed in control antibody treated macrophages. The observed enhancement of phagocytosis appeared comparable to the anti-CD47 antibody tested in these studies (aCD47), which primarily functions by opsonizing CD47-expressing tumor cells for ADCP. In contrast, two different CD47-blocking anti-SIRPA antibodies KWAR23 (See WO2015/138600) and 18D5 (See WO2017/178653) failed to show any enhancement of tumor cell phagocytosis. These results demonstrated that both PS and NSLF Fc variants of anti-SIRPA antibody 3F9-22 retained the properties of enhancing tumor cell phagocytosis in the absence of opsonizing anti-tumor antigen antibodies. As anti-SIRPA antibodies of the present disclosure are non-blocking with respect to SIRPA/CD47 interaction, these results also showed that non-blocking anti-SIRPA antibodies of the present disclosure were effective at increasing or enhancing tumor cell phagocytosis compared to that observed with non-blocking anti-SIRPA antibodies KWAR23 and 18D5.

TABLE 21

| Antibody | EC50 (nM) | Max* |
| --- | --- | --- |
| 3F9-22PS | 0.1144575 | 2.06925 |
| 3F9-22NSLF | 0.457625 | 1.774 |
| KWAR23 | 0.3631 | 1.126 |
| 18D5 | 2.148 | 1.06446667 |
| aCD47 | 0.777775 | 2.6235 |

*Fold increase in phagocytosis over baseline activity

Example 21: Anti-SIRPA Antibody 3F9-22 Variants do not Induce Changes in Red Blood Cell and Platelet Counts Reports have indicated that anti-CD47 antibody 5F9 administered to non-human primates resulted in anemia (Liu et al, 2015, PLOS ONE, DOI:10.1371/journal.pone.0137345) and that anti-SIRPAFc TTI-621 administration to humans resulted in dose-dependent decreases in platelets (Ansell et al, 2016, Blood 128:1812). To examine whether anti-SIRPA antibodies of the present disclosure have any effect on red blood cell counts or platelet counts in vivo, the following studies were performed. Female cynomolgus monkeys were assigned to five groups and were administered control antibody, anti-SIRPA antibody 3F9-22 PS, anti-SIRPA antibody 3F9-22 IgG4, anti-SIRPA antibody 3F9-22 IgG2, or anti-SIRPA antibody 3F9-22 NSLF, as indicated in Table 22 below. Animals were administered the antibodies by intravenous infusion via a saphenous vein.

TABLE 22

| Group | Number of Females | Test Article | Dose Route | Target Dose Level (mg/kg) | Target Dose Concentration (mg/mL) | Target Dose Volume (mL/kg) |
| --- | --- | --- | --- | --- | --- | --- |
| 1 | 3 | IgG | IV | 10 | 2.5 | 4 |
| 2 | 3 | 3F9-22 PS | IV | 10 | 2.5 | 4 |
| 3 | 3 | 3F9-22 IgG4 | IV | 10 | 2.5 | 4 |
| 4 | 3 | 3F9-22 IgG2 | IV | 10 | 2.5 | 4 |
| 5 | 3 | 3F9-22 NSLF | IV | 10 | 2.5 | 4 |

IV = Intravenous; given as a bolus injection.
Notes:
Animals in Groups 1 and 2 were dosed once on Days 1, 8, 15, 22, and 29 (total of 5 doses).
Animals in Groups 3, 4, and 5 were dosed once on Days 1 and 29 (total of 2 doses).

Blood was collected from the animals via a femoral vein for red blood cell (RBC) counts and platelet counts once during the pre-dose phase and then at approximately 72, 168, 240, 408, 576, 672, and 744 hours post antibody administration.

As shown in FIG. 24, red blood cell and platelets counts were not altered by any of anti-SIRPA antibodies 3F9-22 PS, 3F9-22 IgG4, 3F9-22 IgG2, and 3F9-22 NSLF through the course of these experiments.

Certain additional anti-SIRPA antibody sequences of the present disclosure are shown below. Underlined amino acids indicate certain differences in the amino acid sequences of the following anti-SIRPA antibodies.

```
3F9-22-IgG1 WT Heavy Chain
                                               (SEQ ID NO: 47)
EVQLLESGGGLVQPGGSLRLSCAASGFTFSSYAMSWVRQAPGKGLEWVATISEYGGSYTYYAESVKGRFT

ISRDNSKNTLYLQMNSLRAEDTAVYYCARPPYDDYYGGFQYWGQGTLVTVSSASTKGPSVFPLAPSSKST
```

```
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK
```

3F9-22-huIgG1 PS Heavy Chain (SEQ ID NO: 48)

```
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFQYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPASIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK
```

3F9-22 SELF Heavy Chain (SEQ ID NO: 49)

```
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFQYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVEHEDPEVKF
NWYVDGVEVHNAKTKPREEQYNSTYRVVSVLTVLHQDWLNGKEYKCKVSNKAFPAPIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK
```

3F9-22 hIgG1 NSLF Heavy Chain (SEQ ID NO: 53)

```
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFQYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSSKAFPAPIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK
```

3F9-22 hIgG1 LALAPS Heavy Chain (SEQ ID NO: 54)

```
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFQYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPASIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK
```

3F9-22 huIgG1 Light Chain (SEQ ID NO: 50)

```
DIQLTQSPSSLSASVGDRVTITCRASKSVSSGGYSYMHWYQQKPGKAPKLLIYLASNLESGVPSRFSGSG
SGTDFTLTISSVQPEDFATYYCQHNRELPVTFGQGTKLEIKRTVAAPSVFIFPPSDEQLKSGTASVVCLL
```

NNFYPREAKVQWKVDNALQSGNSQESVTEQDSKDSTYSLSSTLTLSKADYEKHKVYACEVTHQGLSSPVT
KSFNRGEC

3F9-14 huIgG1 WT Heavy Chain
(SEQ ID NO: 51)
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGRYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK 3F9-14 PS Heavy Chain
(SEQ ID NO: 57)
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFRYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPASIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK 3F9-14 SELF Heavy Chain
(SEQ ID NO: 52)
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFRYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVEHEDPEVKF
NWYVDGVEVHNAKTKPREEQYNSTYRVVSVLTVLHQDWLNGKEYKCKVSNKAFPAPIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK 3F9-14 NSLF Heavy Chain
(SEQ ID NO: 55)
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFRYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSSKAFPAPIEKTISKAKGQPRE
PQVYTLPPSRDELTKNQVSLTCLVKGFYPSDIAVEWESNGQPENNYKTTPPVLDSDGSFFLYSKLTVDKS
RWQQGNVFSCSVMHEALHNHYTQKSLSLSPGK 3F9-14 LALAPS Heavy Chain
(SEQ ID NO: 56)
EVQLLESGGGLVQPGGSLRLSCAASGFTFSSYAMSWVRQAPGKGLEWVATISEYGGSYTYYAESVKGRFT
ISRDNSKNTLYLQMNSLRAEDTAVYYCARPPYDDYYGGFRYWGQGTLVTVSSASTKGPSVFPLAPSSKST
SGGTAALGCLVKDYFPEPVTVSWNSGALTSGVHTFPAVLQSSGLYSLSSVVTVPSSSLGTQTYICNVNHK
PSNTKVDKKVEPKSCDKTHTCPPCPAPEAAGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPASIEKTISKAKGQPRE -continued

PQVYTLPPSRDELTKNQVSLTCLVKGFYPSDIAVEWESNGQPENNYKTTPPVLDSDGSFFLYSKLTVDKS

RWQQGNVFSCSVMHEALHNHYTQKSLSLSPGK

3F9-14 huIgG1 Light Chain
(SEQ ID NO: 50)

DIQLTQSPSSLSASVGDRVTITCRASKSVSSGGYSYMHWYQQKPGKAPKLLIYLASNLESGVPSRFSGSG

SGTDFTLTISSVQPEDFATYYCQHNRELPVTFGQGTKLEIKRTVAAPSVFIFPPSDEQLKSGTASVVCLL

NNFYPREAKVQWKVDNALQSGNSQESVTEQDSKDSTYSLSSTLTLSKADYEKHKVYACEVTHQGLSSPVT

KSFNRGEC

What is claimed is:

1. An isolated nucleic acid comprising a nucleic acid sequence encoding an antibody that binds to human SIRPA, wherein the antibody comprises a heavy chain variable region and a light chain variable region, wherein the heavy chain variable region comprises: an HVR-H1 comprising the amino acid sequence of SEQ ID NO:20; an HVR-H2 comprising the amino acid sequence of SEQ ID NO: 21; an HVR-H3 comprising an amino acid sequence selected from SEQ ID NOs: 22, 23, and 24; and the light chain variable region comprises: an HVR-L1 comprising the amino acid sequence of SEQ ID NO: 9; an HVR-L2 comprising the amino acid sequence of SEQ ID NO: 10; and an HVR-L3 comprising an amino acid sequence selected from SEQ ID NOs: 11, 12, 13, 14, 15, 16, 17, 18, and 19.

2. The nucleic acid of claim 1, wherein the heavy chain variable region comprises one, two, three or four frame work regions selected from VH FRI comprising the amino acid sequence of SEQ ID NO:25, VH FR2 comprising the amino acid sequence of SEQ ID NO:26, VH FR3 comprising the amino acid sequence of SEQ ID NO:27, and VH FR4 comprising the amino acid sequence of SEQ ID NO:28; and wherein the light chain variable region comprises one, two, three or four frame work regions selected from VL FRI comprising the amino acid sequence of SEQ ID NO:29, VL FR2 comprising the amino acid sequence of SEQ ID NO:30, VL FR3 comprising the amino acid sequence of SEQ ID NO:31, and VL FR4 comprising the amino acid sequence of SEQ ID NO:32.

3. The nucleic acid of claim 1, wherein the heavy chain variable region comprises an amino acid sequence at least 90% or at least 95% or at least 99% identical to an amino acid sequence selected from SEQ ID NOs: 33, 34, and 35.

4. The nucleic acid of claim 1, wherein the light chain variable region comprises an amino acid sequence at least 90% or at least 95% or at least 99% identical to an amino acid sequence selected from SEQ ID NOs: 36, 37, 38, 39, 40, 41, 42, 43, and 44.

5. An isolated nucleic acid comprising a nucleic acid sequence encoding an antibody that binds to human SIRPA, wherein the antibody comprises a heavy chain variable region and a light chain variable region, wherein the heavy chain variable region comprises an amino acid sequence selected from SEQ ID NOs: 33, 34, and 35, and wherein the light chain variable region comprises an amino acid sequence selected from SEQ ID NOs: 36, 37, 38, 39, 40, 41, 42, 43, and 44.

6. The nucleic acid of claim 1, wherein the antibody is a monoclonal antibody.

7. The nucleic acid of claim 1, wherein the antibody is a humanized antibody.

8. The nucleic acid of claim 1, wherein the antibody is a Fab, Fab', Fab'-SH, F (ab') 2, Fv, or scFv fragment.

9. The nucleic acid of claim 1, wherein the antibody is a multivalent antibody.

10. The nucleic acid of claim 1, wherein the antibody is of the IgG class, the IgM class, or the IgA class.

11. The nucleic acid of claim 10, wherein the antibody is of the IgG class and as an IgG1, IgG2, IgG3, or IgG4 isotype.

12. The nucleic acid of claim 1, wherein the antibody binds to an inhibitory Fc receptor.

13. The nucleic acid of claim 12, wherein the inhibitory Fc receptor is inhibitory Fc-gamma receptor IIB (FcgRIIB).

14. The nucleic acid of claim 13, wherein the antibody decreases cellular levels of FcgRIIB.

15. The nucleic acid of claim 1, wherein the anti-SIRPA antibody has a human or mouse IgG1 isotype and comprises one or more amino acid substitutions in the Fc region at an amino acid residue selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, T394D, and any combination thereof, wherein the numbering of the residues is according to EU numbering, or comprises an amino acid deletion in the Fc region at a position corresponding to glycine 236.

16. The nucleic acid of claim 1, wherein the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the amino acid residues is according to EU or Kabat numbering.

17. An isolated nucleic acid comprising a nucleic acid sequence encoding an antibody that binds human SIRPA, wherein the antibody comprises a heavy chain and a light chain, wherein:
 a. the heavy chain comprises the amino acid sequence of SEQ ID NO:47 and the light chain comprises the amino acid sequence of SEQ ID NO:50;
 b. the heavy chain comprises the amino acid sequence of SEQ ID NO:48 and the light chain comprises the amino acid sequence of SEQ ID NO:50;
 c. the heavy chain comprises the amino acid sequence of SEQ ID NO:49 and the light chain comprises the amino acid sequence of SEQ ID NO:50;
 d. the heavy chain comprises the amino acid sequence of SEQ ID NO:53 and the light chain comprises the amino acid sequence of SEQ ID NO:50;
 e. the heavy chain comprises the amino acid sequence of SEQ ID NO:54 and the light chain comprises the amino acid sequence of SEQ ID NO:50;
 f. the heavy chain comprises the amino acid sequence of SEQ ID NO:51 and the light chain comprises the amino acid sequence of SEQ ID NO:50;
 g. the heavy chain comprises the amino acid sequence of SEQ ID NO:52 and the light chain comprises the amino acid sequence of SEQ ID NO:50;
 h. the heavy chain comprises the amino acid sequence of SEQ ID NO:55 and the light chain comprises the amino acid sequence of SEQ ID NO:50;

i. the heavy chain comprises the amino acid sequence of SEQ ID NO:56 and the light chain comprises the amino acid sequence of SEQ ID NO:50; or j. the heavy chain comprises the amino acid sequence of SEQ ID NO:57 and the light chain comprises the amino acid sequence of SEQ ID NO:50.

18. The nucleic acid of claim 1, wherein the anti-SIRPA antibody decreases cell surface levels of SIRPA, decreases intracellular levels of SIRPA, decreases total cellular levels of SIRPA, or any combination thereof.

19. The nucleic acid of claim 1, wherein the anti-SIRPA antibody induces SIRPA degradation, induces SIRPA cleavage, induces SIRPA internalization, induces SIRPA shedding, downregulates SIRPA expression, or any combination thereof.

20. The nucleic acid of claim 1, wherein the antibody reduces cell surface levels of SIRPA in vitro.

21. The nucleic acid of claim 1, wherein the antibody down-regulates expression of SIRPA in human monocytes.

22. The nucleic acid of claim 1, wherein the antibody down-regulates expression of SIRPA in human macrophages by about 70-95%.

23. The nucleic acid of claim 1, wherein the antibody has an affinity (KD) to human SIRPA v1 of less than 6 nM, less than 5 nM, less than 4 nM, less than 3 nM, less than 2 nM, or less than 1 nM.

24. The nucleic acid of claim 1, wherein the antibody has an affinity (KD) to human SIRPA v1 of about 0.1 nM to 2 nM.

25. The nucleic acid of claim 1, wherein the antibody reduces cell surface levels of SIRPA in vitro with a half maximal effective concentration (EC50) of about 0.05 to 0.20 nM for human SIRPA v1, of about 0.05 to 0.10 nM for human SIRPA v2, and/or of about 0.05 to 1 nM for cyno SIRPA as measured by flow cytometry.

26. The nucleic acid of claim 1, wherein the antibody binds human SIRPA, human SIRPA v1, human SIRPA v2, cyno SIRPA, marmoset SIRPA, and human SIRPβ3.

27. The nucleic acid of claim 1, wherein the antibody binds to the D3 domain of human SIRPA v1 of SEQ ID NO:1.

28. The nucleic acid of claim 1, wherein the antibody binds to amino acid residues R282, Q284, and G337 of human SIRPA v1 of SEQ ID NO:1.

29. The nucleic acid of claim 1, wherein the anti-SIRPA antibody increases tumor cell phagocytosis in macrophages, increases tumor cell phagocytosis in M1 macrophages, increases tumor cell phagocytosis in M2 macrophages, down-regulates CD14 expression in macrophages, and/or any combination thereof.

30. The nucleic acid of claim 1, wherein the anti-SIRPA antibody enhances T cell proliferation.

31. The nucleic acid of claim 1, wherein the anti-SIRPA antibody enhances T cell proliferation without blocking the interaction of SIRP☐ and CD47.

32. The nucleic acid of claim 1, wherein the anti-SIRPA antibody stimulates ROS production in monocytes and/or increases IL-8 expression in monocytes.

33. The nucleic acid of claim 1, wherein the anti-SIRPA antibody inhibits tumor growth in vivo.

34. The nucleic acid of claim 1, wherein the anti-SIRPA antibody reduces the number of CD14+ myeloid cells in peripheral blood and/or increases the number of CD14+ myeloid cells in a tumor.

35. The nucleic acid of claim 1, wherein the antibody binds human SIRPA but does not substantially block binding of CD47 to SIRPA.

36. A vector comprising the nucleic acid of claim 1.

37. An isolated host cell comprising the nucleic acid of claim 1.

38. A method of producing an antibody that binds to human SIRPA, comprising culturing the cell of claim 37 so that the antibody is produced.

39. The method of claim 38, further comprising recovering the antibody produced by the cell.

40. The nucleic acid of claim 1, wherein the heavy chain variable region comprises an amino acid sequence at least 95% identical to an amino acid sequence selected from SEQ ID NOs: 33, 34, and 35.

41. The nucleic acid of claim 1, wherein the light chain variable region comprises an amino acid sequence at least 95% identical to an amino acid sequence selected from SEQ ID NOs: 36, 37, 38, 39, 40, 41, 42, 43, and 44.

42. The nucleic acid of claim 1, wherein the heavy chain variable region comprises an amino acid sequence at least 99% identical to an amino acid sequence selected from SEQ ID NOs: 33, 34, and 35.

43. The nucleic acid of claim 1, wherein the light chain variable region comprises an amino acid sequence at least 99% identical to an amino acid sequence selected from SEQ ID NOs: 36, 37, 38, 39, 40, 41, 42, 43, and 44.

44. The nucleic acid of claim 1, wherein the heavy chain variable region comprises: an HVR-H1 comprising the amino acid sequence of SEQ ID NO:20; an HVR-H2 comprising the amino acid sequence of SEQ ID NO:21; an HVR-H3 comprising the amino acid sequence of SEQ ID NO: 24; and the light chain variable region comprises: an HVR-L1 comprising the amino acid sequence of SEQ ID NO: 9; an HVR-L2 comprising the amino acid sequence of SEQ ID NO:10; and an HVR-L3 comprising the amino acid sequence of SEQ ID NO: 16.

45. The nucleic acid of claim 44, wherein the heavy chain variable region comprises one, two, three or four frame work regions selected from VH FRI comprising the amino acid sequence of SEQ ID NO:25, VH FR2 comprising the amino acid sequence of SEQ ID NO:26, VH FR3 comprising the amino acid sequence of SEQ ID NO:27, and VH FR4 comprising the amino acid sequence of SEQ ID NO: 28; and/or wherein the light chain variable region comprises one, two, three or four frame work regions selected from VL FRI comprising the amino acid sequence of SEQ ID NO:29, VL FR2 comprising the amino acid sequence of SEQ ID NO:30, VL FR3 comprising the amino acid sequence of SEQ ID NO:31, and VL FR4 comprising the amino acid sequence of SEQ ID NO:32.

46. The nucleic acid of claim 44, wherein the heavy chain variable region comprises an amino acid sequence at least 90% identical to the amino acid sequence of SEQ ID NO: 35.

47. The nucleic acid of claim 44, wherein the light chain variable region comprises an amino acid sequence at least 90% identical to the amino acid sequence of SEQ ID NO: 41.

48. The nucleic acid of claim 44, wherein the heavy chain variable region comprises an amino acid sequence at least 95% identical to the amino acid sequence of SEQ ID NO: 35.

49. The nucleic acid of claim 44, wherein the light chain variable region comprises an amino acid sequence at least 95% identical to the amino acid sequence of SEQ ID NO: 41.

50. The nucleic acid of claim 44, wherein the heavy chain variable region comprises an amino acid sequence at least 99% identical to the amino acid sequence of SEQ ID NO: 35.

51. The nucleic acid of claim 44, wherein the light chain variable region comprises an amino acid sequence at least 99% identical to the amino acid sequence of SEQ ID NO: 41.

52. The nucleic acid of claim 1, wherein the heavy chain variable region comprises an amino acid sequence of SEQ ID NO: 35, and wherein the light chain variable region comprises an amino acid sequence of SEQ ID NO: 41.

53. The nucleic acid of claim 44, wherein the antibody is of the IgG class, the IgM class, or the IgA class.

54. The nucleic acid of claim 53, wherein the antibody is of the IgG class and has an IgG1, IgG2, IgG3, or IgG4 isotype.

55. The nucleic acid of claim 54, wherein the anti-SIRPA antibody has a human IgG1 isotype and comprises one or more amino acid substitutions in the Fc region at an amino acid residue selected from the group consisting of: N297A, D265A, D270A, L234A, L235A, G237A, P238D, L328E, E233D, G237D, H268D, P271G, A330R, C226S, C229S, E233P, L234V, L234F, L235E, P331S, S267E, L328F, A330L, M252Y, S254T, T256E, N297Q, P238S, P238A, A327Q, A327G, P329A, K322A, N325S, L328F, T394D, and any combination thereof, wherein the numbering of the residues is according to EU numbering, or comprises an amino acid deletion in the Fc region at a position corresponding to glycine 236.

56. The nucleic acid of claim 55, wherein the antibody comprises N325S and L328F substitutions.

57. The nucleic acid of claim 54, which is a full length antibody, and wherein the heavy chain comprises a C-terminal lysine residue.

58. The nucleic acid of claim 54, wherein the heavy chain lacks a C-terminal lysine residue.

59. The nucleic acid of claim 44, wherein the heavy chain comprises the amino acid sequence of SEQ ID NO: 53.

60. The nucleic acid of claim 44, wherein the heavy chain comprises the amino acid sequence of SEQ ID NO: 53 except for the C-terminal lysine residue of SEQ ID NO: 53.

61. The nucleic acid of claim 44, wherein the light chain comprises the amino acid sequence of SEQ ID NO: 50.

62. The nucleic acid of claim 1, wherein the antibody further comprises a heavy chain comprising the amino acid sequence of SEQ ID NO: 53 and a light chain comprising the amino acid sequence of SEQ ID NO: 50.

63. The nucleic acid of claim 1, wherein the antibody further comprises a heavy chain comprising the amino acid sequence of SEQ ID NO: 53 except for the C-terminal lysine residue of SEQ ID NO: 53, and wherein the antibody comprises a light chain comprising the amino acid sequence of SEQ ID NO: 50.

64. The nucleic acid of claim 1, wherein the antibody further comprises a heavy chain consisting of the amino acid sequence of SEQ ID NO: 53 and a light chain consisting of the amino acid sequence of SEQ ID NO: 50.

65. The nucleic acid of claim 1, wherein the antibody further comprises a heavy chain consisting of the amino acid sequence of SEQ ID NO: 53 except for the C-terminal lysine residue of SEQ ID NO: 53, and wherein the antibody comprises a light chain consisting of the amino acid sequence of SEQ ID NO: 50.

66. The nucleic acid of claim 44, wherein the anti-SIRPA antibody decreases cell surface levels of SIRPA, decreases intracellular levels of SIRPA, decreases total cellular levels of SIRPA, or any combination thereof.

67. The nucleic acid of claim 44, wherein the anti-SIRPA antibody induces SIRPA degradation, induces SIRPA cleavage, induces SIRPA internalization, induces SIRPA shedding, downregulates SIRPA expression, or any combination thereof.

68. The nucleic acid of claim 44, wherein the antibody reduces cell surface levels of SIRPA in vitro and/or in vivo.

69. The nucleic acid of claim 44, wherein the antibody down-regulates expression of SIRPA in human monocytes and/or human macrophages.

70. The nucleic acid of claim 69, wherein the antibody down-regulates expression of SIRPA in human macrophages by about 70-95%.

71. The nucleic acid of claim 44, wherein the antibody has an affinity (KD) to human SIRPA v1 of less than 6 nM.

72. The nucleic acid of claim 44, wherein the antibody has an affinity (KD) to human SIRPA v1 of about 0.1 nM to 2 nM.

73. The nucleic acid of claim 44, wherein the antibody reduces cell surface levels of SIRPA in vitro with a half maximal effective concentration (EC50) of about 0.05 to 0.20 nM for human SIRPA v1, of about 0.05 to 0.10 nM for human SIRPA v2, and/or of about 0.05 to 1 nM for cyno SIRPA as measured by flow cytometry.

74. The nucleic acid of claim 44, wherein the antibody binds human SIRPA, human SIRPA v1, human SIRPA v2, cyno SIRPA, marmoset SIRPA, and human SIRPß3.

75. The nucleic acid of claim 44, wherein the antibody binds to the D3 domain of human SIRPA v1 of SEQ ID NO:1.

76. The nucleic acid of claim 75, wherein the antibody binds to amino acid residues R282, Q284, and G337 of human SIRPA v1 of SEQ ID NO:1.

* * * * *

SEQUENCE LISTING

```
Sequence total quantity: 70
SEQ ID NO: 1            moltype = AA   length = 504
FEATURE                 Location/Qualifiers
source                  1..504
                        mol_type = protein
                        organism = Homo sapiens
SEQUENCE: 1
MEPAGPAPGR LGPLLCLLLA ASCAWSGVAG EELQVIQPD KSVLVAAGET ATLRCTATSL    60
IPVGPIQWFR GAGPGRELIY NQKEGHFPRV TTVSDLTKRN NMDFSIRIGN ITPADAGTYY  120
CVKFRKGSPD DVEFKSGAGT ELSVRAKPSA PVVSGPAARA TPQHTVSFTC ESHGFSPRDI  180
TLKWFKNGNE LSDFQTNVDP VGESVSYSIH STAKVVLTRE DVHSQVICEV AHVTLQGDPL  240
RGTANLSETI RVPPTLEVTQ QPVRAENQVN VTCQVRKFYP QRLQLTWLEN GNVSRTETAS  300
TVTENKDGTY NWMSWLLVNV SAHRDDVKLT CQVEHDGQPA VSKSHDLKVS AHPKEQGSNT  360
AAENTGSNER NIYIVVGVVC TLLVALLMAA LYLVRIRQKK AQGSTSSTRL HEPEKNAREI  420
TQDTNDITYA DLNLPKGKKP APQAAEPNNH TEYASIQTSP QPASEDTLTY ADLDMVHLNR  480
TPKQPAPKPE PSFSEYASVQ VPRK                                        504

SEQ ID NO: 2            moltype = AA   length = 122
FEATURE                 Location/Qualifiers
source                  1..122
                        mol_type = protein
                        organism = synthetic construct
SEQUENCE: 2
EVKLVESGGG LVKPGGSLKL SCAASGFTFS SYAMSWVRQT PEKRLEWVAT ISDYGGSYTY   60
YPDSVKGRFT ISRDNAKYTL YLQMSSLRSE DTALYYCARP YDDYYGGFA YWGQGTLVTV  120
SA                                                                122

SEQ ID NO: 3            moltype = AA   length = 122
FEATURE                 Location/Qualifiers
source                  1..122
                        mol_type = protein
                        organism = synthetic construct
SEQUENCE: 3
EVQLLESGGG LVQPGGSLRL SCAASGFTFS SYAMSWVRQA PGKGLEWVST ISDYGGSYTY   60
YADSVKGRFT ISRDNSKNTL YLQMNSLRAE DTAVYYCAKP YDDYYGGFA YWGQGTLVTV  120
SS                                                                122

SEQ ID NO: 4            moltype = AA   length = 122
FEATURE                 Location/Qualifiers
source                  1..122
                        mol_type = protein
                        organism = synthetic construct
SEQUENCE: 4
EVQLLESGGG LVQPGGSLRL SCAASGFTFS SYAMSWVRQA PGKGLEWVAT ISDYGGSYTY   60
YADSVKGRFT ISRDNSKNTL YLQMNSLRAE DTAVYYCARP YDDYYGGFA YWGQGTLVTV  120
SS                                                                122

SEQ ID NO: 5            moltype = AA   length = 111
FEATURE                 Location/Qualifiers
source                  1..111
                        mol_type = protein
                        organism = synthetic construct
SEQUENCE: 5
DIVLTQSPAS LAVSLGQRAT ISCRASKSVS SGYSYMHWY QQKPGQPPKL LIYLASNLES   60
GVPARFSGSG SGTDFTLNIH PVEEEDAATY YCQHNRELPC TFGGGTKLEI K          111

SEQ ID NO: 6            moltype = AA   length = 111
FEATURE                 Location/Qualifiers
source                  1..111
                        mol_type = protein
                        organism = synthetic construct
```

```
SEQUENCE: 6
DIQMTQSPSS LSASVGDRVT ITCRASKSVS SSGYSYMHWY QQKPGKAPKL LIYLASNLES    60
GVPSRFSGSG SGTDFTLTIS SLQPEDFATY YCQHNRELPC TFGQGTKLEI K            111

SEQ ID NO: 7              moltype = AA   length = 111
FEATURE                   Location/Qualifiers
source                    1..111
                          mol_type = protein
                          organism = synthetic construct
SEQUENCE: 7
DIQLTQSPSS LSASVGDRVT ITCRASKSVS SSGYSYMHWY QQKPGKAPKL LIYLASNLES    60
GVPSRFSGSG SGTDFTLTIS SVQPEDFATY YCQHNRELPC TFGQGTKLEI K            111

SEQ ID NO: 8              moltype = AA   length = 111
FEATURE                   Location/Qualifiers
source                    1..111
                          mol_type = protein
                          organism = synthetic construct
SEQUENCE: 8
DIQLTQSPSS LSVSVGDRAT ITCRASKSVS SSGYSYMHWY QQKPGKAPKL LIYLASNLES    60
GVPSRFSGSG SGTDFTLTIS SVQPEDFATY YCQHNRELPC TFGQGTKLEI K            111

SEQ ID NO: 9              moltype = AA   length = 15
FEATURE                   Location/Qualifiers
source                    1..15
                          mol_type = protein
                          organism = synthetic construct
SEQUENCE: 9
RASKSVSSGG YSYMH                                                    15

SEQ ID NO: 10             moltype = AA   length = 7
FEATURE                   Location/Qualifiers
source                    1..7
                          mol_type = protein
                          organism = synthetic construct
SEQUENCE: 10
LASNLES                                                             7

SEQ ID NO: 11             moltype = AA   length = 9
FEATURE                   Location/Qualifiers
source                    1..9
                          mol_type = protein
                          organism = synthetic construct
SEQUENCE: 11
QHNRELPST                                                           9

SEQ ID NO: 12             moltype = AA   length = 9
FEATURE                   Location/Qualifiers
source                    1..9
                          mol_type = protein
                          organism = synthetic construct
SEQUENCE: 12
QHNRELPCT                                                           9

SEQ ID NO: 13             moltype = AA   length = 9
FEATURE                   Location/Qualifiers
source                    1..9
                          mol_type = protein
                          organism = synthetic construct
SEQUENCE: 13
QHNRELPIT                                                           9

SEQ ID NO: 14             moltype = AA   length = 9
FEATURE                   Location/Qualifiers
source                    1..9
                          mol_type = protein
                          organism = synthetic construct
SEQUENCE: 14
QHNRELPPT                                                           9

SEQ ID NO: 15             moltype = AA   length = 9
FEATURE                   Location/Qualifiers
source                    1..9
                          mol_type = protein
                          organism = synthetic construct
SEQUENCE: 15
QHNRELPTT                                                           9

SEQ ID NO: 16             moltype = AA   length = 9
```

-continued

```
FEATURE                 Location/Qualifiers
source                  1..9
                        mol_type = protein
                        organism = synthetic construct
SEQUENCE: 16
QHNRELPVT                                                                9

SEQ ID NO: 17           moltype = AA  length = 9
FEATURE                 Location/Qualifiers
source                  1..9
                        mol_type = protein
                        organism = synthetic construct
SEQUENCE: 17
QHNRELPAT                                                                9

SEQ ID NO: 18           moltype = AA  length = 9
FEATURE                 Location/Qualifiers
source                  1..9
                        mol_type = protein
                        organism = synthetic construct
SEQUENCE: 18
QHNRELPGT                                                                9

SEQ ID NO: 19           moltype = AA  length = 9
FEATURE                 Location/Qualifiers
source                  1..9
                        mol_type = protein
                        organism = synthetic construct
SEQUENCE: 19
QHNRELPWT                                                                9

SEQ ID NO: 20           moltype = AA  length = 10
FEATURE                 Location/Qualifiers
source                  1..10
                        mol_type = protein
                        organism = synthetic construct
SEQUENCE: 20
GFTFSSYAMS                                                              10

SEQ ID NO: 21           moltype = AA  length = 18
FEATURE                 Location/Qualifiers
source                  1..18
                        mol_type = protein
                        organism = synthetic construct
SEQUENCE: 21
TISEYGGSYT YYAESVKG                                                     18

SEQ ID NO: 22           moltype = AA  length = 12
FEATURE                 Location/Qualifiers
source                  1..12
                        mol_type = protein
                        organism = synthetic construct
SEQUENCE: 22
PPYDDYYGGF AY                                                           12

SEQ ID NO: 23           moltype = AA  length = 12
FEATURE                 Location/Qualifiers
source                  1..12
                        mol_type = protein
                        organism = synthetic construct
SEQUENCE: 23
PPYDDYYGGF RY                                                           12

SEQ ID NO: 24           moltype = AA  length = 12
FEATURE                 Location/Qualifiers
source                  1..12
                        mol_type = protein
                        organism = synthetic construct
SEQUENCE: 24
PPYDDYYGGF QY                                                           12

SEQ ID NO: 25           moltype = AA  length = 25
FEATURE                 Location/Qualifiers
source                  1..25
                        mol_type = protein
                        organism = synthetic construct
SEQUENCE: 25
EVQLLESGGG LVQPGGSLRL SCAAS                                             25
```

```
SEQ ID NO: 26              moltype = AA   length = 14
FEATURE                    Location/Qualifiers
source                     1..14
                           mol_type = protein
                           organism = synthetic construct
SEQUENCE: 26
WVRQAPGKGL EWVA                                                        14

SEQ ID NO: 27              moltype = AA   length = 32
FEATURE                    Location/Qualifiers
source                     1..32
                           mol_type = protein
                           organism = synthetic construct
SEQUENCE: 27
RFTISRDNSK NTLYLQMNSL RAEDTAVYYC AR                                    32

SEQ ID NO: 28              moltype = AA   length = 11
FEATURE                    Location/Qualifiers
source                     1..11
                           mol_type = protein
                           organism = synthetic construct
SEQUENCE: 28
WGQGTLVTVS S                                                           11

SEQ ID NO: 29              moltype = AA   length = 23
FEATURE                    Location/Qualifiers
source                     1..23
                           mol_type = protein
                           organism = synthetic construct
SEQUENCE: 29
DIQLTQSPSS LSASVGDRVT ITC                                              23

SEQ ID NO: 30              moltype = AA   length = 15
FEATURE                    Location/Qualifiers
source                     1..15
                           mol_type = protein
                           organism = synthetic construct
SEQUENCE: 30
WYQQKPGKAP KLLIY                                                       15

SEQ ID NO: 31              moltype = AA   length = 32
FEATURE                    Location/Qualifiers
source                     1..32
                           mol_type = protein
                           organism = synthetic construct
SEQUENCE: 31
GVPSRFSGSG SGTDFTLTIS SVQPEDFATY YC                                    32

SEQ ID NO: 32              moltype = AA   length = 10
FEATURE                    Location/Qualifiers
source                     1..10
                           mol_type = protein
                           organism = synthetic construct
SEQUENCE: 32
FGQGTKLEIK                                                             10

SEQ ID NO: 33              moltype = AA   length = 122
FEATURE                    Location/Qualifiers
source                     1..122
                           mol_type = protein
                           organism = synthetic construct
SEQUENCE: 33
EVQLLESGGG LVQPGGSLRL SCAASGFTFS SYAMSWVRQA PGKGLEWVAT ISEYGGSYTY       60
YAESVKGRFT ISRDNSKNTL YLQMNSLRAE DTAVYYCARP PYDDYGGFA  YWGQGTLVTV      120
SS                                                                    122

SEQ ID NO: 34              moltype = AA   length = 122
FEATURE                    Location/Qualifiers
source                     1..122
                           mol_type = protein
                           organism = synthetic construct
SEQUENCE: 34
EVQLLESGGG LVQPGGSLRL SCAASGFTFS SYAMSWVRQA PGKGLEWVAT ISEYGGSYTY       60
YAESVKGRFT ISRDNSKNTL YLQMNSLRAE DTAVYYCARP PYDDYGGFR  YWGQGTLVTV      120
SS                                                                    122

SEQ ID NO: 35              moltype = AA   length = 122
FEATURE                    Location/Qualifiers
source                     1..122
```

```
                        mol_type = protein
                        organism = synthetic construct
SEQUENCE: 35
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP PYDDYYGGFQ YWGQGTLVTV   120
SS                                                                 122

SEQ ID NO: 36           moltype = AA  length = 111
FEATURE                 Location/Qualifiers
source                  1..111
                        mol_type = protein
                        organism = synthetic construct
SEQUENCE: 36
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPS TFGQGTKLEI K            111

SEQ ID NO: 37           moltype = AA  length = 111
FEATURE                 Location/Qualifiers
source                  1..111
                        mol_type = protein
                        organism = synthetic construct
SEQUENCE: 37
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPC TFGQGTKLEI K            111

SEQ ID NO: 38           moltype = AA  length = 111
FEATURE                 Location/Qualifiers
source                  1..111
                        mol_type = protein
                        organism = synthetic construct
SEQUENCE: 38
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPI TFGQGTKLEI K            111

SEQ ID NO: 39           moltype = AA  length = 111
FEATURE                 Location/Qualifiers
source                  1..111
                        mol_type = protein
                        organism = synthetic construct
SEQUENCE: 39
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPP TFGQGTKLEI K            111

SEQ ID NO: 40           moltype = AA  length = 111
FEATURE                 Location/Qualifiers
source                  1..111
                        mol_type = protein
                        organism = synthetic construct
SEQUENCE: 40
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPT TFGQGTKLEI K            111

SEQ ID NO: 41           moltype = AA  length = 111
FEATURE                 Location/Qualifiers
source                  1..111
                        mol_type = protein
                        organism = synthetic construct
SEQUENCE: 41
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPV TFGQGTKLEI K            111

SEQ ID NO: 42           moltype = AA  length = 111
FEATURE                 Location/Qualifiers
source                  1..111
                        mol_type = protein
                        organism = synthetic construct
SEQUENCE: 42
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPA TFGQGTKLEI K            111

SEQ ID NO: 43           moltype = AA  length = 111
FEATURE                 Location/Qualifiers
source                  1..111
                        mol_type = protein
                        organism = synthetic construct
SEQUENCE: 43
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPG TFGQGTKLEI K            111
```

```
SEQ ID NO: 44              moltype = AA   length = 111
FEATURE                    Location/Qualifiers
source                     1..111
                           mol_type = protein
                           organism = synthetic construct
SEQUENCE: 44
DIQLTQSPSS LSASVGDRVT ITCRASKSVS SGGYSYMHWY QQKPGKAPKL LIYLASNLES    60
GVPSRFSGSG SGTDFTLTIS SVQPEDFATY YCQHNRELPW TFGQGTKLEI K             111

SEQ ID NO: 45              moltype = AA   length = 118
FEATURE                    Location/Qualifiers
source                     1..118
                           mol_type = protein
                           organism = synthetic construct
SEQUENCE: 45
EFQLQQSGAE LVKPGASVKI SCKASGYSLT GYNMNWVKQS RGKSLEWIGN INPHYGSSTY    60
NQNFKDKATL TVDKSSSAAY MQFNSLTSED SAVYYCAREG YDGVFDYWGQ GTTLTVSS     118

SEQ ID NO: 46              moltype = AA   length = 106
FEATURE                    Location/Qualifiers
source                     1..106
                           mol_type = protein
                           organism = synthetic construct
SEQUENCE: 46
QIVLSQSPAI LSASPGEKVT MTCRASSSVS YMHWYQQKPG SSPKPWIYVT SNLASGVPTR    60
FSGSGSGTSY SLTISRVEAE DAATYYCQQW SSNPRTFGGG TKLEIK                  106

SEQ ID NO: 47              moltype = AA   length = 452
FEATURE                    Location/Qualifiers
source                     1..452
                           mol_type = protein
                           organism = synthetic construct
SEQUENCE: 47
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFQ YWGQGTLVTV    120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 48              moltype = AA   length = 452
FEATURE                    Location/Qualifiers
source                     1..452
                           mol_type = protein
                           organism = synthetic construct
SEQUENCE: 48
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFQ YWGQGTLVTV    120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPASIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 49              moltype = AA   length = 452
FEATURE                    Location/Qualifiers
source                     1..452
                           mol_type = protein
                           organism = synthetic construct
SEQUENCE: 49
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFQ YWGQGTLVTV    120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VEHEDPEVKF NWYVDGVEVH NAKTKPREEQ   300
YNSTYRVVSV LTVLHQDWLN GKEYKCKVSN KAFPAPIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 50              moltype = AA   length = 218
FEATURE                    Location/Qualifiers
source                     1..218
                           mol_type = protein
                           organism = synthetic construct
SEQUENCE: 50
DIQLTQSPSS LSASVGDRVT ITCRASKSVS SGGYSYMHWY QQKPGKAPKL LIYLASNLES    60
```

```
GVPSRFSGSG SGTDFTLTIS SVQPEDFATY YCQHNRELPV TFGQGTKLEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 51             moltype = AA   length = 452
FEATURE                   Location/Qualifiers
source                    1..452
                          mol_type = protein
                          organism = synthetic construct
SEQUENCE: 51
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFR YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 52             moltype = AA   length = 452
FEATURE                   Location/Qualifiers
source                    1..452
                          mol_type = protein
                          organism = synthetic construct
SEQUENCE: 52
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFQ YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VEHEDPEVKF NWYVDGVEVH NAKTKPREEQ    300
YNSTYRVVSV LTVLHQDWLN GKEYKCKVSN KAFPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 53             moltype = AA   length = 452
FEATURE                   Location/Qualifiers
source                    1..452
                          mol_type = protein
                          organism = synthetic construct
SEQUENCE: 53
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFQ YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSS KAFPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 54             moltype = AA   length = 452
FEATURE                   Location/Qualifiers
source                    1..452
                          mol_type = protein
                          organism = synthetic construct
SEQUENCE: 54
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFQ YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPEAA    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPASIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452

SEQ ID NO: 55             moltype = AA   length = 452
FEATURE                   Location/Qualifiers
source                    1..452
                          mol_type = protein
                          organism = synthetic construct
SEQUENCE: 55
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFR YWGQGTLVTV    120
SSASTKGPSV FPLAPSSKST SGGTAALGCL VKDYFPEPVT VSWNSGALTS GVHTFPAVLQ    180
SSGLYSLSSV VTVPSSSLGT QTYICNVNHK PSNTKVDKKV EPKSCDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSS KAFPAPIEKT ISKAKGQPRE PQVYTLPPSR    360
DELTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                  452
```

```
SEQ ID NO: 56              moltype = AA  length = 452
FEATURE                    Location/Qualifiers
source                     1..452
                           mol_type = protein
                           organism = synthetic construct
SEQUENCE: 56
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFR  YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPEAA   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPASIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 57              moltype = AA  length = 452
FEATURE                    Location/Qualifiers
source                     1..452
                           mol_type = protein
                           organism = synthetic construct
SEQUENCE: 57
EVQLLESGGG LVQPGGSLRL SCAASGFTFS SYAMSWVRQA PGKGLEWVAT ISEYGGSYTY    60
YAESVKGRFT ISRDNSKNTL YLQMNSLRAE DTAVYYCARP YDDYYGGFR  YWGQGTLVTV   120
SSASTKGPSV FPLAPSSKST SGGTAALGCL VKDYFPEPVT VSWNSGALTS GVHTFPAVLQ   180
SSGLYSLSSV VTVPSSSLGT QTYICNVNHK PSNTKVDKKV EPKSCDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPASIEKT ISKAKGQPRE PQVYTLPPSR   360
DELTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 58              moltype = AA  length = 110
FEATURE                    Location/Qualifiers
source                     1..110
                           mol_type = protein
                           organism = synthetic construct
SEQUENCE: 58
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP             110

SEQ ID NO: 59              moltype = AA  length = 343
FEATURE                    Location/Qualifiers
source                     1..343
                           mol_type = protein
                           organism = Homo sapiens
SEQUENCE: 59
EEELQVIQPD KSVLVAAGET ATLRCTATSL IPVGPIQWFR GAGPGRELIY NQKEGHFPRV    60
TTVSDLTKRN NMDFSIRIGN ITPADAGTYY CVKFRKGSPD DVEFKSGAGT ELSVRAKPSA   120
PVVSGPAARA TPQHTVSFTC ESHGFSPRDI TLKWFKNGNE LSDFQTNVDP VGESVSYSIH   180
STAKVVLTRE DVHSQVICEV AHVTLQGDPL RGTANLSETI RVPPTLEVTQ QPVRAENQVN   240
VTCQVRKFYP QRLQLTWLEN GNVSRTETAS TVTENKDGTY NWMSWLLVNV SAHRDDVKLT   300
CQVEHDGQPA VSKSHDLKVS AHPKEQGSNT AAENTGSNER NIY                     343

SEQ ID NO: 60              moltype = AA  length = 342
FEATURE                    Location/Qualifiers
source                     1..342
                           mol_type = protein
                           organism = Macaca fascicularis
SEQUENCE: 60
EEELQVIQPE KSVSVAAGDS ATLNCTVSSL IPVGPIQWFR GAGPGRELIY NLKEGHFPRV    60
TPVSDPTKRN NMDFSIRISN ITPADAGTYY CVKFRKGSPD VELKSGAGTE LSVRAKPSAP   120
VVSGPAVRAT AEHTVSFTCE SHGFSPRDIT LKWFKNGNEL SDFQTNVDPA GKSVSYSIRS   180
TARVVLTRRD VHSQVICEVA HVTLQGDPLR GTANLSEAIR VPPFLEVTQQ SMRADNQVNV   240
TCQVTKFYPQ RLQLTWLENG NVSRTEMASA LPENKDGTYN WTSWLLVNVS AHRDDVKLTC   300
QVEHDGQPAV NKSFSVKVSA HPKEQGSNTA AENTGTNERN IY                      342

SEQ ID NO: 61              moltype = AA  length = 343
FEATURE                    Location/Qualifiers
source                     1..343
                           mol_type = protein
                           organism = Callithrix jacchus
SEQUENCE: 61
EEELQVVQPE KSVSVAAGET ATLHCTVTSL VPVGPIQWFR GAGPGRELIY NQKEGQFPRV    60
TAVADQTKRN NMDHSIRISN ITPADAGTYY CVKFRKASPI DVELKSGPGT ELSVRAKPSA   120
PVVSGPATRV TPEDTVSFTC ESHGFSPRDI TLKWFKNANE LSALQTTVDP AGESVSYSIR   180
STARVGLTRG DVRSQVICEV AHVTLQGDPL RGTANLSEAI RVPPTLEVTH QPMRAENQVN   240
VTCQVKKFYP QSLQLTWLEN GNVSRTETAS TLIENKDGTY NWASWLLVNS SAHRDGVVLT   300
CQVEHDGQPA VSKSLRLEVS AHRKEQGSDT AAEKTGTNER NIY                     343

SEQ ID NO: 62              moltype = AA  length = 342
```

| FEATURE | Location/Qualifiers |
|---|---|
| source | 1..342<br>mol_type = protein<br>organism = Oryctolagus cuniculus |

SEQUENCE: 62

```
QEKLQVTQPD RWVSVAEGEA ATLRCTINTL LPVGPMKWFR GAGPDRKMIY NFKGDQDPRV   60
TNVSDTTKRN NMDFSIRIRD ITPADAGTYY CVKFQKKGAD DEEFKSGGGT QVSVSAKPST  120
PKVSGPGARS TPEQTVDFTC ESHGFSPRNI SLKWFKNGNE LPAFQTSVYP AGESVSYNVT  180
STVKVALASS DVHSQVICEV AHITLQGGSP LRGTANLSET IRVPPTVEVT QQPMGAGTQV  240
NVTCHVDKFY PRDMQLSWLE NGNVSRTETA WTLVENKDGT YNRTSWLLVN SSAHREDVVL  300
SCQVEHDGQP AVTRSHTLQV SAPPKEQGTD TSLDQADNWN VF                    342
```

| SEQ ID NO: 63 | moltype = AA length = 343 |
|---|---|
| FEATURE | Location/Qualifiers |
| source | 1..343<br>mol_type = protein<br>note = subspecies - familiaris<br>organism = Canis lupus |

SEQUENCE: 63

```
EAELQVIQPE KSVSVAAGET ATLRCTLTSL IPVGKVEWFR GTGPGRELIF HFKGGHFPRV   60
TNVSDSTKRN NTDFSIRISN ITPADTGTYY CVKFQKGNPD VELKSGPGTL VTVSAKPSPP  120
VVSGPTARAT PQQTVNFTCK SHGFSPRNIT LRWFKNGNEL TASQTTVYPE EDNASYSISS  180
TTKLVLAPGD VRSQVICEVA HVTLQGGPPL RGTANLSETL RVPPTLEVSQ HPMAGDQVNV  240
TCQVKKFYPQ RLQLTWLENG NVSRTETPSV ASNLLENKDG TFNWTSWLLV NSSTHREDVV  300
FTCQVQHDGQ PAVTKNHTLV ASARQKDQET LKPEDNNDSR SIF                   343
```

| SEQ ID NO: 64 | moltype = AA length = 98 |
|---|---|
| FEATURE | Location/Qualifiers |
| source | 1..98<br>mol_type = protein<br>organism = synthetic construct |

SEQUENCE: 64

```
EVQLLESGGG LVQPGGSLRL SCAASGFTFS SYAMSWVRQA PGKGLEWVSA ISGSGGSTYY   60
ADSVKGRFTI SRDNSKNTLY LQMNSLRAED TAVYYCAK                          98
```

| SEQ ID NO: 65 | moltype = AA length = 15 |
|---|---|
| FEATURE | Location/Qualifiers |
| source | 1..15<br>mol_type = protein<br>organism = synthetic construct |

SEQUENCE: 65

```
YFDYWGQGTL VTVSS                                                   15
```

| SEQ ID NO: 66 | moltype = AA length = 96 |
|---|---|
| FEATURE | Location/Qualifiers |
| source | 1..96<br>mol_type = protein<br>organism = synthetic construct |

SEQUENCE: 66

```
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ RSNWPP                            96
```

| SEQ ID NO: 67 | moltype = AA length = 12 |
|---|---|
| FEATURE | Location/Qualifiers |
| source | 1..12<br>mol_type = protein<br>organism = synthetic construct |

SEQUENCE: 67

```
YTFGQGTKLE IK                                                      12
```

| SEQ ID NO: 68 | moltype = AA length = 111 |
|---|---|
| FEATURE | Location/Qualifiers |
| source | 1..111<br>mol_type = protein<br>organism = synthetic construct |

SEQUENCE: 68

```
EIVLTQSPAT LSLSPGERAT LSCRASKSVS SSGYSYMHWY QQKPGQAPRL LIYLASNLES   60
GIPARFSGSG SGTDFTLTIS SLEPEDFAVY YCQHNRELPC TFGQGTKLEI K           111
```

| SEQ ID NO: 69 | moltype = AA length = 111 |
|---|---|
| FEATURE | Location/Qualifiers |
| source | 1..111<br>mol_type = protein<br>organism = synthetic construct |

SEQUENCE: 69

```
EIVLTQSPAT LSLSPGERAT ISCRASKSVS SSGYSYMHWY QQKPGQAPRL LIYLASNLES   60
GVPARFSGSG SGTDFTLTIS SVEPEDFAVY YCQHNRELPC TFGQGTKLEI K           111
```

| SEQ ID NO: 70 | moltype = AA length = 111 |
|---|---|

-continued

```
FEATURE           Location/Qualifiers
source            1..111
                  mol_type = protein
                  organism = synthetic construct
SEQUENCE: 70
EIVLTQSPAT LSLSPGERAT ISCRASKSVS SSGYSYMHWY QQKPGQAPRL LIYLASNLES    60
GVPARFSGSG SGTDFTLTIS SVEPEDFAVY YCQHNRELPS TFGQGTKLEI K            111
```